(12) United States Patent
Prather et al.

(10) Patent No.: US 10,091,975 B2
(45) Date of Patent: Oct. 9, 2018

(54) PATHOGEN-RESISTANT ANIMALS HAVING MODIFIED CD163 GENES

(71) Applicant: The Curators of the University of Missouri, Columbia, MO (US)

(72) Inventors: Randall S. Prather, Rocheport, MO (US); Kevin D. Wells, Columbia, MO (US); Kristin M. Whitworth, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/216,865

(22) Filed: Jul. 22, 2016

(65) Prior Publication Data

US 2017/0035035 A1 Feb. 9, 2017

Related U.S. Application Data

(60) Provisional application No. 62/202,145, filed on Aug. 6, 2015.

(51) Int. Cl.
| | |
|---|---|
| *A01K 67/027* | (2006.01) |
| *A01K 67/02* | (2006.01) |
| *C12N 5/10* | (2006.01) |
| *C07K 14/705* | (2006.01) |
| *C12N 15/85* | (2006.01) |
| *C12N 15/877* | (2010.01) |

(52) U.S. Cl.
CPC .......... *A01K 67/0276* (2013.01); *A01K 67/02* (2013.01); *C07K 14/70596* (2013.01); *C12N 15/8509* (2013.01); *C12N 15/8778* (2013.01); *A01K 2217/075* (2013.01); *A01K 2227/108* (2013.01); *A01K 2267/02* (2013.01); *C12N 2770/10011* (2013.01)

(58) Field of Classification Search
CPC ............ A01K 67/0276; A01K 2217/15; A01K 2217/075; A01K 2227/108; A01K 67/02; C12N 15/8778; C12N 5/0609; C12N 5/061; C12N 5/0656; C07K 14/70596
USPC .......................... 800/17, 13, 21, 22; 435/325
See application file for complete search history.

(56) References Cited

U.S. PATENT DOCUMENTS

| | | | |
|---|---|---|---|
| 5,945,577 | A | 8/1999 | Stice et al. |
| 6,211,429 | B1 | 4/2001 | Machaty et al. |
| 2003/0237106 | A1 | 12/2003 | Gorczynski |
| 2005/0120400 | A1 | 6/2005 | Day et al. |
| 2005/0260176 | A1 | 11/2005 | Ayares et al. |
| 2009/0104147 | A1 | 4/2009 | Delputte et al. |
| 2010/0158947 | A1 | 6/2010 | Delputte et al. |
| 2011/0016543 | A1 | 1/2011 | Weinstein et al. |
| 2011/0016546 | A1 | 1/2011 | Bedell et al. |
| 2011/0038841 | A1 | 2/2011 | Ayares |
| 2012/0180141 | A1 | 7/2012 | Welsh et al. |
| 2013/0309263 | A1 | 11/2013 | Calvert et al. |
| 2014/0096275 | A1 | 4/2014 | Prather |

FOREIGN PATENT DOCUMENTS

| | | | |
|---|---|---|---|
| CN | | 104593422 A | 1/2015 |
| WO | | 96/07732 A1 | 3/1996 |
| WO | | 97/07668 A1 | 3/1997 |
| WO | | 97/07669 A1 | 3/1997 |
| WO | | 2005/104835 A2 | 11/2005 |
| WO | | 2012/158828 A1 | 11/2012 |
| WO | WO 2012/158828 | * | 11/2012 |
| WO | | 2015/011483 A1 | 1/2015 |
| WO | | 2016/110214 A1 | 7/2016 |

OTHER PUBLICATIONS

Van Gorp et al. (2010) J. Virol., vol. 84(6), 3101-3105.*
Ritter et al. (1999) Biochem. Biophys. Res. Comm., vol. 260, 466-474.*
Kim et al. (2014) Nature Reviews/Genetics, vol. 15, 321-334.*
Whitworth, K. M., et al., "Use of the CRISPR/Cas9 System to Produce Genetically Engineered Pigs from In Vitro-Derived Oocytes and Embryos," Biology of Reproduction, 2014, pp. 1-13, vol. 91, No. 3.
Whitworth, K. M., et al., "Use of the CRISPR/Cas9 System to Produce Pigs With a Genetically Modified CD163 Gene by Using Somatic Cell Nuclear Transfer of In Vitro Derived Oocytes," Abstract, Swine in Biomedical Research Conference, Raleigh, North Carolina, Jul. 20-22, 2014, p. 103.
Whitworth, K. M., et al., "Use of the CRISPR/Cas9 System to Produce Pigs With a Genetically Modified CD163 Gene by Using Somatic Cell Nuclear Transfer of In Vitro Derived Oocytes," Poster, Swine in Biomedical Research Conference, Raleigh, North Carolina, Jul. 20-22, 2014.
Whyte, J. J., et al., "Gene Targeting With Zinc Finger Nucleases to Produce Cloned eGFP Knockout Pigs," Molecular Reproduction and Development, 2011, 3 pages, vol. 78, No. 1.
Whyte, J. J., et al., "Genetic Modifications of Pigs for Medicine and Agriculture," Molecular Reproduction and Development, 2011, pp. 879-891, vol. 78, Nos. 10-11.
Wiedenheft, B., et al., "RNA-guided Genetic Silencing Systems in Bacteria and Archaea," Nature, Feb. 2012, pp. 331-338, vol. 482, No. 7385.
Wills, R. W., et al., "Porcine Reproductive and Respiratory Syndrome Virus—A Persistent Infection," Veterinary Microbiology, 1997, pp. 231-240, vol. 55, Nos. 1-4.
Winckler, C., et al., "The Reliability and Repeatability of a Lameness Scoring System for Use as an Indicator of Welfare in Dairy Cattle," Acta Agriculturae Scandinavica, Section A—Animal Science, 2001, pp. 103-107, vol. 51, Supplement 30.

(Continued)

*Primary Examiner* — Anne Marie S Wehbe
(74) *Attorney, Agent, or Firm* — Senniger Powers LLP

(57) ABSTRACT

Non-human animals and offspring thereof comprising at least one modified chromosomal sequence in a gene encoding a CD163 protein are provided. Animal cells that contain such modified chromosomal sequences are also provided. The animals and cells have increased resistance to pathogens, including porcine reproductive and respiratory syndrome virus (PRRSV). The animals and offspring have chromosomal modifications of a CD163 gene. The invention further relates to methods of breeding to create pathogen-resistant animals and populations of animals made using such methods.

36 Claims, 28 Drawing Sheets

Specification includes a Sequence Listing.

(56) References Cited

OTHER PUBLICATIONS

Wissink, E. H. J., et al., "Identification of Porcine Alveolar Macrophage Glycoproteins Involved in Infection of Porcine Respiratory and Reproductive Syndrome Virus," Archives of Virology, 2003, pp. 177-187, vol. 148, No. 1.
Yang, D., et al., "Generation of PPAR(Gamma) Mono-Allelic Knockout Pigs via Zinc-Finger Nucleases and Nuclear Transfer Cloning," Cell Research, 2011, pp. 979-982, vol. 6.
Yoon, I. L., et al., "Persistent and Contact Infection in Nursery Pigs Experimentally Infected with PRRS Virus," Swine Health and Production, 1993, pp. 5-8, vol. 1.
Yoshioka, K., et al., "Birth of Piglets Derived from Porcine Zygotes Cultured in a Chemically Defined Medium," Biology of Reproduction, 2002, pp. 112-119, vol. 66.
Zhang, Q., et al., "PRRS Virus Receptors and Their Role for Pathogenesis," Veterinary Microbiology, 2015, pp. 229-241, vol. 177.
Zhao, J., et al., "Histone Deacetylase Inhibitors Improve In Vitro and In Vivo Developmental Competence of Somatic Cell Nuclear Transfer Porcine Embryos," Cellular Reprogramming, 2010, pp. 75-83, vol. 12, No. 1.
Zhao, J., et al., "Significant Improvement in Cloning Efficiency of an Inbred Miniature Pig by Histone Deacetylase Inhibitor Treatment After Somatic Cell Nuclear Transfer," Biology of Reproduction, 2009, pp. 525-530, vol. 81.
Co-pending U.S. Appl. No. 14/117,943, filed Nov. 15, 2013.
International Search Report and Written Opinion issued for PCT/US2015/044113, dated Jan. 6, 2016, 13 pages.
International Search Report and Written Opinion issued for PCT/US2016/043467, dated Oct. 25, 2016, 15 pages.
Kim, J.-K., et al., "Defining the Cellular Target(s) of Porcine Reproductive and Respiratory Syndrome Virus Blocking Monoclonal Antibody 7G10," Journal of Virology, Jan. 2006, pp. 689-696, vol. 80, No. 2.
Kristiansen, M., et al., "Identification of the Haemoglobin Scavenger Receptor," Nature, Jan. 2001, pp. 198-201, vol. 409, No. 6817.
Kwon, D.-N., et al., "Production of Biallelic CMP-Neu5Ac Hydroxylase Knock-out Pigs," Scientific Reports, 1981, pp. 1-10, vol. 3.
Ladinig, A., et al., "Pathogenicity of Three Type 2 Porcine Reproductive and Respiratory Syndrome Virus Strains in Experimentally Inoculated Pregnant Gilts," Virus Research, 2015, pp. 24-35, vol. 203.
Lager, K. M., et al., "Evaluation of Protective Immunity in Gilts Inoculated with the NADC-8 Isolate of Porcine Reproductive and Respiratory Syndrome Virus (PRRSV) and Challenge-Exposed with an Antigenically Distinct PRRSV Isolate," American Journal of Veterinary Research, 1999, pp. 1022-1027, vol. 60, No. 8.
Lai, L., et al., "Generation of Cloned Transgenic Pigs Rich in Omega-3 Fatty Acids," Nature Biotechnology, Apr. 2006, pp. 435-436, vol. 24, No. 4.
Lai, L., et al., "Production of alpha-1,3-Galactosyltransferase Knockout Pigs by Nuclear Transfer Cloning," Science, 2002, pp. 1089-1092, vol. 295, No. 5557.
Lai, L., et al., "Creating Genetically Modified Pigs by Using Nuclear Transfer," Reproductive Biology and Endocrinology, 2003, pp. 1-6, vol. 1, No. 82.
Lai, L., et al., "Methods Paper—Production of Cloned Pigs by Using Somatic Cells as Donors," Cloning and Stem Cells, 2003, pp. 233-241, vol. 5, No. 4.
Lai, L. et al., "A Method for Producing Cloned Pigs by Using Somatic Cells as Donors," Methods in Molecular Biology, 2004, pp. 149-163, vol. 254.
Lawson, S. R., et al., "Porcine Reproductive and Respiratory Syndrome Virus Infection of Gnotobiotic Pigs: Sites of Virus replication and Co-localization with MAC-387 Staining at 21 Days Post-infection," Virus Research, 1997, pp. 105-113, vol. 51.
Lee, K., et al., "Engraftment of Human iPS Cells and Allogeneic Porcine Cells into Pigs with Inactivated RAG2 and Accompanying Severe Combined Immunodeficiency," Proceedings of the National Academy of Sciences of the United States of America, 2014, pp. 7260-7265, vol. 111.
Lee, K., et al., "Piglets Produced from Cloned Blastocysts Cultured In Vitro with GM-CSF," Molecular Reproduction and Development, 2013, pp. 145-154, vol. 80, No. 2.
Li, D., et al., "Heritable Gene Targeting in the Mouse and Rat Using a CRISPR-Cas System," Nature Biotechnology, pp. 681-683, vol. 31, No. 8.
Li, R., et al., "Clonsed Transgenic Swine via In Vitro Production and Cryopreservation," Biology of Reproduction, 2006, pp. 226-230, vol. 75.
Lillico, S. G., et al., "Live Pigs Produced From Genome Edited Zygotes," Scientific Reports, 2013, pp. 1-4, vol. 3, No. 2847.
Lunney, J. K., et al., "Genetic Control of Host Resistance to Porcine Reproductive and Respiratory Syndrome Virus (PRRSV) Infection," Virus Research, 2010, pp. 161-169, vol. 154.
Machaty, Z., et al., "Complete Activation of Porcine Oocytes Induced by the Sulfhydryl Reagent, Thimerosal," Biology of Reproduction, 1997, pp. 1123-1127, vol. 57.
Machaty, Z., et al., "Development of Early Porcine Embryos In Vitro and In Vivo," Biology of Reproduction, 1998, pp. 451-455, vol. 59.
Madsen, M., et al., "Molecular Characterization of the Haptoglobin-Hemoglobin Receptor CD163," The Journal of Biological Chemistry, Dec. 3, 2004, pp. 51561-51567, vol. 279, No. 49.
Mansour, S. L., et al., "Disruption of the Proto-Oncogene int-2 in Mouse Embryo-Derived Stem Cells: A General Strategy for Targeting Mutations to Nonselectable Genes," Nature, 1988, pp. 348-352, vol. 336.
Mayes, M. A., et al., "Parthenogenic Activation of Pig Oocytes by Protein Kinase Inhibition," Biology of Reproduction, 1995, pp. 270-275, vol. 53, No. 2.
McGrath, J., et al., "Nuclear Transplantation in the Mouse Embryo by Microsurgery and Cell Fusion," Science, Jun. 1983, pp. 1300-1302, vol. 220, No. 4603.
Meng, X. J., "Heterogeneity of Porcine Reproductive and Respiratory Syndrome Virus: Implications for Current Vaccine Efficacy and Future Vaccine Development [Review]," Veterinary Microbiology, 2000, pp. 309-329, vol. 74, No. 4.
Meng, X. J., et al., "Sequence Comparison of Open Reading Frames 2 to 5 of Low and High Virulence United States Isolates of Porcine Reproductive and Respiratory Syndrome Virus," Journal of General Virology, 1995, pp. 3181-3188, vol. 76, Part 12.
Mengeling, W. L., et al., "Identification and Clinical Assessment of Suspected Vaccine-Related Field Strains of Porcine Reproductive and Respiratory Syndrome Virus," American Journal of Veterinary Research, 1999, pp. 334-340, vol. 60, No. 3.
Merck & Co., Inc., Normal Rectal Temperature Ranges chart, The Merck Veterinary Manual 2009-2015, accessed from <http://www.merckvetmanual.com/mvm/appendixes/reference_guides/normal_rectal_temperature_ranges.html?qt=normal%20rectal%20temperature%20ranges&alt=sh>, 1 page.
Miao, Y.-L. et al., "Centrosome Abnormalities During Porcine Oocyte Aging," Environmental and Molecular Mutagenesis, 2009, pp. 666-671, vol. 50.
Misinzo, G. M., et al., "Involvement of Proteases in Porcine Reproductive and Respiratory Syndrome Virus Uncoating Upon Internalization in Primary Macrophages," Veterinary Research, 2008, 14 pages, vol. 39, No. 55.
Molitor, T. W., et al., "Immunity to PRRSV—Double-Edged Sword," Veterinary Microbiology, 1997, pp. 265-276, vol. 55, Nos. 1-4.
Morgan, S. B., et al., "Pathology and Virus Distribution in the Lung and Lymphoid Tissues of Pigs Experimentally Inoculated with Three Distinct Type 1 PRRS Virus Isolates of Varying Pathogenicity," Transboundary and Emerging Diseases, 2016, pp. 285-295, vol. 63.
Murtaugh, M. P., et al., "Comparison of the Structural Protein Coding Sequences of the VR-2332 and Lelystad Virus Strains of the PRRS Virus," Archives of Virology, 1995, pp. 1451-1460, vol. 140, No. 8.

(56) References Cited

OTHER PUBLICATIONS

Nath, D., et al., "The Amino-Terminal Immunoglobulin-Like Domain of Sialoadhesin Contains the Sialic Acid Binding Site, Comparison with CD22," The Journal of Biological Chemistry, 1995, pp. 26184-26191, vol. 270, No. 44.

Nauwynck, H. J., et al., "Entry of Porcine Reproductive and Respiratory Syndrome Virus into Porcine Alveolar Macrophages via Receptor-Mediated Endocytosis," Journal of General Virology, 1999, pp. 297-305, vol. 80, Part 2.

Nelsen, C. J., et al., "Porcine Reproductive and Respiratory Syndrome Virus Comparison: Divergent Evolution on Two Continents," Journal of Virology, Jan. 1999, pp. 270-280, vol. 73, No. 1.

Neumann, E. J., et al., "Assessment of the Economic Impact of Porcine Reproductive and Respiratory Syndrome on Swine Production in the United States," Journal of the American Veterinary Medical Association, Aug. 1, 2015, pp. 385-392, vol. 227, No. 3.

Nielsen, H. S., et al., "Generation of an Infectious Clone of VR-2332, A Highly Virulent North American-Type Isolate of Porcine Reproductive and Respiratory Syndrome Virus," Journal of Virology, Mar. 2003, pp. 3702-3711, vol. 77, No. 6.

Nielsen, M. J., et al., "The Macrophage Scavenger Receptor CD163: Endocytic Properties of Cytoplasmic Tail Variants," Journal of Leukocyte Biology, Apr. 2006, pp. 837-845, vol. 79, No. 4.

Niu, Y., et al., "Generation of Gene-Modified Cynomolgus Monkey via Cas9/RNA-Modified Gene Targeting in One-Cell Embryos," Cell, Feb. 13, 2014, pp. 836-843, vol. 156.

Nussbaum, D. J_, et al., "Differential Effects of Protein Synthesis Inhibitors on Porcine Oocyte Activation," Molecular Reproduction and Development, 1995, pp. 70-75, vol. 41.

Oetke, C., et al., "Sialoadhesin-Deficient Mice Exhibit Subtle Changes in B- and T-Cell Populations and Reduced Immunoglobulin M Levels," Molecular and Cellular Biology, Feb. 2006, pp. 1549-1557, vol. 26, No. 4.

Park, K.-W., et al., "Developmental Potential of Porcine Nuclear Transfer Embryos Derived from Transgenic Fetal Fibroblasts Infected with the Gene for the Green Fluorescent Protein: Comparison of Different Fusion/Activation conditions," Biology of Reproduction, 2001, pp. 1681-1685, vol. 65, No. 6.

Park, K.-W., et al., "Production of Nuclear Transfer-Derived Swine That Express the Enhanced Green Fluorescent Protein," Animal Biotechnology, 2001, pp. 173-181, vol. 12, No. 2.

Patience, J. F., et al., "Nutrition of the Breeding Herd," Swine Nutrition Guide, 1989, Chapter 6, pp. 149-171, Prairie Swine Centre, University of Saskatchewan, Saskatoon, Saskatchewan, Canada.

Patton, J. B., et al., "Modulation of CD163 Receptor Expression and Replication of Porcine Reproductive and Respiratory Syndrome Virus in Porcine Macrophages," Virus Research, 2009, pp. 161-171, vol. 140.

Plagemann, P. G. W., "Lactate Dehydrogenase-Elevating Virus and Related Viruses," In Fields Virology, 3rd Edition, Fields, B et al., ed, 1996, Chapter 36, pp. 1105-1120.

Prather, R. S., et al., "Genetic Engineering of Pigs for PRRSV Resistance," National Swine Improvement Federation—International PRRS Symposium, Marriott Kansas City, Kansas City, Missouri, Nov. 29-30, 2012, 43 pages.

Prather, R. S., et al., "An Intact Sialoadhesin (Sn/SIGLEC1/CD169) Is Not Required for Attachment/Internalization of the Porcine Reproductive and Respiratory Syndrome Virus," Journal of Virology, Sep. 2013, pp. 9538-9546, vol. 87, No. 17.

Prather, R. S., "Genetic Engineering of Pigs for PRRSV Resistance," North American Porcine Reproductive and Respiratory Syndrome Symposium, Chicago, Illinois, Dec. 6, 2014, 55 pages.

Prather, R.S., et al., "Genetic Engineering the Pig to Better Understand PRRSv Infection," 2014 North American PRRS Symposium, Final Program, Chicago, Illinois, Dec. 5-6, 2014, p. 33.

Albina, E., et al., "Immune Response and Persistence of the Porcine Reproductive and Respiratory Syndrome Virus in Infected Pigs and Farm Units," The Veterinary Record, May 28, 1994, pp. 567-573, vol. 134, No. 22.

Allende, R., et al., "North American and European Porcine Reproductive and Respiratory Syndrome Viruses Differ in Non-Structural Protein Coding Regions," Journal of General Virology, 1999, pp. 307-315, vol. 80.

Allende, R., et al., "Porcine Reproductive and Respiratory Syndrome Virus: Description of Persistence in Individual Pigs Upon Experimental Infection," Journal of Virology, Nov. 2000, pp. 10834-10837, vol. 74, No. 22.

Andreyev, V. G., et al., "Genetic Variation and Phylogenetic Relationships of 22 Porcine Reproductive and Respiratory Syndrome Virus (PRRSV) Field Strains Based on Sequence Analysis of Open Reading Frame 5," Archives of Virology, 1997, pp. 993-1001, vol. 142, No. 5.

Bauer, B. K., et a., "Arginine Supplementation In Vitro Increases Porcine Embryo Development and Affects mRNA Transcript Expression," Reproduction, Fertility, and Development, 2011, p. 107, vol. 23.

Beaton, B. R, et al., "Compound Transgenics: Recombinase-Mediated Gene Stacking," Transgenic Animal Technology, 2014, Chapter 21, p. 565-578, Elsevier.

Benfield, D. A., et al., "Characterization of Swine Infertility and Respiratory Syndrome (SIRS) Virus (Isolate ATCC VR-2332)," Journal of Veterinary Diagnostic Investigation, Apr. 1992, pp. 127-133, vol. 4, No. 2.

Benfield, D. A., et al., "Pathogenesis and Persistence of PRRS," Proceedings, Allen D. Leman Swine Conference, 1998, pp. 169-171.

Berg, H., "500-Biological Implications of Electric Field Effects, Part V. Fusion of Blastomeres and Blastocysts of Mouse Embryos," Bioelectrochemistry and Bioenergetics, 1982, pp. 223-228, vol. 9.

Boddicker, N. J., et al., "Genome-wide Association and Genomic Prediction for Host Response to Porcine Reproductive and Respiratory Syndrome Virus Infection," Genetics Selection Evolution, 2014, 14 pages, vol. 46, No. 18.

Borg, N. A., et al., "CD1d-lipid-antigen Recognition by the Semi-invariant NKT T-cell Receptor," Nature, Jul. 2007, pp. 44-49, vol. 448, No. 7149.

Brinster, R. L., et al., "Factors Affecting the Efficiency of Introducing Foreign DNA Into Mice by Microinjecting Eggs," Proceedings of the National Academy of Sciences of the United States of America, Jul. 1985, pp. 4438-4442, vol. 82, No. 13.

Calvert, J. G., et al., "CD163 Expression Confers Susceptibility to Porcine Reproductive and Respiratory Syndrome Viruses," Journal of Virology, Jul. 2007, pp. 7371-7379, vol. 81, No. 14.

Carter, D. B., et al., "Phenotyping of Transgenic Cloned Piglets," Cloning and Stem Cells, 2002, pp. 131-145, vol. 4, No. 2.

Christopher-Hennings, J., et al., "Persistence of Porcine Reproductive and Respiratory Syndrome Virus in Serum and Semen of Adult Boars," Journal of Veterinary Diagnostic Investigation, Oct. 1995, pp. 456-464, vol. 7, No. 4.

Christopher-Hennings, J., et al., "Effects of a Modified-live Virus Vaccine Against Porcine Reproductive and Respiratory Syndrome in Boars," American Journal of Veterinary Research, 1997, pp. 40-45, vol. 58, No. 1.

Cong, L., et al., "Multiplex Genome Engineering Using CRISPR/Cas Systems," Science, 2013, pp. 819-823, vol. 339, No. 6121.

Crocker, R R., et al., "Properties and Distribution of a Lectin-like Hemagglutinin Differentially Expressed by Murine Stromal Tissue Macrophages," The Journal of Experimental Medicine, 1986, pp. 1862-1875, vol. 164, No. 6.

Crocker, P. R., et al., "Molecular Analysis of Sialoside Binding to Sialoadhesin by NMR and Site-directed Mutagenesis," Biochemical Journal, 1999, pp. 355-361, vol. 341, Part 2.

Dai, Y., et al., "Targeted Disruption of the alpha1,3-galactosyltransferase Gene in Cloned Pigs," Nature Biotechnology, Mar. 2002, pp. 251-255, vol. 20, No. 3.

Das, P. B., et al., "The Minor Envelope Glycoproteins GP2a and GP4 of Porcine Reproductive and Respiratory Syndrome Virus Interact with the Receptor CD163," Journal of Virology, Feb. 2010, pp. 1731-1740, vol. 84, No. 4.

Dee, S. A., et al., "Elmination of Porcine Reproductive and Respiratory Syndrome Virus Using a Test and Removal Process," The Veterinary Record, 1998, pp. 474-476, vol. 143, No. 17.

(56) References Cited

OTHER PUBLICATIONS

Delputte, P. L., et al., "Effect of Virus-specific Antibodies on Attachment, Internalization and Infection of Porcine Reproductive and Respiratory Syndrome Virus in Primary Macrophages," Veterinary Immunology and Immunopathology, 2004, pp. 179-188, vol. 102, No. 3.
Delputte, P. L., et al., "Involvement of the Matrix Protein in Attachment of Porcine Reproductive and Respiratory Syndrome Virus to a Heparinlike Receptor on Porcine Alveolar Macrophages," Journal of Virology, May 2002, pp. 1312-4320, vol. 76, No. 9.
Delputte, P. L., et al., Porcine Arterivirus Infection of Alveolar Macrophages Is Mediated by Sialic Acid on the Virus, Journal of Virology, Aug. 2004, pp. 8094-8101, vol. 78, No. 15.
Delputte, P. L., et al., "Porcine Arterivirus Attachment to the Macrophage-Specific Receptor Sialoadhesin Is Dependent on the Sialic Acid-Binding Activity of the N-Terminal Immunoglobulin Domain of Sialoadhesin," Journal of Virology, Sep. 2007, pp. 9546-9550, vol. 81, No. 17.
Delputte, P. L., et al., "Porcine Sialoadhesin (CD169/Siglec-1) Is an Endocytic Receptor that Allows Targeted Delivery of Toxins and Antigens to Macrophages," PLoS One, Feb. 2011, e16827, pp. 1-12, vol. 6, No. 2.
Etzerodt, A., et al., "Plasma Clearance of Hemoglobin and Haptoglobin in Mice and Effect of CD163 Gene Targeting Disruption," Antioxidants and Redox Signaling, 2013, pp. 2254-2263, vol. 18, No. 17.
Etzerodt, A., et al., "CD163 and Inflammation: Biological, Diagnostic, and Therapeutic Aspects," Antioxidants and Redox Signaling, 2013, pp. 2352-2363, vol. 18, No. 17.
Fabriek, B. O., et al., "The Macrophage Scavenger Receptor CD163," Immunobiology, 2005, pp. 153-160, vol. 210, Nos. 2-4.
Fabriek, B. O., et al., "The Macrophage Scavenger Receptor CD163 Functions as an Innate Immune Sensor for Bacteria," Blood, Jan. 22, 2009, pp. 887-892, vol. 113, No. 4.
Fisher, D., et al., "Membrane Fusion by Viruses and Chemical Agents," Techniques in Cellular Physiology—Part 1, 1981, pp. 1-36, vol. P115.
Gaj, T., et al., "ZEN, TALEN and CRISPR/Cas-based Methods for Genome Engineering," Trends in Biotechnology, 2013, pp. 397-405, vol. 31, No. 7.
Gaudreault, N., et al., "Factors Affecting the Permissiveness of Porcine Alveolar Macrophages for Porcine Reproductive and Respiratory Syndrome Virus," Archives of Virology, 2009, pp. 133-136, vol. 154, No. 1.
Gerrits, R. J., et al., Perspectives for Artificial Insemination and Genomics to Improve Global Swine Populations, Theriogenology, Jan. 2005, pp. 283-299, vol. 63, No. 2.
Graham, C. F., "The Fusion of Cells with One- and Two-Cell Mouse Embryos," The Wistar Institute Symposium Monograph, 1969, pp. 19-35, vol. 9.
Graversen, J. H., et al., "Targeting the Hemoglobin Scavenger Receptor CD163 in Macrophages Highly Increases the Anti-inflammatory Potency of Dexamethasone," Molecular Therapy, 2012, pp. 1550-1558, vol. 20, No. 3.
Groenen, M. A. M., et al., "Analyses of Pig Genomes Provide Insight Into Porcine Demography and Evolution," Nature, 2012, pp. 393-398, vol. 491, No. 7424.
Hai, T., et al., "One-step Generation of Knockout Pigs by Zygote Injection of CRISPR/Cas System," Cell Research, 2014, pp. 372-375, vol. 24, No. 3.
Halbur, P. G., et al., "Comparison of the Pathogenicity of Two US Porcine Reproductive and Respiratory Syndrome Virus Isolates with that of the Lelystad Virus," Veterinary Pathology, 1995, pp. 648-660, vol. 32.
Hammer, R. E., et al., "Production of Transgenic Rabbits, Sheep and Pigs by Microinjection," Nature, Jun. 1985, pp. 680-683, vol. 315, No. 6021.
Hao, Y. H., et al., "Production of Endothelial Nitric Oxide Synthase (eNOS) Over-Expressing Piglets," Transgenic Research, 2006, pp. 739-750, vol. 15, No. 6.
Hauschild, J., et al., "Efficient Generation of a Biallelic Knockout in Pigs Using Zinc-finger Nucleases," Proceedings of the National Academy of Sciences of the United States of America, Sep. 6, 2011, pp. 1-5, vol. 108, No. 36.
Holtkamp, D. J., et al., "Assessment of the Economic Impact of Porcine Reproductive and Respiratory Syndrome Virus on United States Pork Producers," Journal of Swine Health and Production, Mar. and Apr. 2013, pp. 72-84, vol. 21, No. 2.
Huang, Y. W., et al., "Porcine DC-SIGN: Molecular Cloning, Gene Structure, Tissue Distribution and Binding Characteristics," Developmental and Comparative Immunology, 2009, pp. 464-480, vol. 33.
Hwang, W. Y., et al., "Efficient Genome Editing in Zebrafish Using a CRISPR-Cas System," Nature Biotechnology, Mar. 2013, pp. 227-229, vol. 31, No. 3.
Im, G.-S., et al., "In Vitro Development of Preimplantation Porcine Nuclear Transfer Embryos Cultured in Different Media and Gas Atmospheres," Theriogenology, 2004, pp. 1125-1135, vol. 61.
Jeney, V., et al., "Pro-oxidant and Cytotoxic Effects of Circulating Heme," Blood, Aug. 1, 2002, pp. 879-887, vol. 100, No. 3.
Keffaber, K. K., "Reproductive Failure of Unknown Etiology," American Association of Swine Practitioners Newsletter, Sep.-Oct. 1989, pp. 1-10, vol. 1, No. 2.
Kim, H. S., et al., "Enhanced Replication of Porcine Reproductive and Respiratory Syndrome (PRRS) Virus in a Homogeneous Subpopulation of MA-104 Cell Line," Archives of Virology, 1993, pp. 477-483, vol. 133.
Prather, R. S., "Genetic Engineering for Profitable Pork Production: Is Resistance to PRRSv Possible?" Virginia Polytechnic Institute, Blacksburg, Virginia, May 1, 2015, 70 pages.
Prather, R. S., et al., "CRISPR/Cas9-Mediated Genetic Engineering: Is CD163 an Entry Mediator for PRRSv Infection?," International Plant and Animal Genome Conference XXIII, Abstract, Jan. 9-15, 2015, 1 page.
Provost, C., et al., "Identification of a New Cell Line Permissive to Porcine Reproductive and Respiratory Syndrome Virus Infection and Replication Which is Phenotypically Distinct from MARC-145 Cell Line," Virology Journal, 2012, 14 pages, vol. 9.
Reed, L. J., et al., "A Simple Method of Estimating Fifty Percent Endpoints," The American Journal of Hygiene, May 1938, pp. 493-497, vol. 27, No. 3.
Ritter, M., et al., "The Scavenger Receptor CD163: Regulation, Promoter Structure and Genomic Organization," Pathobiology, 1999, pp. 257-261, vol. 67, Nos. 5-6.
Ritter, M., et al., "Genomic Organization and Chromosomal Localization of the Human CD163 (M130) Gene: A Member of the Scavenger Receptor Cysteine-Rich Superfamily," Biochemical and Biophysical Research Communications, 1999, pp. 466-474, vol. 260, No. 2.
Robl, J. M., et al., "Nuclear Transplantation in Bovine Embryos," Journal of Animal Science, Feb. 1987, pp. 642-647, vol. 64, No. 2.
Ropp, S. L., et al., "Characterization of Emerging European-Like Porcine Reproductive and Respiratory Syndrome Virus Isolates in the United States," Journal of Virology, Apr. 2004, pp. 3684-3703, vol. 78, No. 7.
Ross, J. W., et al., "Optimization of Square-wave Electroporation for Transfection of Porcine Fetal Fibroblasts," Transgenic Research, Aug. 2010, pp. 611-620, vol. 19, No. 4.
Rowland, R. R. R., et al., "Control of Porcine Reproductive and Respiratory Syndrome (PRRS) Through Genetic Improvements in Disease Resistance and Tolerance," Frontiers in Genetics, Dec. 2012, pp. 1-6, vol. 3, Article 260.
Rowland, R. R. R., et al., "The Evolution of Porcine Reproductive and Respiratory Syndrome Virus: Quasispecies and Emergence of a Virus Subpopulation During Infection of Pigs with VR-2332," Virology, 1999, pp. 262-266, vol. 259.
Sanchez, C., et al., "The Porcine 2A10 Antigen Is Homologous to Human CD163 and Related to Macrophage Differentiation," Journal of Immunology, 1999, pp. 5230-5267, vol. 162, No. 9.
Sanchez-Torres, C., et al., "Expression of Porcine CD163 on Monocytes/Macrophages Correlates with Permissiveness to African Swine Fever Infection," Archives of Virology, 2003, pp. 2307-2323, vol. 148, No. 12.

(56) References Cited

OTHER PUBLICATIONS

Sangamo BioSciences, Inc., "Sangamo BioSciences Announces Efficient Generation of Transgenic Pigs Using Zinc Finger Nuclease (ZFN) Technology," Press Release, Jul. 21, 2011, 2 pages.
Schaer, C. A., et al., "Constitutive Endocytosis of CD163 Mediates Hemoglobin-Heme Uptake and Determines the Noninflammatory and Protective Transcriptional Response of Macrophages to Hemoglobin," Circulation Research, 2006, pp. 943-950, vol. 99.
Schaer, D. J., et al., "CD163 is the Macrophage Scavenger Receptor for Native and Chemically Modified Hemoglobins in the Absence of Haptoglobin," Blood, Jan. 1, 2006, pp. 373-380, vol. 107, No. 1.
Schaer, D. J., et al., "Hemophagocytic Macrophages Constitute a Major Compartment of Heme Oxygenase Expression in Sepsis," European Journal of Haematology, 2006, pp. 432-436, vol. 77.
Shanmukhappa, K., et al., "Role of CD151, A Tetraspanin, In Porcine Reproductive and Respiratory Syndrome Virus Infection," Virology Journal, 2007, pp. 1-12, vol. 4, No. 62.
Shimozawa, N., et al., "Abnormalities in Cloned Mice Are Not Transmitted to the Progeny," Genesis, 2002, pp. 203-207, vol. 34.
Snijder, E. J., et al., "The Molecular Biology of Arteriviruses [Review]," Journal of General Virology, 1998, pp. 961-979, vol. 79, Part 5.
Soares, M. P., et al., "Heme Oxygenase-1: From Biology to Therapeutic Potential," Trends in Molecular Medicine, 2009, pp. 50-58, vol. 15, No. 2.
Stein, M., et al., "Interleukin 4 Potently Enhances Murine Macrophage Mannose Receptor Activity: A Marker of Alternative Immunologic Macrophage Activation," The Journal of Experimental Medicine, Jul. 1992, pp. 287-292, vol. 176, No. 1.
Stephenson, R. J., et al., "Multiplex Serology for Common Viral Infections in Feral Pigs (Sus scrota) in Hawaii Between 2007 and 2010," Journal of Wildlife, 2015, pp. 239-243, vol. 51, No. 1.
Suarez, P., et al., "Open Reading Frame 5 of Porcine Reproductive and Respiratory Syndrome Virus as a Cause of Virus-Induced Apoptosis," Journal of Virology, May 1996, pp. 2876-2882, vol. 70, No. 5.
Sulahian, T. H., et al., "Human Monocytes Express CD163, Which is Upregulated by IL-10 and Identifical to p155," Cytokine, Sep. 2000, pp. 1312-1321, vol. 12, No. 9.
Sur, J. H., et al., "In Vivo Detection of Porcine Reproductive and Respiratory Syndrome Virus RNA by in Situ Hybridization at Different Times Postinfection," Journal of Clinical Microbiology, Sep. 1996, pp. 2280-2286, vol. 34, No. 9.
Sur, J. H., et al., "Porcine Reproductive and Respiratory Syndrome Virus Replicates in Testicular Germ Cells, Alters Spermatogenesis, and Induces Germ Cell Death by Apoptosis," Journal of Virology, Dec. 1997, pp. 9170-9179, vol. 71, No. 12.
Terns, M. R, et al., "CRISPR-Based Adaptive Immune Systems," Current Opinion in Microbiology, Jun. 2011, pp. 321-327, vol. 14, No. 3.
Trible, B. R., et al., "Recognition of the Different Structural Forms of the Capsid Protein Determines the Outcome Following Infection with Porcine Circovirus Type 2," Journal of Virology, Dec. 2012, pp. 13508-13514, vol. 86, No. 24.
U.S. Department of Agriculture and U.S. Department of Health and Human Services, Dietary Guidelines for Americans 2010, 7th Edition, 112 pages.
Van Breedam, W., et al., "Porcine Reproductive and Respiratory Syndrome Virus Entry into the Porcine Macrophage," Journal of General Virology, 2010, pp. 1659-1667, vol. 91, Part 7.
Van Breedam, W., et al., "The M/GP(5) Glycoprotein Complex of Porcine Reproductive and Respiratory Syndrome Virus Binds the Sialoadhesin Receptor in a Sialic Acid-Dependent Manner," PLoS Pathogens, 2010, e1000730, pp. 1-11, vol. 6, No. 1.
Van Den Heuvel, M. M., et al., "Regulation of CD163 on Human Macrophages: Cross-linking of CD163 Induces Signaling and Activation," Journal of Leukocyte Biology, Nov. 1999, pp. 858-866, vol. 66, No. 5.
Van Den Hoff, M. J. B., et al., "Electroporation in 'Intracellular' Buffer Increases Cell Survival," Nucleic Acids Research, 1992, p. 2902, vol. 20, No. 11.
Van Gorp, H., et al., "Scavenger Receptor CD163, A Jack-of-all-trades and Potential Target for Cell-Directed Therapy," Molecular Immunology, 2010, pp. 1650-1660, vol. 47, Nos. 7-8.
Van Gorp, H., et al., "Identification of the CD163 Protein Domains Involved in Infection of the Porcine Reproductive and Respiratory Syndrome Virus," Journal of Virology, Mar. 2010, pp. 3101-3105, vol. 84, No. 6.
Van Gorp, H., et al., "Sialoadhesin and CD163 Join Forces During Entry of the Porcine Reproductive and Respiratory Syndrome Virus," Journal of General Virology, 2008, pp. 2943-2953, vol. 89, Part 12.
Vanderheijden, N., et al., "Involvement of Sialoadhesin in Entry of Porcine Reproductive and Respiratory Syndrome Virus into Porcine Alveolar Macrophages," Journal of Virology, Aug. 2003, pp. 8207-8215, vol. 77, No. 15.
Vinson, M., et al., "Characterization of the Sialic Acid-Binding Site in Sialoadhesin by Site-Directed Mutagenesis," Journal of Biological Chemistry, 1996, pp. 9267-9272, vol. 271, No. 16.
Walters, E. M., et al., "Advancing Swine Models for Human Health and Diseases," Missouri Medicine, May/Jun. 2013, pp. 212-215, vol. 110, No. 3.
Wang, H., et al., "One-Step Generation of Mice Carrying Mutations in Multiple Genes by CRISPR/Cas-Mediated Genome Engineering," Cell, 2013, pp. 910-918, vol. 153, No. 4.
Welch, S. K. W., et al., "A Brief Review of CD163 and its Role in PRRSV Infection," Virus Research, 2010, pp. 98-103, vol. 154.
Wensvoort, G., et al., "Mystery Swine Disease in the Netherlands: The Isolation of Lelystad Virus," Veterinary Quarterly, 1991, pp. 121-130, vol. 13.
Whitworth, K. M., et al., "Gene-edited Pigs Are Protected From Porcine Reproductive and Respiratory Syndrome Virus," Nature Biotechnology, Jan. 2016, pp. 20-22, vol. 34, No. 1.
Whitworth, K. M., et al., "Disruption the Sialoadhesin and CD163 Genes to Create Pigs Resistant to PRRSV Infectivity," Abstract, Swine in Biomedical Research in Chicago, Illinois, Jul. 17-19, 2011, S1-25, pp. 39-40.
Whitworth, K. M., et al., "Method of Oocyte Activation Affects Cloning Efficiency in Pigs," Molecular Reproduction and Development, May 2009, pp. 490-500, vol. 76, No. 5.
Whitworth, K. M., et al., "Activation Method Does Not Alter Abnormal Placental Gene Expression and Development in Cloned Pigs," Molecular Reproduction and Development, 2010, pp. 1016-1030, vol. 77, No. 12.
Whitworth, K. M., et al., "Pigs Resistant to PRRSV Infectivity," Poster Presented at Swine in Biomedical Research in Chicago, Illinois, Jul. 18, 2011, 1 page.
Whitworth, K. M., et al., "Scriptaid Corrects Gene Expression of a Few Aberrantly Reprogrammed Transcripts in Nuclear Transfer Pig Blastocyst Stage Embryos," Cellular Reprogramming, 2011, pp. 191-204, vol. 13, No. 3.
Whitworth, K. M., et al., "Pigs Resistant to PRRSV Infectivity," University of Missouri Technology Transfer Showcase, 2012, 1 page.

\* cited by examiner

Fig. 4
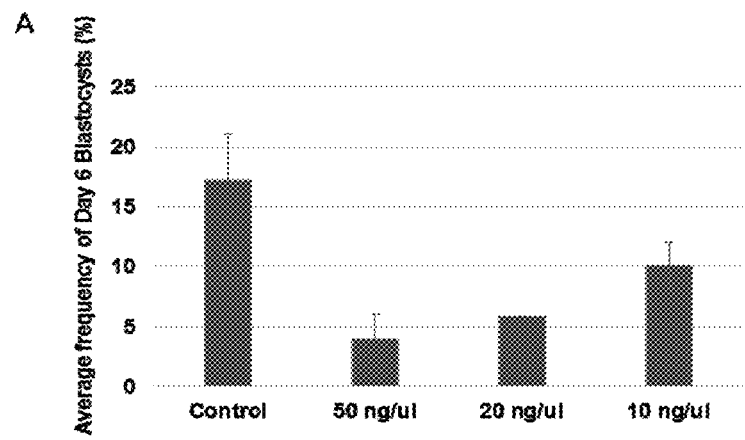
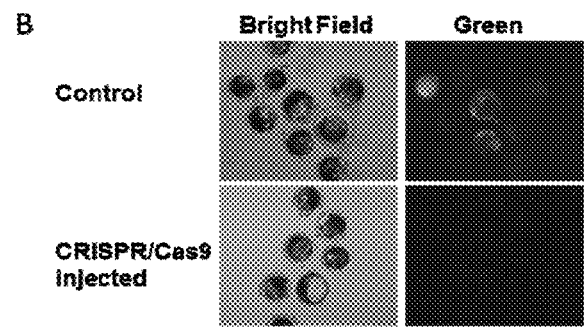
| | SEQ ID NO | |
|---|---|---|
| WT | 16 | GGTCGCCACCATGGTGAGCAAGGGCGAGGAGCTGTTCACCGGGGTGGTGCCCATC |
| #1 | 17 | GGTCGCCACCATGGCCATGAGCAAGGGCGAGGAGCTGTTCACCGGGGTGGTGCC (+3 bp) |
| #2 | 18 | GGTCGCCACCATGG------TGAGCAAGGGCGAGGAGCTGTTCACCGGGGTGGT (-6 bp) |
| #3 | 19 | GGTCGCCACCATGGTTGAGCAAGGGCGAGGAGCTGTTCACCGGGGTGGTGCCCAT (+1 bp) |

A

| SEQ ID NO | | |
|---|---|---|
| WT | 20 | TGCAGGGAACTACAGTGCGGCACTGTGGTTTCCCTCCTGGGGG |
| #1-1 | 21 | TGCAGGGAACTACAGTGCGGCACTG(+16 bp)TGGTTTCCCTCCTGGGGG |
| #1-4 | 22 | TGCAGGGAACTACAGTGCGGC--TGTGGTTTCCCTCCTGGGGG |
| #2-2 | 23 | TGCAGGGAACTACAGTGCGG-AACTACTGTGGTTTCCCTCCTGGGGG |

B

FIG. 7
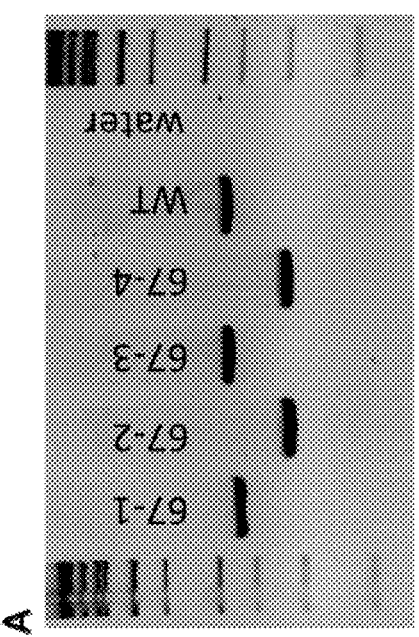
| SEQ ID NO | | |
|---|---|---|
| WT | 33 | TGCTGTGTGCAGGGAACTACAGTGCGGCACTGTGGTTTCCTCCTCCTGGGGGG |
| #67-1 | 34 | TGCTGTGTGCAGGGAACT------------------CTGTGGTTTCCTCCTCCTGGGGGG |
| #67-2 | 35 | -(Δ124 bp)------------------CTGTGGTTTCCTCCTCCTGGGGGG |
|  | 36 | -(Δ123 bp)------------------ACTGTGGTTTCCTCCTCCTGGGGGG |
| #67-3 | 37 | TGCTGTGTGCAGGGAACTACAGTGCGGCACTGTGGTTTCCTCCTCCTGGGGGG |
| #67-4 | 38 | -(Δ130 bp)------------------TCCTGGGGGG |
|  | 39 | -(Δ132 bp)------------------CTGGGGGG |

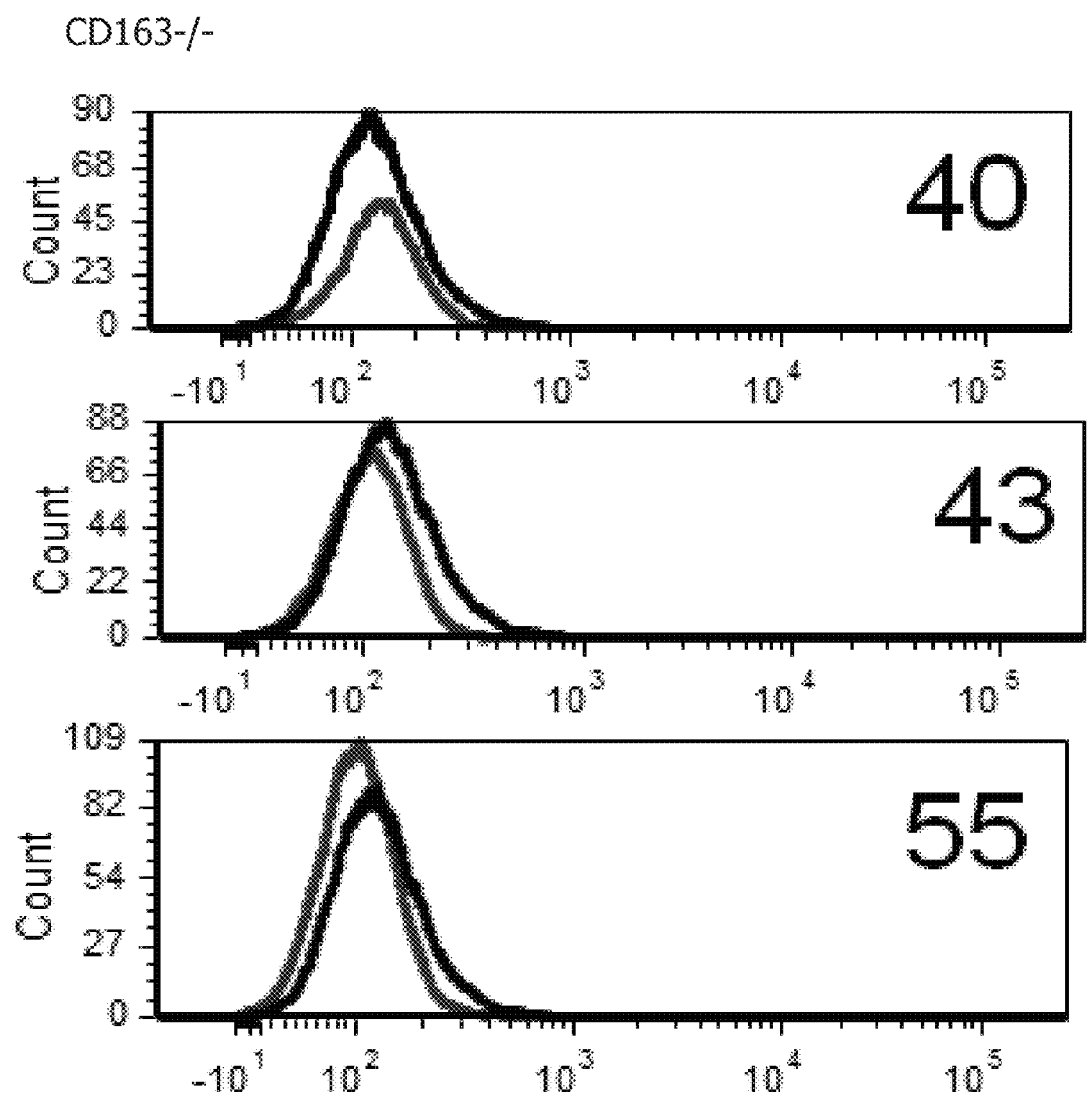

Uncharacterized A

FIG. 16

```
SEQ ID NO. 47
LOCUS       WT_CD163_Referen         4990 bp ds-DNA     linear
DEFINITION  Reference CD163 gene: 3000 bp upstream of exon 7 to the last base of
exon 10
ACCESSION
VERSION
SOURCE      .
  ORGANISM  . pig
COMMENT
COMMENT     ApEinfo:methylated:1
FEATURES             Location/Qualifiers
     misc_feature    1..3000
                     /label=intron 6 misc_feature    3001..3315
                     /label=exon 7 misc_feature    3316..3412
                     /label=intron 7 misc_feature    3413..3727
                     /label=exon 8 misc_feature    3728..4501
                     /label=intron 8 misc_feature    4502..4594
                     /label=exon 9 misc_feature    4595..4676
                     /label=intron 9 misc_feature    4676..4989
                     /label=exon 10

ORIGIN
        1 tatagatgac aaggctttgt gtctgatagg ggccagcgaa ctcagtaaag agggaagatg
       61 agaaagataa tggcagaat ttatccctga agtgtagttt tgacaaacca gtcacaaaga
      121 ggtctaagaa attttggtca caaagttgtt ttgaatccca ggcattttat ttgcaatgat
      181 tgcatatgtt ctggaaagga catctgaacc taagaaatag ttcatttgca ttgtgtttata
      241 ttttactaag gtctgagaaa taatcttgag actgagaatga actctacttc ttcagagtct
      301 ggaaggaata aattatgaaa atgtattaat gcttctttaa accatattgt atatttatct
      361 attactaaac aaaaagaagt agctctatt atttattat ttattatt attatgtct
      421 tttgtctctt tagggccaca cctgtggcat atggaggttc ccaggctaga ggtccaattg
      481 gagatgtagc agccagccta tgccagagcc accgaacac gggatctgag ccacgtctgt
      541 gacttacacc acagctcaca gcaacgcctg atcctcaacc cactgagcga ggccagggat
      601 cgaaccatg tcctcatgga tgctagttgg gttcgttaac tgctgagcca tgatgggaac
      661 tccaaattaa ttattctta tattgttct tcatatattc atttctatag aagaaaataa
      721 atacagattc agtaatgat ggcagctaaa agcttaactt attaatcaaa ggagttaatc
      781 caggcacaaa aattcattc atggctctct gttaaaattt aggtatacgt ttagcaggaa
      841 gaaaaggtta gtagatgcag actattacat ttagaatgga tggacaatga agtcctacta
      901 tacagcacag ggaactatat ccaatctctt gggatagaat atgatggaag acaaaatcag
      961 aacaagagag tatatatata tgtgtctgtg tgtgtgtgtg tgtgtgtgtg tgtgtgtgtg
     1021 tgtgtgactg ggtcaccctg cggcacagca gaaattggca gaacattgta aatcaactat
     1081 actttaatag gaaaaatact ttaagggct aaatttccaa tattctaacc atgtacacag
     1141 agtaaatgtc ataaggatgc cagtctgtgt agagattgat gtgttactag cagattcatg
     1201 aaataaggc tgaggatgta gtcoccaagt cacttctgag tggaagaatt tctccttgt
     1261 cctggactca aatattttag gataaaggaa aaagaagat atttatagaa gggacttgtt
     1321 ttcaagtact tgacaaaatt tcaccattaa agagaaattt gtgggagttc ccatcgtggc
     1381 tcagtggaaa caaatccaac taggaaccat gaggttgtgg gtttgatccc tggcctcact
     1441 cagtgggtta aggatccggt gttgccgtga gctgtggtgt aggttgcaga cacggttctg
     1501 atcctgcgtt gctgtggctg tggctgtggt gtaggccaga agcaaacagc tctgattaga
     1561 cccctagcct ggaaacctcc atatgccaca ggtgcagcc taaaagaca aaaaagaga
```

FIG. 16 cont.

```
1621 aaagacaaaa aaaaaaaaaa aaaaaaaaaa aaaaaaaaaa aaaaaaaaaa gaaccccag
1681 aggtatttat ttgtttttgc cttttttcac tgactgttct ttgtttgttt gtttgagact
1741 gatctagaag actagagatt acaagaaata tgyatttggc tcactctaag aaactgcttt
1801 cattccaagg tttgggtcta tccaaaagtg aatagaatc atatgaatac tagtttatga
1861 gtatttagtg agaggaattt caagctcaaa taatgattca gcaagattaa attaaggagg
1921 gaattttcct tgtgctgag tgggttaagg acccaatgtt gtctctgtga ggatgtaggt
1981 tccatcctgg gctttgctca ttaggttaag gatctggcat tgctgcagct cagacccagt
2041 gctgccctgg ttgtggctta ggccaaagct gcagctcaa ttcaatctct ggcctgggaa
2101 cctccatgtg ctacaaggtg cggccttaaa acgaaaaaaa aaaaattaaa tcaaggactc
2161 aagagtctttt cattatttgt gttgtggaag ctatatttgt tttaaagtct tagttgtgtt
2221 tagaaagcaa gatgttcttc aactcaaatt tcggagggaa cttgttcat acattttaa
2281 tggataagtg gcaaaatttt catgctgagg tgatctatag tgttgtaatg cagaatatag
2341 tcagatcttg aacattttag gaagttggtg agggccaatt gtgtatctgt gccatgctga
2401 taagaatgtc aagggatcac aagaattcgt gttatttgac agcagtcatc tttaaaaggc
2461 atttgagaaa gtccaatttc aaatgcattt cctttcttta aagataaat tgaagaaaat
2521 aagtctttat ttccaagta aattgaattg cctctcagtc tgttaaaaga aactcttacc
2581 ttgatgattg cgctcttaac ctggcaaaga ttgtcttlaa aatctgagct ccatgtcttc
2641 tgctttattt ctggtgtgcc tttgactcca gattacagta aatggaggac tgagtatagg
2701 gctaaaaagt agagagaatg gatgcatatt atctgtggtc tccaatgtga tgaatgaagt
2761 aggcaaatac tcaaaggaaa gagaaagcat gctccaagaa ttatgggttc cagaagcaa
2821 agtcccagaa ttgtctccag ggaaggacag ggaggtctag aatcggctaa gcccactgta
2881 ggcagaaaaa ccaagaggca tgaatggctt cccttctca cttttcactc tctggcttac
2941 tcctatcatg aaggaaaata ttggaatcat attctccctc accgaaatgc tatttttcag
3001 CCCACAGGAA ACCCAGGCTG GTTGGAGGGG ACATTCCCTG CTCTGGTCGT GTTGAAGTAC
3061 AACATGGAGA CACGTGGGGC ACCGTCTGTG ATTCTGACTT CTCTCTGGAG GCGGCCAGCC
3121 TGCTGTGCAG GGAACTACAG TGCGGCACTG TGGTTTCCCT CCTGGGGGA GCTCACTTTG
3181 GAGAAGGAAG TGGACAGATC TGGGCTGAAG AATTCCAGTG TGAGGGCAC GAGTCCCACC
3241 TTTCACTCTG CCCAGTAGCA CCCCGCCCTG ACGGGACATG TAGCCACAGC AGGGACGTCG
3301 CCCGTAGTCTG CTCAAgtgag acccaggaa tgtgttcact ttgttcccat gccatgaaga
3361 gggtagggtt aggtagtcac agacatcttt ttaaagccct gtctcctcc agGATACACA
3421 CAAATCCGCT TGGTCAATGG CAAGACCCCA TGTGAAGGAA GAGTGGAGCT CAACATTCTT
3481 GGGTCCTGGG GGTCCCTCTG CAACTCTCAC TGGGACATGG AAGATGCCCA TGTTTTATGC
3541 CAGCAGCTTA AATGTGGAGT TGCCCTTTCT ATCCGGGAG GAGCACCTTT TGGGAAAGGA
3601 AGTGAGCAGG TCTCGAAGGCA CATGTTTCAC TGCACTGGGA CTGAGAAGCA CATGGGAGAT
3661 TGTTCCGTCA CTGCTCTGGG CGCATCACTC TGTTCTTCAG GGCAAGTGGC CTCTGTAATC
3721 TGCTCAGgta agagaataag ggcagccagt gatgagccac tcatgacggt gccttaagag
3781 tgggtgtacc taggagttcc cattgtggct cagtggtaac aaactcgact ggtatccatg
3841 agggtatggg tttgatccct ggccttgctc aatgggttaa ggatccagca ttgctgtgag
3901 ctgtggtata ggttgcagac tctgctcagg tccatgttg ctgtgattgt ggtgtaggct
3961 gactgctgca gcttcaattt gacccctagc ccgggaattt ccataggcca cacgtgcagc
4021 actaaggaag gaaaaaaaGa aaaaaaaaaa aaagagtgg gtgtgcctat agtgaagaac
4081 agatgtaaaa gggaagtgaa agggattccc ccattctgag ggattgtgag aagtgtgcca
4141 gaatattaac ttcatttgac ttgttacagg gaaagtaaac ttgactttca cggacctcct
4201 agttacctgg tgcttactat atgtcttctc agagtacctg attcattccc agcctggttg
4261 accactccc ctatctctat ggctagttct atccagacca catctatcta acactccagc
4321 tgatcttcct gacacagctg tggcaacct ggatcttta accaactgtg ccaggctgga
4381 gatcaaacct aagcctctgc agcaacccaa gctgctgcag tcagatttt aaccccctgt
4441 gccactgtgg gtatctccga tatttttgtat cttctgtgac tgagtggttt gctgtttgca
4501 gGGAACCAGA GTCAGACACT ATCCCCGTGC AATTCATCAT CCTCGGACCC ATCAAGCTCT
4561 ATTATTTCAG AAGAAAATGG TGTTGCCTGC ATAGtgaga atcagtgacc aacctatgaa
4621 aatgatctca atcctctgaa atgcatttta ttcattttt atttcctctt tgcagGGAGT
4681 GGTCAACTTC GCCTGGTCGA TGGAGTCGT CGTTCTGCTG GGAGAGTAGA GGTCTATCAT
4741 GAGGGCTCCT GGGGCACCAT CTGTGATGAC AGCTGGGACC TGAATGATGC CCATGTGGTG
4801 TGCAAACAGC TgACCTCTCG ATGGGCCATT AATGCCACTG GTTCTCCTCA TTTTGGCCAA
4861 GGAACAGGGC CCATTTGGCT GGATGAGATA AACTGTAATG GAAAAGAATC TCATATTTGG
4921 CAATCCCACT CACATCGTTG GGGGCGGCAC AATTGCACGC ATAAGCACGA TCCAGCAGTC
4981 ATCTGCTCGG
```

PATHOGEN-RESISTANT ANIMALS HAVING MODIFIED CD163 GENES

CROSS-REFERENCE TO RELATED APPLICATION

This application claims the benefit of U.S. Provisional Patent Application Ser. No. 62/202,145, filed on Aug. 6, 2015, which is incorporated herein by reference in its entirety.

FIELD OF THE INVENTION

The present invention relates to non-human animals and offspring thereof comprising at least one modified chromosomal sequence in a gene encoding a CD163 protein. The invention further relates to animal cells that contain such modified chromosomal sequences. The animals and cells have increased resistance to pathogens, including porcine reproductive and respiratory syndrome virus (PRRSV). The animals and offspring have chromosomal modifications of a CD163 gene so that PRRSV entry and replication is inhibited and resultant animals display resistance to the disease and syndrome caused by the virus. The invention further relates to methods of breeding to create pathogen-resistant animals and populations of animals made using such methods. The invention also relates to methods for gene editing of CD163 involving direct injection of embryos and the development of animals, founder animals and lines that are resistant to pathogens such as PRRSV.

BACKGROUND OF THE INVENTION

Porcine reproductive and respiratory syndrome virus (PRRSV) belongs to a group of mammalian arteriviruses, which also include murine lactate dehydrogenase-elevating virus, simian hemorrhagic fever virus and equine arteritis virus. The arteriviruses share important properties related to viral pathogenesis, including a tropism for macrophages and the capacity to cause severe disease and persistent infection. Clinical disease syndromes caused by infection with porcine reproductive and respiratory syndrome virus (PRRSV) were first reported in the United States in 1987 (Keffaber, 1989) and later in Europe in 1990 (Wensvoort et al., 1991). Infection with PRRSV results in respiratory disease including cough and fever, reproductive failure during late gestation, and reduced growth performance. The virus also participates in a variety of polymicrobial disease syndrome interactions while maintaining a life-long subclinical infection (Rowland et al., 2012).

Since its emergence, PRRS has become the most important disease of commercial pigs in North America, Europe and Asia, with only the continents of Australia and Antarctica free from disease. In North America alone PRRSV-related losses are estimated to cost producers $664 M each year (Holtkamp et al., 2013). In 2006, a more severe form of the disease, known as highly pathogenic PRRS (HP-PRRS), decimated pig populations throughout China. Genetic diversity has limited the development of vaccines needed to effectively control and eliminate the disease. While genetic selection for natural resistance might be an option, the results have to date been limited (Boddicker et al., 2014).

Molecular comparisons between North American and European viruses place all PRRSV isolates into one of two genotypes, Type 2 or Type 1, respectively. Even though the two genotypes possess only about 70% identity at the nucleotide level (Nelsen et al., 1999), both share a tropism for CD163-positive cells, establish long-term infections, and produce similar clinical signs.

CD163 is a 130 kDa type 1 membrane protein composed of nine scavenger receptor cysteine-rich (SRCR) domains (Fabriek et al., 2005). Porcine CD163 contains 17 exons that code for a peptide signal sequence followed by nine SRCR domains, two linker domains, also referred to as proline serine threonine (PST) domains, located after SRCR 6 and SRCR 9, and a cytoplasmic domain followed by a short cytoplasmic tail. Surface expression of CD163 is restricted to cells of the monocyte-macrophage lineage. The protein was first identified in human tissues because of its ability to bind a hemoglobin-haptoglobin (HbHp) complexes (Kristiansen et al., 2001). HbHp scavenging is a major function of CD163 and locates to SRCR 3 (Madsen et al., 2004). Metabolites released by macrophages following HbHp degradation include bilirubin, CO, and free iron. One important function of CD163 the prevention of oxidative toxicity that results from free hemoglobin (Kristiansen et al., 2001; Soares et al., 2009).

CD163, as a receptor for PRRSV, was first described by Calvert et. al. (2007). Transfection of non-permissive cell lines with CD163 cDNAs from a variety of species, including simian, human, canine, and mouse can make cells permissive for PRRSV infection (Calvert et al., 2007). In addition to CD163, a second receptor protein, CD169 (also known as sialoadhesin or SIGLEC1), was identified as being a primary PRRSV receptor involved in forming the initial interaction with the GP5-matrix (M) heterodimer, the major protein on the surface of the virion (Delputte et al., 2002). In this model, the subsequent interaction between CD163 and the GP2, 3, 4 heterotrimer in an endosomal compartment mediates uncoating and the release of the viral genome into the cytoplasm (Van Breedam et al., 2010, Allende et al., 1999). A previous model describing PRRSV infection of alveolar macrophages identified SIGLEC1 (CD169) as the primary viral receptor on the surface of macrophages; however, previous work using SIGLEC1$^{-/-}$ pigs showed no difference in virus replication compared to wild type pigs (Prather et a., 2013). These results supported previous in vitro studies showing that PRRSV-resistant cell lines lacking surface CD169 and CD163 supported virus replication after transfection with a CD163 plasmid (Welch et al., 2010).

Many characteristics of both PRRSV pathogenesis (especially at the molecular level) and epizootiology are poorly understood thus making control efforts difficult. Currently producers often vaccinate swine against PRRSV with modified-live attenuated strains or killed virus vaccines, however, current vaccines often do not provide satisfactory protection. This is due to both the strain variation and inadequate stimulation of the immune system. In addition to concerns about the efficacy of the available PRRSV vaccines, there is strong evidence that the modified-live vaccine currently in use can persist in individual pigs and swine herds and accumulate mutations (Mengeling et al., Am. J. Vet. Res, 60(3): 334-340 (1999)), as has been demonstrated with virulent field isolates following experimental infection of pigs (Rowland et al., Virology, 259:262-266 (1999)). Furthermore, it has been shown that vaccine virus is shed in the semen of vaccinated boars (Christopher-Hennings et al., Am. J. Vet. Res, 58(1): 40-45 (1997)). As an alternative to vaccination, some experts are advocating a "test and removal" strategy in breeding herds (Dee and Molitor, Vet. Rec., 143:474-476 (1998)). Successful use of this strategy depends on removal of all pigs that are either acutely or persistently infected with PRRSV, followed by strict controls to prevent reintroduction of the virus. The difficulty, and much of the expense, associated with this strategy is that there is little known about the pathogenesis of persistent PRRSV infection and thus there are no reliable techniques to identify persistently infected pigs.

As can be seen, a need exists in the art for the development of strategies to induce PRRSV resistance to animals.

SUMMARY OF THE INVENTION

Non-human animals, offspring thereof, and animal cells that comprise at least one modified chromosomal sequence in a gene encoding a CD163 protein are provided.

Methods of breeding to create animals or lineages that have reduced susceptibility to infection by a pathogen are also provided. The method comprises genetically modifying an oocyte or a sperm cell to introduce a modified chromosomal sequence in a gene encoding a CD163 protein into at least one of the oocyte and the sperm cell, and fertilizing the oocyte with the sperm cell to create a fertilized egg containing the modified chromosomal sequence in a gene encoding a CD163 protein. Alternatively, the method comprises genetically modifying a fertilized egg to introduce a modified chromosomal sequence in a gene encoding a CD163 protein into the fertilized egg. The method further comprises transferring the fertilized egg into a surrogate female animal, wherein gestation and term delivery produces a progeny animal, screening the progeny animal for susceptibility to the pathogen, and selecting progeny animals that have reduced susceptibility to the pathogen as compared to animals that do not comprise a modified chromosomal sequence in a gene encoding a CD163 protein.

Populations of animals made by the methods of breeding are also provided.

A method of increasing a livestock animal's resistance to infection with a pathogen is further provided. The method comprises genetically editing at least one chromosomal sequence from a gene encoding a CD163 protein so that CD163 protein production or activity is reduced, as compared to CD63 protein production or activity in a livestock animal that does not comprise an edited chromosomal sequence in a gene encoding a CD163 protein.

The modifications to the chromosomal sequence in a gene encoding a CD163 protein provided herein reduce the susceptibility of the animal, offspring, cell, or population (e.g., a porcine animal, offspring, cell or population) to a pathogen (e.g., a virus such as porcine reproductive and respiratory syndrome virus (PRRSV)).

In any of the animals, offspring, cells, populations, and methods provided herein, the modified chromosomal sequence can result in production of substantially no functional CD163 protein by the animal, offspring, cell, or population.

In any of the animals, offspring, cells, populations, and methods provided herein, the modified chromosomal sequence can comprise an in-frame deletion in the gene encoding the CD163 protein.

In any of the porcine animals, offspring, cells, populations, and methods provided herein, the modified chromosomal sequence can comprise SEQ ID NO: 118. Alternatively, the modification of the chromosomal sequence in the gene encoding a CD163 protein can comprise: an 11 base pair deletion from nucleotide 3,137 to nucleotide 3,147 as compared to reference sequence SEQ ID NO: 47; a 2 base pair insertion between nucleotides 3,149 and 3,150 as compared to reference sequence SEQ ID NO: 47, with a 377 base pair deletion from nucleotide 2,573 to nucleotide 2,949 as compared to reference sequence SEQ ID NO: 47 on the same allele; a 124 base pair deletion from nucleotide 3,024 to nucleotide 3,147 as compared to reference sequence SEQ ID NO: 47; a 123 base pair deletion from nucleotide 3,024 to nucleotide 3,146 as compared to reference sequence SEQ ID NO: 47; a 1 base pair insertion between nucleotides 3,147 and 3,148 as compared to reference sequence SEQ ID NO: 47; a 130 base pair deletion from nucleotide 3,030 to nucleotide 3,159 as compared to reference sequence SEQ ID NO: 47; a 132 base pair deletion from nucleotide 3,030 to nucleotide 3,161 as compared to reference sequence SEQ ID NO: 47; a 1506 base pair deletion from nucleotide 1,525 to nucleotide 3,030 as compared to reference sequence SEQ ID NO: 47; a 7 base pair insertion between nucleotide 3,148 and nucleotide 3,149 as compared to reference sequence SEQ ID NO: 47; a 1280 base pair deletion from nucleotide 2,818 to nucleotide 4,097 as compared to reference sequence SEQ ID NO: 47; a 1373 base pair deletion from nucleotide 2,724 to nucleotide 4,096 as compared to reference sequence SEQ ID NO: 47; a 1467 base pair deletion from nucleotide 2,431 to nucleotide 3,897 as compared to reference sequence SEQ ID NO: 47; a 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; a 28 base pair deletion from nucleotide 3,145 to nucleotide 3,172 as compared to reference sequence SEQ ID NO: 47; a 1387 base pair deletion from nucleotide 3,145 to nucleotide 4,531 as compared to reference sequence SEQ ID NO: 47; a 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; a 452 base pair deletion from nucleotide 3,015 to nucleotide 3,466 as compared to reference sequence SEQ ID NO: 47; or any combination thereof.

Nucleic acids are also provided. The nucleic acid molecules comprise a nucleotide sequence selected from the group consisting of: (a) a nucleotide sequence comprising SEQ ID NO: 47; (b) a nucleotide sequence having at least 80% sequence identity to the sequence of SEQ ID NO: 47, wherein said nucleotide sequence contains at least one substitution, insertion, or deletion relative to SEQ ID NO: 47; and (c) a cDNA sequence of (a) or (b).

For example, the nucleic acid molecule can comprise: (a) a nucleotide sequence having at least 87.5% sequence identity to the sequence of SEQ ID NO: 47, wherein said nucleotide sequence contains at least one substitution, insertion, or deletion relative to SEQ ID NO: 47; or (b) a cDNA sequence of (a).

Further nucleic acids are also provided. The nucleic acid can comprise SEQ ID NO: 98, 99, 100, 101, 102, 103, 104, 105, 106, 107, 108, 109, 110, 111, 112, 113, 114, 118, or 119.

Any of the nucleic acid molecules can be isolated nucleic acid molecules.

Other objects and features will be in part apparent and in part pointed out hereinafter.

BRIEF DESCRIPTION OF THE DRAWINGS

FIG. 4. Effect of CRISPR/Cas9 system in porcine embryos. A) Frequency of blastocyst formation after injection of different concentrations of CRISPR/Cas9 system into zygotes. Toxicity of the CRISPR/Cas9 system was lowest at 10 ng/μl. B) The CRISPR/Cas9 system can successfully disrupt expression of eGFP in blastocysts when introduced into zygotes. Original magnification ×4. C) Types of mutations on eGFP generated using the CRISPR/Cas9 system: WT genotype (SEQ ID NO:16), #1 (SEQ ID NO:17), #2 (SEQ ID NO:18), and #3 (SEQ ID NO:19).

FIG. 7. CD163 knockout pigs generated by CRISPR/Cas9 system injected into zygotes. A) PCR amplification of CD163 from the knockout pigs; a clear sign of deletion was detected in litters 67-2 and 67-4. B) Image of CD163 knockout pigs with a surrogate. All the animals are healthy and show no signs of abnormalities. C) Genotype of CD163 knockout pigs. Wild-type (WT) sequence is shown as SEQ ID NO: 33. Two animals (from litters 67-1 (SEQ ID NO:34) and 67-3 (SEQ ID NO:37)) are carrying a homozygous deletion or insertion in CD163. The other two animals (from litters 67-2 and 67-4) are carrying a biallelic modification of CD163: #67-2 A1 (SEQ ID NO:35), #67-2 A2 (SEQ ID NO:36), #67-4 A1 (SEQ ID NO:38), and #67-4 a2 (SEQ ID NO:39). The deletion was caused by introducing two different CRISPRs with Cas9 system. No animals from the zygote injection for CD163 showed a mosaic genotype.

FIG. 16. Genomic Sequence of wild type CD163 exons 7-10 used as a reference sequence (SEQ ID NO: 47). The sequence includes 3000 bp upstream of exon 7 to the last base of exon 10. The underlined regions show the locations of exons 7, 8, 9, and 10, respectively.

FIG. 17. Diagram of CD163 gene modifications illustrating several CD163 gene modifications, the predicted protein product for each modification, and relative macrophage expression for each modification, as measured by the level of surface CD163 on porcine alveolar macrophages (PAMs). Black regions indicate introns and white regions indicate exons. The hatched region indicates the hCD163L1 exon 11 mimic, the homolog of porcine exon 7. The grey region indicates the synthesized intron with PGK Neo construct.

FIG. 18. Diagram of the porcine CD163 protein and gene sequence. A) CD163 protein SRCR (ovals) and PST (squares) domains along with the corresponding gene exons. B) Comparison of the porcine CD163 SRCR 5 (SEQ ID NO: 120) with the human CD163L1 SRCR 8 (SEQ ID NO: 121) homolog.

FIG. 19. Representative results for surface expression of CD163 and CD169 on PAMs from wild-type and CD163-modified pigs. Panels A-E show results for the CD163 gene modifications as illustrated in FIG. 17. Pooled data for d7(1467) and d7(1280) are shown in panel D.

FIG. 20. Serum haptoglobin levels in wild-type and CD163-modified pigs.

FIG. 21. Relative permissiveness of wild-type and HL11m PAMs to infection with Type 2 PRRSV isolates.

FIG. 22. Infection of CD163 modified pigs with Type 1 and Type 2 PRRSV isolates.

FIG. 23. Virus load for WT and CD163-modified pigs infected with Type 2 viruses.

DETAILED DESCRIPTION OF THE INVENTION

Provided herein are animals and methods for producing gene edited animals that have modifications of the CD163 gene and which are resistant to PRRSV and other related respiratory virus infections. The animals have chromosomal modifications (insertions or deletions) that inactivate or otherwise modulate CD163 gene activity. CD163 is required for PRRSV entry into cell and for virus replication. Thus, the null CD163 animals display resistance to PRRSV infection when challenged. These animals can be created using any of a number of protocols which make use of gene editing.

Also provided herein are methods for making a porcine animal comprising introducing to a porcine animal cell or porcine embryo an agent that specifically binds to a chromosomal target site of the cell and causes a double-stranded DNA break or otherwise inactivates or reduces activity of a CD163 gene or protein therein using gene editing methods such as the Clustered Regularly Interspaced Short Palindromic Repeats (CRISPR)/Cas system, Transcription Activator-Like Effector Nucleases (TALENs), Zinc Finger Nucleases (ZFN), recombinase fusion proteins, or meganucleases.

Also described herein is the use of one or more particular CD163 loci in tandem with a polypeptide capable of effecting cleavage and/or integration of specific nucleic acid sequences within the CD163 loci. Examples of the use of CD163 loci in tandem with a polypeptide or RNA capable of effecting cleavage and/or integration of the CD163 loci include a polypeptide selected from the group consisting of zinc finger proteins, meganucleases, TAL domains, TALENs, RNA-guided CRISPR/Cas recombinases, leucine zippers, and others known to those in the art. Particular examples include a chimeric ("fusion") protein comprising a site-specific DNA binding domain polypeptide and cleavage domain polypeptide (e.g., a nuclease), such as a ZFN protein comprising a zinc-finger polypeptide and a FokI nuclease polypeptide. Described herein are polypeptides comprising a DNA-binding domain that specifically binds to a CD163 gene. Such a polypeptide can also comprise a nuclease (cleavage) domain or half-domain (e.g., a homing endonuclease, including a homing endonuclease with a modified DNA-binding domain), and/or a ligase domain, such that the polypeptide may induce a targeted double-stranded break, and/or facilitate recombination of a nucleic acid of interest at the site of the break. A DNA-binding domain that targets a CD163 locus can be a DNA-cleaving functional domain. The foregoing polypeptides can be used to introduce an exogenous nucleic acid into the genome of a host organism (e.g., an animal species) at one or more CD163 loci. The DNA-binding domains can comprise a zinc finger protein with one or more zinc fingers (e.g., 2, 3, 4, 5, 6, 7, 8, 9 or more zinc fingers), which is engineered (non-naturally occurring) to bind to any sequence within a CD163 gene. Any of the zinc finger proteins described herein may bind to a target site within the coding sequence of the target gene or within adjacent sequences (e.g., promoter or other expression elements). The zinc finger protein can bind to a target site in a CD163 gene.

Definitions

Units, prefixes, and symbols may be denoted in their SI accepted form. Unless otherwise indicated, nucleic acids are written left to right in 5' to 3' orientation and amino acid sequences are written left to right in amino to carboxy orientation. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

Figure 1:
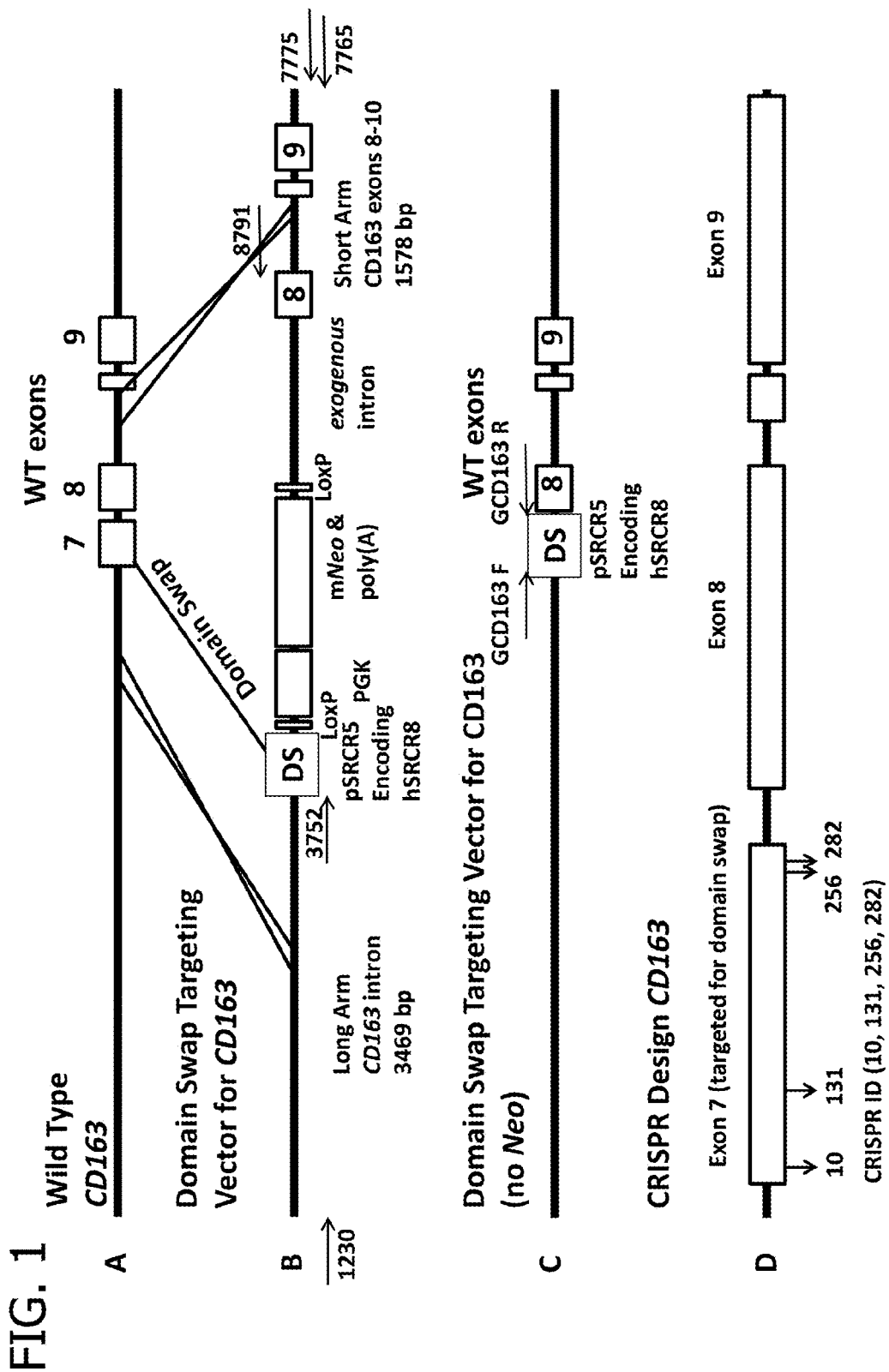
FIG. 1. Targeting vectors and CRISPRs used to modify CD163. Panel A depicts wild type exons 7, 8 and 9 of the CD163 gene that was targeted for modification using CRIS- PRs. Panel B shows the targeting vector designed to replace pig exon 7 (pig domain SRCR5 of CD163) with DNA that encodes human SRCR8 of CD163L. This targeting vector was used in transfections with drug selection by G418. PCR primers for the long range, left arm and right arm assay are labelled with arrows for 1230, 3752, 8791, 7765 and 7775. Panel C depicts a targeting vector identical to the one shown in panel B, but wherein the Neo cassette was removed. This targeting vector was used to target CD163 in cells that were already neomycin resistant. Primers used in small deletions assays are illustrated with arrows and labeled GCD163F and GCD163R. Panel D emphasizes the exons targeted by CRISPRs. Location of CRISPRs 10, 131, 256 and 282 are represented by the downward facing arrows on exon 7. The CRISPR numbers represent the number of base pairs from the intron-exon junction of intron 6 and exon 7.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" means any one of the items, any combination of the items, or all of the items with which this term is associated. The phrase "one or more" is readily understood by one of skill in the art, particularly when read in context of its usage.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The term "conservatively modified variants" applies to both amino acid and nucleic acid sequences. With respect to particular nucleic acid sequences, "conservatively modified variants" refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, for example, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another: [1] Alanine (A), Serine (S), Threonine (T); [2] Aspartic acid (D), Glutamic acid (E); [3] Asparagine (N), Glutamine (Q); [4] Arginine (R), Lysine (K); [5] Isoleucine (I), Leucine (L), Methionine (M), Valine (V); and [6] Phenylalanine (F), Tyrosine (Y), Tryptophan (W). See also, Creighton (1984) Proteins W. H. Freeman and Company.

The term "CRISPR" stands for "clustered regularly interspaced short palindromic repeats." The term "Cas9" refers to "CRISPR associated protein 9." The terms "CRISPR/Cas9" or "CRISPR/Cas9 system" refer to a programmable nuclease system for genetic engineering that includes a Cas9 protein, or derivative thereof, and one or more non-coding RNAs that can provide the function of a CRISPR RNA (crRNA) and trans-activating RNA (tracrRNA) for the Cas9. The crRNA and tracrRNA can be used individually or can be combined to produce a "guide RNA" (gRNA). The crRNA or gRNA provide sequence that is complementary to the genomic target. CRISPR/Cas9 systems are described further hereinbelow.

References herein to a deletion in a nucleotide sequence from nucleotide x to nucleotide y mean that all of the nucleotides in the range have been deleted, including x and y. Thus, for example, the phrase "an 11 base pair deletion from nucleotide 3,137 to nucleotide 3,147 as compared to SEQ ID NO: 47" means that each of nucleotides 3,317 through 3,147 have been deleted, including nucleotides 3,317 and 3,147.

"Disease resistance" is a characteristic of an animal, wherein the animal avoids the disease symptoms that are the outcome of animal-pathogen interactions, such as interactions between a porcine animal and PRRSV. That is, pathogens are prevented from causing animal diseases and the associated disease symptoms, or alternatively, a reduction of the incidence and/or severity of clinical signs or reduction of clinical symptoms. One of skill in the art will appreciate that the compositions and methods disclosed herein can be used with other compositions and methods available in the art for protecting animals from pathogen attack.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

As used herein, "gene editing," "gene edited" "genetically edited" and "gene editing effectors" refer to the use of homing technology with naturally occurring or artificially engineered nucleases, also referred to as "molecular scissors", "homing endonucleases," or "targeting endonucleases." The nucleases create specific double-stranded chromosomal breaks (DSBs) at desired locations in the genome, which in some cases harnesses the cell's endogenous mechanisms to repair the induced break by natural processes of homologous recombination (HR) and/or non-homologous end-joining (NHEJ). Gene editing effectors include Zinc Finger Nucleases (ZENs), Transcription Activator-Like Effector Nucleases (TALENs), the Clustered Regularly Interspaced Short Palindromic Repeats/CAS9 (CRISPR/Cas9) system, and meganucleases (e.g., meganucleases re-engineered as homing endonucleases). The terms also include the use of transgenic procedures and techniques, including, for example, where the change is a deletion or relatively small insertion (typically less than 20 nt) and/or does not introduce DNA from a foreign species. The term also encompasses progeny animals such as those created by sexual crosses or asexual propagation from the initial gene edited animal.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

As used herein "homing DNA technology," "homing technology" and "homing endonuclease" cover any mechanisms that allow a specified molecule to be targeted to a specified DNA sequence including Zinc Finger (ZF) proteins, Transcription Activator-Like Effectors (TALEs) meganucleases, and the CRISPR/Cas9 system.

The terms "increased resistance" and "reduced susceptibility" herein mean, but are not limited to, a statistically significant reduction of the incidence and/or severity of clinical signs or clinical symptoms which are associated with infection by pathogen. For example, "increased resistance" or "reduced susceptibility" can refer to a statistically significant reduction of the incidence and/or severity of clinical signs or clinical symptoms which are associated with infection by PRRSV in an animal comprising at least one modified chromosomal sequence in a gene encoding a CD163 protein as compared to a control animal having an unmodified chromosomal sequence. The term "statistically significant reduction of clinical symptoms" means, but is not limited to, the frequency in the incidence of at least one clinical symptom in the edited group of subjects is at least 10%, preferably at least 20%, more preferably at least 30%, even more preferably at least 50%, and even more preferably at least 70% lower than in the non-edited control group after the challenge with the infectious agent.

As used herein, the term "knock-in" means replacement of an endogenous gene with a transgene or with same endogenous gene with some structural modification/s, but retaining the transcriptional control of the endogenous gene.

"Knock-out" means disruption of the structure or regulatory mechanism of a gene. Knock-outs may be generated through homologous recombination of targeting vectors, replacement vectors or hit-and-run vectors or random insertion of a gene trap vector resulting in complete, partial or conditional loss of gene function.

The term "animal" includes any non-human animal, for example a domestic animal (e.g. a livestock animal). The term "livestock animal" includes any animals traditionally raised in livestock farming, for example a porcine animal, a bovine animal (e.g., beef of dairy cattle), an ovine animal, a caprine animal, an equine animal (e.g., horses or donkeys), buffalo, camels, or an avian animal (e.g., chickens, turkeys, ducks, geese, guinea fowl, or squabs).The term "livestock animal" does not include rats, mice, or other rodents.

As used herein, the term "mutation" includes alterations in the nucleotide sequence of a polynucleotide, such as for example a gene or coding DNA sequence (CDS), compared to the wild-type sequence. The term includes, without limitation, substitutions, insertions, frameshifts, deletions, inversions, translocations, duplications, splice-donor site mutations, point-mutations and the like.

As used herein "operably linked" includes reference to a functional linkage between two nucleic acid sequences, e.g., a promoter sequence and a second sequence, wherein the promoter sequence initiates and mediates transcription of the DNA sequence corresponding to the second sequence. Generally, operably linked means that the nucleic acid sequences being linked are contiguous and, where necessary join two protein coding regions, contiguously and in the same reading frame.

As used herein, "polynucleotide" includes reference to a deoxyribopolynucleotide, ribopolynucleotide, or conservatively modified variants; the term may also refer to analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms also may apply to conservatively modified variants and to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids.

The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of post-translational events, including natural processing event and events brought about by human manipulation which do not occur naturally. Circular, branched and branched circular polypeptides may be synthesized by non-translational natural process and by entirely synthetic methods, as well. Further, this invention contemplates the use of both the methionine-containing and the methionine-less amino terminal variants of the protein of the invention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, these terms encompass any clinical signs of infection, lung pathology, viremia, antibody production, reduction of pathogen load, pathogen shedding, reduction in pathogen transmission, or reduction of any clinical sign symptomatic of PRRSV. Preferably these clinical signs are reduced in one or more animals of the invention by at least 10% in comparison to subjects not having a modification in the CD163 gene and that become infected. More preferably clinical signs are reduced in subjects of the invention by at least 20%, preferably by at least 30%, more preferably by at least 40%, and even more preferably by at least 50%.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to another nucleic acid sequence or other biologics. When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule.

The term "stringent conditions" or "stringent hybridization conditions" includes reference to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e. g., 10 to 50 nucleotides) and at least about 60° C. for long probes (e.g., greater than 50 nucleotides). Stringent conditions may also be achieved with the addition of destabilizing agents such as formamide. Specificity is typically the function of post-hybridization washes, the critical factors being the ionic strength and temperature of the final wash solution. For DNA/DNA hybrids, the thermal melting point (Tm) can be approximated from the equation of Meinkoth and Wahl, Anal. Biochem., 138: 267-284 (1984): $T_m[°C.]=81.5+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1 to 4° C. lower than the $T_m$; moderately stringent conditions can utilize a hybridization and/or wash at 6 to 10° C. lower than the $T_m$; low stringency conditions can utilize a hybridization and/or wash at 11 to 20° C. lower than the $T_m$. Using the equation, hybridization and wash compositions, and desired $T_m$, those of ordinary skill will understand that variations in the stringency of hybridization and/or wash solutions are inherently described. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Zinc finger and TALE binding domains can be "engineered" to bind to a predetermined nucleotide sequence, for example via engineering (altering one or more amino acids) of the recognition helix region of naturally occurring zinc finger or TALE proteins. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

As used herein, "vector" includes reference to a nucleic acid used in transfection of a host cell and into which can be inserted a polynucleotide. Vectors are often replicons. Expression vectors permit transcription of a nucleic acid inserted therein.

"Wild type" means those animals and blastocysts, embryos or cells derived therefrom, which have not been genetically edited or otherwise genetically modified and are usually inbred and outbred strains developed from naturally occurring strains.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

The following terms are used to describe the sequence relationships between a polynucleotide/polypeptide of the present invention with a reference polynucleotide/polypeptide: (a)"reference sequence", (b)"comparison window", (c) "sequence identity", and (d)"percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); and by computerized implementations of these algorithms, including, but not limited to: CLUSTAL in the PC/Gene program by Intelligenetics, Mountain View, Calif.; GAP, BESTFIT, BLAST, FASTA, and TFASTA, and related programs in the GCG Wisconsin Genetics Software Package, Version 10 (available from Accelrys Inc., 9685 Scranton Road, San Diego, Calif., USA). The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215: 403-410 (1990); and, Altschul et al., Nucleic Acids Res. 25: 3389-3402 (1997). Software for performing BLAST analyses is publicly available, for example through the National Center for Biotechnology Information (ncbi.nlm.nih.gov/). This algorithm has been thoroughly described in a number of publications. See, e.g., Altschul S F et al., Gapped BLAST and PSI-BLAST: a new generation of protein database search programs, 25 NUCLEIC ACIDS RES. 3389 (1997); National Center for Biotechnology Information, THE NCBI HANDBOOK [INTERNET], Chapter 16: The BLAST Sequence Analysis Tool (McEntyre J, Ostell J, eds., 2002), available at http://www.ncbi.nlm.nih.gov/books/NBK21097/pdf/ch16.pdf. The BLASTP program for amino acid sequences has also been thoroughly described (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP represents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89: 10915).

Multiple alignment of the sequences can be performed using the CLUSTAL method of alignment (Higgins and Sharp (1989) CABIOS. 5: 151-153) with the default parameters (GAPPENALTY=10, GAP LENGTH PENALTY=10). Default parameters for pairwise alignments using the CLUSTAL method include KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions may be calculated according to the algorithm of Meyers and Miller, Computer Applic. Biol. Sci., 4: 11-17 (1988), for example as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Animals and Cells Having a Modified Chromosomal Sequence in a Gene Encoding a CD163 Protein CD163 has 17 exons and the protein is composed of an extracellular region with 9 scavenger receptor cysteine-rich (SRCR) domains, a transmembrane segment, and a short cytoplasmic tail. Several different variants result from differential splicing of a single gene (Ritter et al. 1999a; Ritter et al. 1999b). Much of this variation is accounted for by the length of the cytoplasmic tail.

CD163 has a number of important functions, including acting as a haptoglobin-hemoglobin scavenger receptor. Elimination of free hemoglobin in the blood is an important function of CD163 as the heme group can be very toxic (Kristiansen et al. 2001). CD163 has a cytoplasmic tail that facilitates endocytosis. Mutation of this tail results in decreased haptoglobin-hemoglobin complex uptake (Nielsen et al. 2006). Other functions of C163 include erythroblast adhesion (SRCR2), being a TWEAK receptor (SRCR1-4 & 6-9), a bacterial receptor (SRCR5), an African Swine Virus receptor (Sanchez-Tones et al. 2003), and a potential role as an immune-modulator (discussed in Van Gorp et al. 2010a). In view of these important functions, it was previously thought that complete knock-out of CD163 would yield animals that would not be viable or would be seriously compromised (see, e.g., PCT Publication No. 2012/158828).

CD163 is a member of the scavenger receptor cysteine-rich (SRCR) superfamily and consists of an intracellular domain and 9 extracellular SRCR domains. In humans endocytosis of CD163 mediated hemoglobin-heme uptake via SRCR3 protects cells from oxidative stress (Schaer et al., 2006a; Schaer et al., 2006b; Schaer et al., 2006c). CD163 also serves as a receptor for tumor necrosis factor-like weak inducer of apoptosis (TWEAK: SRCR1-4 & 6-9), a pathogen receptor (African Swine Fever Virus; bacteria: SRCR2), and erythroblast binding (SRCR2).

CD163 plays a role in infection by many different pathogens and therefore the invention is not limited animals having reduced susceptibility to PRRSV infection, but also includes animals having reduced susceptibility to any pathogen which relies on CD163 either for infection into a cell or for later replication and/or persistence in the cell. The infection process of the PRRSV begins with initial binding to heparan sulfate on the surface of the alveolar macrophage. Prior to 2013 it was thought that secure binding then occurs to sialoadhesin (SIGLEC1, also referred to as CD169 or SN). The virus is then internalized via clatherin-mediated endocytosis. Another molecule, CD163, then facilitates the uncoating of the virus in the endosome (Van Breedam et al. 2010a). The viral genome is released and the cell infected.

Described herein are animals and offspring thereof and cells comprising at least one modified chromosomal sequence in a gene encoding a CD163 protein, e.g., an insertion or a deletion ("INDEL"), which confers improved or complete resistance to infection by a pathogen (e.g., PRRSV) upon the animal. Applicants have demonstrated that CD163 is the critical gene in PRRSV infection and have created founder resistant animals and lines.

The present disclosure provides genetically modified animals, offspring thereof, or animal cells comprising at least one modified chromosomal sequence in a gene encoding a CD163 protein. This invention does not include inactivation or editing of the SIGLEC1 (CD169) gene, which had previously been postulated as critical for PRRSV resistance.

The edited chromosomal sequence may be (1) inactivated, (2) modified, or (3) comprise an integrated sequence resulting in a null mutation. An inactivated chromosomal sequence is altered such that a CD163 protein function as it relates to PRRSV infection is impaired, reduced or eliminated. Thus, a genetically edited animal comprising an inactivated chromosomal sequence may be termed a "knock out" or a "conditional knock out." Similarly, a genetically edited animal comprising an integrated sequence may be termed a "knock in" or a "conditional knock in." Furthermore, a genetically edited animal comprising a modified chromosomal sequence may comprise a targeted point mutation(s) or other modification such that an altered protein product is produced. Briefly, the process can comprise introducing into an embryo or cell at least one RNA molecule encoding a targeted zinc finger nuclease and, optionally, at least one accessory polynucleotide. The method further comprises incubating the embryo or cell to allow expression of the zinc finger nuclease, wherein a double-stranded break introduced into the targeted chromosomal sequence by the zinc finger nuclease is repaired by an error-prone non-homologous end-joining DNA repair process or a homology-directed DNA repair process. The method of editing chromosomal sequences encoding a protein associated with germline development using targeted zinc finger nuclease technology is rapid, precise, and highly efficient.

Alternatively, the process can comprise using a CRISPR/Cas9 system to modify the genomic sequence To use Cas9 to modify genomic sequences, the protein can be delivered directly to a cell. Alternatively, an mRNA that encodes Cas9 can be delivered to a cell, or a gene that provides for expression of an mRNA that encodes Cas9 can be delivered to a cell. In addition, either target specific crRNA and a tracrRNA can be delivered directly to a cell or target specific gRNA(s) can be to a cell (these RNAs can alternatively be produced by a gene constructed to express these RNAs). Selection of target sites and designed of crRNA/gRNA are well known in the art. A discussion of construction and cloning of gRNAs can be found at http://www.genome-engineering.org/crispr/wp-content/uploads/2014/05/CRISPR-Reagent-Description-Rev20140509.pdf.

At least one CD163 locus can be used as a target site for the site-specific editing. The site-specific editing can include insertion of an exogenous nucleic acid (e.g., a nucleic acid comprising a nucleotide sequence encoding a polypeptide of interest) or deletions of nucleic acids from the locus. For example, integration of the exogenous nucleic acid and/or deletion of part of the genomic nucleic acid can modify the locus so as to produce a disrupted (i.e., reduced activity of CD163 protein) CD163 gene.

Provided herein are non-human animals, offspring of said animals, and animal cells comprising at least one modified chromosomal sequence in a gene encoding a CD163 protein.

A non-human animal or offspring thereof or an animal cell comprising at least one modified chromosomal sequence in a gene encoding a CD163 protein is provided. The modified chromosomal sequence results in production of substantially no functional CD163 protein by the animal, offspring, or cell.

Another non-human animal or offspring thereof or an animal cell comprising at least one modified chromosomal sequence in a gene encoding a CD163 protein is provided. The modified chromosomal sequence comprises an in-frame deletion in the gene encoding the CD163 protein.

A porcine animal or offspring thereof or a porcine cell comprising at least one modified chromosomal sequence in a gene encoding a CD163 protein is provided. The modified chromosomal sequence comprises: (a) SEQ ID NO: 118; or (b) a modification selected from the group consisting of: an 11 base pair deletion from nucleotide 3,137 to nucleotide 3,147 as compared to reference sequence SEQ ID NO: 47; a 2 base pair insertion between nucleotides 3,149 and 3,150 as compared to reference sequence SEQ ID NO: 47, with a 377 base pair deletion from nucleotide 2,573 to nucleotide 2,949 as compared to reference sequence SEQ ID NO: 47 on the same allele; a 124 base pair deletion from nucleotide 3,024 to nucleotide 3,147 as compared to reference sequence SEQ ID NO: 47; a 123 base pair deletion from nucleotide 3,024 to nucleotide 3,146 as compared to reference sequence SEQ ID NO: 47; a 1 base pair insertion between nucleotides 3,147 and 3,148 as compared to reference sequence SEQ ID NO: 47; a 130 base pair deletion from nucleotide 3,030 to nucleotide 3,159 as compared to reference sequence SEQ ID NO: 47; a 132 base pair deletion from nucleotide 3,030 to nucleotide 3,161 as compared to reference sequence SEQ ID NO: 47; a 1506 base pair deletion from nucleotide 1,525 to nucleotide 3,030 as compared to reference sequence SEQ ID NO: 47; a 7 base pair insertion between nucleotide 3,148 and nucleotide 3,149 as compared to reference sequence SEQ ID NO: 47; a 1280 base pair deletion from nucleotide 2,818 to nucleotide 4,097 as compared to reference sequence SEQ ID NO: 47; a 1373 base pair deletion from nucleotide 2,724 to nucleotide 4,096 as compared to reference sequence SEQ ID NO: 47; a 1467 base pair deletion from nucleotide 2,431 to nucleotide 3,897 as compared to reference sequence SEQ ID NO: 47; a 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; a 28 base pair deletion from nucleotide 3,145 to nucleotide 3,172 as compared to reference sequence SEQ ID NO: 47; a 1387 base pair deletion from nucleotide 3,145 to nucleotide 4,531 as compared to reference sequence SEQ ID NO: 47; a 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; a 452 base pair deletion from nucleotide 3,015 to nucleotide 3,466 as compared to reference sequence SEQ ID NO: 47; and combinations thereof.

The modification in the chromosomal sequence in the gene encoding the CD163 protein reduces the susceptibility of the animal, offspring, or cell to infection by a pathogen (e.g., a virus such as PRRSV), as compared to the susceptibility of an animal, offspring, or cell that does not comprise a modified chromosomal sequence in a gene encoding a CD163 protein to infection by the pathogen.

For example, the modification in the chromosomal sequence in the gene encoding the CD163 protein can reduce the susceptibility of the animal, offspring, or cell to a Type 1 PRRSV virus, a Type 2 PRRSV, or to both Type 1 and Type 2 PRRSV viruses.

The modification in the chromosomal sequence in the gene encoding the CD163 protein can reduce the animal, offspring or cell to a PRRSV isolate selected from the group consisting of NVSL 97-7895, KS06-72109, P129, VR2332, CO90, AZ25, MLV-ResPRRS, KS62-06274, KS483 (SD23983), CO84, SD13-15, Lelystad, 03-1059, 03-1060, SD01-08, 4353PZ, and combinations thereof.

The animal or offspring can be an embryo, a juvenile, or an adult. Similarly, the cell can comprise an embryonic cell, a cell derived from a juvenile animal, or a cell derived from an adult animal.

The animal or offspring can comprise a domesticated animal. Likewise, the cell can comprise a cell derived from a domesticated animal. The domesticated animal can comprise a livestock animal, for example a porcine animal, a bovine animal (e.g., beef cattle or dairy cattle), an ovine animal, a caprine animal, an equine animal (e.g., a horse or a donkey), buffalo, camels, or an avian animal (e.g., a chicken, a turkey, a duck, a goose, a guinea fowl, or a squab). The livestock animal is preferably a bovine or porcine animal, and most preferably is a porcine animal.

The animal or offspring can comprise a genetically edited animal. The cell can comprise a genetically edited cell.

The animal or cell can be genetically edited using a homing endonuclease. The homing endonuclease can be a naturally occurring endonuclease but is preferably a rationally designed, non-naturally occurring homing endonuclease that has a DNA recognition sequence that has been designed so that the endonuclease targets a chromosomal sequence in gene encoding a CD163 protein. Thus, the homing endonuclease can be a designed homing endonuclease. The homing endonuclease can comprise, for example, a Clustered Regularly Interspaced Short Palindromic Repeats (CRISPR)/Cas9 system, a Transcription Activator-Like Effector Nuclease (TALEN), a Zinc Finger Nuclease (ZFN), a recombinase fusion protein, a meganuclease, or a combination thereof. The animal or cell is preferably an animal or cell that has been genetically edited using a CRISPR/Cas9 system.

The genetically edited animal, offspring thereof, or the genetically edited cell preferably displays increased resistance to a pathogen (e.g., a virus such as PRRSV) as compared to a non-edited animal.

For example, the genetically edited animal can display increased resistance to a Type 1 PRRSV virus, a Type 2 PRRSV, or to both Type 1 and Type 2 PRRSV viruses.

The genetically edited animal can display increased resistance to a PRRSV isolate selected from the group consisting of NVSL 97-7895, KS06-72109, P129, VR2332, CO90, AZ25, MLV-ResPRRS, KS62-06274, KS483 (SD23983), CO84, SD13-15, Lelystad, 03-1059, 03-1060, SD01-08, 4353PZ, and combinations thereof.

The animal, offspring, or cell can be heterozygous for the modified chromosomal sequence. Alternatively, the animal, offspring, or cell can be homozygous for the modified chromosomal sequence.

In any of the animals, offspring, or cells, the modified chromosomal sequence can comprise an insertion in the gene encoding the CD163 protein, a deletion in the gene encoding the CD163 protein, or a combination thereof. For example, the modified chromosomal sequence can comprise a deletion in the gene encoding the CD163 protein (e.g., an in-frame deletion). Alternatively, the modified chromosomal sequence can comprise an insertion in the gene encoding the CD163 protein.

The insertion or deletion can cause CD163 protein production or activity to be reduced, as compared to CD163 protein production or activity in an animal, offspring, or cell that lacks the insertion or deletion.

The insertion or deletion can result in production of substantially no functional CD163 protein by the animal, offspring, or cell. By "substantially no functional CD163 protein," it is meant that the level of CD163 protein in the animal, offspring, or cell is undetectable, or if detectable, is at least about 90% lower than the level observed in an animal, offspring, or cell that does not comprise the insertion or deletion.

Where the animal, offspring, or cell comprises a porcine animal, offspring, or cell, the modified chromosomal sequence can comprise a modification in exon 7 of the gene encoding the CD163 protein, exon 8 of the gene encoding the CD163 protein, an intron that is contiguous with exon 7 or exon 8 of the gene encoding the CD163 protein, or a combination thereof. The modified chromosomal sequence suitably comprises a modification in exon 7 of the gene encoding the CD163 protein.

The modification in exon 7 of the gene encoding the CD163 protein can comprise a deletion (e.g., an in-frame deletion in exon 7). Alternatively, the modification in exon 7 of the gene encoding the CD163 protein can comprise an insertion.

In any of the porcine animals, offspring, or cells, the modified chromosomal sequence can comprise SEQ ID NO: 118. Alternatively, the modified chromosomal sequence can comprise a modification selected from the group consisting of: an 11 base pair deletion from nucleotide 3,137 to nucleotide 3,147 as compared to reference sequence SEQ ID NO: 47; a 2 base pair insertion between nucleotides 3,149 and 3,150 as compared to reference sequence SEQ ID NO: 47, with a 377 base pair deletion from nucleotide 2,573 to nucleotide 2,949 as compared to reference sequence SEQ ID NO: 47 on the same allele; a 124 base pair deletion from nucleotide 3,024 to nucleotide 3,147 as compared to reference sequence SEQ ID NO: 47; a 123 base pair deletion from nucleotide 3,024 to nucleotide 3,146 as compared to reference sequence SEQ ID NO: 47; a 1 base pair insertion between nucleotides 3,147 and 3,148 as compared to reference sequence SEQ ID NO: 47; a 130 base pair deletion from nucleotide 3,030 to nucleotide 3,159 as compared to reference sequence SEQ ID NO: 47; a 132 base pair deletion from nucleotide 3,030 to nucleotide 3,161 as compared to reference sequence SEQ ID NO: 47; a 1506 base pair deletion from nucleotide 1,525 to nucleotide 3,030 as compared to reference sequence SEQ ID NO: 47; a 7 base pair insertion between nucleotide 3,148 and nucleotide 3,149 as compared to reference sequence SEQ ID NO: 47; a 1280 base pair deletion from nucleotide 2,818 to nucleotide 4,097 as compared to reference sequence SEQ ID NO: 47; a 1373 base pair deletion from nucleotide 2,724 to nucleotide 4,096 as compared to reference sequence SEQ ID NO: 47; a 1467 base pair deletion from nucleotide 2,431 to nucleotide 3,897 as compared to reference sequence SEQ ID NO: 47; a 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; a 28 base pair deletion from nucleotide 3,145 to nucleotide 3,172 as compared to reference sequence SEQ ID NO: 47; a 1387 base pair deletion from nucleotide 3,145 to nucleotide 4,531 as compared to reference sequence SEQ ID NO: 47; a 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; a 452 base pair deletion from nucleotide 3,015 to nucleotide 3,466 as compared to reference sequence SEQ ID NO: 47; or combinations thereof.

For example, the modification can comprise the 11 base pair deletion from nucleotide 3,137 to nucleotide 3,147 as compared to reference sequence SEQ ID NO: 47.

The modification can comprise the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele.

The modification can comprise the 124 base pair deletion from nucleotide 3,024 to nucleotide 3,147 as compared to reference sequence SEQ ID NO: 47.

The modification can comprise the 123 base pair deletion from nucleotide 3,024 to nucleotide 3,146 as compared to reference sequence SEQ ID NO: 47.

The modification can comprise the 1 base pair insertion between nucleotides 3,147 and 3,148 as compared to reference sequence SEQ ID NO: 47.

The modification can comprise the 130 base pair deletion from nucleotide 3,030 to nucleotide 3,159 as compared to reference sequence SEQ ID NO: 47.

The modification can comprise the 132 base pair deletion from nucleotide 3,030 to nucleotide 3,161 as compared to reference sequence SEQ ID NO: 47.

The modification can comprise the 1506 base pair deletion from nucleotide 1,525 to nucleotide 3,030 as compared to reference sequence SEQ ID NO: 47.

The modification can comprise the 7 base pair insertion between nucleotide 3,148 and nucleotide 3,149 as compared to reference sequence SEQ ID NO: 47.

The modification can comprise the 1280 base pair deletion from nucleotide 2,818 to nucleotide 4,097 as compared to reference sequence SEQ ID NO: 47.

The modification can comprise the 1373 base pair deletion from nucleotide 2,724 to nucleotide 4,096 as compared to reference sequence SEQ ID NO: 47.

The modification can comprise the 1467 base pair deletion from nucleotide 2,431 to nucleotide 3,897 as compared to reference sequence SEQ ID NO: 47.

The modification can comprise the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47.

The modification can comprise the 28 base pair deletion from nucleotide 3,145 to nucleotide 3,172 as compared to reference sequence SEQ ID NO: 47.

The modification can comprise the 1387 base pair deletion from nucleotide 3,145 to nucleotide 4,531 as compared to reference sequence SEQ ID NO: 47.

The modification can comprise the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113.

The modification can comprise the 1720 base pair deletion from nucleotide 2,440 to nucleotide 4,160 as compared to reference sequence SEQ ID NO: 47.

The modification can comprise the 452 base pair deletion from nucleotide 3,015 to nucleotide 3,466 as compared to reference sequence SEQ ID NO: 47.

The porcine animal, offspring, or cell can comprise any combination of the above insertions and deletions.

SEQ ID NO: 47 provides the nucleotide sequence for the region beginning 3000 base pairs (bp) upstream of exon 7 of the wild-type porcine CD163 gene to the last base of exon 10 of this gene. SEQ ID NO: 47 is used as a reference sequence herein and is shown in FIG. 16.

When the porcine animal, offspring, or cell comprises the 2 base pair insertion between nucleotides 3,149 and 3,150 as compared to reference sequence SEQ ID NO: 47, the 2 base pair insertion can comprise insertion of the dinucleotide AG.

When the porcine animal, offspring, or cell comprises the 1 base pair insertion between nucleotides 3,147 and 3,148 as compared to reference sequence SEQ ID NO: 47, the 1 base pair insertion can comprise insertion of a single adenine residue.

When the porcine animal, offspring, or cell comprises the 7 base pair insertion between nucleotide 3,148 and nucleotide 3,149 as compared to reference sequence SEQ ID NO: 47, the 7 base pair insertion can comprise the sequence TACTACT (SEQ ID NO: 115).

When the porcine animal, offspring, or cell comprises the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47, the 12 base pair insertion can comprise the sequence TGTGGAGAATTC (SEQ ID NO: 116).

When the porcine animal, offspring, or cell comprises the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113, the 11 base pair insertion can comprise the sequence AGCCAGCGTGC (SEQ ID NO: 117).

Where the modified chromosomal sequence in the gene encoding the CD163 protein comprises a deletion, the deletion preferably comprises an in-frame deletion. In-frame deletions are deletions that do not cause a shift in the triplet reading frame, and thus result a protein product that has an internal deletion of one or more amino acids, but that is not truncated. Deletions of three base pairs or multiples of three base pairs within an exon can result in an in-frame mutation, assuming that splicing occurs correctly.

The following INDELs described herein for porcine animals and cells are expected to result in in-frame deletions, since the deletions within exon 7 of the porcine CD163 gene is a multiple of three: the 1506 base pair deletion from nucleotide 1,525 to nucleotide 3,030 as compared to reference sequence SEQ ID NO: 47; the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; the 1373 base pair deletion from nucleotide 2,724 to nucleotide 4,096 as compared to reference sequence SEQ ID NO: 47; the 123 base pair deletion from nucleotide 3,024 to nucleotide 3,146 as compared to reference sequence SEQ ID NO: 47; the 1467 base pair deletion from nucleotide 2,431 to nucleotide 3,897 as compared to reference sequence SEQ ID NO: 47; the 1387 base pair deletion from nucleotide 3,145 to nucleotide 4,531 as compared to reference sequence SEQ ID NO: 47; the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; and the 1720 base pair deletion from nucleotide 2,440 to nucleotide 4,160 as compared to reference sequence SEQ ID NO: 47.

Accordingly, in the porcine animals, offspring, and cells, the insertion or deletion in the gene encoding the CD163 protein can comprise an in-frame deletion in exon 7 selected from the group consisting of the 1506 base pair deletion from nucleotide 1,525 to nucleotide 3,030 as compared to reference sequence SEQ ID NO: 47; the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; the 1373 base pair deletion from nucleotide 2,724 to nucleotide 4,096 as compared to reference sequence SEQ ID NO: 47; the 123 base pair deletion from nucleotide 3,024 to nucleotide 3,146 as compared to reference sequence SEQ ID NO: 47; the 1467 base pair deletion from nucleotide 2,431 to nucleotide 3,897 as compared to reference sequence SEQ ID NO: 47; the 1387 base pair deletion from nucleotide 3,145 to nucleotide 4,531 as compared to reference sequence SEQ ID NO: 47; the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; and combinations thereof.

The porcine animal, offspring, or cell can comprise an insertion or deletion selected from the group consisting of: the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele; the 28 base pair deletion from nucleotide 3,145 to nucleotide 3,172 as compared to reference sequence SEQ ID NO: 47; the 452 base pair deletion from nucleotide 3,015 to nucleotide 3,466 as compared to reference sequence SEQ ID NO: 47; and combinations thereof.

For example, the porcine animal, offspring, or cell can comprise the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele.

The porcine animal, offspring, or cell can comprise the 28 base pair deletion from nucleotide 3,145 to nucleotide 3,172 as compared to reference sequence SEQ ID NO: 47.

The porcine animal, offspring, or cell can comprise comprises the 452 base pair deletion from nucleotide 3,015 to nucleotide 3,466 as compared to reference sequence SEQ ID NO: 47.

The porcine animal, offspring, or cell can comprise any combination any of the modified chromosomal sequences described herein.

For example, the porcine animal, offspring, or cell can comprise the 7 base pair insertion between nucleotide 3,148 and nucleotide 3,149 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The porcine animal, offspring, or cell can comprise the 7 base pair insertion between nucleotide 3,148 and nucleotide 3,149 as compared to reference sequence SEQ ID NO: 47 in one allele of the gene encoding the CD163 protein; and the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113, in the other allele of the gene encoding the CD163 protein.

The porcine animal, offspring, or cell can comprise SEQ ID NO: 118 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The porcine animal, offspring, or cell can comprise SEQ ID NO: 118 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The porcine animal, offspring, or cell can comprise the 1280 base pair deletion from nucleotide 2,818 to nucleotide 4,097 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The porcine animal, offspring, or cell can comprise the 1280 base pair deletion from nucleotide 2,818 to nucleotide 4,097 as compared to reference sequence SEQ ID NO: 47 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The porcine animal, offspring, or cell can comprise the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The porcine animal, offspring, or cell can comprise SEQ ID NO: 118 in one allele of the gene encoding the CD163 protein; and the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47 in the other allele of the gene encoding the CD163 protein.

The porcine animal, offspring, or cell can comprise the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The porcine animal, offspring, or cell can comprise the 1467 base pair deletion from nucleotide 2,431 to nucleotide 3,897 as compared to reference sequence SEQ ID NO: 47 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The porcine animal, offspring, or cell can comprise the 1467 base pair deletion from nucleotide 2,431 to nucleotide 3,897 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The porcine animals, offspring, or cells that comprise any of the insertions or deletions described above can comprise a chromosomal sequence having at a high degree of sequence identity to SEQ ID NO: 47 outside of the insertion or deletion. Thus, for example, the porcine animal, offspring, or cell can comprise a chromosomal sequence having at least 80%, at least 85%, at least 90%, at least 95%, at least 98%, at least 99%, at least 99.9%, or 100% sequence identity to SEQ ID NO: 47 in the regions of the chromosomal sequence outside of the insertion or deletion.

The porcine animal, offspring, or cell can comprise a chromosomal sequence comprising SEQ ID NO: 98, 99, 100, 101, 102, 103, 104, 105, 106, 107, 108, 109, 110, 111, 112, 113, 114, 118, or 119. As is described further in the Examples hereinbelow, SEQ ID NOs. 98-114, and 119 provide nucleotide sequences for a region corresponding to the region of wild-type porcine CD163 provided in SEQ ID NO:47, and include the insertions or deletions in the porcine CD163 chromosomal sequence that are described herein. SEQ ID NO: 118 provides the sequence for a region corresponding to the region of wild-type porcine CD163 provided by SEQ ID NO: 47, wherein exon 7 has been replaced with a synthesized exon encoding a homolog of SRCR 8 of human CD163-like 1 protein (hCD163L1).

For example, the porcine, offspring, animal or cell can comprise a chromosomal sequence comprising SEQ ID NO: 98, 101, 105, 109, 110, 112, 113, or 114. SEQ ID NOs: 98, 101, 105, 109, 110, 112, 113, and 114 provide the nucleotide sequences for in-frame deletions in exon 7 of the porcine CD163 chromosomal sequence.

As another example, the porcine animal, offspring, or cell can comprise a chromosomal sequence comprising SEQ ID NO: 103, 111, or 119.

The porcine animal, offspring, or cell can comprise the 11 base pair deletion in one allele of the gene encoding the CD163 protein and the 2 base pair insertion with the 377 base pair deletion in the other allele of the gene encoding the CD163 protein.

The porcine animal, offspring, or cell can comprise the 124 base pair deletion in one allele of the gene encoding the CD163 protein and the 123 base pair deletion in the other allele of the gene encoding the CD163 protein.

The porcine animal, offspring, or cell can comprise the 1 base pair insertion.

The porcine animal, offspring, or cell can comprise the 130 base pair deletion in one allele of the gene encoding the CD163 protein and the 132 base pair deletion in the other allele of the gene encoding the CD163 protein.

The porcine animal, offspring, or cell can comprise the 1506 base pair deletion.

The porcine animal, offspring, or cell can comprise the 7 base pair insertion.

The porcine animal, offspring, or cell can comprise the 1280 base pair deletion in one allele of the gene encoding the CD163 protein and the 1373 base pair deletion in the other allele of the gene encoding the CD163 protein.

The porcine animal, offspring, or cell can comprise the 1467 base pair deletion.

The porcine animal, offspring, or cell can comprise the 1930 base pair intron 6 deletion from nucleotide 488 to nucleotide 2,417, with a 12 base pair insertion at nucleotide 4,488 and an additional 129 base pair deletion in exon 7.

The porcine animal, offspring, or cell can comprise the 28 base pair deletion in one allele of the gene encoding the CD163 protein and the 1387 base pair deletion in the other allele of the gene encoding the CD163 protein.

The porcine animal, offspring, or cell can comprise the 1382 base pair deletion with the 11 base pair insertion in one allele of the gene encoding the CD163 protein and the 1720 base pair deletion in the other allele of the gene encoding the CD163 protein.

Any of the cells comprising the at least one modified chromosomal sequence in a gene encoding a CD163 protein can comprise a sperm cell. Alternatively, any of these cells can comprise an egg cell (e.g., a fertilized egg).

Any of the cells comprising the at least one modified chromosomal sequence in a gene encoding a CD163 protein can comprise a somatic cell. For example, any of the cells can comprise a fibroblast (e.g., a fetal fibroblast).

Targeted Integration of a Nucleic Acid at a CD163 Locus

Site-specific integration of an exogenous nucleic acid at a CD163 locus may be accomplished by any technique known to those of skill in the art. For example, integration of an exogenous nucleic acid at a CD163 locus can comprise contacting a cell (e.g., an isolated cell or a cell in a tissue or organism) with a nucleic acid molecule comprising the exogenous nucleic acid. Such a nucleic acid molecule can comprise nucleotide sequences flanking the exogenous nucleic acid that facilitate homologous recombination between the nucleic acid molecule and at least one CD163 locus. The nucleotide sequences flanking the exogenous nucleic acid that facilitate homologous recombination can be complementary to endogenous nucleotides of the CD163 locus. Alternatively, the nucleotide sequences flanking the exogenous nucleic acid that facilitate homologous recombination can be complementary to previously integrated exogenous nucleotides. A plurality of exogenous nucleic acids can be integrated at one CD163 locus, such as in gene stacking.

Integration of a nucleic acid at a CD163 locus can be facilitated (e.g., catalysed) by endogenous cellular machinery of a host cell, such as, for example and without limitation, endogenous DNA and endogenous recombinase enzymes. Alternatively, integration of a nucleic acid at a CD163 locus can be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, a nucleic acid comprising a nucleotide sequence encoding at least one nuclease, recombinase, and/or ligase polypeptide may be introduced into the host cell, either concurrently or sequentially with a nucleic acid to be integrated site-specifically at a CD163 locus, wherein the at least one nuclease, recombinase, and/or ligase polypeptide is expressed from the nucleotide sequence in the host cell.

DNA-Binding Polypeptides

Site-specific integration can be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; Tet repressors; Lad; and steroid hormone receptors.

For example, the DNA-binding polypeptide can be a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an α-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites: ZFPs and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the upstream activation sequence (UAS)).

Native GAL4 consists of 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43 (3 Pt 2):729-36. The N-terminal 65 amino acids of GAL4 comprise the GAL4 DNA-binding domain. Keegan et al. (1986) Science 231:699-704; Johnston (1987) Nature 328: 353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that can be used include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-kappaB; and components of the regulatory system described in Wang et al. (1994) Proc. Natl. Acad. Sci. USA 91(17):8180-4, which utilizes a fusion of GAL4, a hormone receptor, and VP16.

The DNA-binding domain of one or more of the nucleases used in the methods and compositions described herein can comprise a naturally occurring or engineered (non-naturally occurring) TAL effector DNA binding domain. See, e.g., U.S. Patent Publication No. 2011/0301073.

Alternatively, the nuclease can comprise a CRISPR/Cas system. Such systems include a CRISPR (clustered regularly interspaced short palindromic repeats) locus, which encodes RNA components of the system, and a Cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60). CRISPR loci in microbial hosts contain a combination of Cas genes as well as non-coding RNA elements capable of programming the specificity of the CRISPR-mediated nucleic acid cleavage.

The Type II CRISPR is one of the most well characterized systems and carries out targeted DNA double-strand break in nature in four sequential steps. First, two non-coding RNAs, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

For use of the CRISPR/Cas system to create targeted insertions and deletions, the two non-coding RNAs (crRNA and the TracrRNA) can be replaced by a single RNA referred to as a guide RNA (gRNA). Activity of the CRISPR/Cas system comprises of three steps: (i) insertion of exogenous DNA sequences into the CRISPR array to prevent future attacks, in a process called "adaptation," (ii) expression of the relevant proteins, as well as expression and processing of the array, followed by (iii) RNA-mediated interference with the foreign nucleic acid. In the bacterial cell, several Cas proteins are involved with the natural function of the CRISPR/Cas system and serve roles in functions such as insertion of the foreign DNA etc.

The Cas protein can be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

A DNA-binding polypeptide can specifically recognize and bind to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

Targeting Endonucleases

A DNA-binding polypeptide that specifically recognizes and binds to a target nucleotide sequence can be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. Functional polypeptides of a chimeric polypeptide can be operatively linked by their expression from a single polynucleotide encoding at least the functional polypeptides ligated to each other in-frame, so as to create a chimeric gene encoding a chimeric protein. Alternatively, the functional polypeptides of a chimeric polypeptide can be operatively linked by other means, such as by cross-linkage of independently expressed polypeptides.

A DNA-binding polypeptide, or guide RNA that specifically recognizes and binds to a target nucleotide sequence can be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR/Cas9, and meganucleases.

As used herein, the term "targeting endonuclease" refers to natural or engineered isolated proteins and mutants thereof that comprise a DNA-binding polypeptide or guide RNA and a nuclease polypeptide, as well as to chimeric polypeptides comprising a DNA-binding polypeptide or guide RNA and a nuclease. Any targeting endonuclease comprising a DNA-binding polypeptide or guide RNA that specifically recognizes and binds to a target nucleotide sequence comprised within a CD163 locus (e.g., either because the target sequence is comprised within the native sequence at the locus, or because the target sequence has been introduced into the locus, for example, by recombination) can be used.

Some examples of suitable chimeric polypeptides include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR/Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

The chimeric polypeptide can comprise a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNAse I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, the near edges of the target sites can be separated by 5-8 nucleotides or by 15-18 nucleotides. However any integral number of nucleotides, or nucleotide pairs, can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/transgenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyses double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, fusion proteins can comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 2007/0134796. Additional restriction enzymes also contain separable binding and cleavage domains, and these are contemplated by the present disclosure. See, for example, Roberts et al. (2003) Nucleic Acids Res. 31:418-420.

The cleavage domain can comprise one or more engineered cleavage half-domain (also referred to as dimerization domain mutants) that minimize or prevent homodimerization, as described, for example, in U.S. Patent Publication Nos. 2005/0064474; 2006/0188987 and 2008/0131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Zinc Finger Nucleases

A chimeric polypeptide can comprise a custom-designed zinc finger nuclease (ZFN) that may be designed to deliver a targeted site-specific double-strand DNA break into which an exogenous nucleic acid, or donor DNA, may be integrated (see US Patent publication 2010/0257638). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. The ZFNs can comprise non-canonical zinc finger DNA binding domains (see US Patent publication 2008/0182332). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

A method for the site-specific integration of an exogenous nucleic acid into at least one CD163 locus of a host can comprise introducing into a cell of the host a ZFN, wherein the ZFN recognizes and binds to a target nucleotide sequence, wherein the target nucleotide sequence is comprised within at least one CD163 locus of the host. In certain examples, the target nucleotide sequence is not comprised within the genome of the host at any other position than the at least one CD163 locus. For example, a DNA-binding polypeptide of the ZFN may be engineered to recognize and bind to a target nucleotide sequence identified within the at least one CD163 locus (e.g., by sequencing the CD163 locus). A method for the site-specific integration of an exogenous nucleic acid into at least one CD163 performance locus of a host that comprises introducing into a cell of the host a ZFN may also comprise introducing into the cell an exogenous nucleic acid, wherein recombination of the exogenous nucleic acid into a nucleic acid of the host comprising the at least one CD163 locus is facilitated by site-specific recognition and binding of the ZFN to the target sequence (and subsequent cleavage of the nucleic acid comprising the CD163 locus).

Optional Exogenous Nucleic Acids for Integration at a CD163 Locus

Exogenous nucleic acids for integration at a CD163 locus include: an exogenous nucleic acid for site-specific integration in at least one CD163 locus, for example and without limitation, an ORF; a nucleic acid comprising a nucleotide sequence encoding a targeting endonuclease; and a vector comprising at least one of either or both of the foregoing. Thus, particular nucleic acids include nucleotide sequences encoding a polypeptide, structural nucleotide sequences, and/or DNA-binding polypeptide recognition and binding sites.

Optional Exogenous Nucleic Acid Molecules for Site-Specific Integration

As noted above, insertion of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient homology-directed repair (HDR) at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See e.g., U.S. Patent Publication Nos. 2010/0047805, 2011/0281361, 2011/0207221, and 2013/0326645. If introduced in linear form, the ends of the donor sequence can be protected (e.g. from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272: 886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (DLV)).

The donor is generally integrated so that its expression is driven by the endogenous promoter at the integration site, namely the promoter that drives expression of the endogenous gene into which the donor is integrated (e.g., CD163). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one CD163 locus, so as to modify the CD163 locus include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the CD163 gene.

An exogenous nucleic acid can be integrated at a CD163 locus, so as to modify the CD163 locus, wherein the nucleic acid comprises a nucleotide sequence encoding a polypeptide of interest, such that the nucleotide sequence is expressed in the host from the CD163 locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass.

Nucleic Acid Molecules Comprising a Nucleotide Sequence Encoding a Targeting Endonuclease A nucleotide sequence encoding a targeting endonuclease can be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. The last codon (i.e., most 3' in the nucleic acid sequence) of a first polynucleotide sequence encoding a nuclease polypeptide, and a second polynucleotide sequence encoding a DNA-binding polypeptide, can be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, consist of any sequence, such that the amino acid sequence encoded is not likely to significantly alter the translation of the targeting endonuclease. Due to the autonomous nature of known nuclease polypeptides and known DNA-binding polypeptides, intervening sequences will not interfere with the respective functions of these structures.

Other Knockout Methods

Various other techniques known in the art can be used to inactivate genes to make knock-out animals and/or to introduce nucleic acid constructs into animals to produce founder animals and to make animal lines, in which the knockout or nucleic acid construct is integrated into the genome. Such techniques include, without limitation, pronuclear microinjection (U.S. Pat. No. 4,873,191), retrovirus mediated gene transfer into germ lines (Van der Putten et al. (1985) Proc. Natl. Acad. Sci. USA 82, 6148-1652), gene targeting into embryonic stem cells (Thompson et al. (1989) Cell 56, 313-321), electroporation of embryos (Lo (1983) Mol. Cell. Biol. 3, 1803-1814), sperm-mediated gene transfer (Lavitrano et al. (2002) Proc. Natl. Acad. Sci. USA 99, 14230-14235; Lavitrano et al. (2006) Reprod. Fert. Develop. 18, 19-23), and in vitro transformation of somatic cells, such as cumulus or mammary cells, or adult, fetal, or embryonic stem cells, followed by nuclear transplantation (Wilmut et al. (1997) Nature 385, 810-813; and Wakayama et al. (1998) Nature 394, 369-374). Pronuclear microinjection, sperm mediated gene transfer, and somatic cell nuclear transfer are particularly useful techniques. An animal that is genomically modified is an animal wherein all of its cells have the genetic modification, including its germ line cells. When methods are used that produce an animal that is mosaic in its genetic modification, the animals may be inbred and progeny that are genomically modified may be selected. Cloning, for instance, may be used to make a mosaic animal if its cells are modified at the blastocyst state, or genomic modification can take place when a single-cell is modified. Animals that are modified so they do not sexually mature can be homozygous or heterozygous for the modification, depending on the specific approach that is used. If a particular gene is inactivated by a knock out modification, homozygosity would normally be required. If a particular gene is inactivated by an RNA interference or dominant negative strategy, then heterozygosity is often adequate.

Typically, in embryo/zygote microinjection, a nucleic acid construct or mRNA is introduced into a fertilized egg; 1 or 2 cell fertilized eggs are used as the nuclear structure containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 OOCYTE MATU- RATION MEDIUM (Minitube, Verona, Wis.) supplemented with 0.1 mg/mL cysteine, 10 ng/mL epidermal growth factor, 10% porcine follicular fluid, 50 µM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium, which will not contain cAMP, PMSG or hCG and incubated for an additional 22 hours. Matured oocytes can be stripped of their cumulus cells by vortexing in 0.1% hyaluronidase for 1 minute.

For swine, mature oocytes can be fertilized in 500 µl Minitube PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to 400,000 sperm. Sperm concentrations can be analyzed by computer assisted semen analysis (SPERMVISION, Minitube, Verona, Wis.). Final in vitro insemination can be performed in a 10 µl volume at a final concentration of approximately 40 motile sperm/oocyte, depending on boar. All fertilizing oocytes can be incubated at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs or mRNA can be injected into one of the pronuclei or into the cytoplasm. Then the injected eggs can be transferred to a recipient female (e.g., into the oviducts of a recipient female) and allowed to develop in the recipient female to produce the transgenic or gene edited animals. In particular, in vitro fertilized embryos can be centrifuged at 15,000×g for 5 minutes to sediment lipids allowing visualization of the pronucleus. The embryos can be injected with using an Eppendorf FEMTOJET injector and can be cultured until blastocyst formation. Rates of embryo cleavage and blastocyst formation and quality can be recorded.

Embryos can be surgically transferred into uteri of asynchronous recipients. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed.

In somatic cell nuclear transfer, a transgenic or gene edited cell such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic or gene edited cell into an enucleated oocyte arrested at meiosis 2. In some conventions, oocytes arrested at meiosis-2 are termed eggs. After producing a porcine or bovine embryo (e.g., by fusing and activating the oocyte), the embryo is transferred to the oviducts of a recipient female, about 20 to 24 hours after activation. See, for example, Cibelli et al. (1998) Science 280, 1256-1258 and U.S. Pat. Nos. 6,548,741, 7,547,816, 7,989,657, or 6,211,429. For pigs, recipient females can be checked for pregnancy approximately 20-21 days after transfer of the embryos.

Standard breeding techniques can be used to create animals that are homozygous for the inactivated gene from the initial heterozygous founder animals. Homozygosity may not be required, however. Gene edited pigs described herein can be bred with other pigs of interest.

Once gene edited animals have been generated, inactivation of an endogenous nucleic acid can be assessed using standard techniques. Initial screening can be accomplished by Southern blot analysis to determine whether or not inactivation has taken place. For a description of Southern analysis, see sections 9.37-9.52 of Sambrook et al., 1989, Molecular Cloning, A Laboratory Manual, second edition, Cold Spring Harbor Press, Plainview; N.Y. Polymerase chain reaction (PCR) techniques also can be used in the initial screening PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) Genetic Engineering News 12, 1; Guatelli et al. (1990) Proc. Natl. Acad. Sci. USA 87:1874; and Weiss (1991) Science 254:1292. At the blastocyst stage, embryos can be individually processed for analysis by PCR, Southern hybridization and splinkerette PCR (see, e.g., Dupuy et al. Proc Natl Acad Sci USA (2002) 99:4495).

Interfering RNAs

A variety of interfering RNA (RNAi) systems are known. Double-stranded RNA (dsRNA) induces sequence-specific degradation of homologous gene transcripts. RNA-induced silencing complex (RISC) metabolizes dsRNA to small 21-23-nucleotide small interfering RNAs (siRNAs). RISC contains a double stranded RNAse (dsRNAse, e.g., Dicer) and ssRNAse (e.g., Argonaut 2 or Ago2). RISC utilizes antisense strand as a guide to find a cleavable target. Both siRNAs and microRNAs (miRNAs) are known. A method of inactivating a gene in a genetically edited animal comprises inducing RNA interference against a target gene and/or nucleic acid such that expression of the target gene and/or nucleic acid is reduced.

For example the exogenous nucleic acid sequence can induce RNA interference against a nucleic acid encoding a polypeptide. For example, double-stranded small interfering RNA (siRNA) or small hairpin RNA (shRNA) homologous to a target DNA can be used to reduce expression of that DNA. Constructs for siRNA can be produced as described, for example, in Fire et al. (1998) Nature 391:806; Romano and Masino (1992) Mol. Microbiol. 6:3343; Cogoni et al. (1996) EMBO J. 15:3153; Cogoni and Masino (1999) Nature 399:166; Misquitta and Paterson (1999) Proc. Natl. Acad. Sci. USA 96:1451; and Kennerdell and Carthew (1998) Cell 95:1017. Constructs for shRNA can be produced as described by McIntyre and Fanning (2006) BMC Biotechnology 6:1. In general, shRNAs are transcribed as a single-stranded RNA molecule containing complementary regions, which can anneal and form short hairpins.

The probability of finding a single, individual functional siRNA or miRNA directed to a specific gene is high. The predictability of a specific sequence of siRNA, for instance, is about 50% but a number of interfering RNAs may be made with good confidence that at least one of them will be effective.

In vitro cells, in vivo cells, or a genetically edited animal such as a livestock animal that express an RNAi directed against a gene encoding CD163 can be used. The RNAi may be, for instance, selected from the group consisting of siRNA, shRNA, dsRNA, RISC and miRNA.

Inducible Systems

An inducible system may be used to inactivate a CD163 gene. Various inducible systems are known that allow spatial and temporal control of inactivation of a gene. Several have been proven to be functional in vivo in porcine animals.

An example of an inducible system is the tetracycline (tet)-on promoter system, which can be used to regulate transcription of the nucleic acid. In this system, a mutated Tet repressor (TetR) is fused to the activation domain of herpes simplex virus VP 16 trans-activator protein to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

The tetracycline-inducible system and the Cre/loxP recombinase system (either constitutive or inducible) are among the more commonly used inducible systems. The tetracycline-inducible system involves a tetracycline-controlled transactivator (tTA)/reverse tTA (rtTA). A method to use these systems in vivo involves generating two lines of genetically edited animals. One animal line expresses the activator (tTA, rtTA, or Cre recombinase) under the control of a selected promoter. Another line of animals expresses the acceptor, in which the expression of the gene of interest (or the gene to be modified) is under the control of the target sequence for the tTA/rtTA transactivators (or is flanked by loxP sequences). Mating the two of animals provides control of gene expression.

The tetracycline-dependent regulatory systems (tet systems) rely on two components, i.e., a tetracycline-controlled transactivator (tTA or rtTA) and a tTA/rtTA-dependent promoter that controls expression of a downstream cDNA, in a tetracycline-dependent manner. In the absence of tetracycline or its derivatives (such as doxycycline), tTA binds to tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. Administration of tetracycline or its derivatives allows temporal control of transgene expression in vivo. rtTA is a variant of tTA that is not functional in the absence of doxycycline but requires the presence of the ligand for transactivation. This tet system is therefore termed tet-ON. The tet systems have been used in vivo for the inducible expression of several transgenes, encoding, e.g., reporter genes, oncogenes, or proteins involved in a signaling cascade.

The Cre/lox system uses the Cre recombinase, which catalyzes site-specific recombination by crossover between two distant Cre recognition sequences, i.e., loxP sites. A DNA sequence introduced between the two loxP sequences (termed foxed DNA) is excised by Cre-mediated recombination. Control of Cre expression in a transgenic and/or gene edited animal, using either spatial control (with a tissue- or cell-specific promoter), or temporal control (with an inducible system), results in control of DNA excision between the two loxP sites. One application is for conditional gene inactivation (conditional knockout). Another approach is for protein over-expression, wherein a foxed stop codon is inserted between the promoter sequence and the DNA of interest. Genetically edited animals do not express the transgene until Cre is expressed, leading to excision of the foxed stop codon. This system has been applied to tissue-specific oncogenesis and controlled antigene receptor expression in B lymphocytes. Inducible Cre recombinases have also been developed. The inducible Cre recombinase is activated only by administration of an exogenous ligand. The inducible Cre recombinases are fusion proteins containing the original Cre recombinase and a specific ligand-binding domain. The functional activity of the Cre recombinase is dependent on an external ligand that is able to bind to this specific domain in the fusion protein.

In vitro cells, in vivo cells, or a genetically edited animal such as a livestock animal that comprises a CD163 gene under control of an inducible system can be used. The genetic modification of an animal may be genomic or mosaic. The inducible system may be, for instance, selected from the group consisting of Tet-On, Tet-Off, Cre-lox, and Hif1 alpha.

Vectors and Nucleic Acids

A variety of nucleic acids may be introduced into cells for knockout purposes, for inactivation of a gene, to obtain expression of a gene, or for other purposes. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3):187; and Hyrup et al. (1996) Bioorgan. Med. Chem. 4:5. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, inducible promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes or heart tissue and can include the albumin or alpha-myosin heavy chain promoters, respectively. A promoter that facilitates the expression of a nucleic acid molecule without significant tissue or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. For example, a fusion of the chicken beta actin gene promoter and the CMV enhancer can be used as a promoter. See, for example, Xu et al. (2001) Hum. Gene Ther. 12:563; and Kiwaki et al. (1996) Hum. Gene Ther. 7:821.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphotransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

A sequence encoding a selectable marker can be flanked by recognition sequences for a recombinase such as, e.g., Cre or Flp. For example, the selectable marker can be flanked by loxP recognition sites (34-bp recognition sites recognized by the Cre recombinase) or FRT recognition sites such that the selectable marker can be excised from the construct. See, Orban, et al., Proc. Natl. Acad. Sci. (1992) 89:6861, for a review of Cre/lox technology, and Brand and Dymecki, Dev. Cell (2004) 6:7. A transposon containing a Cre- or Flp-activatable transgene interrupted by a selectable marker gene also can be used to obtain animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

The exogenous nucleic acid can encode a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™tag (Kodak, New Haven, Conn.).

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult animal cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to an exogenous nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) Nucleic Acids Res. 31:6873); Tol2 (Kawakami (2007) Genome Biology 8 (Suppl.1):S7; Minos (Pavlopoulos et al. (2007) Genome Biology 8 (Suppl.1):S2); Hsmar1 (Miskey et al. (2007)) Mol Cell Biol. 27:4589); and Passport have been developed to introduce nucleic acids into cells, including mice, human, and pig cells. The Sleeping Beauty transposon is particularly useful. A transposase can be delivered as a protein, encoded on the same nucleic acid construct as the exogenous nucleic acid, can be introduced on a separate nucleic acid construct, or provided as an mRNA (e.g., an in vitro-transcribed and capped mRNA).

Insulator elements also can be included in a nucleic acid construct to maintain expression of the exogenous nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region—(MAR) type insulator elements and border-type insulator elements. See, for example, U.S. Pat. Nos. 6,395,549, 5,731,178, 6,100,448, and 5,610,053, and U.S. Publication No. 2004/0203158.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand).

Founder Animals, Animal Lines, Traits, and Reproduction

Founder animals may be produced by cloning and other methods described herein. The founders can be homozygous for a genetic modification, as in the case where a zygote or a primary cell undergoes a homozygous modification. Similarly, founders can also be made that are heterozygous. In the case of the animals comprising at least one modified chromosomal sequence in a gene encoding a CD163 protein, the founders are preferably heterozygous. The founders may be genomically modified, meaning that all of the cells in their genome have undergone modification. Founders can be mosaic for a modification, as may happen when vectors are introduced into one of a plurality of cells in an embryo, typically at a blastocyst stage. Progeny of mosaic animals may be tested to identify progeny that are genomically modified. An animal line is established when a pool of animals has been created that can be reproduced sexually or by assisted reproductive techniques, with heterogeneous or homozygous progeny consistently expressing the modification.

In livestock, many alleles are known to be linked to various traits such as production traits, type traits, workability traits, and other functional traits. Artisans are accustomed to monitoring and quantifying these traits, e.g., Visscher et al., Livestock Production Science, 40 (1994) 123-137, U.S. Pat. No. 7,709,206, US 2001/0016315, US 2011/0023140, and US 2005/153317. An animal line may include a trait chosen from a trait in the group consisting of a production trait, a type trait, a workability trait, a fertility trait, a mothering trait, and a disease resistance trait. Further traits include expression of a recombinant gene product.

Animals with a desired trait or traits may be modified to prevent their sexual maturation. Since the animals are sterile until matured, it is possible to regulate sexual maturity as a means of controlling dissemination of the animals. Animals that have been bred or modified to have one or more traits can thus be provided to recipients with a reduced risk that the recipients will breed the animals and appropriate the value of the traits to themselves. For example, the genome of an animal can be genetically modified, wherein the modification comprises inactivation of a sexual maturation gene, wherein the sexual maturation gene in a wild type animal expresses a factor selective for sexual maturation. The animal can be treated by administering a compound to remedy a deficiency caused by the loss of expression of the gene to induce sexual maturation in the animal.

Breeding of animals that require administration of a compound to induce sexual maturity may advantageously be accomplished at a treatment facility. The treatment facility can implement standardized protocols on well-controlled stock to efficiently produce consistent animals. The animal progeny may be distributed to a plurality of locations to be raised. Farms and farmers (a term including a ranch and ranchers) may thus order a desired number of progeny with a specified range of ages and/or weights and/or traits and have them delivered at a desired time and/or location. The recipients, e.g., farmers, may then raise the animals and deliver them to market as they desire.

A genetically modified livestock animal having an inactivated sexual maturation gene can be delivered (e.g., to one or more locations, to a plurality of farms). The animals can have an age of between about 1 day and about 180 days. The animal can have one or more traits (for example one that expresses a desired trait or a high-value trait or a novel trait or a recombinant trait).

Methods of Breeding and Methods for Increasing an Animal's Resistance to Infection and Populations of Animals Provided herein is a method of breeding to create animals or lineages that have reduced susceptibility to infection by a pathogen. The method comprises genetically modifying an oocyte or a sperm cell to introduce a modified chromosomal sequence in a gene encoding a CD163 protein into at least one of the oocyte and the sperm cell, and fertilizing the oocyte with the sperm cell to create a fertilized egg containing the modified chromosomal sequence in a gene encoding a CD163 protein. Alternatively, the method comprises genetically modifying a fertilized egg to introduce a modified chromosomal sequence in a gene encoding a CD163 protein into the fertilized egg. The method further comprises transferring the fertilized egg into a surrogate female animal, wherein gestation and term delivery produces a progeny animal; screening said progeny animal for susceptibility to the pathogen; and selecting progeny animals that have reduced susceptibility to the pathogen as compared to animals that do not comprise a modified chromosomal sequence in a gene encoding a CD163 protein.

Another method of breeding to create animals or lineages that have reduced susceptibility to infection by a pathogen is provided. The method comprises genetically modifying an oocyte or a sperm cell to introduce a modified chromosomal sequence in a gene encoding a CD163 protein into at least one of the oocyte and the sperm cell, and fertilizing the oocyte with the sperm cell to create a fertilized egg containing the modified chromosomal sequence in a gene encoding a CD163 protein. Alternatively, the method comprises genetically modifying a fertilized egg to introduce a modified chromosomal sequence in a gene encoding a CD163 protein into the fertilized egg. The method further comprises transferring the fertilized egg into a surrogate female animal, wherein gestation and term delivery produces a progeny animal; screening said progeny animal for susceptibility to the pathogen; and selecting progeny animals that have reduced susceptibility to the pathogen as compared to animals that do not comprise a modified chromosomal sequence in a gene encoding a CD163 protein. The modified chromosomal sequence results in production of substantially no functional CD163 protein by the progeny animal.

Yet another method of breeding to create animals or lineages that have reduced susceptibility to infection by a pathogen is provided. The method comprises genetically modifying an oocyte or a sperm cell to introduce a modified chromosomal sequence in a gene encoding a CD163 protein into at least one of the oocyte and the sperm cell, and fertilizing the oocyte with the sperm cell to create a fertilized egg containing the modified chromosomal sequence in a gene encoding a CD163 protein. Alternatively, the method comprises genetically modifying a fertilized egg to introduce a modified chromosomal sequence in a gene encoding a CD163 protein into the fertilized egg. The method further comprises transferring the fertilized egg into a surrogate female animal, wherein gestation and term delivery produces a progeny animal; screening said progeny animal for susceptibility to the pathogen; and selecting progeny animals that have reduced susceptibility to the pathogen as compared to animals that do not comprise a modified chromosomal sequence in a gene encoding a CD163 protein. The modified chromosomal sequence comprises an in-frame deletion in the gene encoding the CD163 protein.

The pathogen preferably comprises a virus, e.g., PRRSV. For example, the modification can reduce susceptibility to a Type 1 PRRSV virus, a Type 2 PRRSV, or to both Type 1 and Type 2 PRRSV viruses.

The modification can reduce susceptibility to a PRRSV isolate selected from the group consisting of NVSL 97-7895, KS06-72109, P129, VR2332, CO90, AZ25, MLV-ResPRRS, KS62-06274, KS483 (SD23983), CO84, SD13-15, Lelystad, 03-1059, 03-1060, SD01-08, 4353PZ, and combinations thereof.

The animal can be an embryo, a juvenile, or an adult.

The animal can comprise a domesticated animal. The domesticated animal can comprise a livestock animal, for example a porcine animal, a bovine animal (e.g., beef cattle or dairy cattle), an ovine animal, a caprine animal, an equine animal (e.g., a horse or a donkey), buffalo, camels, or an avian animal (e.g., a chicken, a turkey, a duck, a goose, a guinea fowl, or a squab). The livestock animal is preferably a bovine or porcine animal, and most preferably is a porcine animal.

The step of genetically modifying the oocyte, sperm cell, or fertilized egg can comprise genetic editing of the oocyte, sperm cell, or fertilized egg. The genetic editing can comprise use of a homing endonuclease. The homing endonuclease can be a naturally occurring endonuclease but is preferably a rationally designed, non-naturally occurring homing endonuclease that has a DNA recognition sequence that has been designed so that the endonuclease targets a chromosomal sequence in gene encoding a CD163 protein. Thus, the homing endonuclease can be a designed homing endonuclease. The homing endonuclease can comprise, for example, a Clustered Regularly Interspaced Short Palindromic Repeats (CRISPR)/Cas9 system, a Transcription Activator-Like Effector Nuclease (TALEN), a Zinc Finger Nuclease (ZFN), a recombinase fusion protein, a meganuclease, or a combination thereof). The genetic editing preferably comprises use of a CRISPR/Cas9 system.

The oocyte, sperm cell, or fertilized egg can be heterozygous for the modified chromosomal sequence. Alternatively, the oocyte, sperm cell, or fertilized egg can be homozygous for the modified chromosomal sequence.

The modified chromosomal sequence can comprise an insertion in the gene encoding the CD163 protein, a deletion in the gene encoding the CD163 protein, or a combination thereof. For example, the modified chromosomal sequence comprises a deletion in the gene encoding the CD163 protein (e.g., an in-frame deletion). Alternatively, the modified chromosomal sequence can comprise an insertion in the gene encoding the CD163 protein.

The insertion or deletion can cause CD163 protein production or activity to be reduced, as compared to CD163 protein production or activity in an animal that lacks the insertion or deletion.

The insertion or deletion can result in production of substantially no functional CD163 protein by the animal. By "substantially no functional CD163 protein," it is meant that the level of CD163 protein in the animal, offspring, or cell is undetectable, or if detectable, is at least about 90% lower than the level observed in an animal, offspring, or cell that does not comprise the insertion or deletion.

Where the animal is a porcine animal, the modified chromosomal sequence can comprise a modification in exon 7 of the gene encoding the CD163 protein, exon 8 of the gene encoding the CD163 protein, an intron that is contiguous with exon 7 or exon 8 of the gene encoding the CD163 protein, or a combination thereof. The modified chromosomal sequence suitably comprises a modification in exon 7 of the gene encoding the CD163 protein.

The modification in exon 7 of the gene encoding the CD163 protein can comprise a deletion (e.g., an in-frame deletion in exon 7). Alternatively, the modification in exon 7 of the gene encoding the CD163 protein can comprise an insertion.

Where the animal is a porcine animal, the modified chromosomal sequence can comprise: (a) SEQ ID NO: 118; or (b) a modification selected from the group consisting of: an 11 base pair deletion from nucleotide 3,137 to nucleotide 3,147 as compared to reference sequence SEQ ID NO: 47; a 2 base pair insertion between nucleotides 3,149 and 3,150 as compared to reference sequence SEQ ID NO: 47, with a 377 base pair deletion from nucleotide 2,573 to nucleotide 2,949 as compared to reference sequence SEQ ID NO: 47 on the same allele; a 124 base pair deletion from nucleotide 3,024 to nucleotide 3,147 as compared to reference sequence SEQ ID NO: 47; a 123 base pair deletion from nucleotide 3,024 to nucleotide 3,146 as compared to reference sequence SEQ ID NO: 47; a 1 base pair insertion between nucleotides 3,147 and 3,148 as compared to reference sequence SEQ ID NO: 47; a 130 base pair deletion from nucleotide 3,030 to nucleotide 3,159 as compared to reference sequence SEQ ID NO: 47; a 132 base pair deletion from nucleotide 3,030 to nucleotide 3,161 as compared to reference sequence SEQ ID NO: 47; a 1506 base pair deletion from nucleotide 1,525 to nucleotide 3,030 as compared to reference sequence SEQ ID NO: 47; a 7 base pair insertion between nucleotide 3,148 and nucleotide 3,149 as compared to reference sequence SEQ ID NO: 47; a 1280 base pair deletion from nucleotide 2,818 to nucleotide 4,097 as compared to reference sequence SEQ ID NO: 47; a 1373 base pair deletion from nucleotide 2,724 to nucleotide 4,096 as compared to reference sequence SEQ ID NO: 47; a 1467 base pair deletion from nucleotide 2,431 to nucleotide 3,897 as compared to reference sequence SEQ ID NO: 47; a 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; a 28 base pair deletion from nucleotide 3,145 to nucleotide 3,172 as compared to reference sequence SEQ ID NO: 47; a 1387 base pair deletion from nucleotide 3,145 to nucleotide 4,531 as compared to reference sequence SEQ ID NO: 47; a 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; a 452 base pair deletion from nucleotide 3,015 to nucleotide 3,466 as compared to reference sequence SEQ ID NO: 47; or combinations thereof.

When the porcine animal comprises the 2 base pair insertion between nucleotides 3,149 and 3,150 as compared to reference sequence SEQ ID NO: 47, the 2 base pair insertion can comprise insertion of the dinucleotide AG.

When the porcine animal comprises the 1 base pair insertion between nucleotides 3,147 and 3,148 as compared to reference sequence SEQ ID NO: 47, the 1 base pair insertion can comprise insertion of a single adenine residue.

When the porcine animal comprises the 7 base pair insertion between nucleotide 3,148 and nucleotide 3,149 as compared to reference sequence SEQ ID NO: 47, the 7 base pair insertion can comprise the sequence TACTACT (SEQ ID NO: 115).

When the porcine animal comprises the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47, the 12 base pair insertion can comprise the sequence TGTGGAGAATTC (SEQ ID NO: 116).

When the porcine animal comprises the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113, the 11 base pair insertion can comprise the sequence AGCCAGCGTGC (SEQ ID NO: 117).

Where the modified chromosomal sequence in the gene encoding the CD163 protein comprises a deletion, the deletion preferably comprises an in-frame deletion. Accordingly, where the animal is a porcine animal, the insertion or deletion in the gene encoding the CD163 protein can comprise an in-frame deletion in exon 7 selected from the group consisting of the 1506 base pair deletion from nucleotide 1,525 to nucleotide 3,030 as compared to reference sequence SEQ ID NO: 47; the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47; the 1373 base pair deletion from nucleotide 2,724 to nucleotide 4,096 as compared to reference sequence SEQ ID NO: 47; the 123 base pair deletion from nucleotide 3,024 to nucleotide 3,146 as compared to reference sequence SEQ ID NO: 47; the 1467 base pair deletion from nucleotide 2,431 to nucleotide 3,897 as compared to reference sequence SEQ ID NO: 47; the 1387 base pair deletion from nucleotide 3,145 to nucleotide 4,531 as compared to reference sequence SEQ ID NO: 47; the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113; a 1720 base pair deletion from nucleotide 2,440 to nucleotide 4,160 as compared to reference sequence SEQ ID NO: 47; and combinations thereof.

When the animal is a porcine animal, the insertion or deletion can be selected from the group consisting of: the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele; the 28 base pair deletion from nucleotide 3,145 to nucleotide 3,172 as compared to reference sequence SEQ ID NO: 47; the 452 base pair deletion from nucleotide 3,015 to nucleotide 3,466 as compared to reference sequence SEQ ID NO: 47; and combinations thereof.

For example, the modified chromosomal sequence can comprise the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 on the same allele.

The modified chromosomal sequence can comprise the 28 base pair deletion from nucleotide 3,145 to nucleotide 3,172 as compared to reference sequence SEQ ID NO: 47.

The modified chromosomal sequence can comprise the 452 base pair deletion from nucleotide 3,015 to nucleotide 3,466 as compared to reference sequence SEQ ID NO: 47.

The modified chromosomal sequence can comprise any combination any of the modified chromosomal sequences described herein.

For example, the modified chromosomal sequence can comprise the 7 base pair insertion between nucleotide 3,148 and nucleotide 3,149 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The modified chromosomal sequence can comprise the 7 base pair insertion between nucleotide 3,148 and nucleotide 3,149 as compared to reference sequence SEQ ID NO: 47 in one allele of the gene encoding the CD163 protein; and the 1382 base pair deletion from nucleotide 3,113 to nucleotide 4,494 as compared to reference sequence SEQ ID NO: 47, wherein the deleted sequence is replaced with an 11 base pair insertion beginning at nucleotide 3,113 in the other allele of the gene encoding the CD163 protein.

The modified chromosomal sequence can comprise SEQ ID NO: 118 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The modified chromosomal sequence can comprise SEQ ID NO: 118 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The modified chromosomal sequence can comprise the 1280 base pair deletion from nucleotide 2,818 to nucleotide 4,097 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The modified chromosomal sequence can comprise the 1280 base pair deletion from nucleotide 2,818 to nucleotide 4,097 as compared to reference sequence SEQ ID NO: 47 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The modified chromosomal sequence can comprise the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The modified chromosomal sequence can comprise SEQ ID NO: 118 in one allele of the gene encoding the CD163 protein; and the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47 in the other allele of the gene encoding the CD163 protein.

The modified chromosomal sequence can comprise the 1930 base pair deletion from nucleotide 488 to nucleotide 2,417 as compared to reference sequence SEQ ID NO: 47, wherein the deleted sequence is replaced with a 12 base pair insertion beginning at nucleotide 488, and wherein there is a further 129 base pair deletion in exon 7 from nucleotide 3,044 to nucleotide 3,172 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The modified chromosomal sequence can comprise the 1467 base pair deletion from nucleotide 2,431 to nucleotide 3,897 as compared to reference sequence SEQ ID NO: 47 in one allele of the gene encoding the CD163 protein; and the 2 base pair insertion between nucleotides 3,149 and 3,150 as compared to reference sequence SEQ ID NO: 47, with the 377 base pair deletion from nucleotide 2,573 to nucleotide 2,949 as compared to reference sequence SEQ ID NO: 47 in the other allele of the gene encoding the CD163 protein.

The modified chromosomal sequence can comprise the 1467 base pair deletion from nucleotide 2,431 to nucleotide 3,897 as compared to reference sequence SEQ ID NO: 47 in one allele of the gene encoding the CD163 protein; and the 11 base pair deletion from nucleotide 3,137 to nucleotide 3,147 as compared to reference sequence SEQ ID NO: 47 in the other allele of the gene encoding the CD163 protein.

The modified chromosomal sequence comprising any of the insertions or deletions described above can comprise a chromosomal sequence having at a high degree of sequence identity to SEQ ID NO: 47 outside of the insertion or deletion. Thus, for example, the oocyte, sperm cell, or fertilized egg can comprise a chromosomal sequence having at least 80%, at least 85%, at least 90%, at least 95%, at least 98%, at least 99%, at least 99.9%, or 100% sequence identity to SEQ ID NO: 47 in the regions of the chromosomal sequence outside of the insertion or deletion.

The modified chromosomal sequence can comprise a chromosomal sequence comprising SEQ ID NO: 98, 99, 100, 101, 102, 103, 104, 105, 106, 107, 108, 109, 110, 111, 112, 113, 114, 118, or 119. As is described further in the Examples hereinbelow, SEQ ID NOs. 98-114, and 119 provide nucleotide sequences for a region corresponding to the region of wild-type porcine CD163 provided in SEQ ID NO:47, and include the insertions or deletions in the porcine CD163 chromosomal sequence that are described herein. SEQ ID NO: 118 provides the sequence for a region corresponding to the region of wild-type porcine CD163 provided by SEQ ID NO: 47, wherein exon 7 has been replaced with a synthesized exon encoding a homolog of SRCR 8 of human CD163-like 1 protein (hCD163L1).

For example, the modified chromosomal sequence can comprise comprises a chromosomal sequence comprising SEQ ID NO: 98, 101, 105, 109, 110, 112, 113, or 114. SEQ ID NOs: 98, 101, 105, 109, 110, 112, 113, or 114 provide the nucleotide sequences for in-frame deletions in exon 7 of the porcine CD163 chromosomal sequence.

As another example, the modified chromosomal sequence can comprise a chromosomal sequence comprising SEQ ID NO: 103, 111, or 119.

The modified chromosomal sequence can comprise the 11 base pair deletion in one allele of the gene encoding the CD163 protein and the 2 base pair insertion with the 377 base pair deletion in the other allele of the gene encoding the CD163 protein.

The modified chromosomal sequence can comprise the 124 base pair deletion in one allele of the gene encoding the CD163 protein and the 123 base pair deletion in the other allele of the gene encoding the CD163 protein.

The modified chromosomal sequence can comprise the 1 base pair insertion.

The modified chromosomal sequence can comprise the 130 base pair deletion in one allele of the gene encoding the CD163 protein and the 132 base pair deletion in the other allele of the gene encoding the CD163 protein.

The modified chromosomal sequence can comprise the 1506 base pair deletion.

The modified chromosomal sequence can comprise the 7 base pair insertion.

The modified chromosomal sequence can comprise the 1280 base pair deletion in one allele of the gene encoding the CD163 protein and the 1373 base pair deletion in the other allele of the gene encoding the CD163 protein.

The modified chromosomal sequence can comprise the 1467 base pair deletion.

The modified chromosomal sequence can comprise the 1930 base pair intron 6 deletion from nucleotide 488 to nucleotide 2,417, with a 12 base pair insertion at nucleotide 4,488 and an additional 129 base pair deletion in exon 7.

The modified chromosomal sequence can comprise the 28 base pair deletion in one allele of the gene encoding the CD163 protein and the 1387 base pair deletion in the other allele of the gene encoding the CD163 protein.

The modified chromosomal sequence can comprise the 1382 base pair deletion with the 11 base pair insertion in one allele of the gene encoding the CD163 protein and the 1720 base pair deletion in the other allele of the gene encoding the CD163 protein.

In any of the methods of breeding, the selected animal can be used as a founder animal.

In any of the methods of breeding the fertilizing can comprise artificial insemination.

A population of animals made by any of the methods of breeding is also provided. The population of animals is preferably resistant to infection by a pathogen, for example a virus such as PRRSV. For example, the population can be resistant to infection by a Type 1 PRRSV virus, a Type 2 PRRSV, or to both Type 1 and Type 2 PRRSV viruses. The population can be resistant to infection by a PRRSV isolate selected from the group consisting of NVSL 97-7895, KS06-72109, P129, VR2332, CO90, AZ25, MLV-ResPRRS, KS62-06274, KS483 (SD23983), CO84, SD13-15, Lelystad, 03-1059, 03-1060, SD01-08, 4353PZ, and combinations thereof.

A method for increasing a livestock animal's resistance to infection with a pathogen is also provided. The method comprises genetically editing at least one chromosomal sequence from a gene encoding a CD163 protein so that CD163 protein production or activity is reduced, as compared to CD63 protein production or activity in a livestock animal that does not comprise an edited chromosomal sequence in a gene encoding a CD163 protein. The pathogen preferably comprises a virus (e.g., PRRSV).

Another method of increasing a livestock animal's resistance to infection with a pathogen comprising is provided. The method comprises genetically editing at least one chromosomal sequence from a gene encoding a CD163 protein so that the livestock animal produces substantially no functional CD163 protein.

Yet another method of increasing a livestock animal's resistance to infection with a pathogen is provided. The method comprises genetically editing at least one chromosomal sequence from a gene encoding a CD163 protein to introduce an in-frame deletion, wherein CD163 protein production or activity is reduced in the livestock animal, as compared to CD63 protein production or activity in a livestock animal that does not comprise an edited chromosomal sequence in a gene encoding a CD163 protein. The in-frame deletion can be, for example, any of the in-frame deletions described herein.

Nucleic Acids

Nucleic acids are provided. The nucleic acid molecule can comprise a nucleotide sequence selected from the group consisting of: (a) a nucleotide sequence comprising SEQ ID NO: 47; (b) a nucleotide sequence having at least 80% sequence identity to the sequence of SEQ ID NO: 47, wherein said nucleotide sequence contains at least one substitution, insertion, or deletion relative to SEQ ID NO: 47; and (c) a cDNA sequence of (a) or (b).

Alternatively, the nucleic acid can comprise (a) a nucleotide sequence having at least 87.5% sequence identity to the sequence of SEQ ID NO: 47, wherein said nucleotide sequence contains at least one substitution, insertion, or deletion relative to SEQ ID NO: 47; and (b) a cDNA sequence of (a).

Any of the nucleic acid molecules described herein can be isolated nucleic acid molecules.

For example, the isolated nucleic acid can comprise a nucleotide sequence comprising SEQ ID NO: 47.

Alternatively, the nucleic acid can comprise a nucleotide sequence having at least 80% sequence identity to the sequence of SEQ ID NO: 47, wherein said nucleotide sequence contains at least one substitution, insertion, or deletion relative to SEQ ID NO: 47. The nucleic acid can comprise a nucleotide sequence having at least 85%, at least 90%, at least 95%, at least 98%, at least 99%, or at least 99.9%, sequence identity to the sequence of SEQ ID NO: 47, wherein said nucleotide sequence contains at least one substitution, insertion, or deletion relative to SEQ ID NO: 47.

The nucleic acid molecule preferably has at least 87.5% sequence identity to the sequence of SEQ ID NO: 47, wherein the nucleotide sequence contains at least one substitution, insertion, or deletion relative to SEQ ID NO: 47.

The substitution, insertion, or deletion preferably reduces or eliminates CD163 protein production or activity, as compared to a nucleic acid that does not comprise the substitution, insertion, or deletion.

The nucleic acid can comprise SEQ ID NO: 98, 99, 100, 101, 102, 103, 104, 105, 106, 107, 108, 109, 110, 111, 112, 113, 114, 118, or 119.

For example, the nucleic acid can comprise SEQ ID NO: 98, 101, 105, 109, 110, 112, 113, or 114.

For example, the nucleic acid can comprise SEQ ID NO: 103, 111, or 119.

The nucleic acid can comprise the cDNA.

Further nucleic acids are provided. The nucleic acid can comprise SEQ ID NO: 98, 99, 100, 101, 102, 103, 104, 105, 106, 107, 108, 109, 110, 111, 112, 113, 114, 118, or 119. For example, the nucleic acid can comprise SEQ ID NO: 98, 101, 105, 109, 110, 112, 113, or 114. As another example, the nucleic acid can comprise SEQ ID NO: 103, 111, or 119.

Having described the invention in detail, it will be apparent that modifications and variations are possible without departing from the scope of the invention defined in the appended claims.

EXAMPLES

The following non-limiting examples are provided to further illustrate the present invention.

Example 1

Use of the CRISPR/Cas9 System to Produce Genetically Engineered Pigs from in Vitro-Derived Oocytes and Embryos Recent reports describing homing endonucleases, such as zinc-finger nucleases (ZFNs), transcription activator-like effector nucleases (TALENs), and components in the clustered regularly interspaced short palindromic repeat (CRISPR)/CRISPR-associated (Cas9) system suggest that genetic engineering (GE) in pigs might now be more efficient. Targeted homing endonucleases can induce double-strand breaks (DSBs) at specific locations in the genome and cause either random mutations through nonhomologous end joining (NHEJ) or stimulation of homologous recombination (HR) if donor DNA is provided. Targeted modification of the genome through HR can be achieved with homing endonucleases if donor DNA is provided along with the targeted nuclease. After introducing specific modifications in somatic cells, these cells were used to produce GE pigs for various purposes via SCNT. Thus, homing endonucleases are a useful tool in generating GE pigs. Among the different homing endonucleases, the CRISPR/Cas9 system, adapted from prokaryotes where it is used as a defense mechanism, appears to be an effective approach. In nature, the Cas9 system requires three components, an RNA (~20 bases) that contains a region that is complementary to the target sequence (cis-repressed RNA [crRNA]), an RNA that contains a region that is complementary to the crRNA (trans-activating crRNA [tracrRNA]), and Cas9, the enzymatic protein component in this complex. A single guide RNA (gRNA) can be constructed to serve the roles of the base-paired crRNA and tracrRNA. The gRNA/protein complex can scan the genome and catalyze a DSB at regions that are complementary to the crRNA/gRNA. Unlike other designed nucleases, only a short oligomer needs to be designed to construct the reagents required to target a gene of interest whereas a series of cloning steps are required to assemble ZFNs and TALENs.

Unlike current standard methods for gene disruption, the use of designed nucleases offers the opportunity to use zygotes as starting material for GE. Standard methods for gene disruption in livestock involve HR in cultured cells and subsequent reconstruction of embryos by somatic cell nuclear transfer (SCNT). Because cloned animals produced through SCNT sometimes show signs of developmental defects, progeny of the SCNT/GE founders are typically used for research to avoid confounding SCNT anomalies and phenotype that could occur if founder animals are used for experiments. Considering the longer gestation period and higher housing costs of pigs compared to rodents, there are time and cost benefits to the reduced need for breeding. A recent report demonstrated that direct injection of ZFNs and TALENs into porcine zygotes could disrupt an endogenous gene and produce piglets with the desired mutations. However, only about 10% of piglets showed biallelic modification of the target gene, and some presented mosaic genotypes. A recent article demonstrated that CRISPR/Cas9 system could induce mutations in developing embryos and produce GE pigs at a higher efficiency than ZFNs or TALENs. However, GE pigs produced from the CRISPR/Cas9 system also possessed mosaic genotypes. In addition, all the above-mentioned studies used in vivo derived zygotes for the experiments, which require intensive labor and numerous sows to obtain a sufficient number of zygotes.

The present example describes an efficient approach to use the CRISPR/Cas9 system in generating GE pigs via both injection of in vitro derived zygotes and modification of somatic cells followed by SCNT. Two endogenous genes (CD163 and CD1D) and one transgene (eGFP) were targeted, and only in vitro derived oocytes or zygotes were used for SCNT or RNA injections, respectively. CD163 appears to be required for productive infection by porcine reproductive and respiratory syndrome virus, a virus known to cause a significant economic loss to swine industry. CD1D is considered a nonclassical major histocompatibility complex protein and is involved in presentation of lipid antigens to invariant natural killer T cells. Pigs deficient in these genes were designed to be models for agriculture and biomedicine. The eGFP transgene was used as a target for preliminary proof-of-concept experiments and optimizations of methods.

Materials and Methods

Chemical and Reagents. Unless otherwise stated, all of the chemicals used in this study were purchased from Sigma.

Design of gRNAs to Build Specific CRISPRs

Guide RNAs were designed to regions within exon 7 of CD163 that were unique to the wild type CD163 and not present in the domain swap targeting vector (described below), so that the CRISPR would result in DSB within wild type CD163 but not in the domain swap targeting vector. There were only four locations in which the targeting vector would introduce a single nucleotide polymorphism (SNP) that would alter an *S. pyogenes* (Spy) protospacer adjacent motif (PAM). All four targets were selected including:

(CRISPR 10)
(SEQ ID NO: 1)
GGAAACCCAGGCTGGTTGGAgGG, (CRISPR 131)
(SEQ ID NO: 2)
GGAACTACAGTGCGGCACTGtGG, (CRISPR 256)
(SEQ ID NO: 3)
CAGTAGCACCCCGCCCTGACgGG
and (CRISPR 282)
(SEQ ID NO: 4)
TGTAGCCACAGCAGGGACGTcGG.

The PAM can be identified by the bold font in each gRNA.

For CD1D mutations, the search for CRISPR targets was arbitrarily limited to the coding strand within the first 1000 bp of the primary transcript. However, RepeatMasker [26] ("Pig" repeat library) identified a repetitive element beginning at base 943 of the primary transcript. The search for CRISPR targets was then limited to the first 942 bp of the primary transcript. The search was further limited to the first 873 bp of the primary transcript since the last Spy PAM is located at base 873. The first target (CRISPR 4800) was selected because it overlapped with the start codon located at base 42 in primary transcript (CCAGCCTCGCCCAGC-GACATgGG (SEQ ID NO:5)). Two additional targets (CRISPRs 5620 and 5626) were selected because they were the most distal to the first selection within the arbitrarily selected region (CTTTCATTTATCTGAACTCAgGG (SEQ ID NO:6) and TTATCTGAACTCAGGGTCCCcGG (SEQ ID NO:7)). These targets overlap. In relation to the start codon, the most proximal Spy PAMs were located in simple sequence that contained extensively homopolymeric sequence as determined by visual appraisal. The forth target (CRISPR 5350) was selected because, in relation to the first target selection, it was the most proximal target that did not contain extensive homopolymeric regions (CAGCTGCAG-CATATATTTAAgGG (SEQ ID NO:8)). Specificity of the designed crRNAs was confirmed by searching for similar porcine sequences in GenBank. The oligonucleotides (Table 1) were annealed and cloned into the p330X vector which contains two expression cassettes, a human codon-optimized *S. pyogenes* (hSpy) Cas9 and the chimeric guide RNA P330X was digested with BbsI (New England Biolabs) following the Zhang laboratory protocol (http://www.addgene.org/crispr/zhang/).

To target eGFP, two specific gRNAs targeting the eGFP coding sequence were designed within the first 60 bp of the eGFP start codon. Both eGFP1 and eGFP2 gRNA were on the antisense strand and eGFP1 directly targeted the start codon. The eGFP1 gRNA sequence was CTCCTCGCCCT-TGCTCACCAtGG (SEQ ID NO:9) and the eGFP2 gRNA sequence was GACCAGGATGGGCACCACCCcGG (SEQ ID NO:10).

TABLE 1

Designed crRNAs.
Primer 1 and primer 2 were annealed
following the Zhang protocol.

| Primer | Sequence (5'-3') | SEQ ID NO. |
|---|---|---|
| CD163 10 1 | CACCGGAAACCCAGGCTGGTTGGA | 48 |
| CD163 10 2 | AAACTCCAACCAGCCTGGGTTTCC | 49 |
| CD163 131 1 | CACCGGAACTACAGTGCGGCACTG | 50 |
| CD163 131 2 | AAACCAGTGCCGCACTGTAGTTCC | 51 |
| CD163 256 1 | CACCGCAGTAGCACCCCGCCCTGAC | 52 |
| CD163 256 2 | AAACGTCAGGGCGGGGTGCTACTGC | 53 |
| CD163 282 1 | CACCGTGTAGCCACAGCAGGGACGT | 54 |
| CD163 282 2 | AAACACGTCCCTGCTGTGGCTACAC | 55 |
| CD1D 4800 1 | CACCGCCAGCCTCGCCCAGCGACAT | 56 |
| CD1D 4800 2 | AAACATGTCGCTGGGCGAGGCTGGC | 57 |
| CD1D 5350 1 | CACCGCAGCTGCAGCATATATTTAA | 58 |
| CD1D 5350 2 | AAACTTAAATATATGCTGCAGCTGC | 59 |
| CD1D 5620 1 | CACCGCTTTCATTTATCTGAACTCA | 60 |
| CD1D 5620 2 | AAACTGAGTTCAGATAAATGAAAGC | 61 |
| CD1D 5626 1 | CACCGTTATCTGAACTCAGGGTCCC | 62 |
| CD1D 5626 2 | AAACGGGACCCTGAGTTCAGATAAC | 63 |
| eGFP 1 1 | CACCGCTCCTCGCCCTTGCTCACCA | 64 |
| eGFP 1 2 | AAACTGGTGAGCAAGGGCGAGGAGC | 65 |
| eGFP 2 1 | CACCGACCAGGATGGGCACCACCC | 66 |
| eGFP 2 2 | AAACGGGTGGTGCCCATCCTGGTCC | 67 |

Synthesis of Donor DNA for CD163 and CD1D Genes

Both porcine CD163 and CD1D were amplified by PCR from DNA isolated from the fetal fibroblasts that would be used for later transfections to ensure an isogenic match between the targeting vector and the transfected cell line. Briefly, LA taq (Clontech) using the forward primer CTCTCCCTCACTCTAACCTACTT (SEQ ID NO:11), and the reverse primer TATTTCTCTCACATGGCCAGTC (SEQ ID NO:12) were used to amplify a 9538 bp fragment of CD163. The fragment was DNA sequence validated and used to build the domain-swap targeting vector (FIG. 1). This vector included 33 point mutations within exon 7 so that it would encode the same amino acid sequence as human CD163L from exon 11. The replacement exon was 315 bp. In addition, the subsequent intron was replaced with a modified myostatin intron B that housed a selectable marker gene that could be removed with Cre-recombinase (Cre) and had previously demonstrated normal splicing when harboring the retained loxP site (Wells, unpublished results). The long arm of the construct was 3469 bp and included the domain swap DS exon. The short arm was 1578 bp and included exons 7 and 8 (FIG. 1, panel B). This plasmid was used to attempt to replace the coding region of exon 7 in the first transfection experiments and allowed for selection of targeting events via the selectable marker (G418). If targeting were to occur, the marker could be deleted by Cre-recombinase. The CD163 DS-targeting vector was then modified for use with cell lines that already contained a SIGLEC1 gene disrupted with Neo that could not be Cre deleted. In this targeting vector, the Neo cassette, loxP and myostatin intron B, were removed, and only the DS exon remained with the WT long and short arm (FIG. 1, panel C).

The genomic sequence for porcine CD1D was amplified with LA taq using the forward primer CTCTCCCT-CACTCTAACCTACTT (SEQ ID NO:13) and reverse primer GACTGGCCATGTGAGAGAAATA (SEQ ID NO:14), resulting in an 8729 bp fragment. The fragment was DNA sequenced and used to build the targeting vector shown in FIG. 2. The Neo cassette is under the control of a phosphoglycerol kinase (PGK) promoter and flanked with loxP sequences, which were introduced for selection. The long arm of the construct was 4832 bp and the short arm was 3563 bp, and included exons 6 and 7. If successful HR occurred, exons 3, 4, and 5 would be removed and replaced with the Neo cassette. If NHEJ repair occurred incorrectly, then exon 3 would be disrupted.

Fetal Fibroblast Collection

Porcine fetal tissue was collected on Day 35 of gestation to create cell lines. Two wild-type (WT) male and female fetal fibroblast cell lines were established from a large white domestic cross. Male and female fetal fibroblasts that had previously been modified to contain a Neo cassette (SIGLEC1−/− genetics) were also used in these studies. Fetal fibroblasts were collected as described with minor modifications; minced tissue from each fetus was digested in 20 ml of digestion media (Dulbecco-modified Eagle medium [DMEM] containing L-glutamine and 1 g/L D-glucose [Cellgro] supplemented with 200 units/ml collagenase and 25 Kunitz units/ml DNaseI) for 5 h at 38.5° C. After digestion, fetal fibroblast cells were washed and cultured with DMEM, 15% fetal bovine serum (FBS), and 40 µg/ml gentamicin. After overnight culture, the cells were typsinized and frozen at −80° C. in aliquots in FBS with 10% dimethyl sulfoxide and stored in liquid nitrogen.

Cell Transfection and Genotyping

Transfection conditions were essentially as previously reported. The donor DNA was always used at a constant amount of 1 µg with varying amounts of CRISPR/Cas9 plasmid (listed below). Donor DNA was linearized with MLUI (CD163) (NEB) or AFLII (CD1D) (NEB) prior to transfection. The gender of the established cell lines was determined by PCR as described previously prior to transfection. Both male and female cell lines were transfected, and genome modification data was analyzed together between the transfections. Fetal fibroblast cell lines of similar passage number (2-4) were cultured for 2 days and grown to 75%-85% confluency in DMEM containing L-glutamine and 1 g/L D-glucose (Cellgro) supplemented with 15% FBS, 2.5 ng/ml basic fibroblast growth factor, and 10 mg/ml gentamicin. Fibroblast cells were washed with phosphate-buffered saline (PBS) (Life Technologies) and trypsinized. As soon as cells detached, the cells were rinsed with an electroporation medium (75% cytosalts [120 mM KCl, 0.15 mM $CaCl_2$, 10 mM $K_2HPO_4$, pH 7.6, 5 Mm $MgCl_2$]) and 25% Opti-MEM (LifeTechnologies). Cell concentration was quantified by using a hemocytometer. Cells were pelleted at 600×g for 5 min and resuspended at a concentration of 1×10$^6$ in electroporation medium. Each electroporation used 200 µl of cells in 2 mm gap cuvettes with three (1 msec) square-wave pulses administered through a BTX ECM 2001 at 250 V. After the electroporation, cells were resuspended in DMEM described above. For selection, 600 µg/ml G418 (Life Technologies) was added 24 h after transfection, and the medium was changed on Day 7. Colonies were picked on Day 14 after transfection. Fetal fibroblasts were plated at 10,000 cells/plate if G418 selection was used and at 50 cells/plate if no G418 selection was used. Fetal fibroblast colonies were collected by applying 10 mm autoclaved cloning cylinders sealed around each colony by autoclaved vacuum grease. Colonies were rinsed with PBS and harvested via trypsin; then resuspended in DMEM culture medium. A part (⅓) of the resuspended colony was transferred to a 96-well PCR plate, and the remaining (⅔) cells were cultured in a well of a 24-well plate. The cell pellets were resuspended in 6 µl of lysis buffer (40 mM Tris, pH 8.9, 0.9% Triton X-100, 0.4 mg/ml proteinase K [NEB]), incubated at 65° C. for 30 min for cell lysis, followed by 85° C. for 10 min to inactivate the proteinase K.

PCR Screening for DS and Large and Small Deletions

Detection of HR-Directed Repair. Long-range PCRs were used to identify mutations on either CD163 or CD1D. Three different PCR assays were used to identify HR events: PCR amplification of regions spanning from the CD163 or CD1D sequences in the donor DNA to the endogenous CD163 or CD1D sequences on either the right or left side and a long-range PCR that amplified large regions of CD163 or CD1D encompassing the designed donor DNAs. An increase in the size of a PCR product, either 1.8 kb (CD1D) or 3.5 kb (CD163), arising from the addition of exogenous Neo sequences, was considered evidence for HR-directed repair of the genes. All the PCR conditions included an initial denaturation of 95° C. for 2 min followed by 33 cycles of 30 sec at 94° C., 30 sec at 50° C., and 7-10 min at 68° C. LA taq was used for all the assays following the manufacturers' recommendations. Primers are shown in Table 2.

TABLE 2

Primers used to identify HR directed repair of CD163 and CD1D

| Primer | Sequence (5'-3') | SEQ ID NO. |
|---|---|---|
| CD163 Long Range Assay Primer 1230 F | TTGTTGGAAGGCTCACTGTCCTTG | 68 |
| CD163 Long Range Assay Primer 7775 R | ACAACTAAGGTGGGCAAAG | 69 |
| CD163 Left Arm Assay Primer 1230 F | TTGTTGGAAGGCTCACTGTCCTTG | 70 |
| CD163 Left Arm Assay Primer 8491 R | GGAGCTCAACATTCTTGGGTCCT | 71 |
| CD163 Right Arm Assay Primer 3752 F | GGCAAAATTTTCATGCTGAGGTG | 72 |
| CD163 Right Arm Assay Primer 7765 R | GCACATCACTTCGGGTTACAGTG | 73 |
| CD1D Long Range Assay Primer F 3991 F | CCCAAGTATCTTCAGTTCTGCAG | 74 |
| CD1D Long Range Assay Primer R 12806 R | TACAGGTAGGAGAGCCTGTTTTG | 75 |
| CD1D Left Arm Assay Primer F 3991 F | CCCAAGTATCTTCAGTTCTGCAG | 76 |
| CD1D Left Arm Assay Primer 7373 R | CTCAAAAGGATGTAAACCCTGGA | 77 |

TABLE 2-continued

Primers used to identify HR directed repair of CD163 and CD1D

| Primer | Sequence (5'-3') | SEQ ID NO. |
|---|---|---|
| CD1D Right Arm Assay Primer 4363 F | TGTTGATGTGGTTTGTTTGCCC | 78 |
| CD1D Right Arm Assay Primer 12806 R | TACAGGTAGGAGAGCCTGTTTTG | 79 |

Small Deletions Assay (NHEJ). Small deletions were determined by PCR amplification of CD163 or CD1D flanking a projected cutting site introduced by the CRISPR/Cas9 system. The size of the amplicons was 435 bp and 1244 bp for CD163 and CD1D, respectively. Lysates from both embryos and fetal fibroblasts were PCR amplified with LA taq. PCR conditions of the assays were an initial denaturation of 95° C. for 2 min followed by 33 cycles of 30 sec at 94° C., 30 sec at 56° C., and 1 min at 72° C. For genotyping of the transfected cells, insertions and deletions (INDELs) were identified by separating PCR amplicons by agarose gel electrophoresis. For embryo genotyping, the resulting PCR products were subsequently DNA sequenced to identify small deletions using forward primers used in the PCR. Primer information is shown in Table 3.

TABLE 3

Primers used to identify mutations through NHEJ on CD163 and CD1D

| Primer | Sequence (5'-3') | SEQ ID NO. |
|---|---|---|
| GCD163F | GGAGGTCTAGAATCGGCTAAGCC | 80 |
| GCD163R | GGCTACATGTCCCGTCAGGG | 81 |
| GCD1DF | GCAGGCCACTAGGCAGATGAA | 82 |
| GCD1DR | GAGCTGACACCCAAGAAGTTCCT | 83 |
| eGFP1 | GGCTCTAGAGCCTCTGCTAACC | 84 |
| eGFP2 | GGACTTGAAGAAGTCGTGCTGC | 85 |

Somatic Cell Nuclear Transfer (SCNT)

To produce SCNT embryos, either sow-derived oocytes (ART, Inc.) or gilt-derived oocytes from a local slaughter house were used. The sow-derived oocytes were shipped overnight in maturation medium (TCM-199 with 2.9 mM Hepes, 5 µg/ml insulin, 10 ng/ml epidermal growth factor [EGF], 0.5 µg/ml porcine follicle-stimulating hormone [p-FSH], 0.91 mM pyruvate, 0.5 mM cysteine, 10% porcine follicular fluid, and 25 ng/ml gentamicin) and transferred into fresh medium after 24 h. After 40-42 h of maturation, cumulus cells were removed from the oocytes by vortexing in the presence of 0.1% hyaluronidase. The gilt-derived oocytes were matured as described below for in vitro fertilization (IVF). During manipulation, oocytes were placed in the manipulation medium (TCM-199 [Life Technologies] with 0.6 mM NaHCO$_3$, 2.9 mM Hepes, 30 mM NaCl, 10 ng/ml gentamicin, and 3 mg/ml BSA, with osmolarity of 305 mOsm) supplemented with 7.0 µg/ml cytochalasin B. The polar body along with a portion of the adjacent cytoplasm, presumably containing the metaphase II plate, was removed, and a donor cell was placed in the perivitelline space by using a thin glass capillary. The reconstructed embryos were then fused in a fusion medium (0.3 M mannitol, 0.1 mM $CaCl_2$, 0.1 mM $MgCl_2$, and 0.5 mM Hepes) with two DC pulses (1-sec interval) at 1.2 kV/cm for 30 lsec using a BTX Electro Cell Manipulator (Harvard Apparatus). After fusion, fused embryos were fully activated with 200 μM thimerosal for 10 min in the dark and 8 mM dithiothreitol for 30 min. Embryos were then incubated in modified porcine zygote medium PZM3-MU1 with 0.5 μM Scriptaid (S7817; Sigma-Aldrich), a histone deacetylase inhibitor, for 14-16 h, as described previously.

In Vitro Fertilization (IVF)

For IVF, ovaries from prepubertal gilts were obtained from an abattoir (Farmland Foods Inc.). Immature oocytes were aspirated from medium size (3-6 mm) follicles using an 18-gauge hypodermic needle attached to a 10 ml syringe. Oocytes with evenly dark cytoplasm and intact surrounding cumulus cells were then selected for maturation. Around 50 cumulus oocyte complexes were place in a well containing 500 μl of maturation medium, TCM-199 (Invitrogen) with 3.05 mM glucose, 0.91 mM sodium pyruvate, 0.57 mM cysteine, 10 ng/ml EGF, 0.5 μg/ml luteinizing hormone (LH), 0.5 μg/ml FSH, 10 ng/ml gentamicin (APP Pharm), and 0.1% polyvinyl alcohol for 42-44 h at 38.5° C., 5% $CO_2$, in humidified air. At the end of the maturation, the surrounding cumulus cells were removed from the oocytes by vortexing for 3 min in the presence of 0.1% hyaluronidase. Then, in vitro matured oocytes were placed in 50 μl droplets of IVF medium (modified Tris-buffered medium containing 113.1 mM NaCl, 3 mM KCl, 7.5 mM CaCl2, 11 mM glucose, 20 mM Tris, 2 mM caffeine, 5 mM sodium pyruvate, and 2 mg/ml bovine serum albumin [BSA]) in groups of 25-30 oocytes. One 100 μl frozen semen pellet was thawed in 3 ml of Dulbecco PBS supplemented with 0.1% BSA. Either frozen WT or fresh eGFP semen was washed in 60% Percoll for 20 min at 650 3 g and in modified Tris-buffered medium for 10 min by centrifugation. In some cases, freshly collected semen heterozygous for a previously described eGFP transgene was washed three times in PBS. The semen pellet was then resuspended with IVF medium to $0.5 \times 10^6$ cells/ml. Fifty microliters of the semen suspension was introduced into the droplets with oocytes. The gametes were coincubated for 5 h at 38.5° C. in an atmosphere of 5% $CO_2$ in air. After fertilization, the embryos were incubated in PZM3-MU1 at 38.5° C. and 5% $CO_2$ in air.

Embryo Transfer

Embryos generated to produce GE CD163 or CD1D pigs were transferred into surrogates either on Day 1 (SCNT) or 6 (zygote injected) after first standing estrus. For Day 6 transfer, zygotes were cultured for five additional days in PZM3-MU1 in the presence of 10 ng/ml ps48 (Stemgent, Inc.). The embryos were surgically transferred into the ampullary-isthmic junction of the oviduct of the surrogate.

In Vitro Synthesis of RNA for CRISPR/Cas9 System

Template DNA for in vitro transcription was amplified using PCR (Table 4). CRISPR/Cas9 plasmid used for cell transfection experiments served as the template for the PCR. In order to express the Cas9 in the zygotes, the mMESSAGE mMACHINE Ultra Kit (Ambion) was used to produce mRNA of Cas9. Then a poly A signal was added to the Cas9 mRNA using a Poly (A) tailing kit (Ambion). CRISPR guide RNAs were produced by MEGAshortscript (Ambion). The quality of the synthesized RNAs were visualized on a 1.5% agarose gel and then diluted to a final concentration of 10 ng/μl (both gRNA and Cas9) and distributed into 3 μl aliquots.

TABLE 4

Primers used to amplify templates for in vitro transcription.

| Primers | Sequence (5'-3') | SEQ ID NO. |
|---|---|---|
| Cas9 | F: TAATACGACTCACTATAGGGAG AATGGACTATAAGGACCACGAC | 86 |
|  | R: GCGAGCTCTAGGAATTCTTAC | 87 |
| eGFP 1 | F: TTAATACGACTCACTATAGGCT CCTCGCCCTTGCTCACCA | 88 |
|  | R: AAAAGCACCGACTCGGTGCC | 89 |
| CD163 10 | F: TTAATACGACTCACTATAGGA AACCCAGGCTGGTTGGA | 90 |
|  | R: AAAAGCACCGACTCGGTGCC | 91 |
| CD163 131 | F: TTAATACGACTCACTATAGGA ACTACAGTGCGGCACTG | 92 |
|  | R: AAAAGCACCGACTCGGTGCC | 93 |
| CD1D 4800 | F: TTAATACGACTCACTATAGGC CAGCCTCGCCCAGCGACAT | 94 |
|  | R: AAAAGCACCGACTCGGTGCC | 95 |
| CD1D 5350 | F: TTAATACGACTCACTATAGGC AGCTGCAGCATATATTTAA | 96 |
|  | R: AAAAGCACCGACTCGGTGCC | 97 |

Microinjection of Designed CRISPR/Cas9 System in Zygotes

Messenger RNA coding for Cas9 and gRNA was injected into the cytoplasm of fertilized oocytes at 14 h postfertilization (presumptive zygotes) using a FemtoJet microinjector (Eppendorf). Microinjection was performed in manipulation medium on the heated stage of a Nikon inverted microscope (Nikon Corporation; Tokyo, Japan). Injected zygotes were then transferred into the PZM3-MU1 with 10 ng/ml ps48 until further use.

Statistical Analysis

The number of colonies with a modified genome was classified as 1, and the colonies without a modification of the genome were classified as 0. Differences were determined by using PROC GLM (SAS) with a P-value of 0.05 being considered as significant. Means were calculated as least-square means. Data are presented as numerical means±SEM.

Results

CRISPR/Cas9-Mediated Knockout of CD163 and CD1D in Somatic Cells

Figure 3:
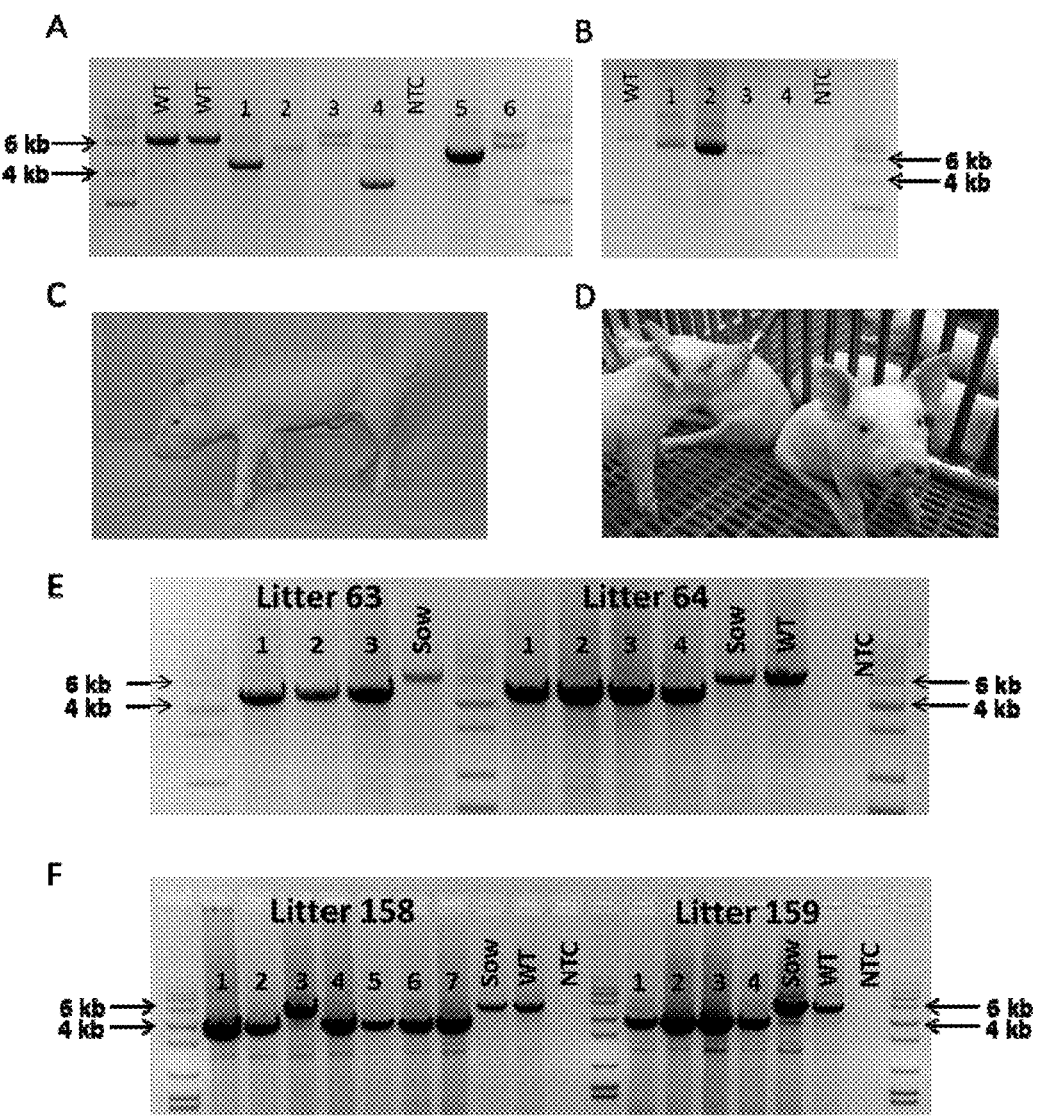
FIG. 3. Generation of CD163 and CD1D knockout pigs by CRISPR/Cas9 and SCNT. A) Targeted deletion of CD163 in somatic cells after transfection with CRISPR/Cas9 and donor DNA. A wild-type (WT) genotype results in a 6545 base pair (bp) band. Lanes 1-6 represent six different colonies from a single transfection with CRISPR 10 with Cas9 and donor DNA containing Neo. Lanes 1, 4, and 5 show a large homozygous deletion of 1500-2000 bp. Lane 2 represents a smaller homozygous deletion. Lanes 3 and 6 represent either a WT allele and a small deletion or a biallelic modification of both alleles. The exact modifications of each colony were only determined by sequencing for colonies used for SCNT. The faint WT band in some of the lanes may represent cross-contamination of fetal fibroblasts from a neighboring WT colony. NTC=no template control. B) Targeted deletion of CD1D in somatic cells after transfection with CRISPR/Cas9 and donor DNA. A WT genotype results in an 8729 bp band. Lanes 1-4 represent colonies with a 500-2000 bp deletion of CD1D. Lane 4 appears to be a WT colony. NTC=no template control. C) Image of CD163 knockout pig produced by SCNT during the study. This male piglet contains a homozygous 1506 bp deletion of CD163. D) Image of CD1D pigs produced during the study. These piglets contain a 1653 bp deletion of CD1D. E) Genotype of two SCNT litters containing the 1506 bp deletion of CD163. Lanes 1-3 (litter 63) and lanes 1-4 (litter 64) represent the genotype for each piglet from each litter. Sow indicates the recipient female of the SCNT embryos, and WT represents a WT control. NTC=no template control. F) Genotype of two SCNT litters containing the 1653 bp deletion of CD1D. Lanes 1-7 (litter 158) and lanes 1-4 (litter 159) represent the genotype for each piglet.

Efficiency of four different CRISPRs plasmids (guides 10, 131, 256, and 282) targeting CD163 was tested at an amount of 2 μg/μl of donor DNA (Table 5). CRISPR 282 resulted in significantly more average colony formation than CRISPR 10 and 256 treatments (P<0.05). From the long-range PCR assay described above, large deletions were found ranging from 503 bp to as much as 1506 bp instead of a DS through HR as was originally intended (FIG. 3, panel A). This was not expected because previous reports with other DNA-editing systems showed much smaller deletions of 6-333 bp using ZFN in pigs. CRISPR 10 and a mix of all four CRISPRs resulted in a higher number of colonies with a modified genome than CRISPR 256 and 282 (Table 5, P<0.002). Transfection with CRISPR 10 and a plasmid containing Neo but no homology to CD163 resulted in no colonies presenting the large deletion. Interestingly, one monoallelic deletion was also detected when the donor DNA was introduced without any CRISPR. This assay likely represents an underestimation of the mutation rate because any potential small deletions by sequencing which could not be detected on an agarose gel in the transfected somatic cells were not screened for.

TABLE 5

Efficiency of four different CRISPR plasmids (guides 10, 131, 256, and 282) targeting CD163. Four different CRISPRs were tested at an amount of 2 μg to 1 μg Donor DNA (shown in FIG. 1).

| Treatment* | Total No. of Colonies | Total No. of Plates | Average No. of Colonies/plate† | No. of Colonies NHEJ | Colony with HR | Percent Colonies with a Modified Genome† | Reps |
|---|---|---|---|---|---|---|---|
| 10 + Donor DNA | 76 | 102 | $0.75^{bc}$ | 11 | 1‡ | $15.79^a$ | 4 |
| 131 + Donor DNA | 102 | 51 | $2.00^{ab}$ | 11 | 0 | $10.78^{ab}$ | 3 |
| 256 + Donor DNA | 43 | 49 | $0.88^c$ | 2 | 0 | $4.65^{bc}$ | 3 |
| 282 + Donor DNA | 109 | 46 | $2.37^a$ | 3 | 0 | $2.75^{bc}$ | 3 |
| mix of 4 + Donor DNA | 111 | 55 | $2.02^{ab}$ | 20 | 0 | $18.02^a$ | 3 |
| Donor DNA | 48 | 52 | $0.92^{bc}$ | 1 | 0 | $2.08^{bc}$ | 3 |
| 10 + Neo (no CD163) | 26 | 20 | $1.3^{n/a}$ | 0 | 0 | $0.00^c$ | 1 |

*Mix of 4 + Donor DNA represents an equal mixing of 0.5 μg of each CRISPR with 1 μg of Donor DNA. The Donor DNA treatment served as the no CRISPR control and the 10 + Neo treatment illustrates that the large deletions observed in the CRISPR treatments were present only when the CD163 Donor DNA was also present.
†ANOVA was performed comparing the average number of colonies/plate to estimate CRISPR toxicity and on the percent colonies with a modified genome. P-values were 0.025 and 0.0002, respectively. n/a = There were no replicates for this treatment so no statistical analysis was performed.
‡The one colony with HR represents a partial HR event.
$a$-$c$Superscript letters indicate a significant difference between treatments for both average number of colonies/plate and percent colonies with a modified genome ($P < 0.05$).

The initial goal was to obtain a domain swap (DS)-targeting event by HR for CD163, but CRISPRs did not increase the efficiency of targeting CD163. It should be noted that various combinations of this targeting vector had been used to modify CD163 by HR by traditional transfections and resulted in 0 targeting events after screening 3399 colonies (Whitworth and Prather, unpublished results). Two pigs were obtained with a full DS resulting from HR that contained all 33 of the mutations that were attempted to be introduced by transfection with CRISPR 10 and the DS-targeting vector as donor DNA.

Next, the efficiency of CRISPR/Cas9-induced mutations without drug selection was tested; the fetal fibroblast cell line used in this study already had an integration of the Neo resistant cassette and a knockout of SIGLEC1. Whether the ratio of CRISPR/Cas9 and donor DNA would increase genome modification or result in a toxic effect at a high concentration was also tested. CRISPR 131 was selected for this trial because in the previous experiment, it resulted in a high number of total colonies and an increased percentage of colonies possessing a modified genome. Increasing amounts of CRISPR 131 DNA from 3:1 to 20:1 did not have a significant effect on fetal fibroblast survivability. The percent of colonies with a genome modified by NHEJ was not significantly different between the various CRISPR concentrations but had the highest number of NHEJ at a 10:1 ratio (Table 6, P=0.33). Even at the highest ratio of CRISPR DNA to donor DNA (20:1), HR was not observed.

Based on this experience, targeted disruption of CD1D in somatic cells was attempted. Four different CRISPRs were designed and tested in both male and female cells. Modifications of CD1D could be detected from three of the applied CRISPRs, but use of CRISPR 5350 did not result in modification of CD1D with a deletion large enough to detect by agarose gel electrophoresis (Table 7). Interestingly, no genetic modification was obtained through HR although donor DNA was provided. However, large deletions similar to the CD163 knockout experiments were observed (FIG. 3, panel B). No targeted modification of CD1D with a large deletion was detected when CRISPR/Cas9 was not used with the donor DNA. Modification of CD1D from CRISPR/Cas9-guided targeting was 4/121 and 3/28 in male and female colonies of cells, respectively. Only INDELs detectable by agarose gel electrophoresis were included in the transfection data.

TABLE 7

Figure 2:
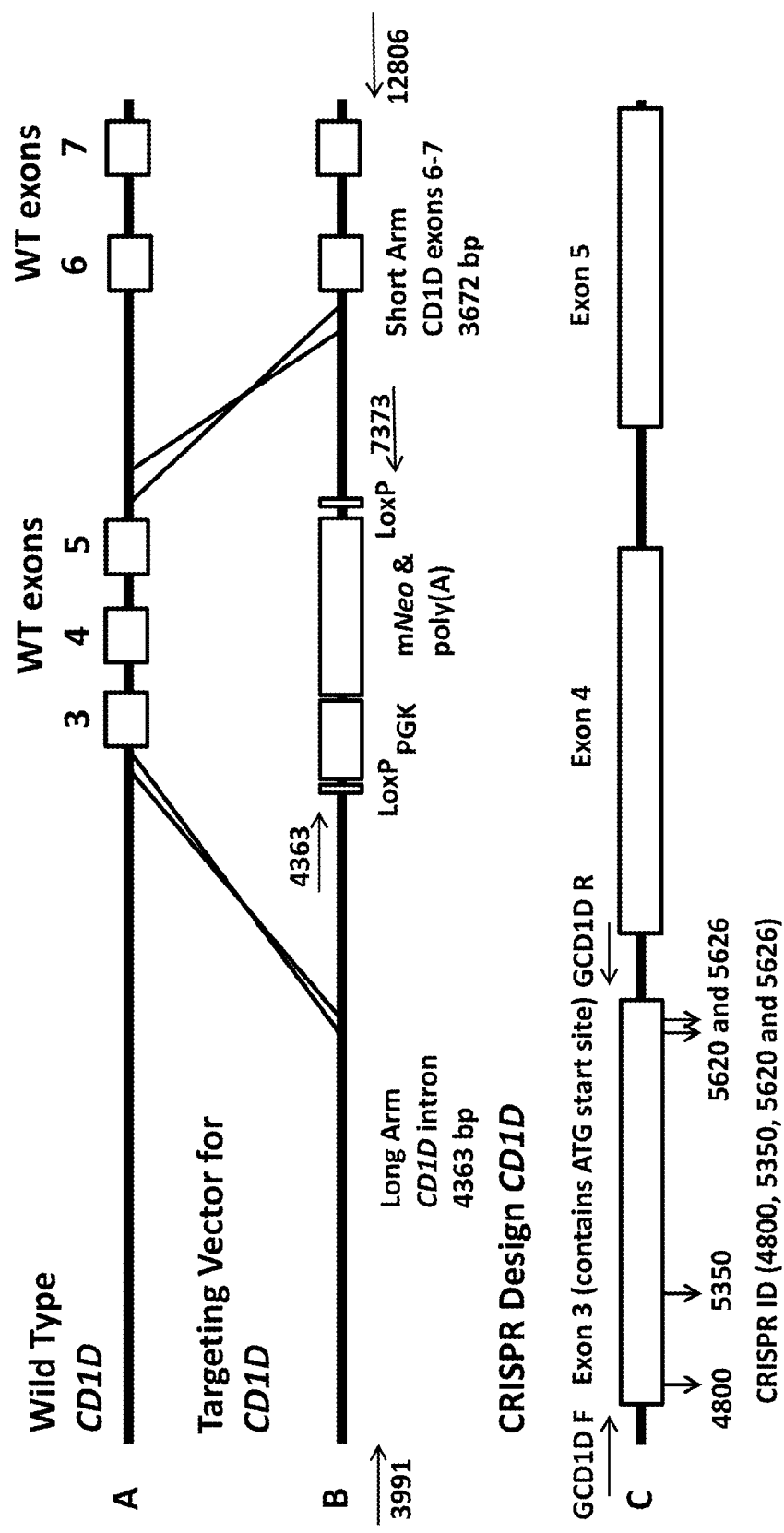
FIG. 2. Targeting vector and CRISPRs used to modify CD1D. Panel A depicts wild type exons 3, 4, 5, 6 and 7 of the CD1D gene that was targeted for modification by CRISPRs. Panel B shows the targeting vector designed to replace exon 3 with the selectable marker Neo. This targeting vector was used in combination with CRISPRs to modify CD1D. PCR primers for the long range, left arm and right arm assay are labeled with arrows for 3991, 4363, 7373 and 12806. Panel C depicts the exons targeted by CRISPRs. Locations of CRISPRs 4800, 5350, 5620 and 5626 are represented by the downward facing arrows on exon 3. Primers used in small deletions assays are illustrated with arrows and labelled GCD1DF and GCD1DR.

Four different CRISPRS were tested at an amount of 2 μg to 1 μg Donor DNA (shown in FIG. 2). The Donor DNA treatment served as the no CRISPR control.

| Gender | Treatment | Total Number of Colonies | INDEL | Efficiency (%) |
|---|---|---|---|---|
| male | 4800 + Donor DNA | 29 | 2 | 6.9 |

TABLE 6

Efficiency of CRISPR/Cas9-induced mutations without drug selection. Four different ratios of Donor DNA to CRISPR 131 DNA were compared in a previously modified cell line without the use of G418 selection.

| Donor DNA:CRISPR Ratio | Number of Plates | Number of Colonies | Mean Number of Colonies/Plate | Number of Colonies NHEJ | Percent Colonies with NHEJ | Colony with HR | Percent Colonies with HR | Reps |
|---|---|---|---|---|---|---|---|---|
| 1:0 | 30 | 79 | 2.6 | 1 | $1.3^a$ | 0 | 0.0 | 2 |
| 1:3 | 30 | 84 | 2.8 | 1 | $1.2^a$ | 0 | 0.0 | 2 |
| 1:5 | 27 | 76 | 2.8 | 2 | $2.6^a$ | 0 | 0.0 | 2 |
| 1:10 | 32 | 63 | 2.0 | 5 | $7.9^a$ | 0 | 0.0 | 2 |
| 1:20 | 35 | 77 | 2.2 | 3 | $3.9^a$ | 0 | 0.0 | 2 |

$a$Significant difference between treatments for percent colonies with NHEJ repair ($P > 0.05$).
$b$There was not a significant difference in the number of genome modified colonies with increasing concentration of CRISPR ($P > 0.33$).

TABLE 7-continued

Four different CRISPRS were tested at an amount of 2 μg to 1 μg Donor DNA (shown in FIG. 2). The Donor DNA treatment served as the no CRISPR control.

| Gender | Treatment | Total Number of Colonies | INDEL | Efficiency (%) |
|---|---|---|---|---|
| male | 5350 + Donor DNA | 20 | 0 | 0 |
| male | 5620 + Donor DNA | 43 | 1 | 2.33 |
| male | 5626 + Donor DNA | 29 | 2 | 6.9 |
| male | Donor DNA | 28 | 0 | 0 |
| female | 4800 + Donor DNA | 2 | 0 | 0 |
| female | 5350 + Donor DNA | 8 | 0 | 0 |
| female | 5620 + Donor DNA | 10 | 0 | 0 |
| female | 5626 + Donor DNA | 8 | 3 | 37.5 |
| female | Donor DNA | 7 | 0 | 0 |

Production of CD163 and CD1D Pigs Through SCNT Using the GE Cells

The cells presenting modification of CD163 or CD1D were used for SCNT to produce CD163 and CD1D knockout pigs (FIG. 3). Seven embryo transfers (CD163 Table 8), six embryo transfers (CD163-No Neo), and five embryo transfers (CD1D) into recipient gilts were performed with SCNT embryos from male and female fetal fibroblasts transfected with CRISPR/Cas9 systems. Six (CD163), two (CD163-No Neo), and four (CD1D) (Table 9) of the recipient gilts remained pregnant to term resulting in pregnancy rates of 85.7%. 33.3%, and 80%, respectively. Of the CD163 recipients, five delivered healthy piglets by caesarean section. One (O044) farrowed naturally. Litter size ranged from one to eight. Four pigs were euthanized because of failure to thrive after birth. One piglet was euthanized due to a severe cleft palate. All the remaining piglets appear healthy (FIG. 3, panel C). Two litters of male piglets resulting from fetal fibroblasts transfected with CRISPR 10 and donor DNA described in FIG. 3, panel B had a 30 bp deletion in exon 7 adjacent to CRISPR 10 and an additional 1476 bp deletion of the preceding intron, thus removing the intron 6/exon 7 junction of CD163 (FIG. 3, panel E). The genotypes and predicted translations are summarized in Table 10. One male piglet and one female litter (4 piglets) were obtained from the CD163-No Neo transfection of previously modified SIGLEC1 cells. All five piglets were double knockouts for SIGLEC1 and CD163. The male piglet had a biallelic modification of CD163 with a 28 bp deletion in exon 7 on one allele and a 1387 bp deletion on the other allele that included a partial deletion of exon 7 and complete deletion of exon 8 and the proceeding intron, thus removing the intron exon junction. The female piglets had a biallelic mutation of CD163, including a 1382 bp deletion with a 11 bp insertion on one allele and a 1720 bp deletion of CD163 on the other allele. A summary of the CD163 modifications and the predicted translations can be found in Table 10. A summary of the CD1D modifications and predicted translations by CRISPR modification can be found in Table 11. Briefly, one female and two male litters were born, resulting in 13 piglets. One piglet died immediately afterbirth. Twelve of the 13 piglets contained either a biallelic or homozygous deletion of CD1D (FIG. 3, panel F). One piglet was WT.

TABLE 8

Embryo Transfer data for CD163.

| Pig ID | Line* | Gender | # Embryos Transferred | Oocyte Source† | Day of Estrus | Piglet Result |
|---|---|---|---|---|---|---|
| O047 | CD163 CRISPR NT | Male | 240 | ART | 2 | 4 live piglets (2 euthanized after birth) |
| O015 | CD163 CRISPR NT | Male | 267 | ART | 1 | 3 live piglets (all healthy) |
| O044 | CD163 CRISPR NT | Male | 206 | ART | 1 | 7 live piglets (1 born dead, 1 euthanized afterbirth) |
| O053 | CD163 CRISPR NT | Male | 224 | ART | 2 | 1 male piglet (euthanized at day 13) |
| O08 | CD163 CRISPR NT | Male | 226 | ART | 1 | 0 piglets |
| O094 | CD163 CRISPR NT | Female | 193 | MU | 2 | 8 live piglets (1 euthanized due to FTT) |
| O086 | CD163 CRISPR NT | Female | 213 | MU | 1 | 9 live piglets (2 euthanized at day 0, 2 due to FTT) |
| O082 | CRISPR Injected CD163 10/131 | Male/Female | 50 Blast | MU | 5 | 0 piglets |
| O083 | CRISPR Injected CD163 10/131 | Male | 46 Blast | MU | 5 | 4 live piglets |
| O99 | CD163 CRISPR NT-no Neo | Male | 156 | ART | 1 | 1 live piglet, 1 dead piglet |
| O128 | CD163 CRISPR NT-no Neo | Male | 196 | ART | 2 | 0 piglets |
| O100 | CD163 CRISPR NT-no Neo | Male | 261 | MU | 3 | 0 piglets |
| O134 | CD163 CRISPR NT-no Neo | Male/Female | 181 | MU | 1 | 0 piglets |
| 200889 | CD163 CRISPR NT-no Neo | Female | 202 | ART | 1 | 4 live piglets |
| O135 | CD163 CRISPR NT-no Neo | Female | 169 | ART | 2 | 0 piglets |

*The CD163 CRISPR NT line represents embryos created by NT with a fetal fibroblast line modified by transfection. CRISPR injected embryos were IVF embryos injected at the 1 cell stage with CD163 guide RNA with CAS9 RNA. CD163 CRISPR NT-no Neo fetal line represents embryos created by NT with a previously modified fetal fibroblast that was already Neo resistant line modified by transfection without the use of a selectable marker.
†MU refers to gilt oocytes that were aspirated and matured at the University of Missouri as described in the IVF se4ction of the Materials and Methods. ART refers to sow oocytes that were purchased and matured as described in the SCNT section of the Materials and Methods.

TABLE 9

Embryo transfer data for CD1D.

| Pig ID | Line* | Gender | # Embryos Transferred | Oocyte Source† | Day of Estrus | Result |
|---|---|---|---|---|---|---|
| 200888 | CD1D CRISPR NT | Male | 201 | ART | 2 | 7 live piglets |
| O61 | CD1D CRISPR NT | Male | 239 | ART | 0 | 4 live piglets |
| O164 | CD1D CRISPR NT | Female | 199 | MU | 2 | 0 piglets |
| O156 | CD1D CRISPR NT | Female | 204 | MU | 2 | 0 piglets |
| O165 | CD1D Injected 4800/5350 | Male/Female | 55 Blast | MU | 6 | 4 piglets (1 female, 3 male) |
| O127 | CD1D Injected 4800/5350 | Male/Female | 55 Blast | MU | 6 | 0 piglets |
| O121 | CD1D CRISPR NT | Female | 212 | ART | 1 | 2 live piglets |

*CD1D CRISPR NT line represents embryos created by NT with a fetal fibroblast line modified by transfection. CRISPR injected embryos were IVF embryos injected at the 1 cell stage with CD1D guide RNA with CAS9 RNA.
†MU refers to gilt oocytes that were aspirated and matured at the University of Missouri as described in the IVF se4ction of the Materials and Methods. ART refers to sow oocytes that were purchased and matured as described in the SCNT section of the Materials and Methods.

TABLE 10

Genotype and Translational Prediction for CD163 modified pigs. Some pigs contain a biallelic type of modification, but only have one allele described and another modified allele that was not amplified by PCR.

| Litter | No. of Piglets | Repair mechanism | Type | Size of INDELs | Description | Protein translation* | Premature stop codon | In reference to SEQ ID NO: 47 | SEQ ID NO† |
|---|---|---|---|---|---|---|---|---|---|
| 63 & 64 | 7 | NHEJ | biallelic | 1506 bp deletion | 30 bp deletion in exon 7 | KO or CD163Δ422-527 | No | Deletion from nt 1,525 to nt 3,030 | 98 |
| 65 | 3 | NHEJ | Biallelic | Other allele 7 bp insertion | Uncharacterized, unamplifiable Insertion into exon 7 | KO | Yes (491) | Insertion between nt 3,148 & 3,149$^a$ | 99 ** |
| 65 | 2 | NHEJ | Biallelic | 503 bp deletion Other allele | Partial deletion of exon 7 and 8 Uncharacterized | KO | Yes (491) | ** | 100 |
| 65 | 2 | NHEJ | Biallelic | 1280 bp deletion | Complete deletion of exons 7 and 8 | CD163Δ422-631 | No | Deletion from nt 2,818 to nt 4,097 | 101 |
| 65 |  | NHEJ |  | 1373 bp deletion | Complete deletion of exons 7 and 8 | CD163Δ422-631 | No | Deletion from nt 2,724 to nt 4,096 | ** |
| 66 | 1 | NHEJ | Homozygous | 2015 bp insertion | Insertion of targeting vector backbone into exon 7 |  |  |  |  |
| 67-1 | 1 | NHEJ | Biallelic | 11 bp deletion | Deletion in exon 7 | KO | Yes (485) | Deletion from nt 3,137 to nt 3,147 | 102 |
|  |  |  |  | 2 bp insertion, 377 bp deletion in intron 6 | Insertion in exon 7 |  |  | 2 bp insertion between nt 3,149 & nt 3,150$^b$ with a 377 bp deletion from nt 2,573 to nt 2,949 | 103 |
| 67-2 | 1 | NHEJ | Biallelic | 124 bp deletion | Deletion in exon 7 | KO | Yes (464) | Deletion from nt 3,024 to nt 3,147 | 104 |
|  |  |  |  | 123 bp deletion | Deletion in exon 7 | CD163Δ429-470 | No | Deletion from nt 3,024 to nt 3,146 | 105 |
| 67-3 | 1 | NHEJ | Biallelic | 1 bp insertion | Insertion into exon 7 | KO | Yes (489) | Insertion between nt 3,147 & 3,148$^c$ | 106 |
| 67-4 | 1 | NHEJ | Biallelic | Other allele 130 bp deletion | Uncharacterized, unamplifiable Deletion in exon 7 | KO | Yes (462) | Deletion from nt 3,030 to nt 3,159 | 107 |
|  |  |  |  | 132 bp deletion | Deletion in exon 7 | CD163Δ430-474 | No | Deletion from nt 3,030 to nt 3,161 | 108 |
| 68 & 69 | 6 | NHEJ | Biallelic | 1467 bp deletion | Complete deletion of exons 7 and 8 | CD163Δ435-478 | No | Deletion from nt 2,431 to nt 3,897 | 109 |
|  |  |  |  | Other allele | Uncharacterized, unamplifiable |  |  |  |  |
| 68 & 69 | 2 | NHEJ | Biallelic | 129 bp deletion, 1930 bp intron 6 deletion | Deletion in exon 7 |  | No | Deletion from nt 488 to nt 2,417 in exon 6, deleted sequence is replaced with a 12 bp insertion$^d$ starting at nt 488, & an additional 129 bp deletion from nt 3,044 to nt 3,172 | 110 |
| 65 & 69 | 3 | WT |  | other allele | Uncharacterized Wild type pigs created from a mixed colony |  |  | SEQ ID NO: 47 | 47 |

TABLE 10-continued

Genotype and Translational Prediction for CD163 modified pigs. Some pigs contain a biallelic type of modification, but only have one allele described and another modified allele that was not amplified by PCR.

| Litter | No. of Piglets | Repair mechanism | Type | Size of INDELs | Description | Protein translation* | Premature stop codon | In reference to SEQ ID NO: 47 | SEQ ID NO† |
|---|---|---|---|---|---|---|---|---|---|
| 70 | 2 | NHEJ | On SIGLEC1−/− Biallelic | 28 bp deletion | Deletion in exon 7 | KO | Yes (528) | Deletion from nt 3,145 to nt 3,172 | 111 |
|  |  |  |  | 1387 bp deletion | Partial deletion in exon 7 and all of exon 8 | KO | No | Deletion from nt 3,145 to nt 4,531 | 112 |
| 73 | 4 | NHEJ | On SIGLEC1−/− Biallelic | 1382 bp deletion +11 bp insertion | Partial deletion in exon 7 and all of CD163^Δ422-631/KO exon 8 | KO | No | Deletion from nt 3,113 to nt 4,494, deleted sequence replaced with an 11 bp insertion^e starting at nt 3,113 | 113 |
|  |  |  |  | 1720 bp deletion | Complete deletion of exons 7 and 8 |  |  | Deletion from nt 2,440 to nt 4,160 | 114 |

* KO, knock-out
** Not included because piglets were euthanized.
† SEQ ID NOs. in this column refer to the SEQ ID NOs. for the sequences that show the INDELs in relation to SEQ ID NO: 47.
^a The inserted sequence was TACTACT (SEQ ID NO: 115)
^b The inserted sequence was AG.
^c The inserted sequence was a single adenine (A) residue.
^d The inserted sequence was TGTGGAGAATTC (SEQ ID NO: 116).
^e The inserted sequence was AGCCAGCGTGC (SEQ ID NO: 117).

TABLE 11

Genotype and Translational Prediction for CD1D modified pigs

| Litter | Number of Piglets | Repair Mechanism | Type | Size of INDEL | Description | Protein Translation |
|---|---|---|---|---|---|---|
| 158, 159 | 11 | NHEJ | homozygous | 1653 bp deletion | Deletion of exon 3,4 and 5 | KO* |
| 167 | 2 | NHEJ | homozygous | 1265 bp deletion | Deletion of exon 5 and 72 bp of exon 6 | KO |
| 166-1 | 1 | NHEJ | biallelic | 24 bp deletion | Removal of start codon in exon 3 | KO |
|  |  |  |  | 27 bp deletion | Disruption of start codon in exon 3 |  |
|  |  |  |  | 362 bp deletion + 5 bp | Deletion of exon 3 |  |
| 166-2 | 1 | NHEJ | biallelic | 6 bp insertion + 2 bp mismatch | Addition of 6 bp before start codon in exon 3 | CD1D$^{ko/+}$ |
|  |  |  |  | 1598 bp deletion | Removal of start codon in exon 3 and deletion of exons 4,5 |  |
| 166-3 | 1 | NHEJ | biallelic | 1 bp insertion | Addition of G/T in exon 3 before start codon in exon 3 | CD1D$^{+/+}$ |
| 166-4 | 1 | NHEJ | homozygous | 1 bp insertion | Addition of A in exon 3 before start codon in exon 3 | CD1D$^{+/+}$ |

*KO, knock-out

Efficiency of CRISPR/Cas9 System in Porcine Zygotes

Based on targeted disruption of CD163 and CD1D in somatic cells using the CRISPR/Cas9 system, this approach was applied to porcine embryogenesis. First, the effectiveness of the CRISPR/Cas9 system in developing embryos was tested. CRISPR/Cas9 system targeting eGFP was introduced into zygotes fertilized with semen from a boar heterozygous for the eGFP transgene. After the injection, subsequent embryos expressing eGFP were monitored. Various concentrations of the CRISPR/Cas9 system were tested and cytotoxicity of the delivered CRISPR/Cas9 system was observed (FIG. 4, panel A); embryo development after CRISPR/Cas9 injection was lower compared to control. However, all the concentrations of CRISPR/Cas9 that were examined were effective in generating modification of eGFP because no embryos with eGFP expression were found in the CRISPR/Cas9-injected group (FIG. 4, panel B); of the noninjected control embryos 67.7% were green, indicating expression of eGFP. When individual blastocysts were genotyped, it was possible to identify small mutations near the CRISPR binding sites (FIG. 4, panel C). Based on the toxicity and effectiveness, 10 ng/µl of gRNA and Cas9 mRNA were used for the following experiments.

When CRISPR/Cas9 components designed to target CD163 were introduced into presumptive zygotes, targeted modification of the genes in the subsequent blastocysts was observed. When individual blastocysts were genotyped for mutation of CD163, specific mutations were found in all the embryos (100% GE efficiency). More importantly, while embryos could be found with homozygous or biallelic modifications (8/18 and 3/18, respectively) (FIG. 5), mosaic (monoallelic modifications) genotypes were also detected (4/18 embryos). Some embryos (8/10) from the pool were injected with 2 ng/µl Cas9 and 10 ng/µl CRISPR and no difference was found in the efficiency of mutagenesis. Next, based on the in vitro results, two CRISPRs representing different gRNA were introduced to disrupt CD163 or CD1D during embryogenesis to induce a specific deletion of the target genes. As a result, it was possible to successfully induce a designed deletion of CD163 and CD1D by introducing two guides. A designed deletion is defined as a deletion that removes the genomic sequence between the two guides introduced. Among the embryos that received two CRISPRs targeting CD163, all but one embryo resulted in a targeted modification of CD163. In addition, 5/13 embryos were found to have a designed deletion on CD163 (FIG. 6, panel A) and 10/13 embryos appeared to have modification of CD163 in either homozygous or biallelic fashion. Targeting CD1D with two CRISPRs was also effective because all the embryos (23/23) showed a modification of CD1D. However, the designed deletion of CD1D could only be found in two embryos (2/23) (FIG. 6, panel B). Five of twenty-three embryos possessing mosaic genotypes were also found, but the rest of embryos had either homozygous or biallelic modification of CD1D. Finally, whether multiple genes can be targeted by the CRISPR/Cas9 system within the same embryo was tested. For this purpose, targeting both CD163 and eGFP was performed in the zygotes that were fertilized with heterozygous eGFP semen. When blastocysts from the injected embryos were genotyped for CD163 and eGFP, it was found that found that CD163 and eGFP were successfully targeted during embryogenesis. Sequencing results demonstrated that multiple genes can be targeted by introducing multiple CRISPRs with Cas9 (FIG. 6, panel C).

Production of CD163 and CD1D Mutants from CRISPR/Cas9-Injected Zygotes

Figure 8:
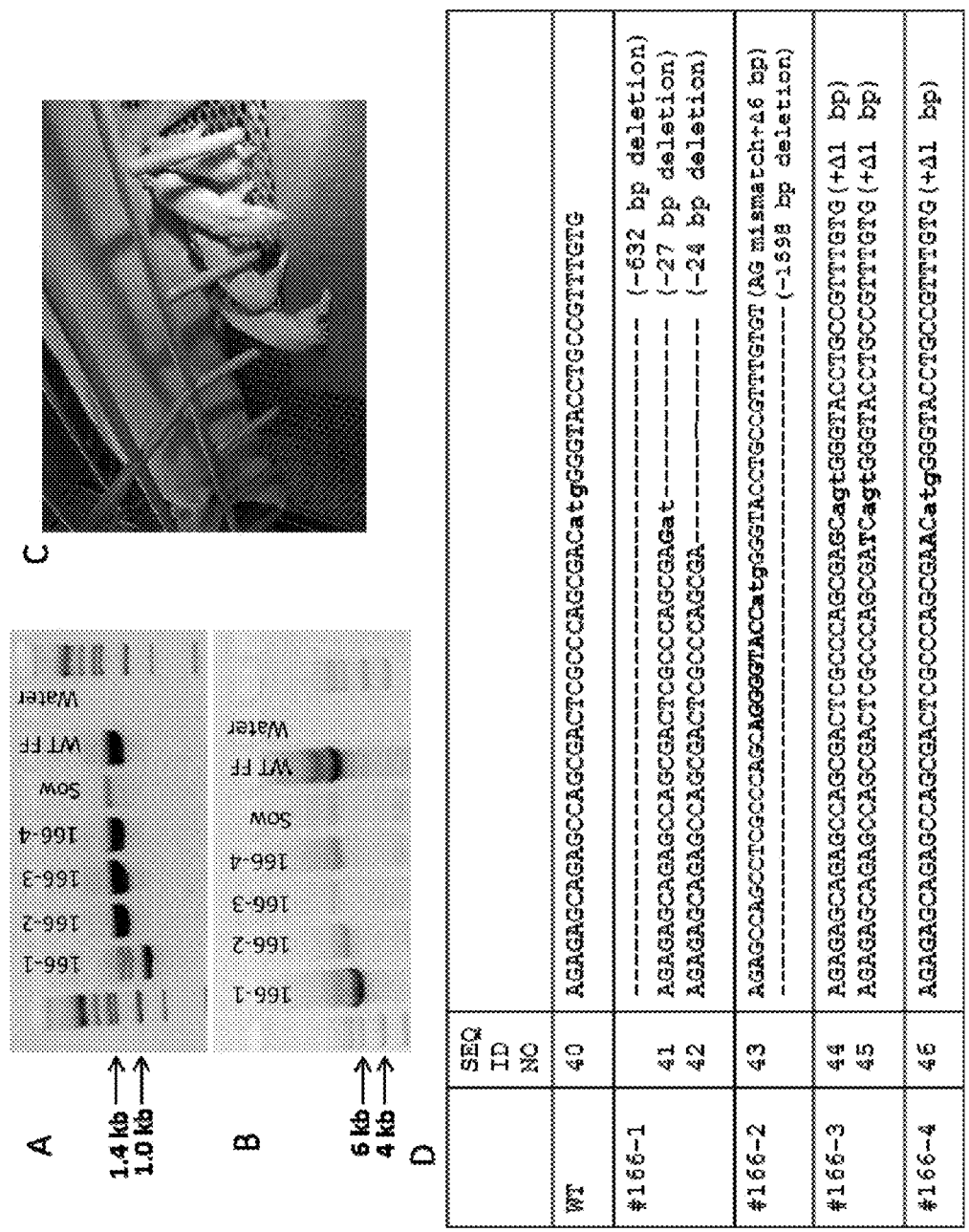
FIG. 8. CD1D knockout pigs generated by CRISPR/Cas9 system injected into zygotes. A) PCR amplification of CD1D from knockout pigs; 166-1 shows a mosaic genotype for CD1D. 166-2, 166-3, and 166-4 do not show a change in size for the amplicon, but sequencing of the amplicon revealed modifications. WT FF=wild-type fetal fibroblasts. B) PCR amplification of the long-range assay showed a clear deletion of one allele in piglets 166-1 and 166-2. C) Image of CD1D knockout pigs with surrogate. D) Sequence data of CD1D knock out pigs; WT (SEQ ID NO:40), #166-1.1 (SEQ ID NO: 41), #166-1.2 (SEQ ID NO:42), #166-2 (SEQ ID NO:43), #166-3.1 (SEQ ID NO:44), #166-3.2 (SEQID NO:45), and #166-4 (SEQ ID NO:46). The atg start codon in exon 3 is shown in bold and also lower case.

Based on the success from the previous in vitro study, some CRISPR/Cas9-injected zygotes were produced and 46-55 blastocysts were transferred per recipient (because this number has been shown to be effective in producing pigs from the in vitro derived embryos). Four embryo transfers were performed, two each for CD163 and CD1D, and a pregnancy for each modification was obtained. Four healthy piglets were produced carrying modifications on CD163 (Table 8). All the piglets, litter 67 from recipient sow ID O083 showed either homozygous or biallelic modification of CD163 (FIG. 7). Two piglets showed the designed deletion of CD163 by the two CRISPRs delivered. All the piglets were healthy. For CD1D, one pregnancy also produced four piglets (litter 166 from recipient sow identification no. 0165): one female and three males (Table 9). One piglet (166-1) did carry a mosaic mutation of CD1D, including a 362 bp deletion that completely removed exon 3 that contains the start codon (FIG. 8). One piglet contained a 6 bp insertion with a 2 bp mismatch on one allele with a large deletion on the other allele. Two additional piglets had a biallelic single bp insertion. There were no mosaic mutations detected for CD163.

Discussion

An increase in efficiency of GE pig production can have a wide impact by providing more GE pigs for agriculture and biomedicine. The data described above show that by using the CRISPR/Cas9 system, GE pigs with specific mutations can be produced at a high efficiency. The CRISPR/Cas9 system was successfully applied to modify genes in both somatic cells and in preimplantation embryos.

When the CRISPR/Cas9 system was introduced into somatic cells, it successfully induced targeted disruption of the target genes by NHEJ but did not increase the ability to target by HR. Targeting efficiency of individual CRISPR/Cas9 in somatic cells was variable, which indicated that the design of the guide can affect the targeting efficiency. Specifically, it was not possible to find targeted modification of CD1D when CRISPR 5350 and Cas9 were introduced into somatic cells. This suggests that it could be beneficial to design multiple gRNAs and validate their efficiencies prior to producing pigs. A reason for the lack of HR-directed repair with the presence of donor DNA is still unclear. After screening 886 colonies (both CD163 and CD1D) transfected with CRISPR and donor DNA, only one colony had evidence for a partial HR event. The results demonstrated that the CRISPR/Cas9 system worked with introduced donor DNA to cause unexpected large deletions on the target genes but did not increase HR efficiency for these two particular targeting vectors. However, a specific mechanism for the large deletion observation is not known. Previous reports from our group suggested that a donor DNA can be effectively used with a ZFN to induce HR-directed repair. Similarly, an increase in the targeting efficiency was seen when donor DNA was used with CRISPR/Cas9 system, but complete HR directed repair was not observed. In a previous study using ZFN, it was observed that targeted modification can occur through a combination of HR and NHEJ because a partial recombination was found of the introduced donor DNA after induced DSBs by the ZFN. One explanation might be that HR and NHEJ pathways are not independent but can act together to complete the repair process after DSBs induced by homing endonucleases. Higher concentrations of CRISPRs might improve targeting efficiency in somatic cells although no statistical difference was found in these experimental results. This may suggest that CRISPR is a limiting factor in CRISPR/Cas9 system, but further validation is needed. Targeted cells were successfully used to produce GE pigs through SCNT, indicating the application of CRISPR/Cas9 does not affect the ability of the cellsto be cloned. A few piglets were euthanized because of health issues; however, this is not uncommon in SCNT-derived piglets.

When the CRISPR/Cas9 system was introduced into developing embryos by zygote injection, nearly 100% of embryos and pigs contained an INDEL in the targeted gene, demonstrating that the technology is very effective during embryogenesis. The efficiency observed during this study surpasses frequencies reported in other studies utilizing homing endonucleases during embryogenesis. A decrease in the number of embryos reaching the blastocyst stage suggested that the concentration of CRISPR/Cas9 introduced in this study may be toxic to embryos. Further optimization of the delivery system may increase survivability of embryos and thus improve the overall efficiency of the process. The nearly 100% mutagenesis rate observed here was different from a previous report in CRISPR/Cas9-mediated knockout in pigs; however, the difference in efficiency between the studies could be a combination of the guide and target that was selected. In the present study, lower concentrations of CRISPR/Cas9 (10 ng/µl each) were effective in generating mutations in developing embryos and producing GE pigs. The concentration is lower than previously reported in pig zygotes (125 ng/µl of Cas9 and 12.5 ng/µl of CRISPR). The lower concentration of CRISPR/Cas9 components could be beneficial to developing embryos because introducing excess amounts of nucleic acid into developing embryos can be toxic. Some mosaic genotypes were seen in CRISPR/Cas9-injected embryos from the in vitro assays; however, only one piglet produced through the approach had a mosaic genotype. Potentially, an injection with CRISPR/Cas9 components may be more effective than introduction of other homing endonucleases because the mosaic genotype was considered to be a main hurdle of using the CRISPR/Cas9 system in zygotes. Another benefit of using the CRISPR/Cas9 system demonstrated by the present results is that no CD163 knockout pigs produced from IVF-derived zygotes injected with CRISPR/Cas9 system were lost, whereas a few piglets resulting from SCNT were euthanized after a few days. This suggests that the technology could not only bypass the need of SCNT in generating knockout pigs but could also overcome the common health issues associated with SCNT Now that injection of CRISPR/Cas9 mRNA into zygotes has been optimized, future experiments will include coinjection of donor DNA as well.

The present study demonstrates that introducing two CRISPRs with Cas9 in zygotes can induce chromosomal deletions in developing embryos and produce pigs with an intended deletion, that is, specific deletion between the two CRISPR guides. This designed deletion can be beneficial because it is possible to specify the size of the deletion rather than relying on random events caused by NHEJ. Specifically, if there is insertion/deletion of nucleotides in a multiple of three caused by a homing endonuclease, the mutation may rather result in a hypomorphic mutation because no frame shift would occur. However, by introducing two CRISPRs, it is possible to cause larger deletions that will have a higher chance of generating non-functional protein. Interestingly, CD1D CRISPRs were designed across a greater area in the genome than CD163; there was a 124 bp distance between CD163 CRISPR 10 and 131 while there was a distance of 550 bp between CRISPR 4800 and 5350 for CD1D. The longer distance between CRISPRs was not very effective in generating a deletion as shown in the study. However, because the present study included only limited number of observations and there is a need to consider the efficacy of individual CRISPRs, which is not addressed here, further study is need to verify the relationship between the distance between CRISPRs and probability of causing intended deletions.

The CRISPR/Cas9 system was also effective in targeting two genes simultaneously within the same embryo with the only extra step being the introduction of one additional CRISPR with crRNA. This illustrates the ease of disrupting multiples genes compared to other homing endonucleases. These results suggest that this technology may be used to target gene clusters or gene families that may have a compensatory effect, thus proving difficult to determine the role of individual genes unless all the genes are disrupted. The results demonstrate that CRISPR/Cas9 technology can be applied in generating GE pigs by increasing the efficiency of gene targeting in somatic cells and by direct zygote injection.

Example 2

Increased Resistance to PRRSV in Swine Having a Modified Chromosomal Sequence in a Gene Encoding a CD163 Protein Porcine Reproductive and Respiratory Syndrome Virus (PRRSV) has ravaged the swine industry over the last quarter of a century. Speculation about the mode of viral entry has included both SIGLEC1 and CD163. While knockout of SIGLEC1 did not affect the response to a viral challenge, it is shown in the present example that CD163 null animals show no clinical signs of infection, lung pathology, viremia or antibody production that are all hallmarks of PRRSV infection. Not only has a PRRSV entry mediator been confirmed; but if similarly created animals were allowed to enter the food supply, then a strategy to prevent significant economic losses and animal suffering has been described.

Materials and Methods

Genotyping

Genotyping was based on both DNA sequencing and mRNA sequencing. The sire's genotype had an 11 bp deletion in one allele that when translated predicted 45 amino acids into domain 5, resulting in a premature stop codon at amino acid 64. In the other allele there was a 2 bp addition in exon 7 and 377 bp deletion in intron before exon 7, that when translated predicted the first 49 amino acids of domain 5, resulting in a premature stop code at amino acid 85. One sow had a 7 bp addition in one allele that when translated predicted the first 48 amino acids of domain 5, resulting in a premature stop codon at amino acid 70. The other allele was uncharacterized (A), as there was no band from exon 7 by either PCR or long range 6.3 kb PCR. The other 3 sows were clones and had a 129 bp deletion in exon 7 that is predicted to result in a deletion of 43 amino acids from domain 5. The other allele was uncharacterized (B).

Growth of PRRSV in Culture and Production of Virus Inoculum for the Infection of Pigs are Covered Under Approved IBC Application 973

A type strain of PRRSV, isolate NVSL 97-7895 (GenBank # AF325691 2001 Feb. 11), was grown as described in approved IBC protocol 973. This laboratory isolate has been used in experimental studies for about 20 years (Ladinig et al., 2015). A second isolate was used for the $2^{nd}$ trial, KS06-72109 as described previously (Prather et al., 2013).

Infection of Pigs with PRRSV

A standardized infection protocol for PRRSV was used for the infection of pigs. Three week old piglets were inoculated with approximately $10^4$ TCID50 of PRRS virus which was administered by intramuscular (IM) and intranasal (IN) routes. Pigs were monitored daily and those exhibiting symptoms of illness are treated according to the recommendations of the CMG veterinarians. Pigs that show severe distress and are in danger of succumbing to infection are humanely euthanized and samples collected. Staff and veterinarians were blind to the genetic status of the pigs to eliminate bias in evaluation or treatment. PRRSV is present in body fluids during infection; therefore, blood samples were collected and stored at −80° C. until measured to determine the amount or degree of viremia in each pig. At the end of the experiment, pigs were weighed and humanely euthanized, and tissues collected and fixed in 10% buffered formalin, embedded in paraffin, and processed for histopathology by a board-certified pathologist.

Phenotype Scoring of the Challenged Pigs

The phenotype of the pigs was blindly scored daily as follows: What is the attitude of the pig? Attitude Score: 0: BAR, 1: QAR, 2: Slightly depressed, 3: Depressed, 4: Moribund. What is the body condition of the pig? Body Condition Score: 1: Emaciated, 2: Thin, 3: Ideal, 4: Fat, 5: Overfat/Obese. What is the rectal temperature of the pig? Normal Body Temperature 101.6-103.6° F. (Fever considered ≥104° F.). Is there any lameness (grade)? What limb? Evaluate limbs for joint swelling and hoof lesions (check bottom and sides of hoof). Lameness Score: 1: No lameness, 2: Slightly uneven when walking, appears stiff in some joints but no lameness, 3: Mild lameness, slight limp while walking, 4: Moderate lameness, obvious limp including toe touching lame, 5: Severe lameness, non-weight bearing on limb, needs encouragement to stand/walk. Is there any respiratory difficulty (grade)? Is there open mouth breathing? Is there any nasal discharge (discharge color, discharge amount: mild/moderate/severe)? Have you noticed the animal coughing? Is there any ocular discharge? Respiratory Score: 0: Normal, 1: mild dyspnea and/or tachypnea when stressed (when handled), 2: mild dyspnea and/or tachypnea when at rest, 3: moderate dyspnea and/or tachypnea when stressed (when handled), 4: moderate dyspnea and/or tachypnea when at rest, 5: severe dyspnea and/or tachypnea when stressed (when handled), 6: severe dyspnea and/or tachypnea when at rest. Is there evidence of diarrhea (grade) or vomiting? Is there any blood or mucus? Diarrhea Score: 0: no feces noted, 1: normal stool, 2: soft stool but formed (soft serve yogurt consistency, creates cow patty), 3: liquid diarrhea of brown/tan coloration with particulate fecal material, 4: liquid diarrhea of brown/tan coloration without particulate fecal material, 5: liquid diarrhea appearing similar to water.

This scoring system was developed by Dr. Megan Niederwerder at KSU and is based on the following publications (Halbur et al., 1995; Merck; Miao et al., 2009; Patience and Thacker, 1989; Winckler and Willen, 2001). Scores and temperatures were analyzed by using ANOVA separated based on genotypes as treatments.

Measurement of PRRSV Viremia

Viremia was determined via two approaches. Virus titration was performed by adding serial 1:10 dilutions of serum to confluent MARC-145 cells in a 96 well-plate. Serum was diluted in Eagle's minimum essential medium supplemented with 8% fetal bovine serum, penicillin, streptomycin, and amphotericin B as previously described (Prather et al., 2013). The cells were examined after 4 days of incubation for the presence of a cytopathic effect by using microscope. The highest dilution showing a cytopathic effect was scored as the titration endpoint. Total RNA was isolated from serum by using the Life Technologies MagMAX-96 viral RNA isolation kit for measuring viral nucleic acid. The reverse transcription polymerase chain reaction was performed by using the EZ-PRRSV MPX 4.0 kit from Tetracore on a CFX-96 real-time PCR system (Bio-Rad) according to the manufacturer's instructions. Each reaction (25 μl) contained RNA from 5.8 μl of serum. The standard curve was constructed by preparing serial dilutions of an RNA control supplied in the kit (Tetracore). The number of templates per PCR are reported.

SIGLEC1 and CD163 Staining of PAM Cells

Porcine alveolar macrophages (PAMs) were collected by excising the lungs and filling them with ~100 ml cold phosphate buffered saline. After recovering the phosphate buffered saline wash cells were pelleted and resuspended in 5 ml cold phosphate buffered saline and stored on ice. Approximately $10^7$ PAMs were incubated in 5 ml of the various antibodies (anti-porcine CD169 (clone 3B11/11, AbD Serotec); anti-porcine CD163 (clone 2A10/11, AbD Serotec)) diluted in phosphate buffered saline with 5% fetal bovine serum and 0.1% sodium azide for 30 min on ice. Cells were washed and resuspended in 1/100 dilution of fluorescein isothiocyanate (FITC)-conjugated to goat anti-mouse IgG (life Technologies) diluted in staining buffer and incubated for 30 min on ice. At least 10 cells were analyzed by using a FACSCalibur flow cytometer and Cell Quest software (Becton Dickinson).

Measurement of PRRSV-Specific Ig

To measure PRRSV-specific Ig recombinant PRRSV N protein was expressed in bacteria. (Trible et al., 2012) and conjugated to magnetic Luminex beads by using a kit (Luminex Corporation). The N protein-coupled beads were diluted in phosphate buffered saline containing 10% goat serum to 2,500 beads/50 µl and placed into the wells of a 96-well round-bottomed polystyrene plate. Serum was diluted 1:400 in phosphate buffered saline containing 10% goat serum and 50 µl was added in duplicate wells and incubated for 30 min with gentle shaking at room temperature. Next the plate was washed (3×) with phosphate buffered saline containing 10% goat serum and 50 µl of biotin-SP-conjugated affinity-purified goat anti-swine secondary antibody (IgG, Jackson ImmunoResearch) or biotin-labeled affinity purified goat anti-swine IgM (KPL) diluted to 2 µg/ml in phosphate buffered saline containing 10% goat serum was added. The plates were washed (3×) after 30 min of incubation and then 50 µl of streptavidin-conjugated phycoerythrin (2 µg/ml (Moss, Inc.) in phosphate buffered saline containing 10% goat serum) was added. The plates were washed 30 min later and microspheres were resuspended in 100 µl of phosphate buffered saline containing 10% goat serum an analyzed by using the MAGPIX and the Luminex xPONENT 4.2 software. Mean fluorescence intensity (MFI) is reported.

Results

Mutations in CD163 were created by using the CRISPR/Cas9 technology as described above in Example 1. Several founder animals were produced from zygote injection and from somatic cell nuclear transfer. Some of these founders were mated creating offspring to study. A single founder male was mated to females with two genotypes. The founder male (67-1) possessed an 11 bp deletion in exon 7 on one allele and a 2 bp addition in exon 7 (and 377 bp deletion in the preceding intron) of the other allele and was predicted to be a null animal (CD163$^{-/-}$). One founder female (65-1) had a 7 bp addition in exon 7 in one allele and an uncharacterized corresponding allele and was thus predicted to be heterozygous for the knockout (CD163$^{-/?}$). A second founder female genotype (3 animals that were clones) contained an as yet uncharacterized allele and an allele with a 129 bp deletion in exon 7. This deletion is predicted to result in a deletion of 43 amino acids in domain 5. Matings between these animals resulted in all piglets inheriting a null allele from the boar and either the 43 amino acid deletion or one of the uncharacterized alleles from the sows. In addition to the wild type piglets that served as positive controls for the viral challenge, this produced 4 additional genotypes (Table 8).

TABLE 12

Genotypes tested for resistance to PRRSV challenge (NVSL and KS06 strains)

| Alleles | | Resistance to PRRSV Challenge as Measured by Viremia | |
|---|---|---|---|
| Paternal | Maternal | NVSL | KS06 |
| Null | Null | Resistant | N/A |
| Null | Δ43 Amino Acids | N/A | Resistant |

TABLE 12-continued

Genotypes tested for resistance to PRRSV challenge (NVSL and KS06 strains)

| Alleles | | Resistance to PRRSV Challenge as Measured by Viremia | |
|---|---|---|---|
| Paternal | Maternal | NVSL | KS06 |
| Null | Uncharacterized A | Susceptible | N/A |
| Null | Uncharacterized B | Susceptible | Susceptible |
| Wild Type | Wild Type | Susceptible | Susceptible |

Figure 9:
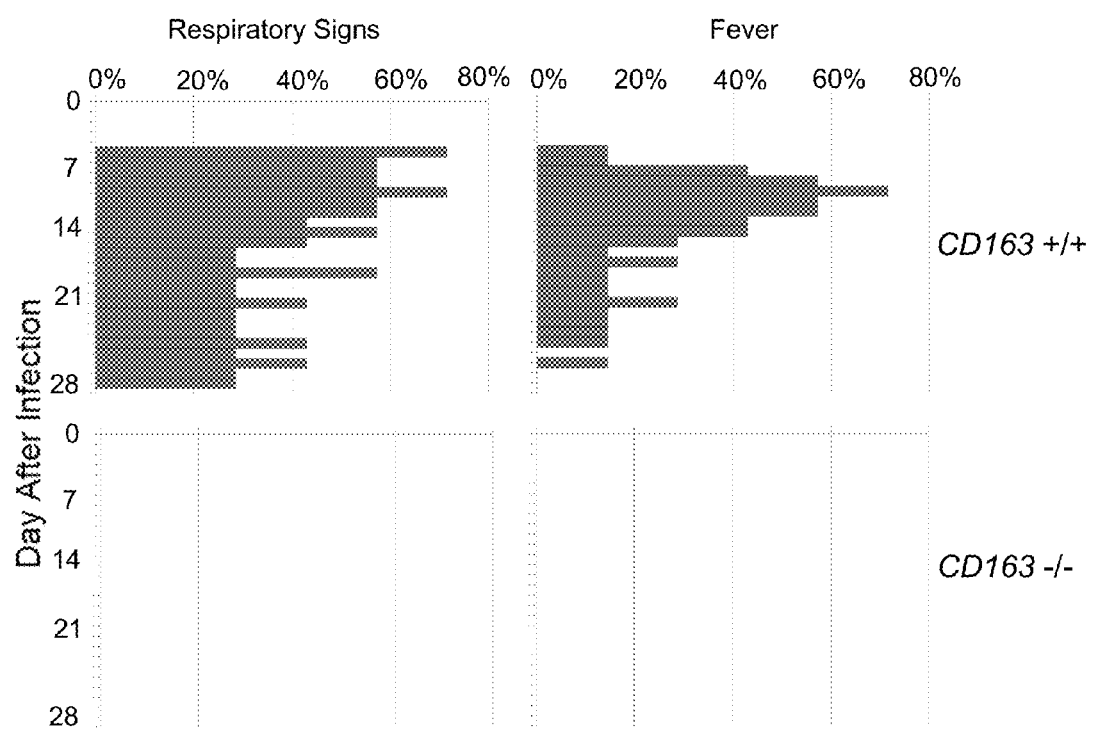
FIG. 9. Clinical signs during acute PRRSV infection. Results for daily assessment for the presence of respiratory signs and fever for CD163+/+ (n=6) and CD163−/− (n=3).
Figure 10:
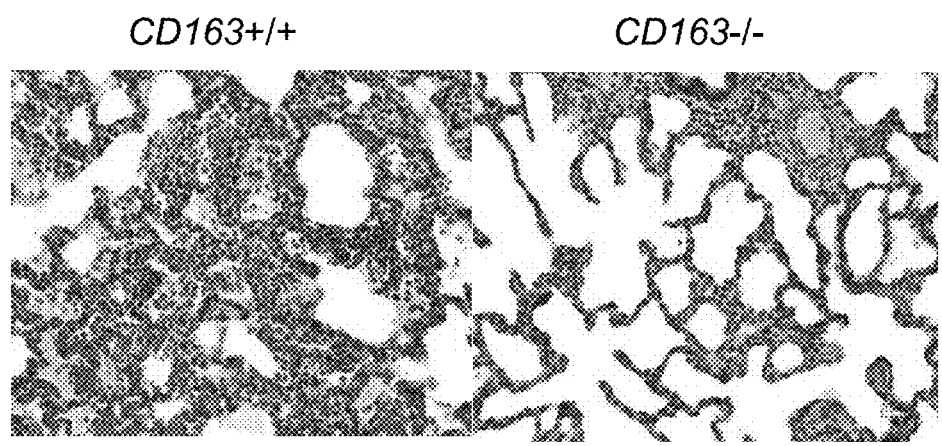
FIG. 10. Lung histopathology during acute PRRSV infection. Representative photomicrographs of H and E stained tissues from wild-type and knockout pigs. The left panel shows edema and infiltration of mononuclear cells. The right panel from a knockout pig shows lung architecture of a normal lung.

At weaning gene edited piglets and wild type age-matched piglets were transported to Kansas State University for a PRRSV challenge. A PRRSV challenge was conducted as previously described (Prather et al., 2013). Piglets, at three weeks of age, were brought into the challenge facility and maintained as a single group. All experiments were initiated after approval of institutional animal use and biosafety committees. After acclimation, the pigs were challenged with a PRRSV isolate, NVSL 97-7895 (Ladinig et al., 2015), propagated on MARC-145 cells (Kim et al., 1993). Pigs were challenged with approximately $10^5$ TCID$_{50}$ of virus. One-half of the inoculum was delivered intramuscularly and the remaining delivered intranasally. All infected pigs were maintained as a single group, which allowed the continuous exposure of virus from infected pen mates. Blood samples were collected at various days up to 35 days after infection and at termination, day 35. Pigs were necropsied and tissues fixed in 10% buffered formalin, embedded in paraffin and processed for histopathology. PRRSV associated clinical signs recorded during the course of the infection included respiratory distress, inappetence, lethargy and fever. The results for clinical signs over the study period are summarized in FIG. 9. As expected, the wild-type Wild Type (CD163+/+) pigs showed early signs of PRRSV infection, which peaked at between days 5 and 14 and persisted in the group during the remainder of the study. The percentage of febrile pigs peaked on about day 10. In contrast, Null (CD163−/−) piglets showed no evidence of clinical signs over the entire study period. The respiratory signs during acute PRRSV infection are reflected in significant histopathological changes in the lung (Table 9). The infection of the wild type pigs showed histopathology consistent with PRRS including interstitial edema with the infiltration of mononuclear cells (FIG. 10). In contrast there was no evidence for pulmonary changes in the Null (CD163−/−) pigs. The sample size for the various genotypes is small; nevertheless the mean scores were 3.85 (n=7) for the wild type, 1.75 (n=4) for the uncharacterized A, 1.33 (n=3) for the uncharacterized B, and 0 (n=3) and for the null (CD163−/−).

TABLE 13

Microscopic Lung evaluation

| Pig | Genotype | Description | Score |
|---|---|---|---|
| 41 | Wild Type | 100% congestion. Multifocal areas of edema. Infiltration of moderate numbers of lymphocytes and macrophages | 3 |
| 42 | Wild Type | 100% congestion. Multifocal areas of edema. Infiltration of moderate numbers of lymphocytes and macrophages | 3 |
| 47 | Wild Type | 75% multifocal infiltration with mononuclear cells and mild edema | 2 |
| 50 | Wild Type | 75% multifocal infiltration of mononuclear cells within alveolar spaces and around small blood vessels perivascular edema | 3 |
| 51 | Wild Type | 25% atelectasis with moderate infiltration of mononuclear cells | 1 |
| 52 | Wild Type | 10% of alveolar spaces collapsed with infiltration of small numbers of mononuclear cells | 1 |
| 56 | Wild Type | 100% diffuse moderate interstitial infiltration of mononuclear cells. Interalveolar septae moderately thickened by hemorrhage and edema. | 4 |
| 45 | Uncharacterized A | 75% multifocal infiltrates of mononuclear cells, especially around bronchi, blood vessels, subpleural spaces, and interalveolar septae. | 3 |
| 49 | Uncharacterized A | 75% multifocal moderate to large infiltration of mononuclear cells. Some vessels with mild edema. | 2 |
| 53 | Uncharacterized A | 10% multifocal small infiltration of mononuclear cells | 1 |
| 57 | Uncharacterized A | 15% infiltration of mononuclear cells | 1 |
| 46 | Uncharacterized B | Moderate interstitial pneumonia | 2 |
| 48 | Uncharacterized B | Perivascular edema and infiltration of mononuclear cells around small and medium sized vessels and around interalveolar septae | 2 |
| 54 | Uncharacterized B | No changes | 0 |
| 40 | Null | No changes | 0 |
| 43 | Null | No changes | 0 |
| 55 | Null | No changes | 0 |

Figure 11:
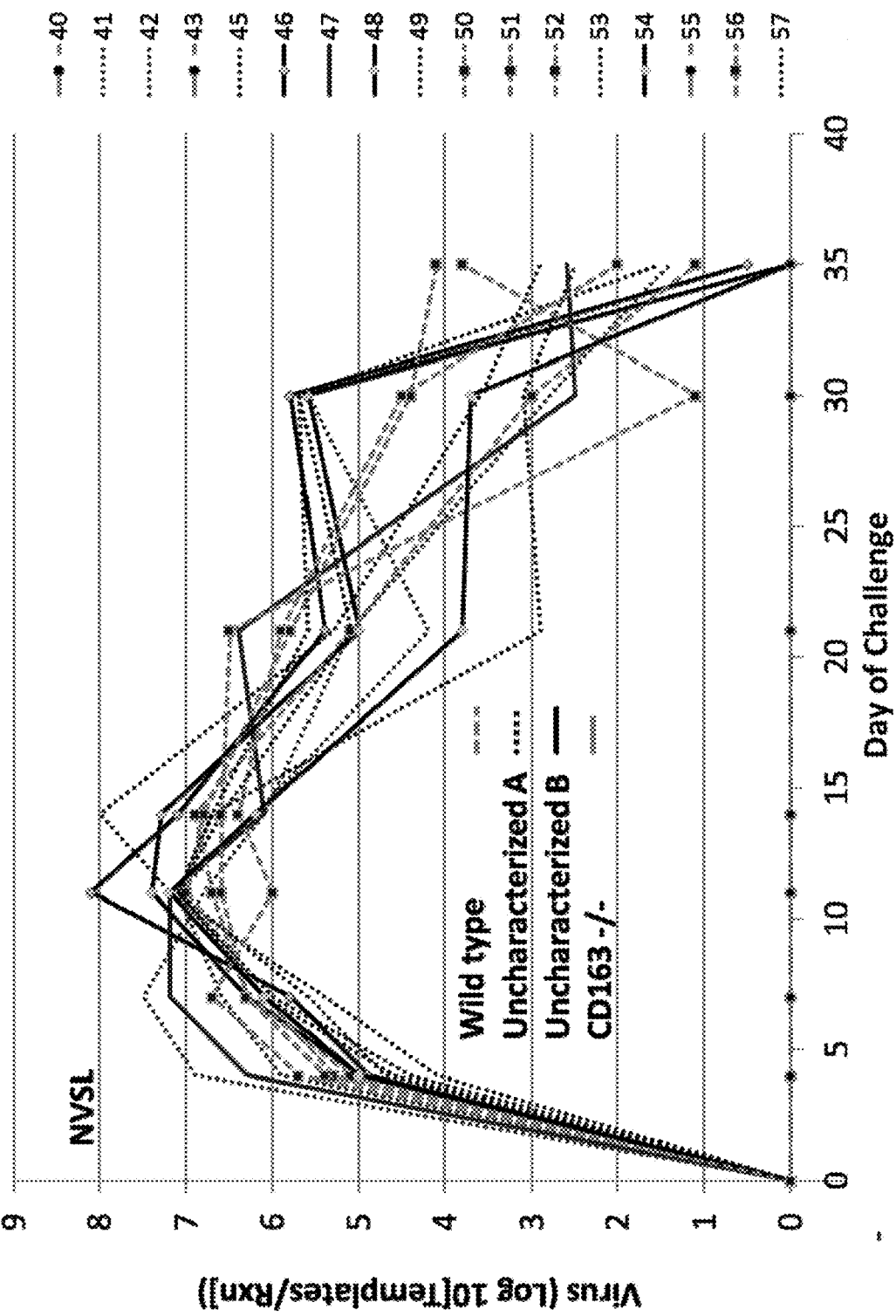
FIG. 11. Viremia in the various genotypes. Note that the CD163−/− piglet data lies along the X axis.
Figure 12:
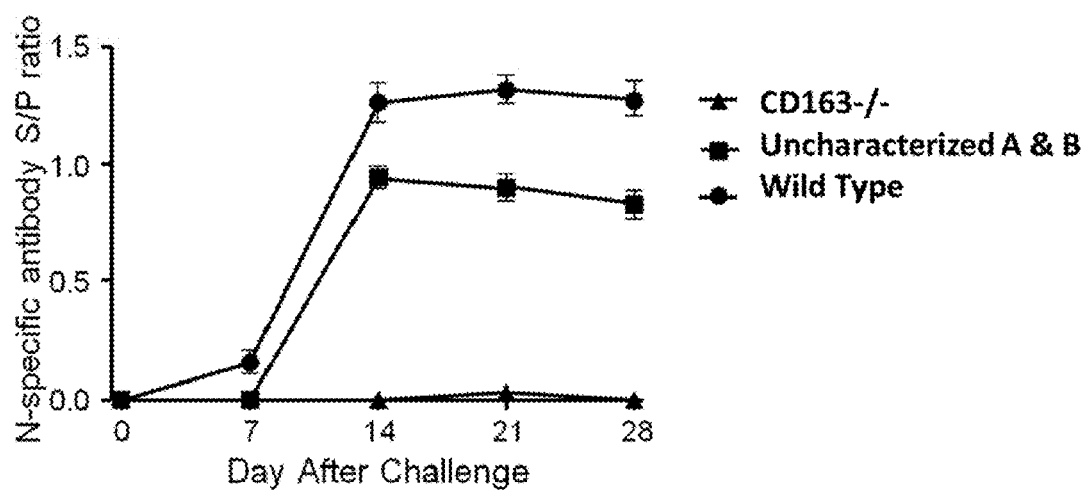
FIG. 12. Antibody production in null, wild type and uncharacterized allele pigs.

Peak clinical signs correlated with the levels of PRRSV in the blood. The measurement of viral nucleic acid was performed by isolation of total RNA from serum followed by amplification of PRRSV RNA by using a commercial reverse transcriptase real-time PRRSV PCR test (Tetracore, Rockville, Md.). A standard curve was generated by preparing serial dilutions of a PRRSV RNA control, supplied in the RT-PCR kit and results were standardized as the number templates per 50 µl PCR reaction. The PRRSV isolate followed the course for PRRSV viremia in the wild type CD163+/+ pigs (FIG. 11). Viremia was apparent at day four, reached a peak at day 11 and declined until the end of the study. In contrast viral RNA was not detected in the CD163$^{-/-}$≥pigs at any time point during the study period. Consistent with the viremia, antibody production by the null and uncharacterized allele pigs was detectable by 14 and increased to day 28. There was no antibody production in the null animals (FIG. 12). Together, these data show that wild type pigs support PRRSV replication with the production of clinical signs consistent with PRRS. In contrast, the knockout pigs produced no viremia and no clinical signs, even though pigs were inoculated and constantly exposed to infected pen mates.

Figure 13:
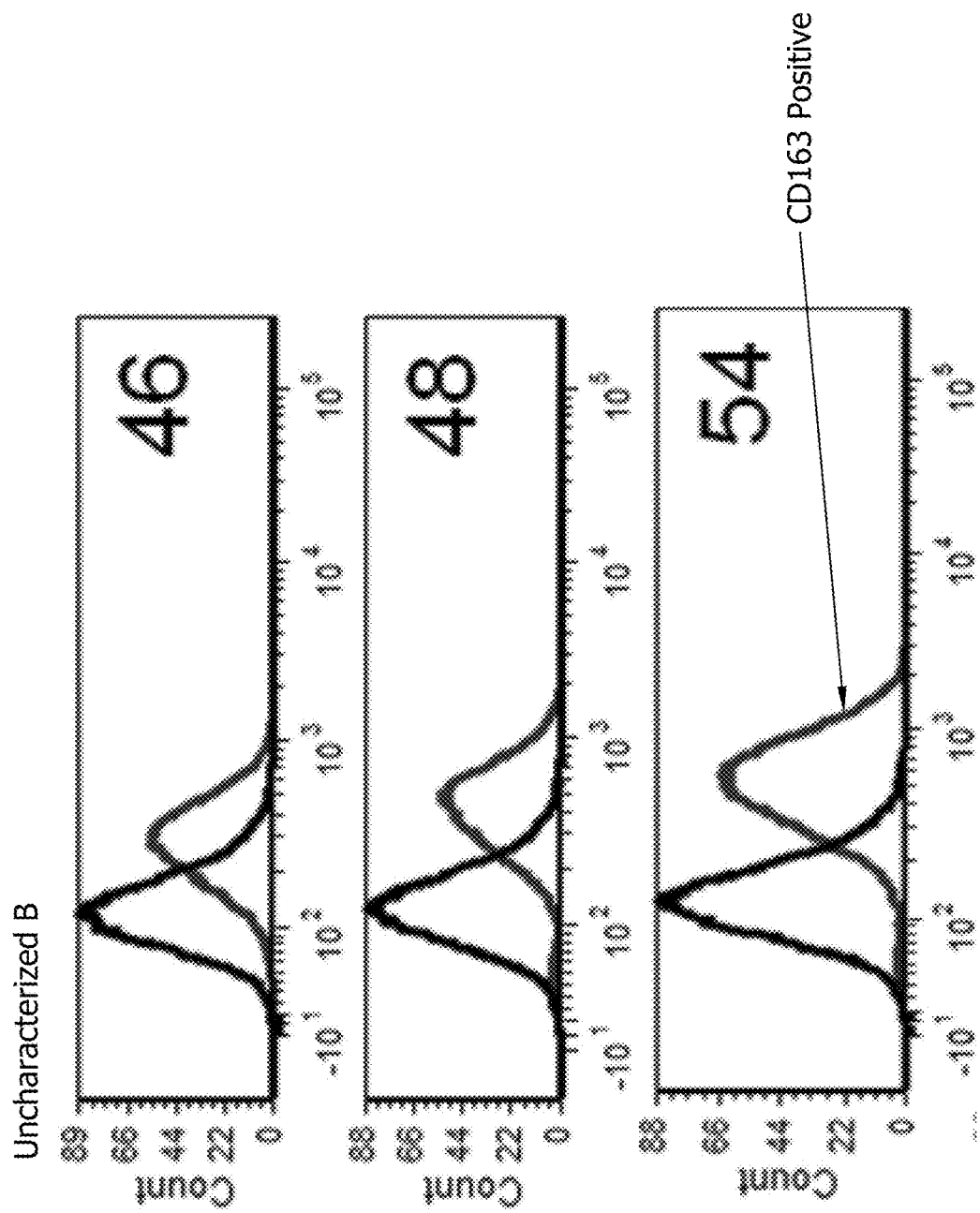
FIG. 13. Cell surface expression of CD163 in individual pigs. Lines appearing towards the right in the uncharacterized A, uncharacterized B, and CD163+/+ panels represent the CD163 antibody while the lines appearing towards the left-hand sides of these panels are the no antibody controls (background). Note that in the CD163−/− animals, the CD163 staining overlaps with the background control, and that the CD163 staining in the uncharacterized alleles is roughly half way between the WT level and the background (also note that this is a log scale, thus less than ~10%).
Figure 13:
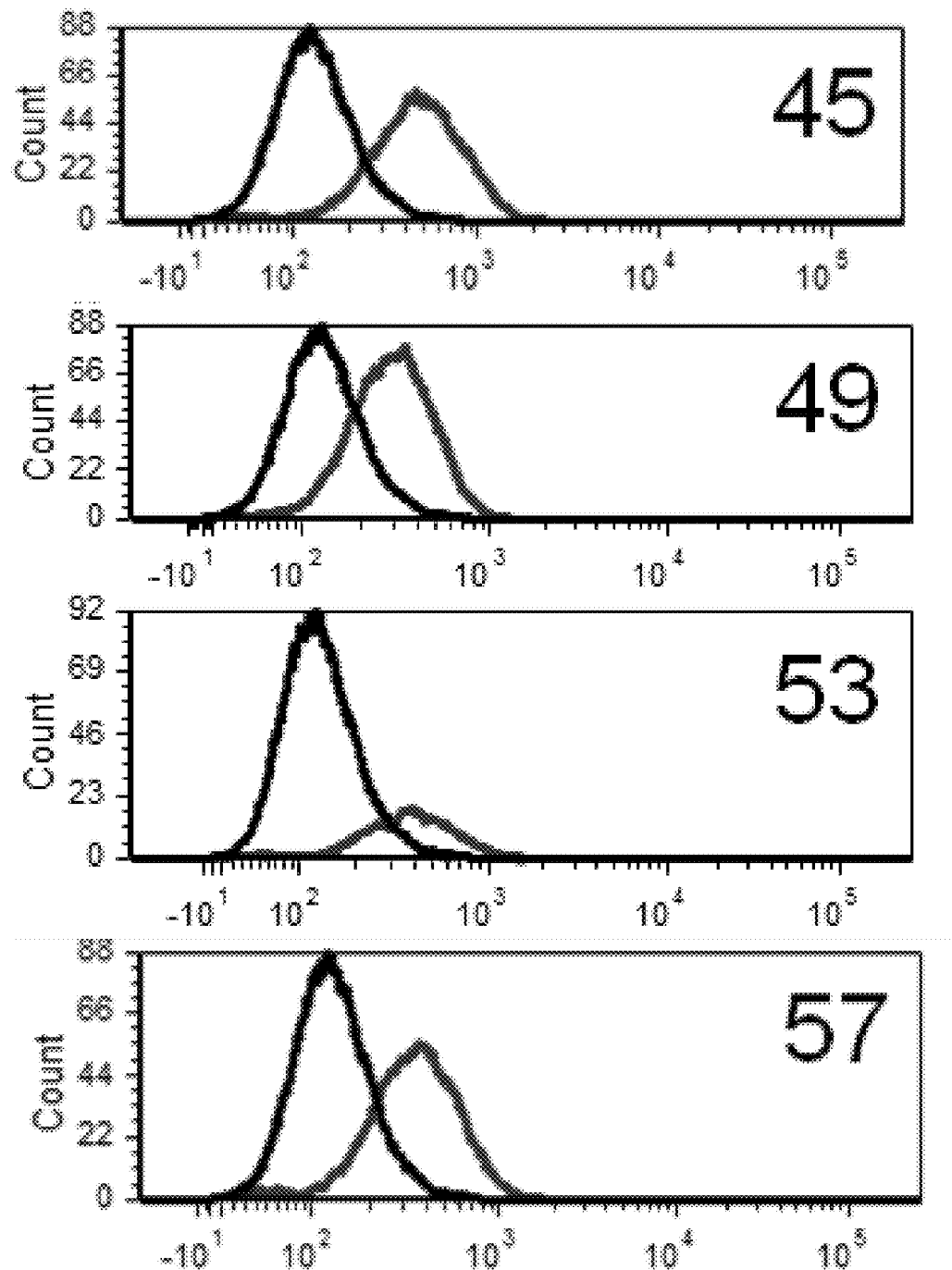
Figure 13:
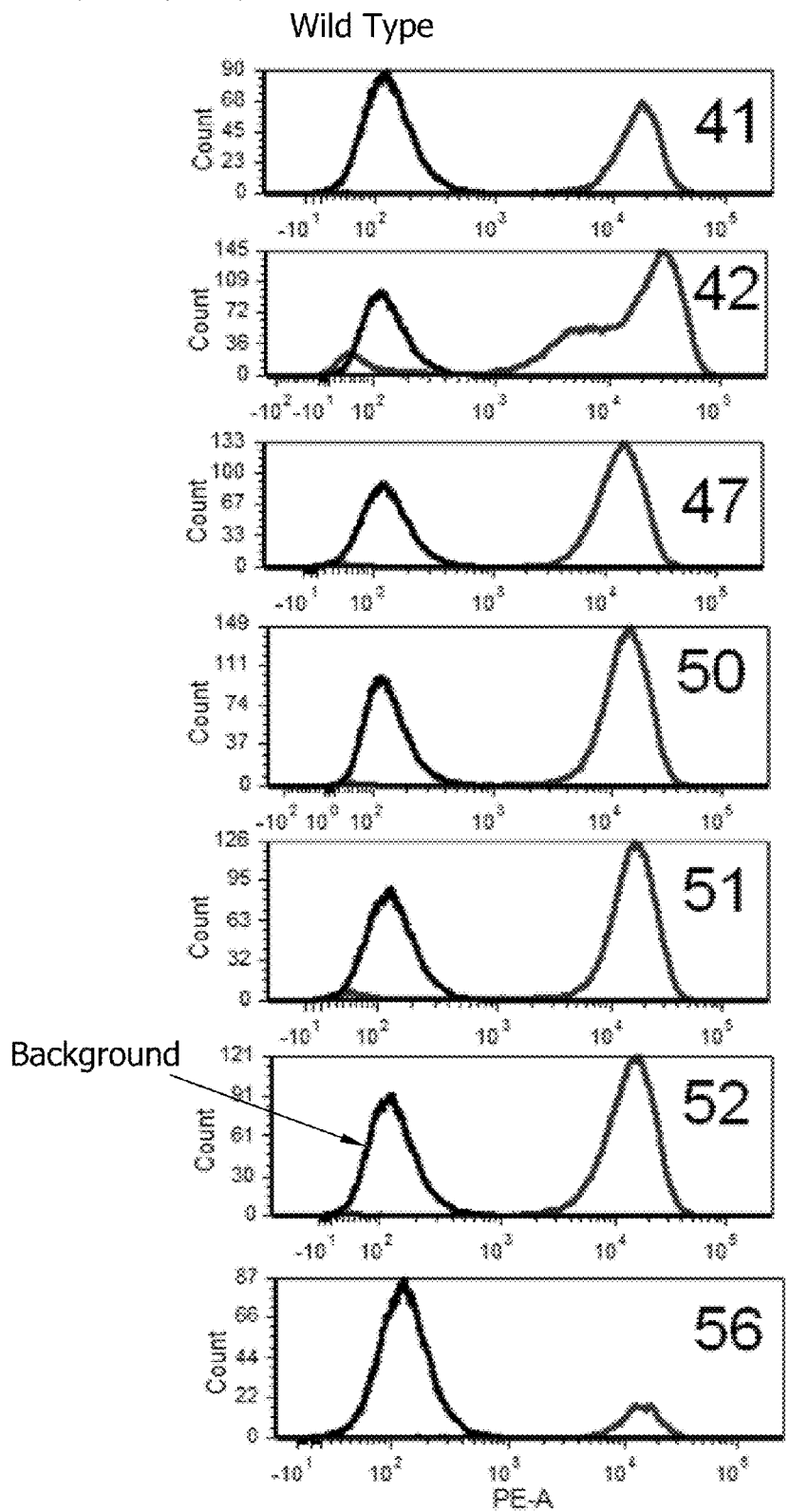
Figure 14:
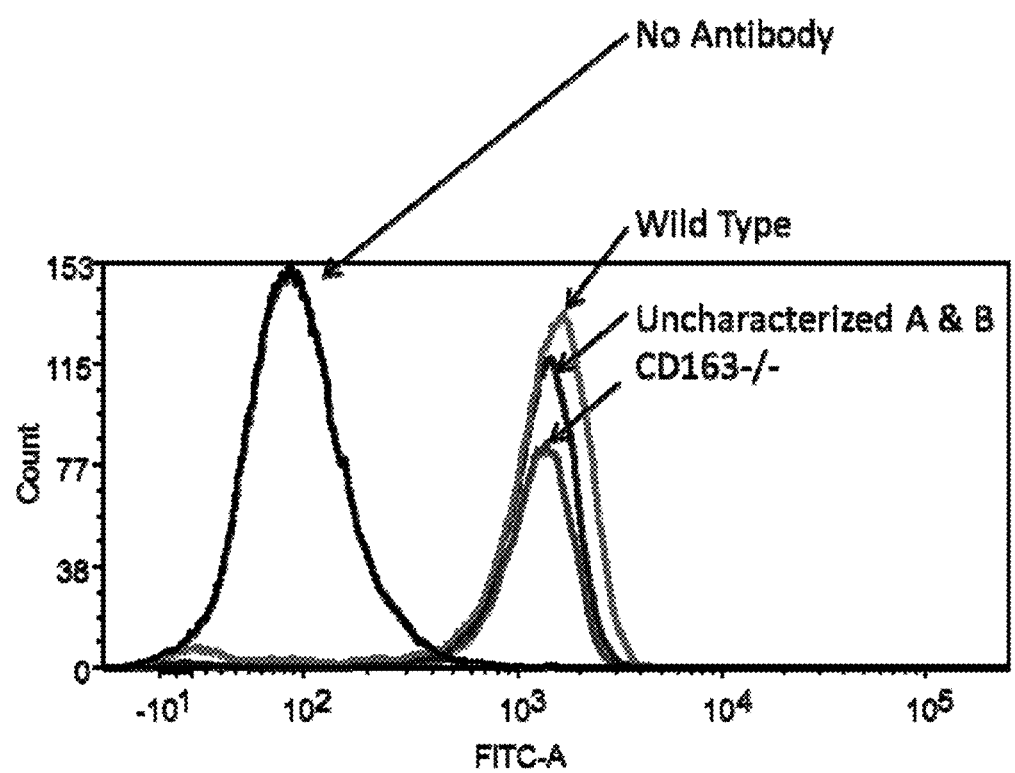
FIG. 14. Level of CD169 on alveolar macrophages from three representative pigs and the no antibody control (FITC labelled anti-CD169).

At the end of the study, porcine alveolar macrophages were removed by lung lavage and stained for surface expression of SIGLEC1 (CD169, clone 3B11/11) and CD163 (clone 2A10/11), as described previously (Prather et al., 2013). Relatively high levels of CD163 expression were detected on CD163+/+ wild type animals (FIG. 13). In contrast, CD163−/− pigs showed only background levels of anti-CD163 staining, thus confirming the knockout phenotype. Expression levels for another macrophage marker CD169 were similar for both wild type and knockout pigs (FIG. 14). Other macrophage surface markers, including MHC II and CD172 were the same for both genotypes (data not shown).

While the sample size was small the wild type pigs tended to gain less weight over the course of the experiment (average daily gain 0.81 kg±0.33, n=7) versus the pigs of the other three genotypes (uncharacterized A 1.32 kg±0.17, n=4; uncharacterized B 1.20 kg±0.16, n=3; null 1.21 kg±0.16, n=3).

Figure 15:
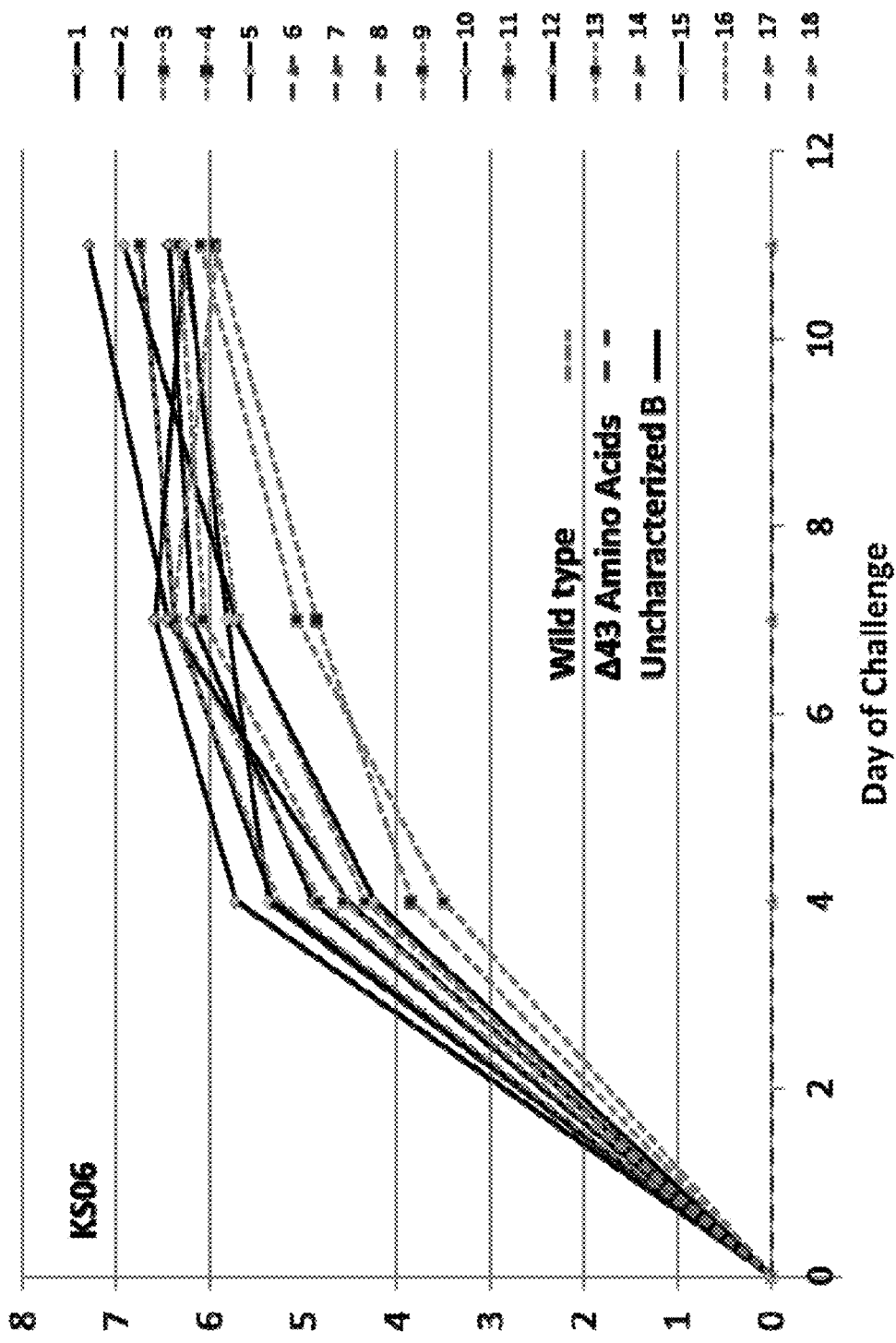
FIG. 15. Viremia in the various genotypes. Note that the Δ43 amino acid piglet data lies along the X-axis.

In a second trial 6 wild type, 6 Δ43 amino acids, and 6 pigs with an uncharacterized allele (B) were challenged as described above, except KS06-72109 was used to inoculate the piglets. Similar to the NVSL data the wild type and uncharacterized B piglets developed viremia. However, in the Δ43 amino acid pigs the KS06 did not result in viremia (FIG. 15; Table 7).

Implications and Conclusion

The most clinically relevant disease to the swine industry is PRRS. While vaccination programs have been successful to prevent or ameliorate most swine pathogens, the PRRSV has proven to be more of a challenge. Here CD163 is identified as an entry mediator for this viral strain. The founder boar was created by injection of CRISPR/Cas9 into zygotes (Whitworth et al., 2014) and thus there is no transgene. Additionally one of the alleles from the sow (also created by using CRISPR/Cas9) does not contain a transgene. Thus piglet #40 carries a 7 bp addition in one allele and a 11 bp deletion in the other allele, but no transgene. These virus-resistance alleles of CD163 represent minor genome edits considering that the swine genome is about 2.8 billion bp (Groenen et al., 2012). If similarly created animals were introduced into the food supply, significant economic losses could be prevented.

Example 3

Increased Resistance to Genotype 1 Porcine Reproductive and PRRS Viruses in Swine with CD163 SRCR Domain 5 Replaced with Human CD163-Like Homology SRCR Domain 8

CD163 is considered the principal receptor for porcine reproductive and respiratory syndrome virus (PRRSV). In this study, pigs were genetically modified (GM) to possess one of the following genotypes: complete knock out (KO) of CD163, deletions within CD163 scavenger receptor cysteine-rich (SRCR) domain 5, or replacement (domain swap) of SRCR domain 5 with a synthesized exon encoding a homolog of human CD163-like (hCD163L1) SRCR 8 domain. Immunophenotyping of porcine alveolar macrophages (PAMs) showed that pigs with the KO or SRCR domain 5 deletions did not express CD163 and PAMs did not support PRRSV infection. PAMs from pigs that possessed the hCD163L1 domain 8 homolog expressed CD163 and supported the replication of Type 2, but not Type 1 genotype viruses. Infection of CD163-modified pigs with representative Type 1 and Type 2 viruses produced similar results. Even though Type 1 and Type 2 viruses are considered genetically and phenotypically similar at several levels, including the requirement of CD163 as a receptor, the results demonstrate a distinct difference between PRRSV genotypes in the recognition of the CD163 molecule.

Materials and Methods
Genomic Modifications of the Porcine CD163 Gene

Figure 17:
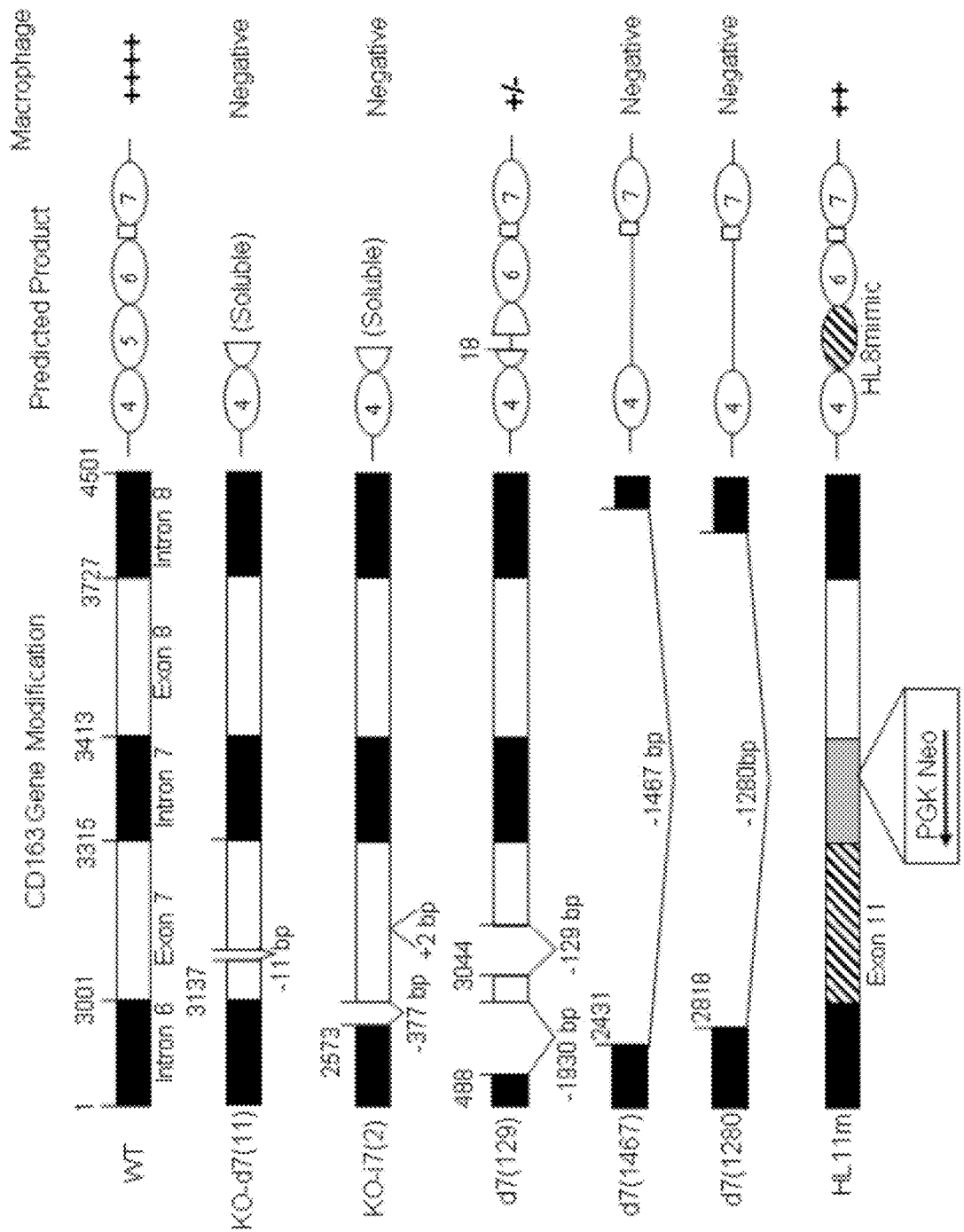

Experiments involving animals and viruses were performed in accordance with the Federation of Animal Science Societies Guide for the Care and Use of Agricultural Animals in Research and Teaching, the USDA Animal Welfare Act and Animal Welfare Regulations, and were approved by the Kansas State University and University of Missouri Institutional Animal Care and Use Committees and Institutional Biosafety Committees. Mutations in CD163 used in this study were created using the CRISPR/Cas9 technology as described hereinabove in the preceding examples. The mutations are diagrammed in FIG. 17. The diagrammed genomic region shown in FIG. 17 covers the sequence from intron 6 to intron 8 of the porcine CD163 gene. The introns and exons diagrammed in FIG. 17 are not drawn to scale. The predicted protein product is illustrated to the right of each genomic structure. Relative macrophage expression, as measured by the level of surface CD163 on PAMs, is shown on the far right of FIG. 17. The black regions indict introns; the white regions indicate exons; the hatched region indicates hCD163L1 exon 11 mimic, the homolog of porcine exon 7; and the gray region indicates a synthesized intron with the PGK Neo construct as shown in FIG. 17.

The CD163 gene construct KO-d7(11) shown in FIG. 17 possesses an 11 base pair deletion in exon 7 from nucleotide 3,137 to nucleotide 3,147. The CD163 gene construct KO-i7(2), possesses a 2 base pair insertion in exon 7 between nucleotides 3,149 and 3,150 as well as a 377 base pair deletion in the intron upstream of exon 7, from nucleotide 2,573 to nucleotide 2,949. These edits are predicted to cause frameshift mutations and premature stop codons, resulting in only partial translation of SRCR 5 and the KO phenotype. Three other mutations produced deletions in exon 7. The first, d7(129), has a 129 base pair deletion in exon 7 from nucleotide 3,044 to nucleotide 3,172. The d7(129) construct also has a deletion from nucleotide 488 to nucleotide 2,417 in exon 6, wherein the deleted sequence is replaced with a 12 bp insertion. The other two deletion constructs, d7(1467) and d7(1280), have complete deletions of exons 7 and 8 as illustrated in FIG. 17. d7(1467) has a 1467 base pair deletion from nucleotide 2,431 to nucleotide 3,897, and d7(1280) has a 1280 base pair deletion from nucleotide 2,818 to nucleotide 4,097. For these deletion constructs the other CD163 exons remained intact.

The last construct shown in FIG. 17, HL11m, was produced using a targeting event that deleted exon 7 and replaced it with a synthesized exon that encoded a homolog of SRCR 8 of the human CD163-like 1 protein (hCD163L1 domain 8 is encoded by hCD163L1 exon 11). The SRCR 8 peptide sequence was created by making 33 nucleotide changes in the porcine exon 7 sequence. A neomycin cassette was included in the synthesized exon to enable screening for the modification. SEQ ID NO: 118 provides the nucleotide sequence for the HL11m construct in the region corresponding to the same region in reference sequence SEQ ID NO: 47.

Figure 18:
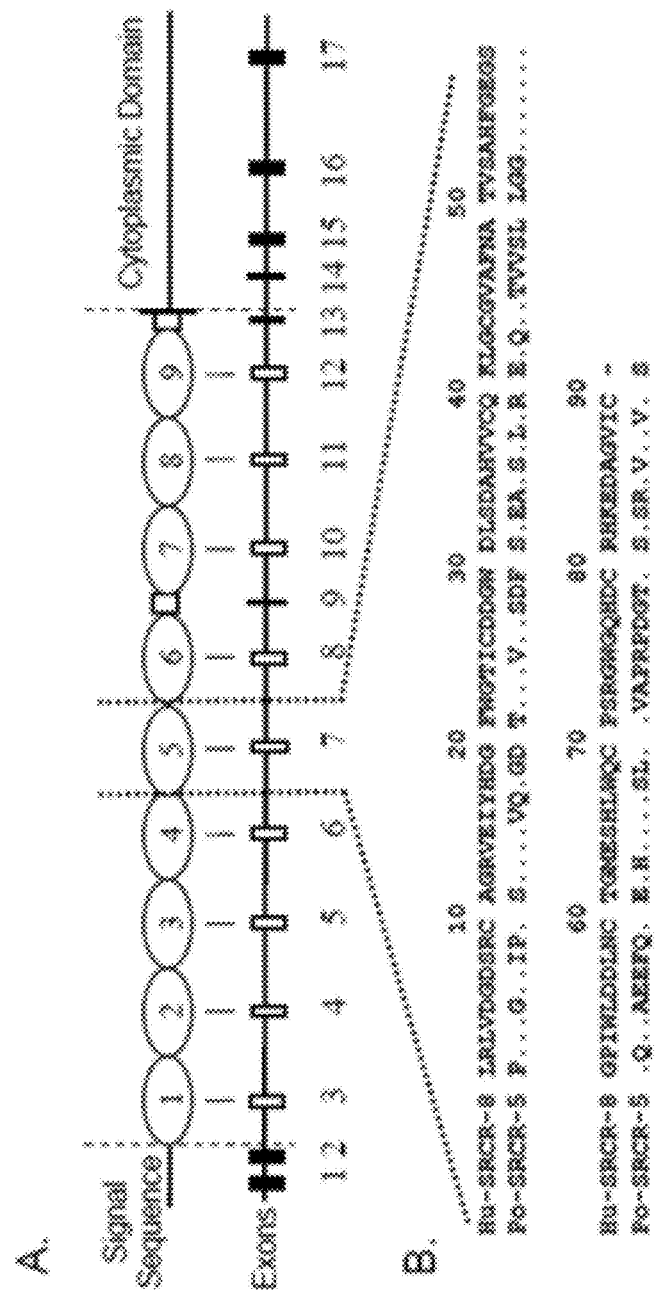

A diagram of the porcine CD163 protein and gene is provided FIG. 18. The CD163 protein SCRC (ovals) and PST (squares) domains along with the corresponding gene exons are shown in panel A of FIG. 18. A peptide sequence comparison for porcine CD163 SRCR 5 (SEQ ID NO: 120) and human CD163 SRCR 8 homolog (SEQ ID NO: 121) is shown in panel B of FIG. 18. The figure is based on GenBank accession numbers AJ311716 (pig CD163) and GQ397482 (hCD163-L1).

Viruses

The panel of viruses used in this example is listed in Table 14. Isolates were propagated and titrated on MARC-145 cells (Kim et al., 1993). For titration, each virus was serially diluted 1:10 in MEM supplemented with 7% FBS, Pen-Strep (80 Units/ml and 80 µg/ml, respectively), 3 µg/ml FUNGIZONE (amphotericin B), and 25 mM HEPES. Diluted samples were added in quadruplicate to confluent MARC-145 cells in a 96 well plate to a final volume of 200 µl per well and incubated for four days at 37° C. in 5% $CO_2$. The titration endpoint was identified as the last well with a cytopathic effect (CPE). The 50% tissue culture infectious dose ($TCID_{50}$/ml) was calculated using a method as previously described (Reed and Muench 1938).

TABLE 14

PRRSV isolates.

| Virus | Genotype | Year Isolated | GenBank No. |
| --- | --- | --- | --- |
| NVSL 97-7895 | 2 | 1997 | AY545985 |
| KS06-72109 | 2 | 2006 | KM252867 |
| P129 | 2 | 1995 | AF494042 |
| VR2332 | 2 | 1992 | AY150564 |
| CO90 | 2 | 2010 | KM035799 |
| AZ25 | 2 | 2010 | KM035800 |
| MLV-ResPRRS | 2 | NA* | AF066183 |
| KS62-06274 | 2 | 2006 | KM035798 |
| KS483 (SD23983) | 2 | 1992 | JX258843 |
| CO84 | 2 | 2010 | KM035802 |
| SD13-15 | 1 | 2013 | NA |
| Lelystad | 1 | 1991 | M96262 |
| 03-1059 | 1 | 2003 | NA |
| 03-1060 | 1 | 2003 | NA |
| SD01-08 | 1 | 2001 | DQ489311 |
| 4353PZ | 1 | 2003 | NA |

*NA, Not available

Infection of Alveolar Macrophages

The preparation and infection of macrophages were performed as previously described (Gaudreault, et al., 2009 and Patton, et al., 2008). Lungs were removed from euthanized pigs and lavaged by pouring 100 ml of cold phosphate buffered saline (PBS) into the trachea. The tracheas were clamped and the lungs gently massaged. The alveolar contents were poured into 50 ml centrifuge tubes and stored on ice. Porcine alveolar macrophages (PAMs) were sedimented by centrifugation at 1200×g for 10 minutes at 4° C. The pellets were re-suspended and washed once in cold sterile PBS. The cell pellets were re-suspended in freezing medium containing 45% RPMI 1640, 45% fetal bovine serum (FBS), and 10% dimethylsulfoxide (DMSO) and stored in liquid nitrogen until use. Frozen cells were thawed on ice, counted and adjusted to $5\times10^5$ cells/ml in media (RPMI 1640 supplemented with 10% FBS, PenStrep, and FUNGIZONE; RPMI-FBS). Approximately $10^3$ PAMs per well were added to 96 well plates and incubated overnight at 37° C. in 5% $CO_2$. The cells were gently washed to remove non-adherent cells. Serial 1:10 dilutions of virus were added to triplicate wells. After incubation overnight, the cells were washed with PBS and fixed for 10 minutes with 80% acetone. After drying, wells were stained with PRRSV N-protein specific SDOW-17 mAb (Rural Technologies Inc.) diluted 1:1000 in PBS with 1% fish gelatin (PBS-FG; Sigma Aldrich). After a 30 minute incubation at 37° C., the cells were washed with PBS and stained with ALEXAFLUOR 488-labeled anti-mouse IgG (Thermofisher Scientific) diluted 1:200 in PBS-FG. Plates were incubated for 30 minutes in the dark at 37° C., washed with PBS, and viewed under a fluorescence microscope. The 50% tissue culture infectious dose ($TCID_{50}$)/ml was calculated according to a method as previously described (Reed and Muench 1938).

Measurement of CD169 and CD163 Surface Expression on PAMs

Staining for surface expression of CD169 and CD163 was performed as described previously (Prather et al., 2013). Approximately $1\times10^6$ PAMs were placed in 12 mm×75 mm polystyrene flow cytometry (FACS) tubes and incubated for 15 minutes at room temp in 1 ml of PBS with 10% normal mouse serum to block Fc receptors. Cells were pelleted by centrifugation and re-suspended in 5 µl of FITC-conjugated mouse anti-porcine CD169 mAb (clone 3B11/11; AbD Serotec) and 5 µl of PE-conjugated mouse anti-porcine CD163 mAb (Clone: 2A10/11, AbD Serotec). After 30 minutes incubation the cells were washed twice with PBS containing 1% bovine serum albumin (BSA Fraction V; Hyclone) and immediately analyzed on a BD LSR Fortessa flow cytometer (BD Biosciences) with FCS Express 5 software (De Novo Software). A minimum of 10,000 cells were analyzed for each sample.

Measurement of PRRS Viremia

RNA was isolated from 50 µl of serum using Ambion's MagMAX 96 Viral Isolation Kit (Applied Biosystems) according to the manufacturer's instructions. PRRSV RNA was quantified using EZ-PRRSV MPX 4.0 Real Time RT-PCR Target-Specific Reagents (Tetracore) performed according to the manufacturer's instructions. Each plate contained Tetracore Quantification Standards and Control Sets designed for use with the RT-PCR reagents. PCR was carried out on a CFX96 Touch Real-Time PCR Detection System (Bio-Rad) in a 96-well format using the recommended cycling parameters. The PCR assay results were reported as $log_{10}$ PRRSV RNA copy number per 50 µl reaction volume, which approximates the number of copies per ml of serum. The area under the curve (AUC) for viremia over time was calculated using GraphPad Prism version 6.00 for Windows.

Measurement of PRRSV Antibody

The microsphere fluorescent immunoassay (FMIA) for the detection of antibodies against the PRRSV nucleocapsid (N) protein was performed as described previously (Stephenson et al., 2015). Recombinant PRRSV N protein was coupled to carboxylated Luminex MAGPLEX polystyrene microsphere beads according to the manufacturer's directions. For FMIA, approximately 2500 antigen-coated beads, suspended in 50 µL PBS with 10% goat serum (PBS-GS), were placed in each well of a 96-well polystyrene round bottom plate. Sera were diluted 1:400 in PBS-GS and 50 µl added to each well. The plate was wrapped in foil and incubated for 30 minutes at room temperature with gentle shaking. The plate was placed on a magnet and beads were washed three times with 190 µl of PBS-GS. For the detection of IgG, 50 µl of biotin-SP-conjugated affinity purified goat anti-swine secondary antibody (IgG, Jackson ImmunoResearch) was diluted to 2 µg/ml in PBS-GS and 100 µl added to each well. The plate was incubated at room temperature for 30 minutes and washed three times followed by the addition of 50 µl of streptavidin-conjugated phycoerythrin (2 ug/ml in PBS-GS; SAPE). After 30 minutes, the microspheres were washed, resuspended in 100 µl of PBS-GS, and analyzed using a MAGPIX instrument (LUMINEX) and LUMINEX xPONENT 4.2 software. The mean fluorescence intensity (MFI) was calculated on a minimum of 100 microsphere beads.

Measurement of Haptoglobin (HP)

The amount of Hp in serum was measured using a porcine-specific Hp ELISA kit (Genway Biotech Inc.) and steps performed according to the manufacturer's instructions. Serum samples were diluted 1:10,000 in 1× diluent solution and pipetted in duplicate on a pre-coated anti-pig Hp 96 well ELISA plate, incubated at room temperature for 15 minutes, then washed three times. Anti-Hp-HRP conjugate was added to each well and incubated in the dark at room temperature for 15 minutes. The plate was washed and 100 µl chromogen-substrate solution added to each well. After incubating in the dark for 10 minutes, 100 µl of stop solution was added to each well. The plate was read at 450 nm on a Fluostar Omega filter-based microplate reader (BMG Labtech).

Results

Phenotypic Properties of PAMs from CD163 Gene-Modified Pigs

The forward and side scatter properties of cells in the lung lavage material were used to gate on the mononuclear subpopulation of cells. Representative CD169 and CD163 staining results for the different gene modifications shown in FIG. 17 are presented in FIG. 19. In the representative example presented in panel A of FIG. 19, greater than 91% of PAMs from the WT pigs were positive for both CD169 and CD163. Results for 12 WT pigs used in this study showed a mean of 85+/–8% of double-positive cells. As shown in panel B of FIG. 19, PAMs from the CD163 KO pigs showed no evidence of CD163, but retained normal surface levels of CD169. Although it was predicted that the CD163 polypeptides derived from the d7(1467) and d7(1280) deletion genotypes should produce modified CD163 polypeptides anchored to the PAM surface, immunostaining results showed no surface expression of CD163 (see FIG. 19, panel D). Since MAb 2A10 recognizes an epitope located in the first three SRCR domains, the absence of detection was not the result of the deletion of an immunoreactive epitope. The d7(129) genotype was predicted to possess a 43 amino acid deletion in SRCR 5 (see FIG. 17). In the example presented in panel C of FIG. 19, only 2.4% of cells fell in the double-positive quadrant. The analysis of PAMs from nine d7(129) pigs used in this study showed percentages of double-positive cells ranging from 0% to 3.6% (mean=0.9%). The surface expression of CD169 remained similar to WT PAMs. For the purpose of this study, pigs possessing the KO, d7(1467), d7(1280), and d7(129) genotypes were all categorized as possessing a CD163-null phenotype.

Figure 19:
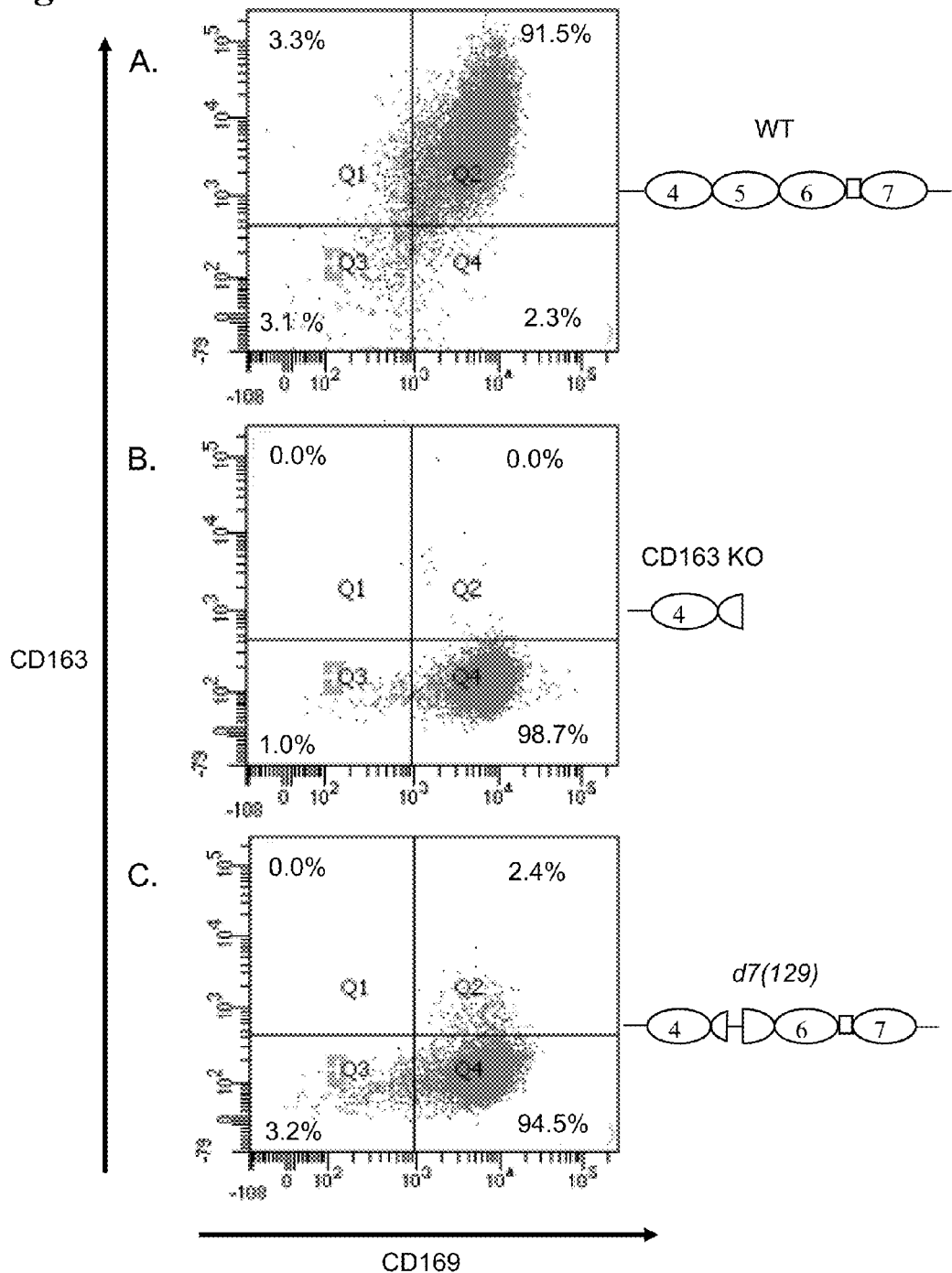
Figure 19:
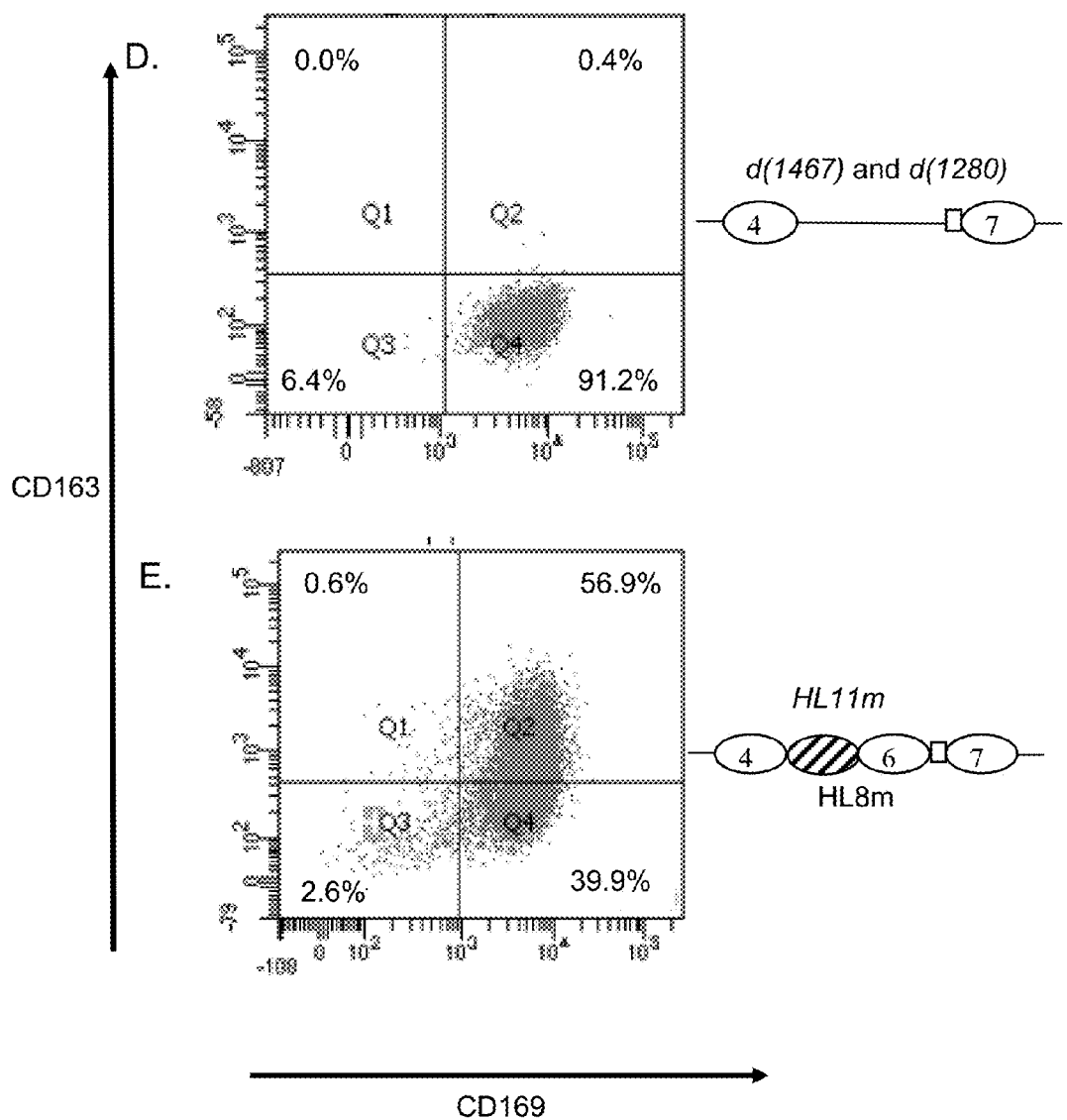

The CD163 modification containing the hCD163L1 domain 8 peptide sequence HL11m, showed dual expression of CD163+ and CD169+ on PAMs (panel E of FIG. 19). However, in all of the HL11m pigs analyzed in this study, the surface expression of CD163 was markedly reduced compared to the WT PAMs. The levels of CD163 fell on a continuum of expression, ranging from no detectable CD163 to pigs possessing moderate levels of CD163. In the example shown in panel E of FIG. 19, approximately 60% of cells were in the double-positive quadrant while 40% of cells stained for only CD169. The analysis of PAMs from a total 24 HL11m pigs showed 38+/−12% of PAM cells were positive only for CD169 and 54+/−14% were double-positive (CD169+CD163+).

Circulating Haptoglobin Levels in WT and CD163-Modified Pigs

Figure 20:
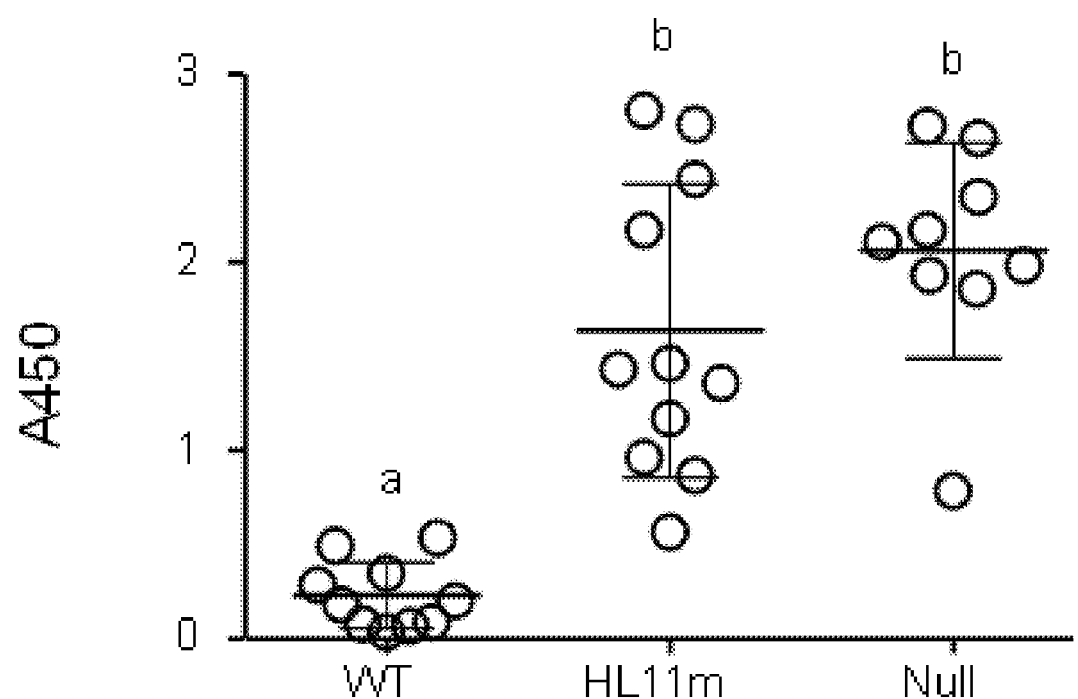

As a scavenging molecule, CD163 is responsible for removing HbHp complexes from the blood (Fabriek, et al., 2005; Kristiansen et al., 2001; and Madsen et al., 2004). The level of Hp in serum provides a convenient method for determining the overall functional properties of CD163-expressing macrophages. Hp levels in sera from WT, HL11m and CD163-null pigs were measured at three to four weeks of age, just prior to infection with PRRSV. The results, presented in FIG. 20, showed that sera from WT pigs had the lowest amounts of Hb (mean A450=23+/−0.18, n=10). The mean and standard deviation for each group were WT, 0.23+/−0.18, n=10; HL11m, 1.63+/−0.8, n=11; and 2.06+/−0.57, n=9, for the null group. The null group was composed of genotypes that did not express CD163 (CD163 null phenotype pigs). Hp measurements were made on a single ELISA plate. Groups with the same letter were not significantly different (p>0.05, Kruskal-Wallis one-way ANOVA with Dunnett's post-test). The mean A450 value was for WT pigs was significantly different from that of the HL11m and CD163-null pigs (p<0.05). Although the mean A450 value was lower for the HL11m group compared to the CD163-null group (A450=1.6+/−0.8 versus 2.1+/−0.6), the difference was not statistically significant. Since the interaction between HbHp and CD163 occurs through SRCR 3 (Madsen et al., 2004), increased circulating Hp in the HL11m pigs compared to WT pigs was likely not a consequence of a reduced affinity of CD163 for Hb/Hp, but the result of reduced numbers of CD163+ macrophages along with reduced CD163 expression on the remaining macrophages (see panel E of FIG. 19).

Infection of PAMs with Type 1 and Type 2 Viruses

The permissiveness of the CD163-modified pigs for PRRSV was initially evaluated by infecting PAM cells in vitro with a panel of six Type 1 and nine Type 2 PRRSV isolates (see Table 14 for the list of viruses). The viruses in the panel represent different genotypes, as well as differences in nucleotide and peptide sequences, pathogenesis, and years of isolation. The data presented in Table 15 show the results form experiments using PAMs from three pigs for each CD163 genotype group. The viruses listed correspond to the PRRSV isolates listed in Table 14. The results are shown as mean+/−standard deviation of the percent of PAMs infected. The CD163-null PAMs were from pigs expressing the d7(129) allele (see FIGS. 17 and 19 for CD163 gene constructs and CD163 expression on PAMs, respectively).

TABLE 15

Infection of PAMs from wild-type and GM pigs with different PRRSV isolates

| | Genotype/Phenotype (% Infection) | | |
|---|---|---|---|
| | WT (%) | HL11m | Null |
| Type 1 | | | |
| 13-15 | 56 +/− 9 | 0 | 0 |
| Lelystad | 62 +/− 15 | 0 | 0 |
| 03-1059 | 50 +/− 18 | 0 | 0 |
| 03-1060 | 61 +/− 12 | 0 | 0 |
| 01-08 | 64 +/− 20 | 0 | 0 |
| 4353-PZ | 62 +/− 15 | 0 | 0 |
| Type 2 | | | |
| NVSL 97 | 59 +/− 15 | 8 +/− 08 | 0 |
| KS-06 | 56 +/− 20 | 12 +/− 09 | 0 |
| P129 | 64 +/− 11 | 8 +/− 06 | 0 |
| VR2332 | 54 +/− 05 | 6 +/− 03 | 0 |
| CO 10-90 | 43 +/− 18 | 8 +/− 08 | 0 |
| CO 10-84 | 51 +/− 22 | 7 +/− 04 | 0 |
| MLV-ResP | 55 +/− 12 | 3 +/− 01 | 0 |
| KS62 | 49 +/− 03 | 10 +/− 11 | 0 |
| KS483 | 55 +/− 23 | 6 +/− 03 | 0 |

As expected, the WT PAMs were infected by all viruses. In contrast, the CD163-null phenotype pigs were negative for infection by all viruses. A marked difference was observed in the response of PAMs from the HL11m pigs. None of the Type 1 viruses were able to infect the HL11m PAMs; whereas, all viruses in the Type 2 panel infected the HL11m PAMs, albeit at much lower percentages compared to the WT PAMs.

Figure 21:
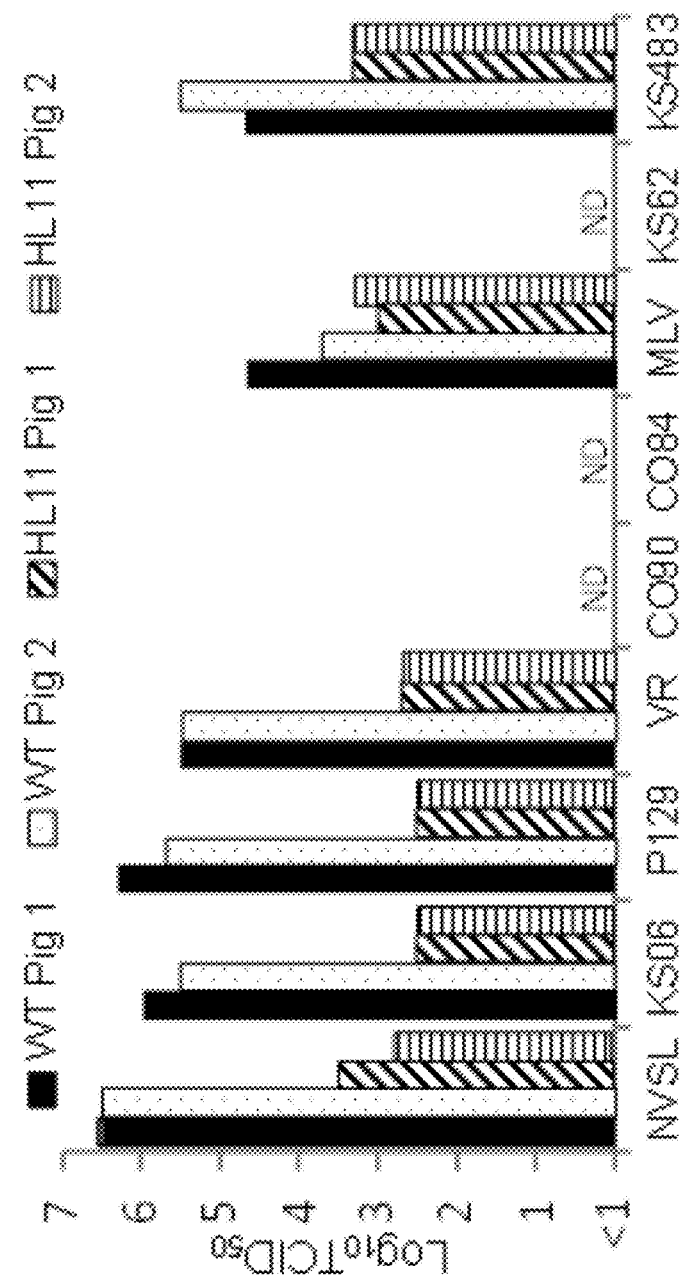

Permissiveness was also evaluated by comparing virus titration endpoints between WT and HL11m PAMs for the same Type 2 viruses. Results are shown for two WT and two HL11m pigs (FIG. 21). The $\log_{10}$ $TCID_{50}$ values were calculated based on the infection of macrophage cultures with the same virus sample. Infection results represent two different pigs from each genotype. Viruses used for infection are listed in Table 14. The $\log_{10}$ $TCID_{50}$ values for PAMs from the HL11m pigs were 1-3 logs lower compared to WT PAMs infected with the same virus. The only exception was infection with a modified-live virus vaccine strain. When taken altogether, the results suggest that PAMs from HL11m pigs possess a reduced susceptibility or permissiveness to infection with Type 2 viruses.

Infection of CD163-Modified Pigs with Type 1 and Type 2 Viruses

Figure 22:
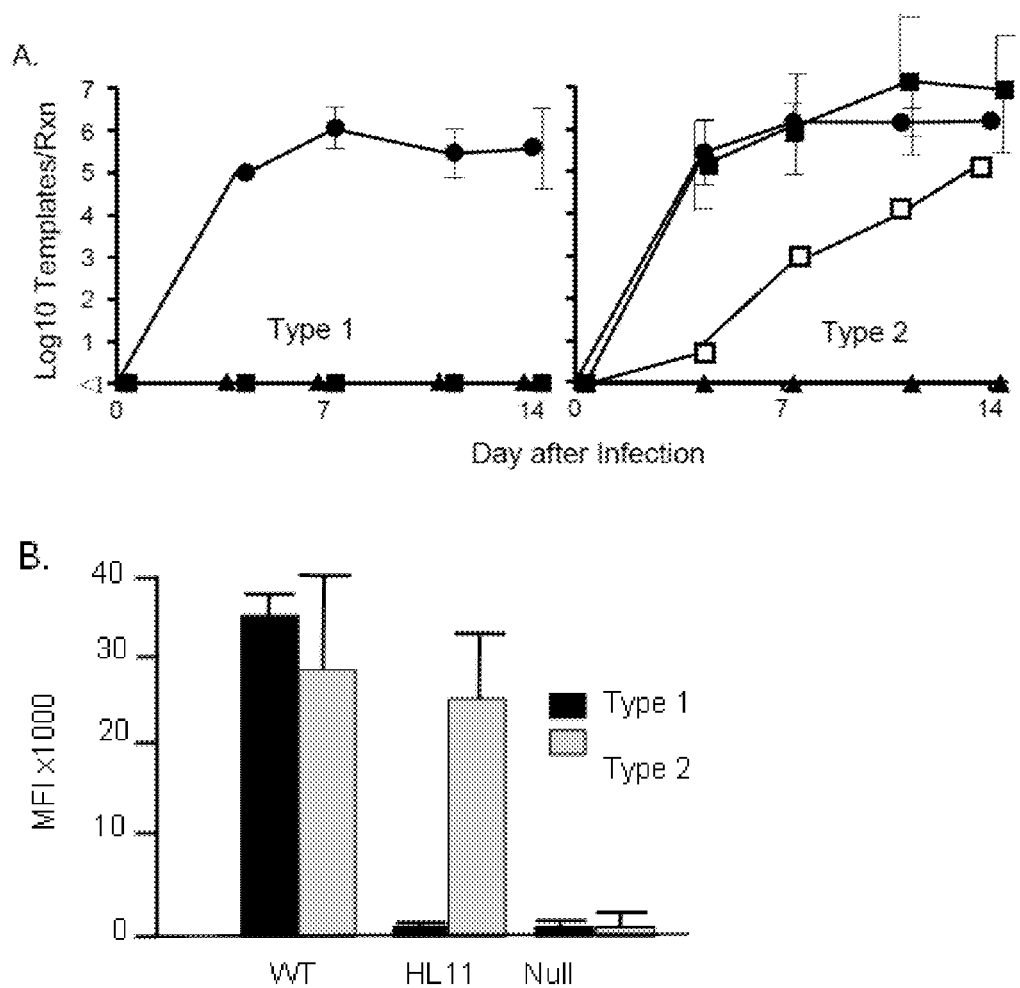

WT (circles), HL11m (squares), and CD163-null (triangles) pigs were infected with representative Type 1 (SD13-15) (FIG. 22, panel A, left graph) and Type 2 (NVSL 97-7895) (FIG. 22, panel A, right graph) viruses. The null phenotype pigs were derived from the KO and d(1567) alleles (see FIG. 17). Pigs from the three genotypes inoculated with the same virus were co-mingled in one pen, which allowed for the continuous exposure of CD163-modified pigs to virus shed from WT pen mates. The number of pigs infected with representative Type 1 virus were: WT (n=4), HL11m (n=5), and Null (n=3); and Type 2 virus: WT (n=4), HL11m (n=4), and Null (n=3). As shown in FIG. 22, the CD163-null pigs infected with either the Type 1 or Type 2 virus were negative for viremia at all time points and did not seroconvert. As expected, the WT pigs were productively infected possessing mean viremia levels approaching $10^6$ templates per 50 µl PCR reaction at 7 days after infection for both viruses. By 14 days, all WT pigs had seroconverted (see FIG. 22, panel B). Consistent with the PAM infection results (Table 15), the five HL11m pigs infected with the Type 1 virus showed no evidence of viremia or PRRSV antibody. All HL11m pigs infected with the Type 2 isolate, NVSL, supported infection and seroconverted (FIG. 22, panel B). The presence of a reduced permissive of the HL11m pigs was unclear. Mean viremia for three of the four HL11m pigs were similar to the WT pigs. However, for one HL11m pig, #101 (open squares in FIG. 22, panel A right graph), viremia was greatly reduced compared to the other pigs in HL11m genotype group. An explanation for the 3 to 4 log reduction in viremia for Pig #101 was not clear, but suggested that some HL11m pigs may be less permissive for PRRSV, an observation supporting the in vitro PAM infection results (Table 15). Since all pigs were inoculated with the same amount of virus and remained co-mingled with the WT pigs, the lower viremia in Pig #101 was not the result of receiving a lower amount of virus or less exposure to virus. Flow cytometry of macrophages showed that CD163 expression for Pig #101 was comparable to the other HL11m pigs (data not shown). There was no difference in the sequence in the exon 11 mimic sequence.

Figure 23:
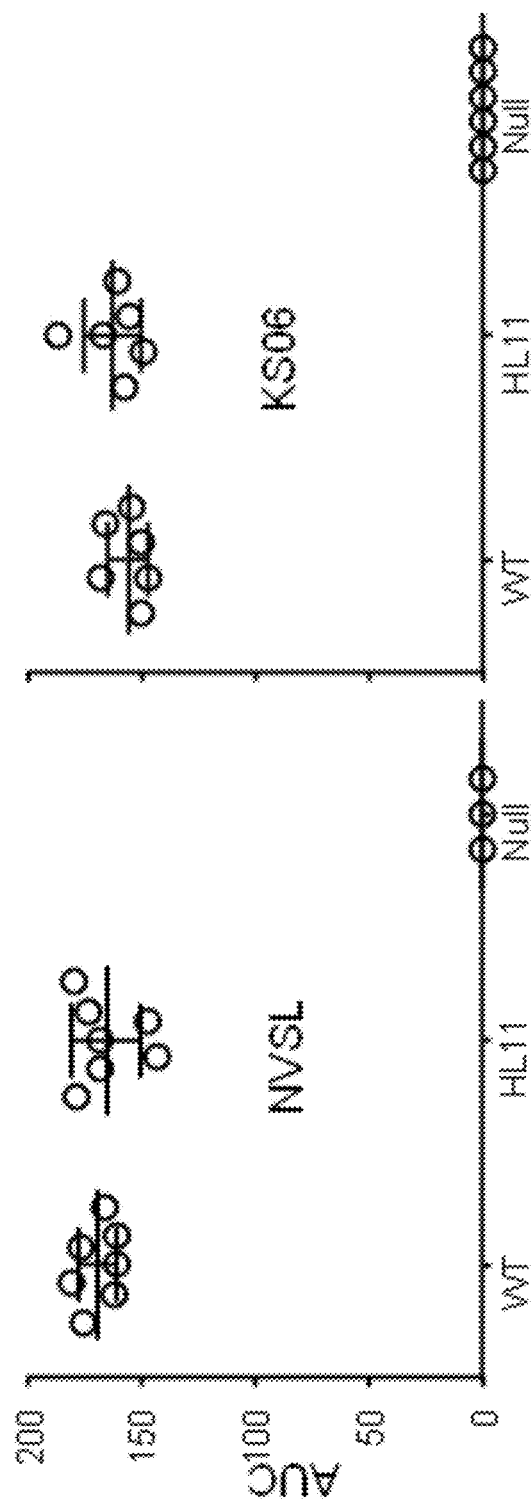

Additional virus infection trials were conducted using two viruses, NVSL 97-7895 and KS06-72109. Results are shown in FIG. 23. Pigs were followed for 35 days after infection and data reported as the area under the curve (AUC) for viremia measurements taken at 3, 7, 11, 14, 21, 28 and 35 days after infection. As shown in FIG. 23, for NVSL, the mean AUC value for the seven WT pigs infected with NVSL was 168+/−8 versus 165+/−15 for the seven HL11m pigs. For KS06, the mean AUC values for the six WT and six HL11m pigs were 156+/−9 and 163+/−13, respectively. For both viruses, there was no statistically significant difference between the WT and HL11m pigs (p>0.05). When taken altogether, the results showed that the HL11m pigs failed to support infection with Type 1 PRRSV, but retained permissiveness for infection with Type 2 viruses. Even though there was a reduction in the PRRSV permissiveness of PAMs from HL11m pigs infected in vitro with the Type 2 isolates, this difference did not translate to the pig. For the results shown in FIG. 23, virus load was determined by calculating the area under the curve (AUC) for each pig over a 35 day infection period. The AUC calculation was performed using $\log_{10}$ PCR viremia measurements taken at 0, 4, 7, 10, 14, 21, 28 and 35 days after infection. The horizontal lines show mean and standard deviation. Key: WT=wild-type pigs, HL11=HL11m genotype pigs; Null=CD163-null genotype.

Discussion

CD163 is a macrophage surface protein important for scavenging excess Hb from the blood and modulating inflammation in response to tissue damage. It also functions as a virus receptor. CD163 participates in both pro- and anti-inflammatory responses (Van Gorp et al., 2010). CD163-positive macrophages are placed within the alternatively activated M2 group of macrophages, which are generally described as highly phagocytic and anti-inflammatory. M2 macrophages participate in the cleanup and repair after mechanical tissue damage or infection (Stein et al., 1992). In an anti-inflammatory capacity, CD163 expression is upregulated by anti-inflammatory proteins, such as IL-10 (Sulahian, et al., 2002). During inflammation, CD163 decreases inflammation by reducing oxidative through the removal of circulating heme from the blood. Heme degradation products, such as bilverdin, bilirubin, and carbon monoxide are potent anti-inflammatory molecules (Soares and Bach, 2009 and Jeney et al., 2002). In a pro-inflammatory capacity, the crosslinking of CD163 on the macrophage surface by anti-CD163 antibody or bacteria results in the localized release of pro-inflammatory cytokines, including IL-6, GM-CSF, TNFα and IL-1β (Van den Heuvel et al., 1999 and Fabriek et al., 2009).

GM pigs that lack CD163 fail to support the replication of a Type 2 PRRSV isolate (Whitworth et al., 2016). In this study, in vitro infection trials demonstrate the resistance of CD163 null phenotype macrophages to an extensive panel of Type 1 and Type 2 PRRSV isolates, further extending resistance to potentially include all PRRSV isolates (Table 15). Resistance of the CD163-null phenotype macrophages to Type 1 and Type 2 viruses was confirmed in vivo (FIG. 22 and FIG. 23). Based on these results, the contribution of other PRRSV receptors previously described in the literature (Zhang and Yoo, 2015) can be ruled out. For example, Shanmukhappa et al. (2007) showed that non-permissive BHK cells transfected with a CD151 plasmid acquired the ability to support PRRSV replication, and incubation with a polyclonal anti-CD151 antibody was shown to significantly reduce the infection of MARC-145 cells. In addition, a simian cell line, SJPL, originally developed for use in propagating swine influenza viruses, was previously shown to support PRRSV replication (Provost, et al., 2012). Important properties of the SJPL cell line included the presence of CD151 and the absence of sialoadhesin and CD163. When taken together, these data provided convincing evidence that the presence of CD151 alone is sufficient to support PRRSV replication. The results from this study showing the absence of PRRSV infection in macrophages and pigs possessing a CD163 null phenotype indicates that CD151 as an alternative receptor for PRRSV is not biologically relevant.

The viral proteins GP2a and GP4, which form part of the GP2a, GP3, GP4 heterotrimer complex on the PRRSV surface, can be co-precipitated with CD163 in pull-down assays from cells transfected with GP2 and GP4 plasmids (Das, et al., 2009). Presumably, GP2 and GP4 form an interaction with one or more of the CD163 SRCR domains. In vitro infectivity assays incorporating a porcine CD163 cDNA backbone containing a domain swap between porcine SRCR 5 and the homolog from hCD163-L1 SRCR 8 further localized the region utilized by Type 1 viruses to SRCR 5 (Van Gorp, et al., 2010). It is interesting to speculate that the stable interaction between GP2/GP4 and CD163 occurs through SRCR 5. Additional viral glycoproteins, such as GP3 and GP5, may further stabilize the virus-receptor complex or may function as co-receptor molecules. The requirement for SRCR 5 was investigated in this study by infecting macrophages and pigs possessing the HL11m allele, which recreated the CD163L1 SRCR 8 domain swap by making 33 bp substitutions in porcine exon 7. The HL11m allele also included a neomycin cassette for selection of cells positive for the genetic modification (FIG. 17). The HL11m pigs expressed CD163 on PAMs, albeit at reduced levels compared to WT PAMs (FIG. 19, compare panels A and E). Reduced expression was likely due to the presence of the neomycin cassette, which was located between the exon 11 mimic and the following intron. HL11m pigs were not permissive for infection with a Type 1 virus, confirming the importance of SRCR 5. However, HL11m macrophages and HL11m pigs did support infection with Type 2 viruses. Based on virus titration and percent infection results, the PAMs from the HL11m pigs showed an overall decrease in permissiveness for virus compared to the WT macrophages (Table 15 and FIG. 17). Decreased permissiveness may be due to reduced levels of CD163 on the HL11m macrophages, combined with a reduced affinity of virus for the modified CD163 protein. Assuming that Type 2 viruses possesses a requirement of SRCR 5 and that L1 SRCR 8 can function as a suitable substitute, the lower affinity may be explained by the difference in peptide sequences between human SRCR 8 and porcine SRCR 5 (see FIG. 18, panel B). However, the reduced permissiveness of PAMs did not translate to the pig. Mean viremia for the HL11m pigs was not significantly different when compared to WT pigs (FIG. 23). In addition to PAMs, PRRSV infection of intravascular, septal and lymphoid tissue macrophages contribute to viremia (Lawson et al., 1997 and Morgan et al., 2014). The potential contributions of these and other CD163-positive cells populations in maintaining the overall virus load in HL11m pigs deserves further study.

Even though CD163 plasmids possessing deletions of SRCR domains are stably expressed in HEK cells (Van Gorp et al., 2010), the deletion of exons 7 and 8 in d7(1467) and d7(1280) resulted in a lack of detectable surface expression of CD163 (FIG. 19, panel D). Since the 2A10 mAB used for flow cytometry recognizes the three N-terminal SRCR domains (Van Gorp et al., 2010), and possibly the $7^{th}$ and $8^{th}$ domains (Sanchez, et al., 1999), the absence of detection was not due to the removal of a 2A10 epitope in the mutated proteins. While a small amount of CD163 expression could be detected on PAMs from some of the d7(129) pigs (see FIG. 19, panel C), the quantity of expressed protein was not sufficient to support PRRSV infection in PAMs or pigs. The absence of CD163 expression in the exon 7 and 8 deletion mutants is not fully understood, but is likely the result of mRNA and/or protein degradation.

In 2003, CD163 was identified as a receptor for African swine fever virus (ASFV; Sanchez-Torres et al., 2003). This conclusion was based on the observation that infected macrophages possess a mature CD163-positive phenotype, and anti-CD163 antibodies, such as 2A10, block ASFV infection of macrophages in vitro. It remains to be determined if CD163-null pigs are resistant to ASFV infection.

Cell culture models incorporating modifications to the PRRSV receptor have provided valuable insight into the mechanisms of PRRSV entry, replication and pathogenesis. One unique aspect of this study was the conduct of parallel experiment in vivo using receptor-modified pigs. This research has important impacts on the feasibility of developing preventative cures for one of the most serious diseases to ever face the global swine industry.

Examples disclosed herein are provided by way of exemplification and are not intended to limit the scope of the invention.

In view of the above, it will be seen that the several objects of the invention are achieved and other advantageous results attained.

As various changes could be made in the above products and methods without departing from the scope of the invention, it is intended that all matter contained in the above description and shown in the accompanying drawing[s] shall be interpreted as illustrative and not in a limiting sense.

REFERENCES

Allende R, et al., 1999. North American and European porcine reproductive and respiratory syndrome viruses differ in non-structural protein coding regions. J. Gen. Virol. 80: 307-315.

Bauer B K, et al., Arginine supplementation in vitro increases porcine embryo development and affects mRNA transcript expression. Reprod Fertil Dev 2011; 23:107.

Beaton B P, et al., Compound transgenics: recombinase-mediated gene stacking. In: Pinkert C A (ed.). Transgenic Animal Technology: A Laboratory Handbook, 3rd ed. Waltham, Mass.: Elsevier; 2014:565-578.

Benfield D A, et al., 1992. Characterization of swine infertility and respiratory syndrome (SIRS) virus (Isolate ATCC VR-2332). J Vet Diag Invest 4:127-133.

Boddicker, et al., 2014. Genome-wide association and genomic prediction for host response to porcine reproductive and respiratory syndrome virus infection. Genetics, selection, evolution: GSE 46, 18.

Borg N A, et al., CD1d-lipid-antigen recognition by the semi-invariant NKT T-cell receptor. Nature 2007; 448: 44-49.

Brinster R L, et al., Factors affecting the efficiency of introducing foreign DNA into mice by microinjecting eggs. Proc Natl Acad Sci USA 1985; 82:4438-4442.

Calvert J G, et al., 2007. CD163 expression confers susceptibility to porcine reproductive and respiratory syndrome viruses. J Virol. 81:7371-7379.

Carter D B, et al., Phenotyping of transgenic cloned piglets. Cloning Stem Cells 2002; 4:131-145.

Cong L, et al., Multiplex genome engineering using CRISPR/Cas systems. Science 2013; 339:819-823.

Dai Y, et al., Targeted disruption of the alpha1,3-galactosyltransferase gene in cloned pigs. Nat Biotechnol 2002; 20:251-255.

Das P B, et al., 2009. The minor envelope glycoproteins GP2a and GP4 of porcine reproductive and respiratory syndrome virus interact with the receptor CD163. J Virol. 84:1731-40.

Delputte P L, et al., 2002. Involvement of the matrix protein in attachment of porcine reproductive and respiratory syndrome virus to a heparin-like receptor on porcine alveolar macrophages. J Virol. 76:4312-4320.

Etzerodt, A., et al., 2013. Plasma clearance of hemoglobin and haptoglobin in mice and effect of CD163 gene targeting disruption. Antioxidants & redox signaling 18, 2254-2263.

Etzerodt, A., et al., 2013. CD163 and inflammation: biological, diagnostic, and therapeutic aspects. Antioxidants & redox signaling 18, 2352-2363.

Fabriek B O, et al., 2005. The macrophage scavenger receptor CD163. Immunobiology. 210:153-160.

Fabriek B O, et al., 2009. The macrophage scavenger receptor CD163 functions as an innate immune sensor for bacteria. Blood. 113:887-892.

Gaj T, et al., ZFN, TALEN, and CRISPR/Cas-based methods for genome engineering. Trends Biotechnol 2013; 31: 397-405.

Gaudreault N, et al., 2009. Factors affecting the permissiveness of porcine alveolar macrophages for porcine reproductive and respiratory syndrome virus. Archiv Virol. 154:133-136.

Graversen, J. H., et al., 2012. Targeting the hemoglobin scavenger receptor CD163 in macrophages highly increases the anti-inflammatory potency of dexamethasone. Molecular therapy: the journal of the American Society of Gene Therapy 20, 1550-1558.

Groenen, M. A., et al., 2012. Analyses of pig genomes provide insight into porcine demography and evolution. Nature 491, 393-398.

Hai T, et al., One-step generation of knockout pigs by zygote injection of CRISPR/Cas system. Cell Res 2014; 24: 372-375.

Halbur, P. G., et al., 1995. Comparison of the pathogenicity of two US porcine reproductive and respiratory syndrome virus isolates with that of the Lelystad virus. Veterinary pathology 32, 648-660.

Hammer R E, et al., Production of transgenic rabbits, sheep and pigs by microinjection. Nature 1985; 315:680-683.

Hauschild J, et al., Efficient generation of a biallelic knockout in pigs using zinc-finger nucleases. Proc Natl Acad Sci USA 2011; 108:12013-12017.

Holtkamp, D. J., et al., 2013. Assessment of the economic impact of porcine reproductive and respiratory syndrome virus on United States pork producers. Journal of Swine Health and Production 21, 72-84.

Hwang W Y, et al., Efficient genome editing in zebrafish using a knockout pigs via zinc-finger nucleases and nuclear transfer cloning. Cell Res 2011; 21:979-982.

Hwang W Y, et al., Efficient genome editing in zebrafish using a CRISPR-Cas system. Nat Biotechnol 2013; 31:227-229.

Jeney V, et al., 2002. Pro-oxidant and cytotoxic effects of circulating heme. Blood. 100:879-887.

Keffaber, K. K., 1989. Reproductive failure of unknown etiology. American Association of Swine Practitioners Newsletter 1, 1-10.

Kim, H. S., et al., 1993. Enhanced replication of porcine reproductive and respiratory syndrome (PRRS) virus in a homogeneous subpopulation of MA-104 cell line. Arch Virol 133, 477-483.

Kristiansen M, et al., 2001. Identification of the haemoglobin scavenger receptor. Nature. 409:198-201.

Kwon D N, et al., Production of biallelic CMP-Neu5Ac hydroxylase knock-out pigs. Sci Rep 2013; 3:1981.

Ladinig, A., et al., 2015. Pathogenicity of three type 2 porcine reproductive and respiratory syndrome virus strains in experimentally inoculated pregnant gilts. Virus Res 203, 24-35.

Lai L, et al., Production of alpha-1,3-galactosyltransferase knockout pigs by nuclear transfer cloning. Science 2002; 295:1089-1092.

Lai L, et al., Creating genetically modified pigs by using nuclear transfer. Reprod Biol Endocrinol 2003; 1:82.

Lai L, et al., Production of cloned pigs by using somatic cells as donors. Cloning Stem Cells 2003; 5:233-241.

Lawson S R, et al., 1997. Porcine reproductive and respiratory syndrome virus infection of gnotobiotic pigs: sites of virus replication and co-localization with MAC-387 staining at 21 days post-infection. Virus Res. 51:105-113.

Lee K, et al., Engraftment of human iPS cells and allogeneic porcine cells into pigs with inactivated RAG2 and accompanying severe combined immunodeficiency. Proc Natl Acad Sci USA 2014; 111:7260-7265.

Lee K, et al., Piglets produced from cloned blastocysts cultured in vitro with GM-CSF. Mol Reprod Dev 2013; 80: 145-154.

Li D, et al., Heritable gene targeting in the mouse and rat using a CRISPR-Cas system. Nat Biotechnol 2013; 31:681-683.

Lillico S G, et al., Live pigs produced from genome edited zygotes. Sci Rep 2013; 3:2847.

Machaty Z, et al., Complete activation of porcine oocytes induced by the sulfhydryl reagent, thimerosal. Biol Reprod 1997; 57:1123-1127.

Madsen M, et al., 2004. Molecular characterization of the haptoglobin-hemoglobin receptor CD163. Ligand binding properties of the scavenger receptor cysteine-rich domain region. J Biol Chem. 279:51561-51567.

Merck, The Merck Veterinary Manual. http://www.merck-manuals.com/vet/appendixes/reference_guides/normal_rectal_temperature_ranges.html.

Miao, Y. L., et al., 2009. Centrosome abnormalities during porcine oocyte aging. Environmental and molecular mutagenesis 50, 666-671.

Morgan S B, et al., 2014. Pathology and Virus Distribution in the Lung and Lymphoid Tissues of Pigs Experimentally Inoculated with Three Distinct Type 1 PRRS Virus Isolates of Varying Pathogenicity. Transbound Emerg Dis. November 10. pp 1-11.

Nelsen C J, et al., 1999. Porcine reproductive and respiratory syndrome virus comparison: divergent evolution on two continents. J. Virol. 73, 270-280.

Neumann E J, et al., Assessment of the economic impact of porcine reproductive and respiratory syndrome on swine production in the United States. J Am Vet Med Assoc 2005; 227:385-392.

Niu Y, et al., Generation of gene-modified Cynomolgus monkey via Cas9/RNA-mediated gene targeting in one-cell embryos. Cell 2014; 156:836-843.

Patience, J. F., et al., 1989. Swine Nutrition Guide, in: Center, P.S. (Ed.), University of Saskatchewan, Saskatoon, CA, pp. 149-171.

Patton J P, et al., 2008. Modulation of CD163 receptor expression and replication of porcine reproductive and respiratory syndrome virus in porcine macrophages. Virus Res. 140: 161-171.

Prather R S, et al., An intact sialoadhesin (Sn/SIGLEC1/CD169) is not required for attachment/internalization of the porcine reproductive and respiratory syndrome virus. J Virol 2013; 87:9538-9546.

Prather, R. S., et al., 2013. An intact sialoadhesin (Sn/SIGLEC1/CD169) is not required for attachment/internalization of the porcine reproductive and respiratory syndrome virus. J Virol 87, 9538-9546.

Provost C, et al., 2012. Identification of a new cell line permissive to porcine reproductive and respiratory syndrome virus infection and replication which is phenotypically distinct from MARC-145 cell line. Virol J. 9:267.

Reed J L, et al., 1938. A simple method of estimating fifty percent endpoints. The American Journal of Hygiene 27:493-497.

Ross J W, et al., Optimization of square-wave electroporation for transfection of porcine fetal fibroblasts. Transgenic Res 2010; 19:611-620.

Rowland, R. R., et al., 2012. Control of porcine reproductive and respiratory syndrome (PRRS) through genetic improvements in disease resistance and tolerance. Frontiers in genetics 3, 260.

Sanchez C, et al., 1999. The porcine 2A10 antigen is homologous to human CD163 and related to macrophage differentiation. Journal of Immunology 162:5230-5237.

Sanchez-Torres C, et al., 2003. Expression of porcine CD163 on monocytes/macrophages correlates with permissiveness to African swine fever infection. Arch Virol. 148:2307-2323.

Schaer, C. A., et al., 2006a. Constitutive endocytosis of CD163 mediates hemoglobin-heme uptake and determines the noninflammatory and protective transcriptional response of macrophages to hemoglobin. Circulation research 99, 943-950.

Schaer, D. J., et al., 2006b. CD163 is the macrophage scavenger receptor for native and chemically modified hemoglobins in the absence of haptoglobin. Blood 107, 373-380.

Schaer, D. J., et al., 2006c. Hemophagocytic macrophages constitute a major compartment of heme oxygenase expression in sepsis. European journal of haematology 77, 432-436.

Shanmukhappa, K, et al., 2007. Role of CD151, A tetraspanin, in porcine reproductive and respiratory syndrome virus infection. Virol J. 4:62.

Shimozawa N, et al., Abnormalities in cloned mice are not transmitted to the progeny. Genesis 2002; 34:203-207.

Smit, A F A, et al., RepeatMasker Open-3.0. 1996-2010. Current Version: open-4.0.5 (RMLib: 20140131 and Dfam: 1.2). http://www.repeatmasker.org>. CD163: accessed Jul. 25, 2014; CD1D: accessed Aug. 27, 2013.

Soares M P, et al., 2009. Heme oxygenase-1: from biology to therapeutic potential. Trends Mol Med. 15:50-58.

Stein M, et al., 1992. Interleukin 4 potently enhances murine macrophage mannose receptor activity: a marker of alternative immunologic macrophage activation. J Exp Med. 176:287-292.

Stephenson R, et al., 2015. Multiplex serology for common viral infections in feral pigs in Hawaii between 2007 and 2010. Accepted for publication. J Wildlife Dis 51:239-2343.

Sulahian T Hl, et al., 2002. 2002. Human monocytes express CD163, which is upregulated by IL-10 and identical to p155. Cytokine. 2000 12:1312-1321.

Terns M P, et al., CRISPR-based adaptive immune systems. Curr Opin Microbiol 2011; 14:321-327.

Trible, B. R., et al., 2012. Recognition of the different structural forms of the capsid protein determines the outcome following infection with porcine circovirus type 2. J Virol 86, 13508-13514.

U.S. Department of Agriculture and U.S. Department of Health and Human Services. Dietary Guidelines for Americans, 2010. 7th Edition, Van Breedam W, et al., Porcine reproductive and respiratory syndrome virus entry into the porcine macrophage. J Gen Virol 2010; 91:1659-1667.

Van Breedam, W., et al., 2010. Porcine reproductive and respiratory syndrome virus entry into the porcine macrophage. J Gen Virol 91, 1659-1667.

Van den Heuvel M M, et al., 1999. Regulation of CD163 on human macrophages: cross-linking of CD163 induces signaling and activation. J Leukoc Biol. 66:858-866.

van den Hoff M J, et al., Electroporation in 'intracellular' buffer increases cell survival. Nucleic Acids Res 1992; 20:2902.

Van Gorp, H., et al., 2010. Scavenger receptor CD163, a Jack-of-all-trades and potential target for cell-directed therapy. Mol Immunol 47, 1650-1660.

Van Gorp H, et al., 2010. Identification of the CD163 protein domains involved in infection of the porcine reproductive and respiratory syndrome virus. J Virol. 84:3101-3105.

Walters E M, et al., Advancing swine models for human health and diseases. Mo Med 2013; 110:212-215.

Wang H, et al., One-step generation of mice carrying mutations in multiple genes by CRISPR/Cas-mediated genome engineering. Cell 2013; 153: 910-918.

Welch S K, et al., 2010. A brief review of CD163 and its role in PRRSV infection. Virus Res. 154:98-103.

Wells, K. D., et al., 2014. Use of the CRISPR/Cas9 system to produce genetically engineered pigs from in vitro-derived oocytes and embryos. Biol Reprod 91,78.

Wensvoort, G., et al., 1991. Mystery swine disease in The Netherlands: the isolation of Lelystad virus. Veterinary Quarterly 13, 121-130.

Whitworth K M, et al., 2016. CD163 facilitates both entry and replication of porcine reproductive and respiratory syndrome virus. Nature Biotech. 34:20-22.

Whitworth K M, et al., Method of oocyte activation affects cloning efficiency in pigs. Mol Reprod Dev 2009; 76:490-500.

Whitworth K M, et al., Activation method does not alter abnormal placental gene expression and development in cloned pigs. Mol Reprod Dev 2010; 77:1016-1030.

Whitworth K M, et al., Scriptaid corrects gene expression of a few aberrantly reprogrammed transcripts in nuclear transfer pig blastocyst stage embryos. Cell Reprogram 2011; 13:191-204.

Whitworth, K. M., et al., 2014. Use of the CRISPR/Cas9 system to produce genetically engineered pigs from in vitro-derived oocytes and embryos. Biol Reprod 91,78.

Whyte J J, et al., Genetic modifications of pigs for medicine and agriculture. Mol Reprod Dev 2011; 78:879-891.

Whyte J J, et al., Gene targeting with zinc finger nucleases to produce cloned eGFP knockout pigs. Mol Reprod Dev 2011; 78:2.

Wiedenheft B, et al., RNA-guided genetic silencing systems in bacteria and archaea. Nature 2012; 482:331-338.

Winckler, C., et al., 2001. The reliability and repeatability of a lameness scoring system for use as an indicator of welfare in dairy cattle. Acta Agricultura Scandinavica Section A. Animal Science, 103-107.

Yang D, et al., Generation of PPARgamma mono-allelic knockout pigs via zinc-finger nucleases and nuclear transfer cloning. Cell Res 2011; 21:979-982.

Yoshioka K, et al., Birth of piglets derived from porcine zygotes cultured in a chemically defined medium. Biol Reprod 2002; 66:112-119.

Zhang Q, et al., 2015. PRRS virus receptors and their role for pathogenesis. Vet Microbiol. 177:229-241.

Zhao J, et al., Histone deacetylase inhibitors improve in vitro and in vivo developmental competence of somatic cell nuclear transfer porcine embryos. Cell Reprogram 2010; 12:75-83.

Zhao J, et al., Significant improvement in cloning efficiency of an inbred miniature pig by histone deacetylase inhibitor treatment after somatic cell nuclear transfer. Biol Reprod 2009; 81:525-530.

TABLE OF SEQUENCES

| SEQ | TYPE | DESCRIPTION |
| --- | --- | --- |
| SEQ ID NO: 1 | nucleotide | CRISPR 10 |
| SEQ ID NO: 2 | nucleotide | CRISPR 131 |
| SEQ ID NO: 3 | nucleotide | CRISPR 256 |
| SEQ ID NO: 4 | nucleotide | CRISPR 282 |
| SEQ ID NO: 5 | nucleotide | CRISPR 4800 |
| SEQ ID NO: 6 | nucleotide | CRISPR 5620 |
| SEQ ID NO: 7 | nucleotide | CRISPR 5626 |
| SEQ ID NO: 8 | nucleotide | CRISPR 5350 |
| SEQ ID NO: 9 | nucleotide | eGFP1 |
| SEQ ID NO: 10 | nucleotide | eGFP2 |
| SEQ ID NO: 11 | nucleotide | forward primer 9538 fragment |
| SEQ ID NO: 12 | nucleotide | reverse primer 9538 fragment |
| SEQ ID NO: 13 | nucleotide | forward primer 8729 fragment |
| SEQ ID NO: 14 | nucleotide | forward primer 8729 fragment |
| SEQ ID NO: 15 | nucleotide | WILD TYPE CD163 |
| SEQ ID NO: 16 | nucleotide | FIG. 4, panel C WT |
| SEQ ID NO: 17 | nucleotide | FIG. 4, panel C #1 |
| SEQ ID NO: 18 | nucleotide | FIG. 4, panel C #2 |

TABLE OF SEQUENCES

Figure 5:
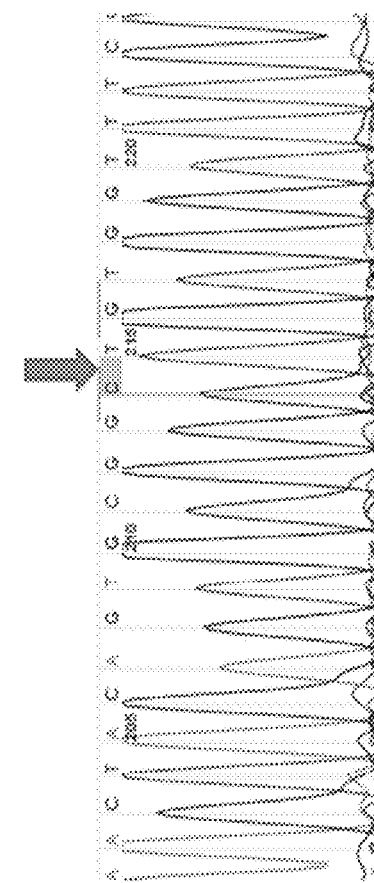
FIG. 5. Effect of CRISPR/Cas9 system in targeting CD163 in porcine embryos. A) Examples of mutations generated on CD163 by the CRISPR/Cas9 system: WT genotype (SEQ ID NO:20), #1-1 (SEQ ID NO:21), #1-4 (SEQ ID NO:22), and #2-2 (SEQ ID NO:23). All the embryos examined by DNA sequencing showed mutation on the CD163 (18/18). CRISPR 131 is highlighted in bold. B) Sequencing read of a homozygous deletion caused by the CRISPR/Cas9 system. The image represents #1-4 from panel A carrying a 2 bp deletion of CD163.
Figure 6:
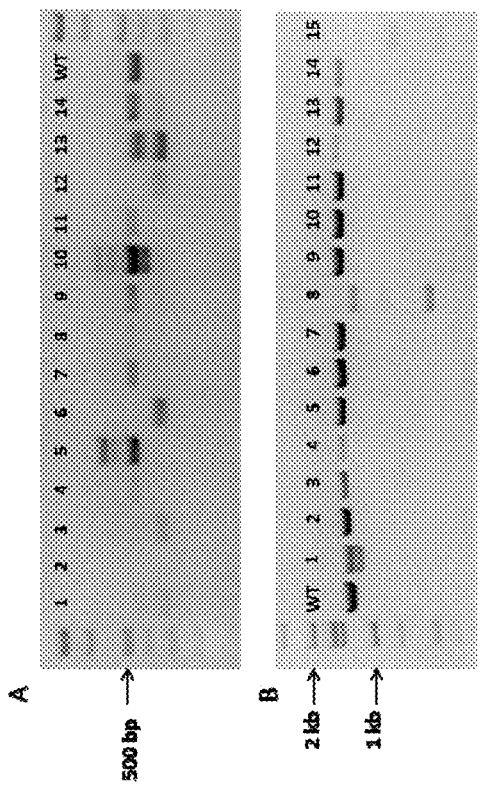
FIG. 6. Effect of CRISPR/Cas9 system when introduced with two types of CRISPRs. A) PCR amplification of CD163 in blastocysts injected with CRISPR/Cas9 as zygotes. Lanes 1, 3, 6, and 12 show the designed deletion between two different CRISPRs. B) PCR amplification of CD1D in blastocysts injected with CRISPR/Cas9 as zygotes. CD1D had a lower frequency of deletion as determined by gel electrophoresis when compared to CD163 (3/23); lanes 1, 8, and 15 show obvious deletions in CD1D. C) CRISPR/Cas9 system successfully targeted two genes when the system was provided with two CRISPRs targeting CD163 and eGFP. The modifications of CD163 and eGFP are shown: CD163 WT (SEQ ID NO:24), CD163 #1 (SEQ ID NO:25), CD163 #2 (SEQ ID NO:26), CD163 #3 (SEQ ID NO:27), eGFP WT (SEQ ID NO:28), eGFP #1-1 (SEQ ID NO:29), eGFP #1-2 (SEQ ID NO: 30), eGFP #2 (SEQ ID NO:31), and eGFP #3 (SEQ ID NO:32).

| SEQ | TYPE | DESCRIPTION |
|---|---|---|
| SEQ ID NO: 19 | nucleotide | FIG. 4, panel C #3 |
| SEQ ID NO: 20 | nucleotide | FIG. 5, panel A WT |
| SEQ ID NO: 21 | nucleotide | FIG. 5, panel A #1-1 |
| SEQ ID NO: 22 | nucleotide | FIG. 5, panel A #1-4 |
| SEQ ID NO: 23 | nucleotide | FIG. 5, panel A #2-2 |
| SEQ ID NO: 24 | nucleotide | FIG. 6, panel C CD163 WT |
| SEQ ID NO: 25 | nucleotide | FIG. 6, panel C CD163 #1 |
| SEQ ID NO: 26 | nucleotide | FIG. 6, panel C CD163 #2 |
| SEQ ID NO: 27 | nucleotide | FIG. 6, panel C CD163 #3 |
| SEQ ID NO: 28 | nucleotide | FIG. 6, panel C eGFP WT |
| SEQ ID NO: 29 | nucleotide | FIG. 6, panel C eGFP #1-1 |
| SEQ ID NO: 30 | nucleotide | FIG. 6, panel C eGFP #1-2 |
| SEQ ID NO: 31 | nucleotide | FIG. 6, panel C eGFP #2 |
| SEQ ID NO: 32 | nucleotide | FIG. 6, panel C eGFP #3 |
| SEQ ID NO: 33 | nucleotide | FIG. 7, panel C WT |
| SEQ ID NO: 34 | nucleotide | FIG. 7, panel C #67-1 |
| SEQ ID NO: 35 | nucleotide | FIG. 7, panel C #67-2 a1 |
| SEQ ID NO: 36 | nucleotide | FIG. 7, panel C #67-2 a2 |
| SEQ ID NO: 37 | nucleotide | FIG. 7, panel C #67-3 |
| SEQ ID NO: 38 | nucleotide | FIG. 7, panel C #67-4 a1 |
| SEQ ID NO: 39 | nucleotide | FIG. 7, panel C #67-4 a2 |
| SEQ ID NO: 40 | nucleotide | FIG. 8, panel D WT |
| SEQ ID NO: 41 | nucleotide | FIG. 8, panel D #166-1.1 |
| SEQ ID NO: 42 | nucleotide | FIG. 8, panel D #166-1.2 |
| SEQ ID NO: 43 | nucleotide | FIG. 8, panel D #166-2 |
| SEQ ID NO: 44 | nucleotide | FIG. 8, panel D #166-3.1 |
| SEQ ID NO: 45 | nucleotide | FIG. 8, panel D #166-3.2 |
| SEQ ID NO: 46 | nucleotide | FIG. 8, panel D #166-4 |
| SEQ ID NO: 47 | nucleotide | FIG. 16 WT CD163 partial |
| SEQ ID NOs. 48-67 | nucleotide | Primer sequences (Table 1) |
| SEQ ID NOs. 68-79 | nucleotide | Primer sequences (Table 2) |
| SEQ ID NOs. 80-85 | nucleotide | Primer sequences (Table 3) |
| SEQ ID NOs. 86-97 | nucleotide | Primer sequences (Table 4) |
| SEQ ID NO: 98 | nucleotide | Allele with 1506 bp deletion |
| SEQ ID NO: 99 | nucleotide | Allele with 7 bp insertion |
| SEQ ID NO: 100 | nucleotide | Allele with 1280 bp deletion |
| SEQ ID NO: 101 | nucleotide | Allele with 1373 bp deletion |
| SEQ ID NO: 102 | nucleotide | Allele with 11 bp deletion |
| SEQ ID NO: 103 | nucleotide | Allele with 2 bp insertion & 377 bp deletion |
| SEQ ID NO: 104 | nucleotide | Allele with 124 bp deletion |
| SEQ ID NO: 105 | nucleotide | Allele with 123 bp deletion |
| SEQ ID NO: 106 | nucleotide | Allele with 1 bp insertion |
| SEQ ID NO: 107 | nucleotide | Allele with 130 bp deletion |
| SEQ ID NO: 108 | nucleotide | Allele with 132 bp deletion |
| SEQ ID NO: 109 | nucleotide | Allele with 1467 bp deletion |
| SEQ ID NO: 110 | nucleotide | Allele with 1930 bp deletion in exon 6, 129 bp deletion in exon 7, and 12 bp insertion |
| SEQ ID NO: 111 | nucleotide | Allele with 28 bp deletion |
| SEQ ID NO: 112 | nucleotide | Allele with 1387 bp deletion |
| SEQ ID NO: 113 | nucleotide | Allele with 1382 bp deletion & 11 bp insertion |
| SEQ ID NO: 114 | nucleotide | Allele with 1720 bp deletion |
| SEQ ID NO: 115 | nucleotide | Inserted sequence for SEQ. 99 |
| SEQ ID NO: 116 | nucleotide | Inserted sequence for SEQ.110 |
| SEQ ID NO: 117 | nucleotide | Inserted sequence for SEQ.113 |
| SEQ ID NO: 118 | nucleotide | Domain swap sequence |
| SEQ ID NO: 119 | nucleotide | Allele with 452 bp deletion |
| SEQ ID NO: 120 | peptide | Porcine CD163 SRCR 5 |
| SEQ ID NO: 121 | peptide | Human CD163L1 SRCR 8 homolog |

What is claimed is:

1. A porcine animal or offspring thereof or a porcine cell comprising a modified chromosomal sequence in at least one allele of a gene encoding a CD163 protein, wherein the modified chromosomal sequence in the at least one allele comprises a deletion and the deletion consists of
  an 11 base pair deletion from nucleotide 3,137 to nucleotide 3,147 as compared to reference sequence SEQ ID NO: 47.

2. The animal, offspring, or cell of claim 1, wherein the modification reduces the susceptibility of the animal, offspring, or cell to infection by a virus, as compared to the susceptibility of an animal, offspring, or cell that does not comprise a modified chromosomal sequence in a gene encoding a CD163 protein to infection by the virus.

3. The animal, offspring, or cell of claim 2, wherein the virus comprises a porcine reproductive and respiratory syndrome virus (PRRSV).

4. The animal, offspring, or cell of claim 3, wherein the modification reduces the susceptibility of the animal, offspring, or cell to a Type 1 PRRSV virus, a Type 2 PRRSV, or to both Type 1 and Type 2 PRRSV viruses.

5. The animal, offspring, or cell of claim 4, wherein the modification reduces the susceptibility of the animal, offspring or cell to a PRRSV isolate selected from the group consisting of NVSL 97-7895, KS06-72109, P129, VR2332, CO90, AZ25, MLV-ResPRRS, KS62-06274, KS483 (SD23983), CO84, SD13-15, Lelystad, 03-1059, 03-1060, SD01-08, 4353PZ, and combinations of any thereof.

6. The animal, offspring, or cell of claim 1, wherein the animal or offspring comprises a genetically edited animal or offspring or wherein the cell comprises a genetically edited cell.

7. The animal, offspring, or cell of claim 6, wherein the animal or cell has been genetically edited using a designed homing endonuclease, wherein the homing endonuclease comprises a Clustered Regularly Interspaced Short Palindromic Repeats (CRISPR)/Cas system, a Transcription Activator-Like Effector Nuclease (TALEN), a Zinc Finger Nuclease (ZFN), a recombinase fusion protein, a meganuclease, or a combination thereof.

8. The animal, offspring, or cell of claim 7, wherein the animal or cell has been genetically edited using a CRISPR/Cas system.

9. The animal, offspring, or cell of claim 8, wherein the CRISPR/Cas system comprises a CRISPR/Cas9 system.

10. The animal, offspring, or cell of claim 8, wherein said edited animal, offspring, or cell displays increased resistance to PRRSV as compared to a non-edited animal.

11. The animal, offspring, or cell of claim 1, wherein the deletion causes CD163 protein production or activity to be reduced, as compared to CD163 protein production or activity in an animal, offspring, or cell that lacks the deletion.

12. The animal, offspring, or cell of claim 1, wherein the deletion results in production of substantially no functional CD163 protein by the animal, offspring, or cell.

13. The porcine animal, offspring, or cell of claim 1, wherein the animal, offspring, or cell comprises a chromosomal sequence having at least 80% sequence identity to SEQ ID NO: 47 in the regions of said chromosomal sequence outside of the deletion.

14. The cell of claim 1.

15. The cell of claim 14, wherein said cell is a sperm cell.

16. The cell of claim 14, wherein said cell is an egg cell.

17. The cell of claim 16, wherein said egg cell is a fertilized egg.

18. The cell of claim 14, wherein said cell is a somatic cell.

19. The cell of claim 18, wherein the somatic cell comprises a fibroblast.

20. The cell of claim 19, wherein the fibroblast comprises a fetal fibroblast.

21. The non-human animal of claim 1.

22. The offspring of claim 1.

23. The animal, offspring, or cell of claim 1, comprising a chromosomal sequence comprising SEQ ID NO: 102.

24. The animal, offspring, or cell of claim 1, wherein the animal or offspring is a juvenile or an adult or wherein the cell comprises a cell derived from a juvenile animal or a cell derived from an adult animal.

25. The animal, offspring, or cell of claim 1, wherein the animal or offspring is an embryo or where the cell comprises an embryonic cell.

26. The animal, offspring, or cell of claim 1, wherein the animal, offspring, or cell is heterozygous for the modified chromosomal sequence.

27. The animal, offspring, or cell of claim 25, wherein the embryo or the embryonic cell is heterozygous for the modified chromosomal sequence.

28. The animal, offspring, or cell of claim 1, wherein the animal, offspring, or cell is homozygous for the modified chromosomal sequence.

29. The animal, offspring, or cell of claim 1, wherein the animal, offspring, or cell comprises:
the 11 base pair deletion from nucleotide 3,137 to nucleotide 3,147 as compared to reference sequence SEQ ID NO: 47 in one allele of the gene encoding the CD163 protein; and
an insertion in the other allele of the gene encoding the CD163 protein, the insertion consisting of a 7 base pair insertion between nucleotide 3,148 and nucleotide 3,149 as compared to reference sequence SEQ ID NO: 47.

30. The animal, offspring, or cell of claim 29, wherein the 7 base pair insertion between nucleotide 3,148 and nucleotide 3,149 as compared to reference sequence SEQ ID NO: 47 consists of the sequence TACTACT (SEQ ID NO: 115).

31. The animal, offspring, or cell of claim 1, wherein the animal, offspring, or cell comprises:
the 11 base pair deletion from nucleotide 3,137 to nucleotide 3,147 as compared to reference sequence SEQ ID NO: 47 in one allele of the gene encoding the CD163 protein; and
a deletion in the other allele of the gene encoding the CD163 protein, the deletion consisting of a 1280 base pair deletion from nucleotide 2,818 to nucleotide 4,097 as compared to reference sequence SEQ ID NO: 47.

32. The animal, offspring, or cell of claim 1, wherein the animal, offspring, or cell comprises:
the 11 base pair deletion from nucleotide 3,137 to nucleotide 3,147 as compared to reference sequence SEQ ID NO: 47 in one allele of the gene encoding the CD163 protein; and
deletions in the other allele of the gene encoding the CD163 protein, the deletions consisting of:
a 1930 base pair deletion from nucleotide 488 to nucleotide 2,417 as compared to reference sequence SEQ ID NO: 47, wherein the deleted sequence is replaced with a 12 base pair insertion beginning at nucleotide 488; and
a 129 base pair deletion in exon 7 from nucleotide 3,044 to nucleotide 3,172 as compared to reference sequence SEQ ID NO: 47.

33. The animal, offspring, or cell of claim 32, wherein the 12 base pair insertion beginning at nucleotide 488 consists of the sequence TGTGGAGAATTC (SEQ ID NO: 116).

34. The animal, offspring, or cell of claim 1, wherein the animal, offspring, or cell comprises:
the 11 base pair deletion from nucleotide 3,137 to nucleotide 3,147 as compared to reference sequence SEQ ID NO: 47 in one allele of the gene encoding the CD163 protein; and
a deletion in the other allele of the gene encoding the CD163 protein, the deletion consisting of a 1467 base pair deletion from nucleotide 2,431 to nucleotide 3,897 as compared to reference sequence SEQ ID NO: 47 in the other allele of the gene encoding the CD163 protein.

35. The animal, offspring, or cell of claim 1, wherein the animal, offspring, or cell comprises:
the 11 base pair deletion from nucleotide 3,137 to nucleotide 3,147 as compared to reference sequence SEQ ID NO: 47 in one allele of the gene encoding the CD163 protein; and
an insertion and a deletion in the other allele of the gene encoding the CD163 protein, the insertion consisting of a 2 base pair insertion between nucleotides 3,149 and 3,150 as compared to reference sequence SEQ ID NO: 47 and the deletion consisting of a 377 base pair deletion from nucleotide 2,573 to nucleotide 2,949 as compared to reference sequence SEQ ID NO: 47.

36. The animal, offspring, or cell of claim 35, wherein the 2 base pair insertion between nucleotides 3,149 and 3,150 as compared to reference sequence SEQ ID NO: 47 consists of the dinucleotide AG.

* * * * *

SEQUENCE LISTING

```
<160> NUMBER OF SEQ ID NOS: 121

<210> SEQ ID NO 1
<211> LENGTH: 23
<212> TYPE: DNA
<213> ORGANISM: Sus scrofa

<400> SEQUENCE: 1
ggaaacccag gctggttgga ggg                                              23

<210> SEQ ID NO 2
<211> LENGTH: 23
<212> TYPE: DNA
<213> ORGANISM: Sus scrofa

<400> SEQUENCE: 2
ggaactacag tgcggcactg tgg                                              23

<210> SEQ ID NO 3
<211> LENGTH: 23
<212> TYPE: DNA
<213> ORGANISM: Sus scrofa

<400> SEQUENCE: 3
cagtagcacc ccgccctgac ggg                                              23

<210> SEQ ID NO 4
<211> LENGTH: 23
<212> TYPE: DNA
<213> ORGANISM: Sus scrofa

<400> SEQUENCE: 4
```

-continued tgtagccaca gcagggacgt cgg                                          23

<210> SEQ ID NO 5
<211> LENGTH: 23
<212> TYPE: DNA
<213> ORGANISM: Sus scrofa

<400> SEQUENCE: 5
ccagcctcgc ccagcgacat ggg                                          23

<210> SEQ ID NO 6
<211> LENGTH: 23
<212> TYPE: DNA
<213> ORGANISM: Sus scrofa

<400> SEQUENCE: 6
ctttcattta tctgaactca ggg                                          23

<210> SEQ ID NO 7
<211> LENGTH: 23
<212> TYPE: DNA
<213> ORGANISM: Sus scrofa

<400> SEQUENCE: 7
ttatctgaac tcagggtccc cgg                                          23

<210> SEQ ID NO 8
<211> LENGTH: 23
<212> TYPE: DNA
<213> ORGANISM: Sus scrofa

<400> SEQUENCE: 8
cagctgcagc atatatttaa ggg                                          23

<210> SEQ ID NO 9
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 9
ctcctcgccc ttgctcacca tgg                                          23

<210> SEQ ID NO 10
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 10
gaccaggatg ggcaccaccc cgg                                          23

<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
ctctccctca ctctaaccta ctt                                          23

```
<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
tatttctctc acatggccag tc                                          22

<210> SEQ ID NO 13
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 13
ctctccctca ctctaaccta ctt                                         23

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
gactggccat gtgagagaaa ta                                          22

<210> SEQ ID NO 15
<211> LENGTH: 27767
<212> TYPE: DNA
<213> ORGANISM: Sus scrofa

<400> SEQUENCE: 15
atacaagtgc cttttacaga caatctgcac aagttatttg ttagacatat ttgattatag      60
aattaatatt aaaagggggtt ataacaatca agcattgata atttaattat gtttgcctat    120
tttactttag ttttttgaca taactgtgta actattgcga tttttttatt cctaatgtaa    180
ttagttcaaa acaaagtgca gaaatttaaa atattcaatt caacaacagt atataagtca    240
atattccccc cttaaatttt tacaaatctt tagggagtgt ttctcaattt ctcaatttct    300
ttggttgttt catgtcccat atggaagaaa acatgggtgt gaaagggaag cttactcttt    360
tgattacttc ccttttctgg ttgactccac ctccattatg aagcctttct gtattttgt     420 ggaagtgaaa tgatttttag aattcttagt ggttctcttc ttcaggagaa catttctagg    480
taataataca agaagattta aatggcataa aaccttggaa tggacaaact cagaatggtg    540
ctacatgaaa actctggatc tgcaggtaaa atcttctcat ttattctata tttaccttt     600 aaatagagtg tagcaatatt ccgacagtca atcaatctga tttaatagtg attggcatct    660
ggagaagaag taacagggaa aaaggcaata agctttataa ggggaacttt tatcttccat    720
agactcaaaa ttgaagacgt gactagaaga ttgctagatt tggcatcagt tttgtaaaat    780
tgctgaggtg aaattaagta aagggatgaaa attaactaaa ttgtgttgag tatgaaacta    840
gtagttgtta gaaaagatag aacatgaagg aatgaatatt gattgaaagt tgatgaccta    900
gaggacattt agactaacac ctctgagtgt caaagtctaa tttatgattt acatcgatgc    960
gttaaactca tttaacattc ttactttttt ccctcaagc atttaagctg aagtataaca    1020
tttcacatga aagcctggat tataaaatgca cagttcagtg acctatctca gaggagtgac    1080
```

```
tgccatagca ttttttttgt cttttttgcct tcagagccac agcaacgcgg gatccgaagc   1140
cgcgtctgcg acccacacca cagctcacgg caatgccgga tctttaaccc actgagcgag   1200
gccggggatc gaacccgcag tctcatggtt cctagtagga ttcgttaacc actgcgccac   1260
gacgggaact cctaccatag cattttttact tttaagttac tgttggttta gagtaagaag   1320
gagaaatgag agtgatggag cgtttgctat atttggagac aaggtcctat attggaggtt   1380
ctcaaatata aattttgtcg cttttttcctc caatgtattg ttcaactact atttagcagg   1440
ccactgtgcc aggtactggt gaaactggtg aacatgatag atgtaattca ttccctcatg   1500
gaactttcca tctaacaatg tggatcaggt aggcttggag atgagaatgc cagtggttga   1560
ctatgactct gtggctgaag ggagagctac tcacttcgta gtttcatcaa tgtcttttttg   1620 gttttccagg ttttaagccc tgctcttgca attcttttcc cttctccaac tttcttctaa   1680
tttctcaccc ctaggatgcc tataaacatg agtattttca aagctacttc actgaggtta   1740
tatgatcctg gtgtgaattt ttcctgcctg acttgccatt tagaaggaag tgtttcctgg   1800
aatttccatt gtggcttggt ggttaaagac cctgcattgt ctctgtgagg atgtgggttc   1860
aatctctggc tcattcagt gagtgggtta aggatctggt gtcgctgcaa gctgtggcta   1920
agatcccaca ttgccatgtc tgtggtgtag actggcacct ggagctctga tttgaccaca   1980
atcttaggaa cttcagatgt ggccataaaa aggaaaaaaa agttaggaag gttttctgt   2040 cttgtttgga ccttcgttaa tctcaaacct ttggaaccat ctctcctcca aaacctcctt   2100
tgggtaagac tgtatgtttg ccctctctct tcttttcgca gactttagaa gatgttctgc   2160
ccatttaagt tccttcactt tggctgtagt cgctgttctc agtgcctgct tggtcactag   2220
ttctcttggt gagtactttg acaaatttac ttgtaaccga gcccaactgt gacaagaaac   2280
actgaaaagc aaataattgc tcctgaagtc tagatagcat ctaaaaacat gcttcatggt   2340
ttcaaggatc atatattgaa accccaggga tcctctagag tcgacctgca gcatgcaggg   2400
gggggggggg gggggggggg gggggggggg gggggggggg gggggggggg gggggggggg   2460
gggggggggg gggggggggg gggggggggg ggggggggg gtgcataagg aaagactatc   2520
tcaacgtctt attcctcagc ttacattaga tttgaaactc tagtcaccta aaatgcaaat   2580
ctcatttact taccatcaga gatattaatg acctatagaa ttcagcataa ataaagtttc   2640
atgtatggat attagcttat ggttctagtc actgctaatt gaaacctgtg atattgctgt   2700 ttgtttttgac tcctatgaaa taacattctc ccattgtacc atggatgggt ccagaaacat   2760
ttctcaaatc ctggcttgaa aaaataaata agtaatctaa agaataataa ttctctactt   2820
gctctttgaa tcttgaccaa ttgctgcatt tacctattgt tacaggagga aaagacaagg   2880
agctgaggct aacgggtggt gaaaacaagt gctctggaag agtggaggtg aaagtgcagg   2940
aggagtgggg aactgtgtgt aataatggct gggacatgga tgtggtctct gttgtttgta   3000
ggcagctggg atgtccaact gctatcaaag ccactggatg ggctaatttt agtgcaggtt   3060
ctggacgcat ttggatggat catgtttctt gtcgagggaa tgagtcagct ctctgggact   3120
gcaaacatga tggatgggga aagcataact gtactcacca acaggatgct ggagtaacct   3180
gctcaggtaa gacatacaca aataagtcaa gcctatacat gaaatgcttt gtgggaaaaa   3240
atgtatagat gagttaaaaa caaaaggaa ccagttttct ataagtcatc tagtccatgt   3300
ataaaattac ccaatccatt actaaaagac cacttctggt attttacaca tgacaaagcc   3360
catattaaaa aaaaaaaatt cagaagagat tctgaatgct ataataaatg agcaagtgac   3420
```

-continued

```
tagcttcaat tttatattag gtcattctac cttctacttc tacatgaaaa tatcataatg    3480
tctaagttaa ttccttgtcc cctttcccaa taaagcactg ctttcatgca ctggcctatg    3540
aatcatgaac ttttttgccct ttaactgatg atcaacttac caaatcaaga aataaatatt    3600
cttagcactg atccttttt gttgttgttg gaggaagaat gttttgcaaa gtagaattgc    3660
ttttttctgt ttaacagtgc tattcatttc atttacatgg tcgttttaat ttataaaaca    3720
tttcataagt ttcacctcat atgcccttac aataactcag gaagttatat gttagacctt    3780
tctgctgaca aatcccagag tcatgtttct gacccagttc agattccttg gcttcccatt    3840
tctctttgct catgtcattg acctttatgc agccctctta cctcccacct ttctattaca    3900
gaccatctcc tccataggac tggtgttaga aagtactaat ctctacccag gcattgtggt    3960
gcaatgtggg cagcacaggc tggtatctag aaaaatgctg aagtgaattc cagctcagct    4020
gctcgttaat actatcgttt taagtaagct gttcaatcct ttgaaattca ctttctgagc    4080
actcagtgat ataataaatg tagagctact ggtacactgt ctggtatgta ataggtgtta    4140
ccaattaacc ttagtttcct catgggtcac tggttctcat acctagaca actcatttct    4200
ctttcttcct ctttctcttt ctccattctc ctcctcttc ttcctcttct tcttgtctgt    4260
tattgttata tcattttgct gagaaagtta agaaataaca actctaacct ctacatcgac    4320
cacctagagc aaagttaaaa ataataataa accttgccag actcttacta taattgttgc    4380
tgtctataga gttgactgtt taagttaaga catcagtata tattttaat ttttgtgttt    4440
ttttttcat acttttacat gaggatcctt tataaagga tgagttaaac aaacttgatt    4500
tttgaagttt ataccccctga ggctcaactg cataataata gaaagggatc catagcctct    4560
caaggactta actagtttca tgagttttca gaatctgaat ttctgagatt ctccaccca    4620
attaaagctc aagcctcaga acatatatcc ttctcttggt aaattctatt cttatcacat    4680
gcgtaataat aaaaaagaga gatgttggag acagattttt ttcctcacat tctgtctcta    4740
ctgttttcta ggtgtttgat tctgtgttat ttaacctcag tttgcttatc tgtgaagtag    4800
ggattatggt aataacatat aatgctttat gttgtaaaga ctaaagaaga tagcatatgt    4860
aacacatttg gaacagggaa tgcatatttt gattgtgagc tcttattatt attaccattc    4920
agccctaata aaaatcttgg taagtggaag gctttggatt tcagaacttt taaaatctaa    4980
ttacttttttc aaaaagaaac ttcctagggt tttttttttt taaccacaaa gtgtttctat    5040
tttttaggtg tcccaaaatt tcgttccaaa tatcttttc tcagatattt tagtcctcat    5100
agaacaccta gggatagtgg atagagaaaa ttttctttat taaaaagctg ttctttgcta    5160
aaaattgtag caggtacttt tgggaggggg gaaaactttg attcagaaac tgctaagaca    5220
tggagtgttt tgactaattt ttcctcaatt tttaatgttt tttataccat agggtacttt    5280
tgcaaactat tatgcatact tatatatttt tacttttttc ctgtcttta acttccaaat    5340
tcaacttcag acaattattc atgcactaaa ctgtttgtag taagaaagat taaaattaaa    5400
aaattaacca ttcaacaaat gactggtttg ccatttttac tactttgttg tatgaacaat    5460
ttttttttct acaaatgaat actttgagtc tgatttatcc attcctacat aaaagttttt    5520
actatatctt agtattggaa ggaaacaaaa caaaacacaa tgtaaattt aatctataaa    5580
ttttgggggg gtaaatatac atagatgaaa gtcttaacca ttaattagag tcaaaagatt    5640
aaaattctcc aatatgtgaa cttaggctgc atccaaaatg aagcatcatt tttaaggaca    5700
gcatcaaaag tgaccagagg aattttactt tctttctttt tttttttttt gaatttagt    5760
ttctaaactc acttctgaat aaatacaact tctaaattct cgtctttct ctactctaga    5820
```

```
tggatctgat ttagagatga ggctggtgaa tggaggaaac cggtgcttag gaagaataga    5880
agtcaaattt caaggaacgt ggggaacagt gtgtgatgat cacttcaaca taaatcatgc    5940
ttctgtggtt tgtaaacaac ttgaatgtgg aagtgctgtc agtttctctg gttcagctaa    6000
ttttggagaa ggttctggac caatctggtt tgatgatctt gtatgcaatg gaaatgagtc    6060
agctctctgg aactgcaaac atgaaggatg gggaaagcac aattgcgatc atgctgagga    6120
tgctggagtg atttgcttaa gtaaggactg acctgggttt gttctgttct ccatgagagg    6180
gcaaaaaaag gggagtaaaa gtcttaaaag ctcaaactgt taaaaacata atgatgattg    6240
cttcttttat catcttatta ttatctaatt tcaggtcgaa attctagtac ctgtgcagtt    6300
ttttacctta actgaaatta agataaatag gatagggagg aaggatgagc agtgacattt    6360
aggtccaagt catgaggtta gaaggaaatg ttcagagaat agcccattcc ctcagccctc    6420
aaagaaagaa agaaagaaaa agaaaaaaaa aagaaagct taactagaaa attttgttct    6480
ctggatgttt tagaggcaaa ccatcccttt atcattccta cctacaaagc cttctcttaa    6540
tcacattacc cacccttttcc tactatagtc agggggggggg ggggggggggg ggggggggggg    6600 gggggggggg gggggggggg gggggggggg gggggggggg gggggggggg gggggggggg    6660
gggggggggg gtgaaaaaag aaccaaacaa tttcaacaaa aaaccaaaca attccaacaa    6720
aattggtcca ataagcaaac ctctagataa atttcagtgc cctggatgtt ttgttaggaa    6780
ctcttcctac aatgcgtgct ttccattctg aaaagtccta tctacttgcc tgatccactt    6840
ctccttccat cctaaacgat tttcagtggt agtatattac tgttgtctct gtctctactt    6900
atatatcttc cccttttcac tcactcctct caggtacagc tcttcagttt gcccttattc    6960
ttgtttcctt gtcaatgact tgttttgtgt ccctcttaca gatggagcag acctgaaact    7020
gagagtggta gatggagtca ctgaatgttc aggaagattg gaagtgaaat tccaaggaga    7080
atggggaaca atctgtgatg atggctggga tagtgatgat gccgctgtgg catgtaagca    7140
actgggaggt ccaactgctg tcactgccat tgtcgagtta acgccagtga gggactggac    7200
acattggctc acacacatac agccatgaca cgatctgctc tatggtccga tgattaaagg    7260
gggggggggg gggggggggg gggggggggg gggggggggg gggggggggg gggggggggg    7320
gggggggggg gggggggggg gggggggggg ggggggggag aagagctggt ggacatttct    7380
ggaaaggaac caaacccgg aagggccttg ttcttcagga tttgggatgg attggggagg    7440
gagaaaattg tttctaatat ttccttggtgg gaattctttt acagttgtga caaatctttc    7500
acatattctt catttgagta gtttggaggg ttgtctgact gttttctata ataaatgtcc    7560
caagtgctat gaggtaccac atttcaaatt ctaattctac ctgaagctcc aaaaagacaa    7620
aatgttatag gtcttttctt tatatctaat ttgcttatgg ttttagcca ttgacaattt    7680 tttttttctta actcttgaaa ctataacct atttctaacc aaattcatgt tctatactgg    7740
ctcttcaaaa acccaggaga tgggaaagcc agaatctcca gtgtttcagc ttctgggaag    7800
gagcaagttt ttaaaaatac cctctgggag ctaaattcca catgtatcta tggcctaagt    7860
gtatgtttat tttgcagatg gatcagatct ggaactgaga cttaaaggtg gaggcagcca    7920
ctgtgctggg acagtggagg tggaaattca gaaactggta ggaaaagtgt gtgatagaag    7980
ctggggactg aaagaagctg atgtggtttg caggcagctg ggatgtggat ctgcactcaa    8040
aacatcatat caagtttatt ccaaaaccaa ggcaacaaac acatggctgt ttgtaagcag    8100
ctgtaatgga aatgaaactt ctcttgggga ctgcaagaat tggcagtggg gtggacttag    8160
```

```
ttgtgatcac tatgacgaag ccaaaattac ctgctcaggt aagaatttca atcaatgtgt      8220
taggaaattg cattctactt tcttttacat gtagctgtcc agttttccca gcaccacttg      8280
ttgaagagac tgtcttttct tcatcatata gtcctacatc ctttgtcata aattaattga      8340
ccataggtgt gtgggtttat atctgggctc tctattctgt tcctttgatc tatatgtctg      8400
tttttatgcc agcaccatgc tgttttgatt actatagctt tgtagtatca tctgaagtca      8460
ggaaacatga ttcctccagc tttgttcttc tttctcaaga ttgttttgtc tattcagagt      8520
ttatgttccc atgcagattt aattttttaaa tttatttaat ttttattttt tattttttaat    8580
ttaaattaat ttaaatttt tatttcccaa cgtacagcca aggggccag ggtaaccttt         8640
acatgtatac attaaaaatt tcaggttttt cccccaccca tttctttctg ttggcaagta      8700
aattttgaa caaagtttcc caatgctttt taagggaat tcccttgggg gggggggg           8760
gggggggggg gggggggggg gggggggggg gggggggggg gggggggggg gggggggggg      8820
gggggggggg gggggggggg gggggggggg gggggggg agacgaaatt gactatattt        8880
tctttgttgg gaatctttta cagttgtgac aaatctttca catattcttc atttgagtag      8940
tttggagggt tgtctgactg ttttctataa taaatgtccc aagtgctatg aggtaccaca      9000
tttcaaattc taattctacc tgaagctcca aaaagacaaa atgttatagg tcttttcttt      9060
atatctaatt tgcttatggt ttttagccat tgacaattt tttttcttaa ctcttgaaac       9120
tataccccta tttctaacca aattcatgtt ctatactggc tcttcaaaaa cccaggagat      9180
gggaaagcca gaatctccag tgtttcagct tctgggaagg agcaagtttt taaaaatacc      9240
ctctgggagc taaattccac atgtatctat ggcctaagtg tatgtttatt ttgcagatgg      9300
atcagatctg gaactgagac ttaaaggtgg aggcagccac tgtgctggga cagtggaggt     9360
ggaaattcag aaactggtag gaaaagtgtg tgatagaagc tggggactga agaagctga       9420
tgtggtttgc aggcagctgg gatgtggatc tgcactcaaa acatcatatc aagtttattc     9480
caaaccaag gcaacaaaca catggctgtt tgtaagcagc tgtaatggaa atgaaacttc       9540
tctttgggac tgcaagaatt ggcagtgggg tggacttagt tgtgatcact atgacgaaac     9600
caaaattacc tgctcaggta agaatttcaa tcaatgtgtt aggaaaattg cattctactt     9660
tcttttacat gtagctgtcc agttttccca gcaccacttg ttgaaaaaac tgtcttttc      9720
ttcatcatat agtcctacat cccttggcca taaattaatt gaccataagg ggtgtgggtt     9780
taatatccgg ggctcctcaa ttcgggtccc ttggatccta aaagccggtt ttataacccg     9840
acacatggcc tgttttgac taaataaaac ctttggaaaa caatcccgaa ggtcgaggaa       9900
catggaatcc ccccaacaaa ggaccttctt tccccaaaaa tgcggctcag ccaactcaaa     9960
aagattttat gaatcacaaa ccgcacatta tcttcctaaa attactattc ctatgtttta    10020
atttgcaaag tcattccgat atagttggcg cagagtaact catttagata tccaccccac    10080
cagttcctca ctcaagtaag gggggggggg gggggggggg gggggggggg gggggggggg    10140
gggggggggg gggggggggg gggggggggg gggggggggg gggggggggg gggggggggc    10200
ccccatgtga gattttgtgt gtcctttaag agtggagtct ctatttccca ctgctctctg    10260
gttctcccca aagtaagccc tgctggcttt caaaacttct gggagcttgc cttcttgta     10320
taggactcct gggctaggga gtctaatgtt tggcttagac cccttactgc ttgggaagaa    10380
tctctgcaac tgtaatgaat tatcttccta tttgtgggtt gctgaggata tggtcttaac    10440
tgttctgtgt tctaccccct ctatccatct tgttgtggtt ccttctttat atctttagtt    10500
gtagaaaagt ttttcttatc aacagttgct ctgtaaattg taacttgggt gtacacctag    10560
```

```
taggaggtga gctcagggtc ttcctactct gccatcttgg ccatgtcctc taaacatttt    10620
ggtgtatttc actgcaacct ttttaaaaat ctcaaaagtg agctgtgatt ggctagtctt    10680
gtggataatc tctagcattt gatgctaatc atatttatac aaatactttg ttgaaaagtg    10740
atgccttttt aactattatt aaaaaacgta ttgacataac tattgctatt atactgaaaa    10800
gaaagacctt agagaaaata gcataagagc aaaaccatta acatggaga catctagtca     10860 tagggtggaa attttatgtg gtccatatcc cctaaccagt ggctttacac caggcacatc    10920
ctaactaaga tctgctccca agtgtcttcc ctgatgcttt aaattgtgtt acatggaaac    10980
tatcctttga tgaagaaatg caaccttta aaatacaaca ttgaaacttt tgtgctttaa     11040
ttttgctttt caacatttt tcttttaaa agaagaaatt tatttgtttt tttaaatttt      11100
aatggccacg gcatatggaa gttctcaggc cagggataga attcaagcca caggtgcgac    11160
ccatgccaca actgctgcaa caccagatcc tttaacccac tgcaccaggc cagggattga    11220
agccttgcct tactgacaat ctgagccact tcagtcagat aaagaaattt cttcattaag    11280
cagagtattc acatggttta aacttcaaaa tattaaagtg taaactcttt ccccaccact    11340
gtccccagct caccaactct acttaccaca gacaactgat gtggttaggg tatttaaata    11400
gtaaatccaa gaaaatataa acaaatccgt atatataggt ttcaccccat tttattatcc    11460
taatgttgca tatcatataa actatactgt cccttgggta ttcacttagt aaaatatttt    11520
gatcataatt tcctatcagt atttaaagag ctttctgaaa ttatttctgt ataacatttc    11580
ttttctcatc ggtaggggg gggggggggg gggggggggg gggggggggg gggggggggg     11640
gggggggggg gggggggggg gggggggggg gggggggggg gggggggggg gggaatggg     11700 aagaaaaaac caccatggtt aattttttt atccctctac acccgggaaa attacccttg     11760
gggccacact tttctataga aaggggatta tttaaaaggg tctgaaaaag aattttttt     11820 tcgaaggggg aaatatttgg cctaacttag tcacataagc catgttctct ggcaagttag    11880
gtaacataca tttttgtcat tgggggcaac aaaaacaatt ttccttttgg accttttggg    11940
actccgcatt ggttagggaa ggggaagtat attggaattc ggaaaattcc ttccaaatta    12000
aaaaaggttt gttattttca tattaaccta tttcatatta attagcatga attccagcgc    12060
cattaaaagg gaaaacacct ggagtggtaa gaaaaaagtt tttttttctc tttttttttt    12120
ttttttttta atggccacat ctgtggcatg tgaagttccc aggctagggg tcgaatagga    12180
gctacagctg ccagcttgca ccacagccac aacaatgcca gagccaagcc tcatctgcga    12240
cctataccac aactcatggc aatgctggtt ccttaaccc ctgagtgagg cctgggtca     12300 aacccacatc ctcatggata ctaaccggct ttgttaccgc tgagccatga gggaaactcc    12360 cttttctca ttgaaaataa gtcaaataga taagcagctt aaggctgttt gggtgattct     12420
gtggtccagt aattatcaaa tcctactgga caagaataga gaatgtgcaa atgagggaac    12480
gtgttggtga gatcaggctc tgcccactga gctatcctct gtcatgggcc ctgtgctgtt    12540
ctcagagctg tacttcctag ggcattgttc tcatttcaat tctgagttca gtgtggagag    12600
tatacgtgtg tgggggctgc acgcttttca caacccactt tctgctgata ctgatttagg    12660
gatccttgga ttgctttaca gttgagtcat cattaactag tgtcacttgc cttcaaagtc    12720
agcaaaataa ttgtctccaa actagtaggc ttctagtgta tttgctttaa tccaatgcca    12780
tgtgaaagta acatggtcaa agaataagtt atataccttg acctaccctg tgaccaggct    12840
cttcctctta atttattgac cactgcctta aggtcatttg aaaccatggg tttgggagga    12900
```

```
aggcaaggcc taaatcccgt ctttgttgga aggctcactg tccttgtctt tagagcatca    12960
ttttttttta aactggggta cagtttattt acagtgttgt gtcaattcct gctgtacagc    13020
acagtgaccc agtcatacac atacatacat tcttttttctc atactatctt caatttttatt  13080 ttctgctaag tctgccatttt tatcatcacc tcagtttgaa ggacaggata tttagagtttt  13140 gttttttttt tccccccaat cctgcaattt ctaaattata agactctcaa ttagccgtat    13200
ataacagctg caggcacagg atgtctccct cacaaaattg gtattttttcc ttccatttct   13260 tcttgcagtt tggctatttc ttgtctgagt tcatctctct ttttaagtgt taaaaagggc   13320
aaggaggatt catgctatgt caacattatg attttttctt ttctatactt gataagagta   13380
tacttttccc aaatgtcatc caactttttca gcatcagttt ggacatggtt ttcttttcaa  13440 ggtggtatttt ctctaatgtc acttgaataa caagactcgt tagttctcca ggctacaata  13500
tcctagtctg agtatattct gcatgttaat tctattcagc cacatccata atttaggttt   13560
tattcctgga acacctcact tttttttttt ttttggtct ttttatagcc ataaccatgg     13620
catatggagg ttcccaggct aggggtctaa tctgagcttt agccactggc ccatgccaca   13680
gccacagcca tgccacatct gagccacatc tgtgaccttt tccacagctc acagaaacac    13740
cagatcccta acccactgag tgaggccagg ggtcaaacct gtaacccttc catggttcct   13800
agtcagattc gttcctctgt accacgatgg gaattcctaa tacctcactt atgataacac   13860
attctgaatt atttaggatt ctattatact gcatgtaata gaaatcccaa atagcaaaat   13920
ttgcaactta aggcaggttc ctgtctttac aaaatcatgt ttttcctttgc tatatgtgca  13980 ctttgctttc ctctgtgaat tccctttttt gttatatttc tatagctttt ggaaacactt   14040
ttacttattt gggggggcct agattttttaa ccctctcctt gttttttctag aaatagagtt  14100 tataatttta tttcttcatt tacttgatac tttcaagaga ttcccaggaa aaaaattatg   14160
gaaatactgt ctctgtgcct gccaagttca aactaagaat tgtataatct gttttaattc   14220
ttaagcattt atagatgaca aggctttgtg tctgataggg gccagcgaac tcagtaaaga   14280
gggaagatga gaaagataat ggcaagaatt tatccctgaa gtgtagtttt gacaaaccag   14340
tcacaaagag gtctaagaaa ttttggtcac aaagttgttt tgaatcccag gcatttttatt  14400 tgcaatgatt gcatatgttc tggaaaggac atctgaacct aagaaatagt tcatttgcat   14460
tgtgttatat tttactaagg tctgagaaat aatcttgaga tgagaatgaa ctctacttct   14520
tcagagtctg gaaggaataa attatgaaaa tgtattaatg cttctttaaa ccatattgta   14580
tatttatcta ttactaaaca aaagaagta gctctattta tttatttatt tatttattta     14640
tttatgtctt ttgtctctttt agggccacac ctgtggcata tggaggttcc caggctagag   14700
gtccaattgg agatgtagca gccagcctat gccagagcca ccgcaacacg ggatctgagc   14760
cacgtctgtg acttacacca cagctcacag caacgcctga tcctcaaccc actgagcgag   14820
gccagggatc gaacccatgt cctcatggat gctagttggg ttcgttaact gctgagccat    14880
gatgggaact ccaaattaat tatttcttat atttgttctt catatattca tttctataga   14940
aagaaataaa tacagattca gttaatgatg gcaggtaaaa gcttaactta ttaatcaaag   15000
gagttaatcc aggcacaaaa attcaattca tggctctctg ttaaaattta ggtataggtt   15060
tagcaggaag aaaaggttag tagatgcaga ctattacatt tagaatggat ggacaatgaa   15120
gtcctactat acagcacagg gaactatatc caatctcttg ggatagaata tgatggaaga   15180
caaaatcaga acaagagagt atatatatat gtgtgtgtgt gtgtgtgtgt gtgtgtgtgt   15240
gtgtgtgtgt gtgtgactgg gtcaccctgc ggcacagcag aaattggcag aacattgtaa   15300
```

```
atcaactata ctttaatagg aaaaatactt ttaagggcta aatttccaat attctaacca   15360
tgtacacaga gtaaatgtca taaggatgcc agtctgtgta gagattgatg tgttactagc   15420
agattcatga aataaaggct gaggatgtag tccccaagtc acttctgagt ggaagaattt   15480
ctcctttgtc ctggactcaa atattttagg ataaaggaaa aaagaagata tttatagaag   15540
ggacttgttt tcaagtactt gacaaaattt caccattaaa gagaaatttg tgggagttcc   15600
catcgtggct cagtggaaac aaatccaact aggaaccatg aggttgtggg tttgatccct   15660
ggcctcactc agtgggttaa ggatccggtg ttgccgtgag ctgtggtgta ggttgcagac   15720
acggttctga tcctgcgttg ctgtggctgt ggctgtggtg taggccagca gcaaacagct   15780
ctgattagac ccctagcctg aaacctcca tatgccacag gtgcagccct aaaaagacaa   15840
aaaaagagaa aagacaaaaa aaaaaaaaa aaaaaaaaa aaaaaaaaaa aaaaaaaag    15900 aacccccaga ggtatttatt tgttttttgcc ttttttcact gactgttctt tgtttgtttg   15960
tttgagactg atctagaaga ctagagatta caagaaatat ggatttggct cactctaaga   16020
aactgctttc attccaaggt ttgggtctat ccaaaagtgg aatagaatca tatgaatact   16080
agtttatgag tatttagtga gaggaatttc aagctcaaat aatgattcag caagattaaa   16140
ttaaggaggg aatttttcctt gtggctgagt gggttaagga cccaatgttg tctctgtgag   16200
gatgtaggtt ccatcctggg ctttgctcat taggttaagg atctggcatt gctgcagctc   16260
agacccagtg ctgccctggt tgtggcttag gccaaagctg cagctccaat tcaatctctg   16320
gcctgggaac ctccatgtgc tacaaggtgc ggccttaaaa ggaaaaaaaa aaaattaaat   16380
caaggactca agagtctttc attatttgtg ttgtggaagc tatatttgtt ttaaagtctt   16440
agttgtgttt agaaagcaag atgttcttca actcaaattt gggagggaac ttgtttcata   16500 cattttttaat ggataagtgg caaaatttttc atgctgaggt gatctatagt gttgtaatgc   16560
agaatatagt cagatcttga acattttagg aagttggtga gggccaattg tgtatctgtg   16620
ccatgctgat aagaatgtca agggatcaca agaattcgtg ttatttgaca gcagtcatct   16680
ttaaaaggca tttgagaaag tccaatttca aatgcatttc ctttctttaa aagataaatt   16740
gaagaaaata agtctttatt tcccaagtaa attgaattgc ctctcagtct gttaaaagaa   16800
actcttacct tgatgattgc gctcttaacc tggcaaagat tgtctttaaa atctgagctc   16860
catgtcttct gctttatttc tggtgtgcct ttgactccag attacagtaa atggaggact   16920
gagtataggg ctaaaaagta gagagaatgg atgcatatta tctgtggtct ccaatgtgat   16980
gaatgaagta ggcaaatact caaggaaag agaaagcatg ctccaagaat tatgggttcc   17040
agaaggcaaa gtcccagaat tgtctccagg gaaggacagg gaggtctaga atcggctaag   17100
cccactgtag gcagaaaaac caagaggcat gaatggcttc cctttctcac ttttcactct   17160
ctggcttact cctatcatga aggaaaatat tggaatcata ttctccctca ccgaaatgct   17220 attttttcagc ccacaggaaa cccaggctgg ttggagggga cattccctgc tctggtcgtg   17280
ttgaagtaca acatggagac acgtggggca ccgtctgtga ttctgacttc tctctggagg   17340
cggccagcgt gctgtgcagg gaactacagt gcggcactgt ggtttccctc ctgggggag   17400 ctcactttgg agaaggaagt ggacagatct gggctgaaga attccagtgt gaggggcacg   17460
agtcccacct ttcactctgc ccagtagcac cccgccctga cgggacatgt agccacagca   17520
gggacgtcgg cgtagtctgc tcaagtgaga cccagggaat gtgttcactt tgttcccatg   17580
ccatgaagag ggtagggtta ggtagtcaca gacatctttt taaagccctg tctccttcca   17640
```

```
ggatacacac aaatccgctt ggtgaatggc aagacccat gtgaaggaag agtggagctc    17700
aacattcttg ggtcctgggg gtccctctgc aactctcact gggacatgga agatgcccat    17760
gttttatgcc agcagcttaa atgtggagtt gcccttccta tcccgggagg agcaccttt    17820 gggaaaggaa gtgagcaggt ctggaggcac atgtttcact gcactgggac tgagaagcac    17880
atgggagatt gttccgtcac tgctctgggc gcatcactct gttcttcagg gcaagtggcc    17940
tctgtaatct gctcaggtaa gagaataagg gcagccagtg atgagccact catgacggtg    18000
ccttaagagt gggtgtacct aggagttccc attgtggctc agtggtaaca aactcgactg    18060
gtatccatga gggtatgggt ttgatccctg gccttgctca atgggttaag gatccagcat    18120
tgctgtgagc tgtggtatag gttgcagact ctgctcaggt cccatgttgc tgtgattgtg    18180
gtgtaggctg actgctgcag cttcaatttg accctagcc cgggaatttc cataggccac     18240
acgtgcagca ctaaggaagg aaaaaagaa aaaaaaaaa aaagagtggg tgtgcctata     18300
gtgaagaaca gatgtaaaag ggaagtgaaa gggattcccc cattctgagg gattgtgaga    18360
agtgtgccag aatattaact tcatttgact tgttacaggg aaagtaaact tgactttcac    18420
ggacctccta gttacctggt gcttactata tgtcttctca gagtacctga ttcattccca    18480
gcctggttga cccatccccc tatctctatg gctatgttta tccagagcac atctatctaa    18540
cactccagct gatcttcctg acacagctgt ggcaaccctg gatcctttaa ccaactgtgc    18600
caggctggag atcaaaccta agcctctgca gcaacccaag ctgctgcagt cagatttta    18660 accccctgtg ccactgtggg tatctccgat atttgtatc ttctgtgact gagtggtttg    18720
ctgtttgcag ggaaccagag tcagacacta tccccgtgca attcatcatc ctcggaccca    18780
tcaagctcta ttatttcaga agaaaatggt gttgcctgca taggtgagaa tcagtgacca    18840
acctatgaaa atgatctcaa tcctctgaaa tgcattttat tcatgttta tttcctcttt    18900 gcagggagtg gtcaacttcg cctggtcgat ggaggtggtc gttgtgctgg gagagtagag    18960
gtctatcatg agggctcctg gggcaccatc tgtgatgaca gctgggacct gaatgatgcc    19020
catgtggtgt gcaaacagct gagctgtgga tgggccatta atgccactgg ttctgctcat    19080
tttggggaag aacagggcc catttggctg gatgagataa actgtaatgg aaaagaatct    19140
catatttggc aatgccactc acatggttgg gggcggcaca attgcaggca taaggaggat    19200
gcaggagtca tctgctcggg taagttctgc acatcacttc gggttacagt gatttaagaa    19260
acaactaagg tggggcaaag ggtagtgagg catatccatc agagcaaatt ccttgaaata    19320
cggactcaga gggaaccatt gtgagattga ggttcccaga ggtgtggatt taatgaatta    19380
gtgttacctc atgtacaagg tagtatacta ccagaaagat aaaaattcag aagcgagttt    19440
gcagcaaaac tcatagggag aacttctttt ataataata tgaagctgga tatttagtgc    19500
accacctgat gaccacttta ttaataaata aagagttcct gttgtggcgc agcggaaatg    19560
aatccgacaa ataatcatga gtttgcgggt tgatccctg acctcgctca gtgggttggg    19620
gatctggtgt tgccatgagc tgtggtgtag gtcgcagatg ctgcttggat cctgctttgc    19680
tgtggctgtg gtataggctt gtggctacag ctccgatttg accgctagcc tgggaacctc    19740
catatgctgc gggggtggcc ctcaaaagaa aaataaataa ataagtaaat aaataagtag    19800
tttaaaaagg acaagaagaa atatatttgg tgttatattc tacagagaca agataatca    19860 ccatgcccga ttgattttc aaggcatata aatgagacgt catgggagca aaatggtca     19920 taatacaatg cccttgtttt gtgtacatgg taagatttta gaaagcattg tgaggtaaaa    19980
aagtgtactc agttataata tattggggaa aacagtacta tgagaagtaa aaaaatctac    20040
```

```
atgccggaag ttattttttt aatgtctctt ttagagtcgc acatgcggca tatggaggtt    20100
cccaggctag gggtcgaatc agagctatag ccactggctt atggcacagc cacaacaaca    20160
ctagatctga gccacatcag cgacctatac tatagctcat ggcaatgcca gatccttaac    20220
ctactgagcc aagccatggg tcaaatccag gtcctcacgg atcctaggca aattcatttc    20280
tgctgagcca cgaagggaac tcctcagaag tgattttgat gttactttct tttcatgaca    20340
aatctggtaa agtacataca catagaaact gaagtgtcag aaagggaaat atttcatttt    20400
aaggtaatgt atacaaaaca gtggttttac catctgagta tctcgctaaa ttttaactat    20460
caaggacaat tgccaaaaaa aaaaaaaaaa gagagagaga gagaacagaa tagggttatg    20520
aagctaaaat cacagggtta tgaagctaaa atcacagtaa tttagggaga aaaaaatcca    20580
aagcatgtaa ttgataaaag gttctgagcc tttgtttgag atttagaatt caacttagaa    20640
ataccggtgg tattttaaag cagtccataa gtataaaatc caaggctaaa aaaccagaag    20700
gtatttgtag aacaaatata ttttaataag ctctaccaag tcatccagaa gctattaaag    20760
aattactggt cactgacata gtgtacctgt tttcaaggcc attcttacat cagaataaag    20820
ggagagcacc ctctgaatct tcagaaaaga tgtgaaagtg ctaattctct atttcatccc    20880
agagttcatg tctctgagac tgatcagtga aaacagcaga gagacctgtg cagggcgcct    20940
ggaagttttt tacaacggag cttggggcag cgttggcaag aatagcatgt ctccagccac    21000
agtgggggtg gtatgcaggc agctaggctg tgcagacaga ggggacatca gccctgcatc    21060
ttcagacaag acagtgtcca ggcacatgtg ggtggacaat gttcagtgtc ctaaaggacc    21120
tgacacacta tggcagtgcc catcatctcc atggaagaag agactggcca gcccctcaga    21180
ggagacatgg atcacatgtg ccagtgagta tccattcttt agcgccactg ttatcttctg    21240
atctacctaa gcagaagttt tataatctgt agttaatccc tattctacct ggatgatggg    21300
attcattctg tttaatttgg tgtgcaggta ttcagcatca gtgatcattt tcccaaagac    21360
catcatgctc tgatggtctt ctcaaaagtt ctaatcagtt gcttcctccg tgaacagttg    21420
aggagcagag aatatgtaat tcagaatttg actattgaat catcccattt ttctttcaca    21480
tagtcttttg ttgcactgaa tataaggaga gaagcagtca gaaagatcaa tcctgaatta    21540
tttctccatt ctacatctgt tttaaatttc aaaaaaaaaa attgttatag gtgatttaca    21600
atgtctgtca atttctgctc tacagcaaag tgacccagtt atttacatat acattctgtt    21660
tctcatattt ttaaaccagg agatttctat ctgcctggcg gtttgaggga atttaacatt    21720
atgcatttat gttaacttta ttcacctgat gttttctaag tcatactgag attcttatgc    21780
ccaggatgga atacacctgg tttgctggaa agacatgtgc tttcataaag acgaattttg    21840
gaaaaaatat aaaatttaaa aggcccatta ataagcaaa  gttttaagag atttcaaaaa    21900
aaatttcatc tctctctttt cctctttgac ctcttgggca cgttcatctt ctcaaatatg    21960
atcttggtgt ttctgacttt tcagacaaaa taagacttca agaaggaaac actaattgtt    22020
ctggacgtgt ggagatctgg tacggaggtt cctggggcac tgtgtgtgac gactcctggg    22080
accttgaaga tgctcaggtg gtgtgccgac agctgggctg tggctcagct ttggaggcag    22140
gaaaagaggc cgcatttggc caggggactg gccccatatg gctcaatgaa gtgaagtgca    22200
agggaatga  aacctccttg tgggattgtc ctgccagatc ctgggccac  agtgactgtg    22260
gacacaagga ggatgctgct gtgacgtgtt caggtgaggg cagagagtct ggattgagct    22320
tggaagctct ggcagcaaag agagggtggg cggtgacctg cattgggtaa agattggaag    22380
```

```
gtccagccta aggatctggt ggtggggga gacatgatgt ttcagtctga agaatgatga    22440
aaacctgtgt ggttacgcat gggccttcgc cgaggaaagg gacataacta ccatgtatcc    22500
tcctgcagag ggaggaagaa ctaggggatt ctagttttgt gtgggaagga gcagtttact    22560
tggctcagga ggcactaaag gctcagatag gaaacagaga tctgttccat tcttactccc    22620
agaactgatt ctcttctctt ttctcctaca gaaattgcaa agagccgaga atccctacat    22680
gccacaggta tatcaaaaag tttaagaaca tgggacccat tgtctgcatt ttgtggaatc    22740
cctcttatta agacattctg ggtcagaagt tctgaggatt tgacatttac ttcagctatc    22800
tgttatctta cccaagagag ggatggtaac taggaaccca ggtctttag ctaagacatt    22860 atcacctctt gtgatgttta cttgttctca ggtcgctcat cttttgttgc acttgcaatc    22920
tttggggtca ttctgttggc ctgtctcatc gcattcctca tttggactca gaagcgaaga    22980
cagaggcagc ggctctcagg tctgaacaaa attacggtct ctctaatgtt tctatgggag    23040
aagaagcctc tctggataat aaaacaaaaa aattacattc aagtatcagt tggccagaaa    23100
gagggaacct agaagaggtt taagcagttt ctccgaaaca gggaacaaga attcagaaa     23160 gaaaaggcac attggctgta ctgatgatac ctgcactcgc tatgtatgtt taatggggga    23220
cagtagaaaa ttgatagttt agaaggagta tgcttatatg gttctggatg aatcctgtat    23280
ccccccaaac atttattttc tcttactata tacttattac taatttaact cttctgtcaa    23340
gccatgtgct aggttctgaa gatggttcag acttggataa ccaagtgctt ttgttttcat    23400
ggaatttcca gtttagtgga agagataaat atgtaaacaa ataaatgggg gggggggggg    23460
gggggggggg gggggggggg gggggggggg gggggggggg gggggggggg gggggggggg    23520
gggggggggg gggggggggg gggggggggg gggggggggg gggggggggg gggggggggg    23580
gggggggggg gggggggggg gggggggggg gggggggggg gggggggggg gggggggggg    23640
gggggggggg gggggggggg gggggggggg gggggggggg gggggggggg gggggggggg    23700
gggggggggg gggggggggg gggggggggg gggggggggg gggggggggg gggggggggg    23760
gggggggggg gggggggggg gggggggggg gggggggggg gggggggggg gggggggggg    23820
gggggggggg gggggggggg gggggggggg gggggggggg gggggggggg gggggggggg    23880
gggggggggg gggggggggg gggggggggg gggggggggg gggggggggg gggggggggg    23940
gggggggggg gggggggggg gggggggggg gggggggggg gggggggggg gggggggggg    24000
gggggggggg gggggggggg gggggggggg gggggggggg ggggggggtt ggcgggcccc    24060
cctcgaggtc gacggtatcg ataagcttga tatcgaattc gtgagccaga ggacgagact    24120
agagatggat gatgactacg ttatgcttgc actgctgggg aaaagcacac atagggaggg    24180
aacgttttat tatgacccag tccctaacct atgacctctg ttatcagttt tctcaggagg    24240
agagaattct gtccatcaaa ttcaataccg ggagatgaat tcttgcctga agcagatga     24300 aacggatatg ctaaatccct caggtccgtg ggttctttga ggggctgtag ccctgggtt     24360 cagatcagca gctgcagttg aggttgaggc atgctacttt gcatagcagt agaaagaaat    24420
ctcaactgta ataggaagct tgggatgcat atgaggaaga aaggcaagaa tgaactacaa    24480
attattctta gggaagataa aaattgcagt catggggaga cctctggctg agagggccgt    24540
gattatttct gacagaggga ttatggagta gaatatgatg gcttggacct ttttcacta     24600 aaacaagtca gtcttctcaa aggtagttta gcttttcata tatctttcac agtttcttcc    24660
attcccattt cctgccattt tcctttctct aactttatt tattatattt tttcctaaaa     24720
gtttaaattt tctatatctt tatcccttca gaagccatcc ctagtcacag gactagtctc    24780
```

```
atttcccatt atgtaatgct tctttctctg tctgttgact tctatttaga accagtgcac    24840
taaatctgcc tttaggaaca tacctctgct aggttgcaag aaatatccca ttccccactc    24900
actctgtgaa gactcaatgc ttctcaatat tccttacctc ctgagaggga cttgcctcac    24960
ttctttaatc caagggactc gattttgcc aaaactaagt caggaaaacc tacataagac     25020
ataggaaaga cttgctgtgc ttcttaaacc ccactgtttg ttttcctaat tgtgaacagt    25080
atttttaaag ttaacaagag agcttctaag gcacttgagg ggagatctga tttatttccc    25140
agtaattatt ttcttccttt cagaaaattc cactgaataa gatggttta acggatgtgg     25200 gactaatttt tgtgtctaaa tctcttccta tttctggatg aaaaaaagga gaccactctg    25260
aagtacaatg aaaaggaaaa tgggaattat aacctggtga ggtgagtagg aagaatttat    25320
tcatcattgc tgaaaacagg tacattcctt ttgaaagttg agaactcctc tggtattaga    25380
aaaaaaaaaa gaacgtatat acacatatat ttccatgtct atgtttatgt ttgtaaatcc    25440
atattcagaa tatgcaacaa ctttttataa ctatgacttc agtccatctt ttagttacat    25500
atatattcta aacaacaact attgctaaga gaagctgggt aagtaaatgt gaataaatct    25560
tctaaagata ttacaggaag ttcctgctgc ggctcagtgg gttaaagact tgatgtcttt    25620
gtgaagatga gggctcgagc cctggcctca ctcagtgagt taaggatcta gcattgctgt    25680
aagctgcagc gtaggttgca gatagggctc agatccagtg ttgctgtggc tgtgccctca    25740
gttgcagctc tgattcaacc cttaggcgag gaacttccat atgcagcaaa tgtggccatt    25800
aaaaaaaaaa aaaacattat aggagtcatt tcataaaaga gataagacgt ttctatagtt    25860
atatagtgca tactctggta aagatagtat aggatactat aggaatatag aaagcttgcc    25920
tatgaaaatt tgggaagatt gtggaaagaa catctcaaaa tatggcatag aaaagaatca    25980
tatctttgag gaacagtaag tttttcattc aaaaccgtgt attgaacata cttgtggtga    26040
caagtggtgt cctgagtact aaaaattcag tgataaaaga tgctcttgac aaagacatgg    26100
ctgttgaata gaaggtctca ctgtcaatgt gtgggaatta tggacagcct atgtggacac    26160
agggaataga tgagactcta ggctggaagg ctgcattgag cccaataatg aatggtcctg    26220
tctgatatat ttcatgctca tatttattt tagggactat tggggaggtg gtgggttttg     26280
gaagattaag ctgaggcaag acacaatcag attgcctttt ataatttact ttcaggagga    26340
aagtctaact aaaaaaagaa ttcgatatca agcttatcga taccgtcgac ctcgaggagg    26400
cccgcctgcc cttttggggg ggggggggg gggggggggg gggggggggg gggggggggg     26460
gggggggggg gggggggggg gggggggggg gggggggggg gggggggggg ggggggcagca    26520 ccaattttat tattggcggg aataaagaga aaatgtaat ttcaaagatt gctgttggaa     26580
atgaggggtg tggtagcttt tggagaaagc attctggaga cttctattaa ttttttttt     26640 ttaagtgctt caaagatcct ttgatccaac aattctactc ctaaaaattt cttccataca    26700
gataaagcca tttgtctgta tataacaaat agaagagaat tccttttttgc agccttgtta    26760 gtagtgcccc caaactggaa acaaagtgaa tatcagtcag tggggtagcg gctggaaaaa    26820
ttttagtgca cccaaccaac aaagaaaaac catgcacaaa aattcaataa atatcatctc    26880
acttttgtgt tcatgttatt gaatataatt aaacataatg tttacatcta taaaattatc    26940
atatgtatac atgtaaagaa acattaaaac attttaaca gactgtaaac ttgaggactg     27000
tgaatgactt ttgattgata atctcaaaca tatggatact attctgatgt aataaataat    27060
gattaaattt tttccctaaa gagtaatcac tactgaatcg ttgcctcaga atcatatgga    27120
```

```
ggtgctttta aaaaaggcat ttctgcactg ttgttctctg aatagaagt aattcttatg    27180 tacactgaag tttgaaaatc attgcattta agtgttctgt tcaggaaagt agtgtgcttt    27240
ttaatatttg tgagtgaatg agtaacacaa tacattatat cacattttaa tgtaattcta    27300
cacatgtgca tatgaagaga aaagtaacat tttttctat ttatgtcttt agttcagcct     27360
ttaagatacc ttgatgaaga cctggactat tgaatgagca agaatctgcc tcttacactg    27420
aagattacaa tacagtcctc tgtctcctgg tattccaaag actgctgttg aatttctaaa    27480
aaatagattg gtgaatgtga ctactcaaag ttgtatgtaa gactttcaag ggcattaaat    27540
aaaaaagaat attgctgatt cttgttcttg attttctgaa tttctgaatc tcttattggg    27600
cttctaattt aaaaaaaaat atctgggcgc ccgcagatat cgaactcttg ggcagtgtga    27660
ccaaacgaag acatatccaa tcaagcatgc aaatggacca gcccactgta ctagcacgct    27720
gtggcagcca atctgaccga gaaagcagac aaccgcaggg agcaacg                 27767
```

<210> SEQ ID NO 16
<211> LENGTH: 55
<212> TYPE: DNA
<213> ORGANISM: Sus scrofa

<400> SEQUENCE: 16

```
ggtcgccacc atggtgagca agggcgagga gctgttcacc ggggtggtgc ccatc         55
```

<210> SEQ ID NO 17
<211> LENGTH: 54
<212> TYPE: DNA
<213> ORGANISM: Sus scrofa

<400> SEQUENCE: 17

```
ggtcgccacc atggccatga gcaagggcga ggagctgttc accggggtgg tgcc          54
```

<210> SEQ ID NO 18
<211> LENGTH: 48
<212> TYPE: DNA
<213> ORGANISM: Sus scrofa

<400> SEQUENCE: 18

```
ggtcgccacc atggtgagca agggcgagga gctgttcacc ggggtggt                 48
```

<210> SEQ ID NO 19
<211> LENGTH: 55
<212> TYPE: DNA
<213> ORGANISM: Sus scrofa

<400> SEQUENCE: 19

```
ggtcgccacc atggttgagc aagggcgagg agctgttcac cggggtggtg cccat         55
```

<210> SEQ ID NO 20
<211> LENGTH: 43
<212> TYPE: DNA
<213> ORGANISM: Sus scrofa

<400> SEQUENCE: 20

```
tgcagggaac tacagtgcgg cactgtggtt tccctcctgg ggg                      43
```

<210> SEQ ID NO 21
<211> LENGTH: 60
<212> TYPE: DNA
<213> ORGANISM: Sus scrofa

<400> SEQUENCE: 21

```
tgcagggaac tacagtgcgg cactgtaaac cactactact gtggtttccc tcctgggggg    60
```

<210> SEQ ID NO 22
<211> LENGTH: 41
<212> TYPE: DNA
<213> ORGANISM: Sus scrofa

<400> SEQUENCE: 22

```
tgcagggaac tacagtgcgg ctgtggtttc cctcctgggg g                        41
```

<210> SEQ ID NO 23
<211> LENGTH: 46
<212> TYPE: DNA
<213> ORGANISM: Sus scrofa

<400> SEQUENCE: 23

```
tgcagggaac tacagtgcgg aactactgtg gtttccctcc tggggg                   46
```

<210> SEQ ID NO 24
<211> LENGTH: 31
<212> TYPE: DNA
<213> ORGANISM: Sus scrofa

<400> SEQUENCE: 24

```
gaaacccagg ctggttggag gggacattcc c                                   31
```

<210> SEQ ID NO 25
<211> LENGTH: 24
<212> TYPE: DNA
<213> ORGANISM: Sus scrofa

<400> SEQUENCE: 25

```
gaaacccagg ctggggacat tccc                                           24
```

<210> SEQ ID NO 26
<211> LENGTH: 13
<212> TYPE: DNA
<213> ORGANISM: Sus scrofa

<400> SEQUENCE: 26

```
aggggacatt ccc                                                       13
```

<210> SEQ ID NO 27
<211> LENGTH: 13
<212> TYPE: DNA
<213> ORGANISM: Sus scrofa

<400> SEQUENCE: 27

```
gaaacccatt ccc                                                       13
```

<210> SEQ ID NO 28
<211> LENGTH: 31
<212> TYPE: DNA
<213> ORGANISM: Sus scrofa

<400> SEQUENCE: 28

```
ggtcgccacc atggtgagca agggcgagga g                                   31
```

<210> SEQ ID NO 29
<211> LENGTH: 32
<212> TYPE: DNA
<213> ORGANISM: Sus scrofa

<400> SEQUENCE: 29
ggtcgccacc atggctgagc aagggcgagg ag					32

<210> SEQ ID NO 30
<211> LENGTH: 29
<212> TYPE: DNA
<213> ORGANISM: Sus scrofa

<400> SEQUENCE: 30
ggtcgccacc atggtgagag ggcgaggag						29

<210> SEQ ID NO 31
<211> LENGTH: 32
<212> TYPE: DNA
<213> ORGANISM: Sus scrofa

<400> SEQUENCE: 31
ggtcgccacc atggttgagc aagggcgagg ag					32

<210> SEQ ID NO 32
<211> LENGTH: 48
<212> TYPE: DNA
<213> ORGANISM: Sus scrofa

<400> SEQUENCE: 32
ggtcgccacc atggtgagca agggcgagga gaacccaggc tggttgga			48

<210> SEQ ID NO 33
<211> LENGTH: 49
<212> TYPE: DNA
<213> ORGANISM: Sus scrofa

<400> SEQUENCE: 33
tgctgtgcag ggaactacag tgcggcactg tggtttccct cctgggggg			49

<210> SEQ ID NO 34
<211> LENGTH: 38
<212> TYPE: DNA
<213> ORGANISM: Sus scrofa

<400> SEQUENCE: 34
tgctgtgcag ggaactctgt ggtttccctc ctgggggg				38

<210> SEQ ID NO 35
<211> LENGTH: 22
<212> TYPE: DNA
<213> ORGANISM: Sus scrofa

<400> SEQUENCE: 35
ctgtggtttc cctcctgggg gg						22

<210> SEQ ID NO 36
<211> LENGTH: 23
<212> TYPE: DNA
<213> ORGANISM: Sus scrofa

<400> SEQUENCE: 36
actgtggttt ccctcctggg ggg						23

<210> SEQ ID NO 37
<211> LENGTH: 50
<212> TYPE: DNA
<213> ORGANISM: Sus scrofa

```
<400> SEQUENCE: 37
tgctgtgcag ggaactacag tgcggcaact gtggtttccc tcctgggggg          50

<210> SEQ ID NO 38
<211> LENGTH: 10
<212> TYPE: DNA
<213> ORGANISM: Sus scrofa

<400> SEQUENCE: 38
tcctgggggg                                                      10

<210> SEQ ID NO 39
<211> LENGTH: 8
<212> TYPE: DNA
<213> ORGANISM: Sus scrofa

<400> SEQUENCE: 39 ctgggggg                                                         8

<210> SEQ ID NO 40
<211> LENGTH: 52
<212> TYPE: DNA
<213> ORGANISM: Sus scrofa

<400> SEQUENCE: 40
agagagcaga gccagcgact cgcccagcga catggggtac ctgccgtttg tg        52

<210> SEQ ID NO 41
<211> LENGTH: 33
<212> TYPE: DNA
<213> ORGANISM: Sus scrofa

<400> SEQUENCE: 41
agagagcaga gccagcgact cgcccagcga gat                            33

<210> SEQ ID NO 42
<211> LENGTH: 30
<212> TYPE: DNA
<213> ORGANISM: Sus scrofa

<400> SEQUENCE: 42
agagagcaga gccagcgact cgcccagcga                                30

<210> SEQ ID NO 43
<211> LENGTH: 50
<212> TYPE: DNA
<213> ORGANISM: Sus scrofa

<400> SEQUENCE: 43
agagccagcc tcgcccagca ggggtaccat ggggtacctg ccgtttgtgt          50

<210> SEQ ID NO 44
<211> LENGTH: 53
<212> TYPE: DNA
<213> ORGANISM: Sus scrofa

<400> SEQUENCE: 44
agagagcaga gccagcgact cgcccagcga gcagtgggta cctgccgttt gtg      53

<210> SEQ ID NO 45
<211> LENGTH: 53
<212> TYPE: DNA
```

<213> ORGANISM: Sus scrofa

<400> SEQUENCE: 45

| agagagcaga gccagcgact cgcccagcga tcagtgggta cctgccgttt gtg | 53 |
|---|---|

<210> SEQ ID NO 46
<211> LENGTH: 53
<212> TYPE: DNA
<213> ORGANISM: Sus scrofa

<400> SEQUENCE: 46

| agagagcaga gccagcgact cgcccagcga acatggggta cctgccgttt gtg | 53 |
|---|---|

<210> SEQ ID NO 47
<211> LENGTH: 4990
<212> TYPE: DNA
<213> ORGANISM: Sus scrofa

<400> SEQUENCE: 47

| tatagatgac aaggctttgt gtctgatagg ggccagcgaa ctcagtaaag agggaagatg | 60 |
|---|---|
| agaaagataa tggcaagaat ttatccctga agtgtagttt tgacaaacca gtcacaaaga | 120 |
| ggtctaagaa attttggtca caagttgtt ttgaatccca ggcattttat ttgcaatgat | 180 |
| tgcatatgtt ctggaaagga catctgaacc taagaaatag ttcatttgca ttgtgttata | 240 |
| ttttactaag gtctgagaaa taatcttgag atgagaatga actctacttc ttcagagtct | 300 |
| ggaaggaata aattatgaaa atgtattaat gcttctttaa accatattgt atatttatct | 360 |
| attactaaac aaaagaagt agctctattt atttatttat ttatttattt atttatgtct | 420 |
| tttgtctctt tagggccaca cctgtggcat atggaggttc ccaggctaga ggtccaattg | 480 |
| gagatgtagc agccagccta tgccagagcc accgcaacac gggatctgag ccacgtctgt | 540 |
| gacttacacc acagctcaca gcaacgcctg atcctcaacc cactgagcga ggccagggat | 600 |
| cgaacccatg tcctcatgga tgctagttgg gttcgttaac tgctgagcca tgatgggaac | 660 |
| tccaaattaa ttatttctta tatttgttct tcatatattc atttctatag aaagaaataa | 720 |
| atacagattc agttaatgat ggcaggtaaa agcttaactt attaatcaaa ggagttaatc | 780 |
| caggcacaaa aattcaattc atggctctct gttaaatttt aggtataggt ttagcaggaa | 840 |
| gaaaaggtta gtagatgcag actattacat ttagaatgga tggacaatga agtcctacta | 900 |
| tacagcacag ggaactatat ccaatctctt gggatagaat atgatggaag acaaaatcag | 960 |
| aacaagagag tatatatata tgtgtgtgtg tgtgtgtgtg tgtgtgtgtg tgtgtgtgtg | 1020 |
| tgtgtgactg ggtcaccctg cggcacagca gaaattggca gaacattgta aatcaactat | 1080 |
| actttaatag gaaaaatact tttaagggct aaatttccaa tattctaacc atgtacacag | 1140 |
| agtaaatgtc ataaggatgc cagtctgtgt agagattgat gtgttactag cagattcatg | 1200 |
| aaataaaggc tgaggatgta gtccccaagt cacttctgag tggaagaatt ctccttttgt | 1260 |
| cctggactca aatattttag gataaaggaa aaaagaagat atttatagaa gggacttgtt | 1320 |
| ttcaagtact tgacaaaatt tcaccattaa agagaaattt gtgggagttc ccatcgtggc | 1380 |
| tcagtggaaa caaatccaac taggaaccat gaggttgtgg gtttgatccc tggcctcact | 1440 |
| cagtgggtta aggatccggt gttgccgtga gctgtggtgt aggttgcaga cacggttctg | 1500 |
| atcctgcgtt gctgtggctg tggctgtggt gtaggccagc agcaaacagc tctgattaga | 1560 |
| cccctagcct ggaaacctcc atatgccaca ggtgcagccc taaaaagaca aaaaagaga | 1620 |
| aagacaaaa aaaaaaaaa aaaaaaaaa aaaaaaaaa aaaaaaaaa gaaccccag | 1680 |

-continued

```
aggtatttat ttgtttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg aatagaatc atatgaatac tagtttatga    1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acattttttaa  2280 tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc agaaggcaa    2820 agtcccagaa ttgtctccag ggaaggacag ggaggtctag aatcggctaa gcccactgta   2880
ggcagaaaaa ccaagaggca tgaatggctt cccttttctca cttttcactc tctggcttac  2940
tcctatcatg aaggaaaaata ttggaatcat attctccctc accgaaatgc tatttttcag  3000
cccacaggaa acccaggctg gttggagggg acattccctg ctctggtcgt gttgaagtac   3060
aacatggaga cacgtgggcc accgtctgtg attctgactt ctctctggag gcggccagcg   3120
tgctgtgcag ggaactacag tgcggcactg tggtttccct cctgggggga gctcactttg   3180
gagaaggaag tggacagatc tgggctgaag aattccagtg tgagggcac gagtcccacc    3240 tttcactctg cccagtagca ccccgccctg acgggacatg tagccacagc agggacgtcg   3300
gcgtagtctg ctcaagtgag acccagggaa tgtgttcact ttgttcccat gccatgaaga   3360
gggtagggtt aggtagtcac agacatcttt ttaaagccct gtctccttcc aggatacaca   3420
caaatccgct tggtgaatgg caagacccca tgtgaaggaa gagtggagct caacattctt   3480
gggtcctggg ggtccctctg caactctcac tgggacatgg aagatgccca tgttttatgc   3540
cagcagctta aatgtggagt tgcccttttct atcccgggag gagcaccttt tgggaaagga  3600
agtgagcagg tctggaggca catgtttcac tgcactggga ctgagaagca catgggagat   3660
tgttccgtca ctgctctggg cgcatcactc tgttcttcag ggcaagtggc ctctgtaatc   3720
tgctcaggta agagaataag ggcagccagt gatgagccac tcatgacggt gccttaagag   3780
tgggtgtacc taggagttcc cattgtggct cagtggtaac aaactcgact ggtatccatg   3840
agggtatggg tttgatccct ggccttgctc aatgggttaa ggatccagca ttgctgtgag   3900
ctgtggtata ggttgcagac tctgctcagg tcccatgttg ctgtgattgt ggtgtaggct   3960
gactgctgca gcttcaattt gaccccctagc ccgggaattc ccataggcca cacgtgcagc  4020
```

-continued

```
actaaggaag gaaaaaaga aaaaaaaaa aaaagagtgg gtgtgcctat agtgaagaac      4080
agatgtaaaa gggaagtgaa agggattccc ccattctgag ggattgtgag aagtgtgcca      4140
gaatattaac ttcatttgac ttgttacagg gaaagtaaac ttgactttca cggacctcct      4200
agttacctgg tgcttactat atgtcttctc agagtacctg attcattccc agcctggttg      4260
acccatcccc ctatctctat ggctatgttt atccagagca catctatcta acactccagc      4320
tgatcttcct gacacagctg tggcaaccct ggatccttta accaactgtg ccaggctgga      4380
gatcaaacct aagcctctgc agcaacccaa gctgctgcag tcagattttt aaccccctgt      4440
gccactgtgg gtatctccga tattttgtat cttctgtgac tgagtggttt gctgtttgca      4500
gggaaccaga gtcagacact atccccgtgc aattcatcat cctcggaccc atcaagctct      4560
attatttcag aagaaaatgg tgttgcctgc ataggtgaga atcagtgacc aacctatgaa      4620
aatgatctca atcctctgaa atgcatttta ttcatgtttt atttcctctt tgcagggagt      4680
ggtcaacttc gcctggtcga tggaggtggt cgttgtgctg ggagagtaga ggtctatcat      4740
gagggctcct ggggcaccat ctgtgatgac agctgggacc tgaatgatgc ccatgtggtg      4800
tgcaaacagc tgagctgtgg atgggccatt aatgccactg ttctgctca ttttggggaa      4860 ggaacagggc ccatttggct ggatgagata aactgtaatg gaaaagaatc tcatatttgg      4920
caatgccact cacatggttg ggggcggcac aattgcaggc ataaggagga tgcaggagtc      4980
atctgctcgg                                                             4990
```

```
<210> SEQ ID NO 48
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 48
caccggaaac ccaggctggt tgga                                             24

<210> SEQ ID NO 49
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 49
aaactccaac cagcctgggt ttcc                                             24

<210> SEQ ID NO 50
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 50
caccggaact acagtgcggc actg                                             24

<210> SEQ ID NO 51
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 51
```

-continued aaaccagtgc cgcactgtag ttcc                                              24

<210> SEQ ID NO 52
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 52
caccgcagta gcaccccgcc ctgac                                             25

<210> SEQ ID NO 53
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 53
aaacgtcagg gcggggtgct actgc                                             25

<210> SEQ ID NO 54
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 54
caccgtgtag ccacagcagg gacgt                                             25

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 55
aaacacgtcc ctgctgtggc tacac                                             25

<210> SEQ ID NO 56
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 56
caccgccagc ctcgcccagc gacat                                             25

<210> SEQ ID NO 57
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 57
aaacatgtcg ctgggcgagg ctggc                                             25

<210> SEQ ID NO 58
<211> LENGTH: 25
<212> TYPE: DNA

<213> ORGANISM: Artificial sequence
<220> FEATURE:
<223> OTHER INFORMATION: Synthetic oligonucleotide

<400> SEQUENCE: 58
caccgcagct gcagcatata tttaa                                                25

<210> SEQ ID NO 59
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 59
aaacttaaat atatgctgca gctgc                                                25

<210> SEQ ID NO 60
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 60
caccgctttc atttatctga actca                                                25

<210> SEQ ID NO 61
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 61
aaactgagtt cagataaatg aaagc                                                25

<210> SEQ ID NO 62
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 62
caccgttatc tgaactcagg gtccc                                                25

<210> SEQ ID NO 63
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 63
aaacgggacc ctgagttcag ataac                                                25

<210> SEQ ID NO 64
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 64
caccgctcct cgcccttgct cacca                                                25

<210> SEQ ID NO 65
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 65
aaactggtga gcaagggcga ggagc                                    25

<210> SEQ ID NO 66
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 66
caccggacca ggatgggcac caccc                                    25

<210> SEQ ID NO 67
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 67
aaacgggtgg tgcccatcct ggtcc                                    25

<210> SEQ ID NO 68
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 68
ttgttggaag gctcactgtc cttg                                     24

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
acaactaagg tggggcaaag                                          20

<210> SEQ ID NO 70
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 70
ttgttggaag gctcactgtc cttg                                     24

<210> SEQ ID NO 71
<211> LENGTH: 23
<212> TYPE: DNA
<213> ORGANISM: Artificial sequence
<220> FEATURE:

<223> OTHER INFORMATION: Synthetic oligonucleotide

<400> SEQUENCE: 71
ggagctcaac attcttgggt cct                                              23

<210> SEQ ID NO 72
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 72
ggcaaaattt tcatgctgag gtg                                              23

<210> SEQ ID NO 73
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 73
gcacatcact tcgggttaca gtg                                              23

<210> SEQ ID NO 74
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 74
cccaagtatc ttcagttctg cag                                              23

<210> SEQ ID NO 75
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 75
tacaggtagg agagcctgtt ttg                                              23

<210> SEQ ID NO 76
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 76
cccaagtatc ttcagttctg cag                                              23

<210> SEQ ID NO 77
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 77
ctcaaaagga tgtaaaccct gga                                              23

```
<210> SEQ ID NO 78
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 78
tgttgatgtg gtttgtttgc cc                                              22

<210> SEQ ID NO 79
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 79
tacaggtagg agagcctgtt ttg                                             23

<210> SEQ ID NO 80
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 80
ggaggtctag aatcggctaa gcc                                             23

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ggctacatgt cccgtcaggg                                                 20

<210> SEQ ID NO 82
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 82
gcaggccact aggcagatga a                                               21

<210> SEQ ID NO 83
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 83
gagctgacac ccaagaagtt cct                                             23

<210> SEQ ID NO 84
<211> LENGTH: 22
<212> TYPE: DNA
<213> ORGANISM: Artificial sequence
<220> FEATURE:
<223> OTHER INFORMATION: Synthetic oligonucleotide
```

<400> SEQUENCE: 84
ggctctagag cctctgctaa cc                                          22

<210> SEQ ID NO 85
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 85
ggacttgaag aagtcgtgct gc                                          22

<210> SEQ ID NO 86
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 86
taatacgact cactataggg agaatggact ataaggacca cgac                  44

<210> SEQ ID NO 87
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 87
gcgagctcta ggaattctta c                                           21

<210> SEQ ID NO 88
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 88
ttaatacgac tcactatagg ctcctcgccc ttgctcacca                       40

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
aaaagcaccg actcggtgcc                                             20

<210> SEQ ID NO 90
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 90
ttaatacgac tcactatagg aaacccaggc tggttgga                         38

<210> SEQ ID NO 91
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 91
aaaagcaccg actcggtgcc                                                    20

<210> SEQ ID NO 92
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 92
ttaatacgac tcactatagg aactacagtg cggcactg                                38

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
aaaagcaccg actcggtgcc                                                    20

<210> SEQ ID NO 94
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 94
ttaatacgac tcactatagg ccagcctcgc ccagcgacat                              40

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
aaaagcaccg actcggtgcc                                                    20

<210> SEQ ID NO 96
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 96
ttaatacgac tcactatagg cagctgcagc atatatttaa                              40

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
```
aaaagcaccg actcggtgcc                                                   20

<210> SEQ ID NO 98
<211> LENGTH: 3484
<212> TYPE: DNA
<213> ORGANISM: Sus scrofa

<400> SEQUENCE: 98

| | | | | | |
|---|---|---|---|---|---|
| tatagatgac | aaggctttgt | gtctgatagg | ggccagcgaa | ctcagtaaag | agggaagatg | 60 |
| agaaagataa | tggcaagaat | ttatccctga | agtgtagttt | tgacaaacca | gtcacaaaga | 120 |
| ggtctaagaa | attttggtca | caaagttgtt | ttgaatccca | ggcattttat | ttgcaatgat | 180 |
| tgcatatgtt | ctggaaagga | catctgaacc | taagaaatag | ttcatttgca | ttgtgttata | 240 |
| ttttactaag | gtctgagaaa | taatcttgag | atgagaatga | actctacttc | ttcagagtct | 300 |
| ggaaggaata | aattatgaaa | atgtattaat | gcttctttaa | accatattgt | atatttatct | 360 |
| attactaaac | aaaagaagt | agctctattt | atttatttat | ttatttattt | atttatgtct | 420 |
| tttgtctctt | tagggccaca | cctgtggcat | atggaggttc | ccaggctaga | ggtccaattg | 480 |
| gagatgtagc | agccagccta | tgccagagcc | accgcaacac | gggatctgag | ccacgtctgt | 540 |
| gacttacacc | acagctcaca | gcaacgcctg | atcctcaacc | cactgagcga | ggccagggat | 600 |
| cgaacccatg | tcctcatgga | tgctagttgg | gttcgttaac | tgctgagcca | tgatgggaac | 660 |
| tccaaattaa | ttatttctta | tatttgttct | tcatatattc | atttctatag | aaagaaataa | 720 |
| atacagattc | agttaatgat | ggcaggtaaa | agcttaactt | attaatcaaa | ggagttaatc | 780 |
| caggcacaaa | aattcaattc | atggctctct | gttaaaattt | aggtataggt | ttagcaggaa | 840 |
| gaaaaggtta | gtagatgcag | actattacat | ttagaatgga | tggacaatga | agtcctacta | 900 |
| tacagcacag | ggaactatat | ccaatctctt | gggatagaat | atgatggaag | acaaaatcag | 960 |
| aacaagagag | tatatatata | tgtgtgtgtg | tgtgtgtgtg | tgtgtgtgtg | tgtgtgtgtg | 1020 |
| tgtgtgactg | ggtcaccctg | cggcacagca | gaaattggca | gaacattgta | aatcaactat | 1080 |
| actttaatag | gaaaaatact | tttaagggct | aaatttccaa | tattctaacc | atgtacacag | 1140 |
| agtaaatgtc | ataaggatgc | cagtctgtgt | agagattgat | gtgttactag | cagattcatg | 1200 |
| aaataaaggc | tgaggatgta | gtccccaagt | cacttctgag | tggaagaatt | tctcctttgt | 1260 |
| cctggactca | atattttag | gataaaggaa | aaagaagat | atttatagaa | gggacttgtt | 1320 |
| ttcaagtact | tgacaaaatt | tcaccattaa | agagaaattt | gtgggagttc | ccatcgtggc | 1380 |
| tcagtggaaa | caaatccaac | taggaaccat | gaggttgtgg | gtttgatccc | tggcctcact | 1440 |
| cagtgggtta | aggatccggt | gttgccgtga | gctgtggtgt | aggttgcaga | cacggttctg | 1500 |
| atcctgcgtt | gctgtggctg | tggcacattc | cctgctctgg | tcgtgttgaa | gtacaacatg | 1560 |
| gagacacgtg | gggcaccgtc | tgtgattctg | acttctctct | ggaggcggcc | agcgtgctgt | 1620 |
| gcagggaact | acagtgcggc | actgtggttt | ccctcctggg | gggagctcac | tttggagaag | 1680 |
| gaagtggaca | gatctgggct | gaagaattcc | agtgtgaggg | gcacgagtcc | cacctttcac | 1740 |
| tctgcccagt | agcaccccgc | cctgacggga | catgtagcca | cagcagggac | gtcggcgtag | 1800 |
| tctgctcaag | tgagacccag | ggaatgtgtt | cactttgttc | ccatgccatg | aagagggtag | 1860 |
| ggttaggtag | tcacagacat | cttttttaaag | ccctgtctcc | ttccaggata | cacacaaatc | 1920 |
| cgcttggtga | atggcaagac | cccatgtgaa | ggaagagtgg | agctcaacat | tcttgggtcc | 1980 |
| tggggggtccc | tctgcaactc | tcactgggac | atggaagatg | cccatgtttt | atgccagcag | 2040 |
| cttaaatgtg | gagttgccct | ttctatcccg | ggaggagcac | cttttgggaa | aggaagtgag | 2100 |

```
caggtctgga ggcacatgtt tcactgcact gggactgaga agcacatggg agattgttcc    2160
gtcactgctc tgggcgcatc actctgttct tcagggcaag tggcctctgt aatctgctca    2220
ggtaagagaa taagggcagc cagtgatgag ccactcatga cggtgcctta agagtgggtg    2280
tacctaggag ttcccattgt ggctcagtgg taacaaactc gactggtatc catgagggta    2340
tgggtttgat ccctggcctt gctcaatggg ttaaggatcc agcattgctg tgagctgtgg    2400
tataggttgc agactctgct caggtcccat gttgctgtga ttgtggtgta ggctgactgc    2460
tgcagcttca atttgacccc tagcccggga atttccatag ccacacgtg cagcactaag    2520 gaaggaaaaa aagaaaaaaa aaaaaaaaga gtgggtgtgc ctatagtgaa gaacagatgt    2580
aaaagggaag tgaaagggat tcccccattc tgagggattg tgagaagtgt gccagaatat    2640
taacttcatt tgacttgtta cagggaaagt aaacttgact ttcacggacc tcctagttac    2700
ctggtgctta ctatatgtct tctcagagta cctgattcat tcccagcctg gttgacccat    2760 cccctatct ctatggctat gtttatccag agcacatcta tctaacactc agctgatct     2820 tcctgacaca gctgtggcaa ccctggatcc tttaaccaac tgtgccaggc tggagatcaa    2880
acctaagcct ctgcagcaac ccaagctgct gcagtcagat ttttaacccc ctgtgccact    2940
gtgggtatct ccgatatttt gtatcttctg tgactgagtg gtttgctgtt tgcagggaac    3000
cagagtcaga cactatcccc gtgcaattca tcatcctcgg acccatcaag ctctattatt    3060
tcagaagaaa atggtgttgc ctgcataggt gagaatcagt gaccaaccta tgaaaatgat    3120
ctcaatcctc tgaaatgcat tttattcatg ttttatttcc tctttgcagg gagtggtcaa    3180
cttcgcctgg tcgatggagg tggtcgttgt gctgggagag tagaggtcta tcatgagggc    3240
tcctggggca ccatctgtga tgacagctgg gacctgaatg atgcccatgt ggtgtgcaaa    3300
cagctgagct gtgatgggc cattaatgcc actggttctg ctcattttgg ggaaggaaca    3360
gggcccattt ggctgatga gataaactgt aatggaaaag aatctcatat ttggcaatgc    3420
cactcacatg gttgggggcg gcacaattgc aggcataagg aggatgcagg agtcatctgc    3480
tcgg                                                                 3484
```

<210> SEQ ID NO 99
<211> LENGTH: 4997
<212> TYPE: DNA
<213> ORGANISM: Sus scrofa

<400> SEQUENCE: 99

```
tatagatgac aaggctttgt gtctgatagg ggccagcgaa ctcagtaaag agggaagatg     60
agaaagataa tggcaagaat ttatccctga agtgtagttt tgacaaacca gtcacaaaga    120
ggtctaagaa attttggtca caaagttgtt ttgaatccca ggcattttat ttgcaatgat    180
tgcatatgtt ctggaaagga catctgaacc taagaaatag ttcatttgca ttgtgtttata  240 ttttactaag gtctgagaaa taatcttgag atgagaatga actctacttc ttcagagtct    300
ggaaggaata aattatgaaa atgtattaat gcttctttaa accatattgt atatttatct    360
attactaaac aaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
```

```
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaagaagat atttatagaa gggacttgtt    1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaagaga    1620 aaagacaaaa aaaaaaaaa aaaaaaaaa aaaaaaaaa aaaaaaaaaa gaaccccag      1680 aggtatttat ttgttttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt ccttcttta aagataaat tgaagaaaat    2520 aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tattttcag    3000 cccacaggaa acccaggctg gttggagggg acattccctg ctctggtcgt gttgaagtac   3060
```

| | |
|---|---|
| aacatggaga cacgtggggc accgtctgtg attctgactt ctctctggag gcggccagcg | 3120 |
| tgctgtgcag ggaactacag tgcggctact actactgtgg tttccctcct gggggagct | 3180 |
| cactttggag aaggaagtgg acagatctgg gctgaagaat tccagtgtga ggggcacgag | 3240 |
| tcccaccttt cactctgccc agtagcaccc cgccctgacg ggacatgtag ccacagcagg | 3300 |
| gacgtcggcg tagtctgctc aagtgagacc cagggaatgt gttcactttg ttcccatgcc | 3360 |
| atgaagaggg tagggttagg tagtcacaga catcttttta aagccctgtc tccttccagg | 3420 |
| atacacacaa atccgcttgg tgaatggcaa gaccccatgt gaaggaagag tggagctcaa | 3480 |
| cattcttggg tcctgggggt ccctctgcaa ctctcactgg gacatggaag atgcccatgt | 3540 |
| tttatgccag cagcttaaat gtggagttgc ccttttctatc ccgggaggag cacctttgg | 3600 |
| gaaaggaagt gagcaggtct ggaggcacat gtttcactgc actgggactg agaagcacat | 3660 |
| gggagattgt tccgtcactg ctctgggcgc atcactctgt tcttcagggc aagtggcctc | 3720 |
| tgtaatctgc tcaggtaaga gaataagggc agccagtgat gagccactca tgacggtgcc | 3780 |
| ttaagagtgg gtgtacctag gagttcccat tgtggctcag tggtaacaaa ctcgactggt | 3840 |
| atccatgagg gtatgggttt gatccctggc cttgctcaat gggttaagga tccagcattg | 3900 |
| ctgtgagctg tggtataggt tgcagactct gctcaggtcc catgttgctg tgattgtggt | 3960 |
| gtaggctgac tgctgcagct tcaatttgac ccctagcccg ggaatttcca taggccacac | 4020 |
| gtgcagcact aaggaaggaa aaaagaaaa aaaaaaaaa agagtgggtg tgcctatagt | 4080 |
| gaagaacaga tgtaaaaggg aagtgaaagg gattcccca ttctgaggga ttgtgagaag | 4140 |
| tgtgccagaa tattaacttc atttgacttg ttacaggaa agtaaacttg actttcacgg | 4200 |
| acctcctagt tacctggtgc ttactatatg tcttctcaga gtacctgatt cattcccagc | 4260 |
| ctggttgacc catcccccta tctctatggc tatgtttatc cagagcacat ctatctaaca | 4320 |
| ctccagctga tcttcctgac acagctgtgg caaccctgga tcctttaacc aactgtgcca | 4380 |
| ggctggagat caaacctaag cctctgcagc aacccaagct gctgcagtca gatttttaac | 4440 |
| cccctgtgcc actgtgggta tctccgatat tttgtatctt ctgtgactga gtggtttgct | 4500 |
| gtttgcaggg aaccagagtc agacactatc cccgtgcaat tcatcatcct cggacccatc | 4560 |
| aagctctatt atttcagaag aaaatggtgt tgcctgcata ggtgagaatc agtgaccaac | 4620 |
| ctatgaaaat gatctcaatc ctctgaaatg cattttattc atgttttatt tcctctttgc | 4680 |
| agggagtggt caacttcgcc tggtcgatgg aggtggtcgt tgtgctggga gagtagaggt | 4740 |
| ctatcatgag ggctcctggg gcaccatctg tgatgacagc tgggacctga atgatgccca | 4800 |
| tgtggtgtgc aaacagctga gctgtggatg ggccattaat gccactggtt ctgctcattt | 4860 |
| tggggaagga acagggccca tttggctgga tgagataaac tgtaatggaa aagaatctca | 4920 |
| tatttggcaa tgccactcac atggttgggg gcggcacaat tgcaggcata aggaggatgc | 4980 |
| aggagtcatc tgctcgg | 4997 |

<210> SEQ ID NO 100
<211> LENGTH: 3710
<212> TYPE: DNA
<213> ORGANISM: Sus scrofa

<400> SEQUENCE: 100

| | |
|---|---|
| tatagatgac aaggctttgt gtctgatagg ggccagcgaa ctcagtaaag agggaagatg | 60 |
| agaaagataa tggcaagaat ttatccctga agtgtagttt tgacaaacca gtcacaaaga | 120 |

```
ggtctaagaa attttggtca caaagttgtt ttgaatccca ggcattttat ttgcaatgat        180
tgcatatgtt ctggaaagga catctgaacc taagaaatag ttcatttgca ttgtgttata        240
ttttactaag gtctgagaaa taatcttgag atgagaatga actctacttc ttcagagtct        300
ggaaggaata aattatgaaa atgtattaat gcttctttaa accatattgt atatttatct        360
attactaaac aaaaagaagt agctctattt atttatttat ttatttattt atttatgtct        420
tttgtctctt tagggccaca cctgtggcat atggaggttc ccaggctaga ggtccaattg        480
gagatgtagc agccagccta tgccagagcc accgcaacac gggatctgag ccacgtctgt        540
gacttacacc acagctcaca gcaacgcctg atcctcaacc cactgagcga ggccagggat        600
cgaacccatg tcctcatgga tgctagttgg gttcgttaac tgctgagcca tgatgggaac        660
tccaaattaa ttatttctta tatttgttct tcatatattc atttctatag aaagaaataa        720
atacagattc agttaatgat ggcaggtaaa agcttaactt attaatcaaa ggagttaatc        780
caggcacaaa aattcaattc atggctctct gttaaaattt aggtataggt ttagcaggaa        840
gaaaaggtta gtagatgcag actattacat ttagaatgga tggacaatga agtcctacta        900
tacagcacag ggaactatat ccaatctctt gggatagaat atgatggaag acaaaatcag        960
aacaagagag tatatatata tgtgtgtgtg tgtgtgtgtg tgtgtgtgtg tgtgtgtgtg       1020
tgtgtgactg ggtcaccctg cggcacagca gaaattggca gaacattgta aatcaactat       1080
actttaatag gaaaaatact tttaagggct aaatttccaa tattctaacc atgtacacag       1140
agtaaatgtc ataaggatgc cagtctgtgt agagattgat gtgttactag cagattcatg       1200
aaataaaggc tgaggatgta gtccccaagt cacttctgag tggaagaatt ctcctttgt        1260 cctggactca aatattttag gataaaggaa aaagaagat atttatagaa gggacttgtt        1320
ttcaagtact tgacaaaatt tcaccattaa agagaaattt gtgggagttc ccatcgtggc       1380
tcagtggaaa caaatccaac taggaaccat gaggttgtgg gtttgatccc tggcctcact       1440
cagtgggtta aggatccggt gttgccgtga gctgtggtgt aggttgcaga cacggttctg       1500
atcctgcgtt gctgtggctg tggctgtggt gtaggccagc agcaaacagc tctgattaga       1560
cccctagcct ggaaacctcc atatgccaca ggtgcagccc taaaaagaca aaaaagaga        1620 aaagacaaaa aaaaaaaaaa aaaaaaaaaa aaaaaaaaa aaaaaaaaaa gaaccccag         1680 aggtatttat ttgttttgc cttttttcac tgactgttct ttgtttgttt gtttgagact        1740
gatctagaag actagagatt acaagaaata tggatttggc tcactctaag aaactgcttt       1800
cattccaagg tttgggtcta tccaaaagtg gaatagaatc atatgaatac tagtttatga       1860
gtatttagtg agaggaattt caagctcaaa taatgattca gcaagattaa attaaggagg       1920
gaattttcct tgtggctgag tgggttaagg acccaatgtt gtctctgtga ggatgtaggt       1980
tccatcctgg gctttgctca ttaggttaag gatctggcat tgctgcagct cagacccagt       2040
gctgccctgg ttgtggctta ggccaaagct gcagctccaa ttcaatctct ggcctgggaa       2100
cctccatgtg ctacaaggtg cggccttaaa aggaaaaaaa aaaattaaa tcaaggactc        2160 aagagtcttt cattatttgt gttgtggaag ctatatttgt tttaaagtct tagttgtgtt       2220
tagaaagcaa gatgttcttc aactcaaatt tgggagggaa cttgtttcat acatttttaa       2280
tggataagtg gcaaaatttt catgctgagg tgatctatag tgttgtaatg cagaatatag       2340
tcagatcttg aacattttag gaagttggtg agggccaatt gtgtatctgt gccatgctga       2400
taagaatgtc aagggatcac aagaattcgt gttatttgac agcagtcatc tttaaaggc        2460 atttgagaaa gtccaatttc aaatgcattt ccttcctta aaagataaat tgaagaaaat       2520
```

```
aagtctttat ttcccaagta aattgaattg cctctcagtc tgttaaaaga aactcttacc    2580
ttgatgattg cgctcttaac ctggcaaaga ttgtctttaa aatctgagct ccatgtcttc    2640
tgctttattt ctggtgtgcc tttgactcca gattacagta aatggaggac tgagtatagg    2700
gctaaaaagt agagagaatg gatgcatatt atctgtggtc tccaatgtga tgaatgaagt    2760
aggcaaatac tcaaaggaaa gagaaagcat gctccaagaa ttatgggttc cagaagggaa    2820
agggattccc ccattctgag ggattgtgag aagtgtgcca gaatattaac ttcatttgac    2880
ttgttacagg gaaagtaaac ttgactttca cggacctcct agttacctgg tgcttactat    2940
atgtcttctc agagtacctg attcattccc agcctggttg acccatcccc ctatctctat    3000
ggctatgttt atccagagca catctatcta acactccagc tgatcttcct gacacagctg    3060
tggcaaccct ggatccttta accaactgtg ccaggctgga gatcaaacct aagcctctgc    3120
agcaacccaa gctgctgcag tcagattttt aacccctgt gccactgtgg gtatctccga    3180
tattttgtat cttctgtgac tgagtggttt gctgtttgca gggaaccaga gtcagacact    3240
atccccgtgc aattcatcat cctcggaccc atcaagctct attatttcag aagaaaatgg    3300
tgttgcctgc ataggtgaga tcagtgacc aacctatgaa aatgatctca atcctctgaa    3360
atgcatttta ttcatgtttt atttcctctt tgcagggagt ggtcaacttc gcctggtcga    3420
tggaggtggt cgttgtgctg ggagagtaga ggtctatcat gagggctcct ggggcaccat    3480
ctgtgatgac agctgggacc tgaatgatgc ccatgtggtg tgcaaacagc tgagctgtgg    3540
atgggccatt aatgccactg gttctgctca tttggggaa ggaacagggc ccatttggct    3600
ggatgagata aactgtaatg gaaaagaatc tcatatttgg caatgccact cacatggttg    3660
ggggcggcac aattgcaggc ataaggagga tgcaggagtc atctgctcgg             3710
```

<210> SEQ ID NO 101
<211> LENGTH: 3617
<212> TYPE: DNA
<213> ORGANISM: Sus scrofa

<400> SEQUENCE: 101

```
tatagatgac aaggctttgt gtctgatagg ggccagcgaa ctcagtaaag agggaagatg      60
agaaagataa tggcaagaat ttatccctga agtgtagttt tgacaaacca gtcacaaaga    120
ggtctaagaa attttggtca caaagttgtt ttgaatccca ggcattttat ttgcaatgat    180
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaaagaagt agctctattt attttattat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagtggg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
```

```
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaagaagat atttatagaa gggacttgtt    1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaacctcc atatgccaca ggtgcagccc taaaaagaca aaaaagaga     1620
aaagacaaaa aaaaaaaaa aaaaaaaaa aaaaaaaaa aaaaaaaaa gaaccccag        1680
aggtatttat ttgttttgc cttttttcac tgactgttct ttgtttgttt gtttgagact    1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acattttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt ccttcttta aagataaat tgaagaaaat     2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gattgaaagg gattccccca ttctgaggga ttgtgagaag   2760
tgtgccagaa tattaacttc atttgacttg ttacagggaa agtaaacttg actttcacgg   2820
acctcctagt tacctggtgc ttactatatg tcttctcaga gtacctgatt cattcccagc   2880
ctggttgacc catccccta tctctatggc tatgtttatc cagagcacat ctatctaaca    2940
ctccagctga tcttcctgac acagctgtgg caaccctgga tccttttaacc aactgtgcca  3000
ggctggagat caaacctaag cctctgcagc aacccaagct gctgcagtca gattttaac    3060
cccctgtgcc actgtgggta tctccgatat tttgtatctt ctgtgactga gtggtttgct   3120
gtttgcaggg aaccagagtc agacactatc cccgtgcaat tcatcatcct cggacccatc   3180
aagtctatt atttcagaag aaaatggtgt tgcctgcata ggtgagaatc agtgaccaac    3240
ctatgaaaat gatctcaatc ctctgaaatg cattttattc atgtttatt tcctctttgc    3300
```

-continued

```
agggagtggt caacttcgcc tggtcgatgg aggtggtcgt tgtgctggga gagtagaggt    3360
ctatcatgag ggctcctggg gcaccatctg tgatgacagc tgggacctga atgatgccca    3420
tgtggtgtgc aaacagctga gctgtggatg ggccattaat gccactggtt ctgctcattt    3480
tggggaagga acagggccca tttggctgga tgagataaac tgtaatggaa aagaatctca    3540
tatttggcaa tgccactcac atggttgggg gcggcacaat tgcaggcata aggaggatgc    3600
aggagtcatc tgctcgg                                                  3617

<210> SEQ ID NO 102
<211> LENGTH: 4979
<212> TYPE: DNA
<213> ORGANISM: Sus scrofa

<400> SEQUENCE: 102
tatagatgac aaggctttgt gtctgatagg ggccagcgaa ctcagtaaag agggaagatg      60
agaaagataa tggcaagaat ttatccctga agtgtagttt tgacaaacca gtcacaaaga     120
ggtctaagaa attttggtca caaagttgtt ttgaatccca ggcattttat ttgcaatgat     180
tgcatatgtt ctggaaagga catctgaacc taagaaatag ttcatttgca ttgtgttata     240
ttttactaag gtctgagaaa taatcttgag atgagaatga actctacttc ttcagagtct     300
ggaaggaata aattatgaaa atgtattaat gcttctttaa accatattgt atatttatct     360
attactaaac aaaaagaagt agctctattt atttatttat ttatttattt atttatgtct     420
tttgtctctt tagggccaca cctgtggcat atggaggttc ccaggctaga ggtccaattg     480
gagatgtagc agccagccta tgccagagcc accgcaacac gggatctgag ccacgtctgt     540
gacttacacc acagctcaca gcaacgcctg atcctcaacc cactgagcga ggccagggat     600
cgaacccatg tcctcatgga tgctagttgg gttcgttaac tgctgagcca tgatgggaac     660
tccaaattaa ttatttctta tatttgttct tcatatattc atttctatag aaagaaataa     720
atacagattc agttaatgat ggcaggtaaa agcttaactt attaatcaaa ggagttaatc     780
caggcacaaa aattcaattc atggctctct gttaaaattt aggtataggt ttagcaggaa     840
gaaaaggtta gtagatgcag actattacat ttagaatgga tggacaatga agtcctacta     900
tacagcacag ggaactatat ccaatctctt gggatagaat atgatggaag acaaaatcag     960
aacaagagag tatatatata tgtgtgtgtg tgtgtgtgtg tgtgtgtgtg tgtgtgtgtg    1020
tgtgtgactg ggtcaccctg cggcacagca gaaattggca gaacattgta aatcaactat    1080
actttaatag gaaaaatact tttaagggct aaatttccaa tattctaacc atgtacacag    1140
agtaaatgtc ataaggatgc cagtctgtgt agagattgat gtgttactag cagattcatg    1200
aaataaaggc tgaggatgta gtccccaagt cacttctgag tggaagaatt tctcctttgt    1260
cctggactca aatattttag gataaaggaa aaagaagat atttatagaa gggacttgtt    1320
ttcaagtact tgcaaaaatt tcaccattaa agagaaattt gtgggagttc ccatcgtggc    1380
tcagtggaaa caaatccaac taggaaccat gaggttgtgg gtttgatccc tggcctcact    1440
cagtgggtta aggatccggt gttgccgtga gctgtggtgt aggttgcaga cacggttctg    1500
atcctgcgtt gctgtggctg tggctgtggt gtaggccagc agcaaacagc tctgattaga    1560
cccctagcct ggaaacctcc atatgccaca ggtgcagccc taaaaagaca aaaaagaga    1620 aaagacaaaa aaaaaaaaaa aaaaaaaaa aaaaaaaaa aaaaaaaaaa gaaccccag    1680 aggtatttat ttgttttgc cttttttcac tgactgttct ttgtttgttt gtttgagact    1740
```

```
gatctagaag actagagatt acaagaaata tggatttggc tcactctaag aaactgcttt    1800
cattccaagg tttgggtcta tccaaaagtg aatagaatc atatgaatac tagtttatga     1860
gtatttagtg agaggaattt caagctcaaa taatgattca gcaagattaa attaaggagg    1920
gaattttcct tgtggctgag tgggttaagg acccaatgtt gtctctgtga ggatgtaggt    1980
tccatcctgg gctttgctca ttaggttaag gatctggcat tgctgcagct cagacccagt    2040
gctgccctgg ttgtggctta ggccaaagct gcagctccaa ttcaatctct ggcctgggaa    2100
cctccatgtg ctacaaggtg cggccttaaa aggaaaaaaa aaaattaaa tcaaggactc      2160 aagagtcttt cattatttgt gttgtggaag ctatatttgt tttaaagtct tagttgtgtt    2220
tagaaagcaa gatgttcttc aactcaaatt tgggagggaa cttgtttcat acattttaa     2280 tggataagtg gcaaaatttt catgctgagg tgatctatag tgttgtaatg cagaatatag    2340
tcagatcttg aacattttag gaagttggtg agggccaatt gtgtatctgt gccatgctga    2400
taagaatgtc aagggatcac aagaattcgt gttatttgac agcagtcatc tttaaaaggc    2460
atttgagaaa gtccaatttc aaatgcattt cctttcttta aagataaat tgaagaaaat     2520 aagtctttat ttcccaagta aattgaattg cctctcagtc tgttaaaaga aactcttacc    2580
ttgatgattg cgctcttaac ctggcaaaga ttgtctttaa aatctgagct ccatgtcttc    2640
tgctttattt ctggtgtgcc tttgactcca gattacagta aatggaggac tgagtatagg    2700
gctaaaaagt agagagaatg gatgcatatt atctgtggtc tccaatgtga tgaatgaagt    2760
aggcaaatac tcaaaggaaa gagaaagcat gctccaagaa ttatgggttc cagaaggcaa    2820
agtcccagaa ttgtctccag ggaaggacag ggaggtctag aatcggctaa gcccactgta    2880
ggcagaaaaa ccaagaggca tgaatggctt ccctttctca cttttcactc tctggcttac    2940
tcctatcatg aaggaaaata ttggaatcat attctccctc accgaaatgc tattttcag    3000 cccacaggaa acccaggctg gttggagggg acattccctg ctctggtcgt gttgaagtac    3060
aacatggaga cacgtggggc accgtctgtg attctgactt ctctctggag gcggccagcg    3120
tgctgtgcag ggaactctgt ggtttccctc ctgggggag ctcactttgg agaaggaagt     3180
ggacagatct gggctgaaga attccagtgt gaggggcacg agtcccacct ttcactctgc    3240
ccagtagcac cccgccctga cgggacatgt agccacagca gggacgtcgg cgtagtctgc    3300
tcaagtgaga cccagggaat gtgttcactt tgttcccatg ccatgaagag ggtagggtta    3360
ggtagtcaca gacatctttt taaagccctg tctccttcca ggatacacac aaatccgctt    3420
ggtgaatggc aagaccccat gtgaaggaag agtggagctc aacattcttg ggtcctgggg    3480
gtccctctgc aactctcact gggacatgga agatgcccat gttttatgcc agcagcttaa    3540
atgtggagtt gcccttttcta tcccgggagg agcaccttttt gggaaaggaa gtgagcaggt   3600
ctggaggcac atgtttcact gcactgggac tgagaagcac atgggagatt gttccgtcac    3660
tgctctgggc gcatcactct gttcttcagg gcaagtggcc tctgtaatct gctcaggtaa    3720
gagaataagg gcagccagtg atgagccact catgacggtg ccttaagagt gggtgtacct    3780
aggagttccc attgtggctc agtggtaaca aactcgactg gtatccatga gggtatgggt    3840
ttgatccctg gccttgctca atgggttaag gatccagcat tgctgtgagc tgtggtatag    3900
gttgcagact ctgctcaggt cccatgttgc tgtgattgtg gtgtaggctg actgctgcag    3960
cttcaatttg accccctagcc cgggaatttc cataggccac acgtgcagca ctaaggaagg   4020
aaaaaaagaa aaaaaaaaa aaagagtggg tgtgcctata gtgaagaaca gatgtaaaag     4080
ggaagtgaaa gggattcccc cattctgagg gattgtgaga agtgtgccag aatattaact    4140
```

```
tcatttgact tgttacaggg aaagtaaact tgactttcac ggacctccta gttacctggt    4200
gcttactata tgtcttctca gagtacctga ttcattccca gcctggttga cccatccccc    4260
tatctctatg gctatgttta tccagagcac atctatctaa cactccagct gatcttcctg    4320
acacagctgt ggcaaccctg gatcctttaa ccaactgtgc caggctggag atcaaaccta    4380
agcctctgca gcaacccaag ctgctgcagt cagatttttta accccctgtg ccactgtggg    4440
tatctccgat attttgtatc ttctgtgact gagtggtttg ctgtttgcag ggaaccagag    4500
tcagacacta tccccgtgca attcatcatc ctcggaccca tcaagctcta ttatttcaga    4560
agaaaatggt gttgcctgca taggtgagaa tcagtgacca acctatgaaa atgatctcaa    4620
tcctctgaaa tgcattttat tcatgttttta tttcctcttt gcagggagtg gtcaacttcg    4680
cctggtcgat ggaggtggtc gttgtgctgg gagagtagag gtctatcatg agggctcctg    4740
gggcaccatc tgtgatgaca gctgggacct gaatgatgcc catgtggtgt gcaaacagct    4800
gagctgtgga tgggccatta tgccactggt tctgctcat tttggggaag gaacagggcc    4860
catttggctg gatgagataa actgtaatgg aaaagaatct catatttggc aatgccactc    4920
acatggttgg gggcggcaca attgcaggca taaggaggat gcaggagtca tctgctcgg    4979

<210> SEQ ID NO 103
<211> LENGTH: 4615
<212> TYPE: DNA
<213> ORGANISM: Sus scrofa

<400> SEQUENCE: 103
tatagatgac aaggctttgt gtctgatagg ggccagcgaa ctcagtaaag agggaagatg      60
agaaagataa tggcaagaat ttatccctga agtgtagttt tgacaaacca gtcacaaaga     120
ggtctaagaa attttggtca caagttgtt ttgaatccca ggcattttat ttgcaatgat     180
tgcatatgtt ctggaaagga catctgaacc taagaaatag ttcatttgca ttgtgttata     240
ttttactaag gtctgagaaa taatcttgag atgagaatga actctacttc ttcagagtct     300
ggaaggaata aattatgaaa atgtattaat gcttctttaa accatattgt atatttatct     360
attactaaac aaaaagaagt agctctattt atttatttat ttatttattt atttatgtct     420
tttgtctctt tagggccaca cctgtggcat atggaggttc ccaggctaga ggtccaattg     480
gagatgtagc agccagccta tgccagagcc accgcaacac gggatctgag ccacgtctgt     540
gacttacacc acagctcaca gcaacgcctg atcctcaacc cactgagcga ggccagggat     600
cgaacccatg tcctcatgga tgctagttgg gttcgttaac tgctgagcca tgatgggaac     660
tccaaattaa ttatttctta tatttgttct tcatatattc atttctatag aaagaaataa     720
atacagattc agttaatgat ggcaggtaaa agcttaactt attaatcaaa ggagttaatc     780
caggcacaaa aattcaattc atggctctct gttaaaattt aggtataggt ttagcaggaa     840
gaaaaggtta gtagatgcag actattacat ttagaatgga tggacaatga agtcctacta     900
tacagcacag ggaactatat ccaatctctt gggatagaat atgatggaag acaaaatcag     960
aacaagagag tatatatata tgtgtgtgtg tgtgtgtgtg tgtgtgtgtg tgtgtgtgtg    1020
tgtgtgactg ggtcaccctg cggcacagca gaaattggca gaacattgta aatcaactat    1080 acttttaatag gaaaaatact tttaagggct aaatttccaa tattctaacc atgtacacag    1140
agtaaatgtc ataaggatgc cagtctgtgt agagattgat gtgttactag cagattcatg    1200
aaataaaggc tgaggatgta gtccccaagt cacttctgag tggaagaatt tctcctttgt    1260
```

```
cctggactca aatattttag gataaaggaa aaaagaagat atttatagaa gggacttgtt    1320
ttcaagtact tgacaaaatt tcaccattaa agagaaattt gtgggagttc ccatcgtggc    1380
tcagtggaaa caaatccaac taggaaccat gaggttgtgg gtttgatccc tggcctcact    1440
cagtgggtta aggatccggt gttgccgtga gctgtggtgt aggttgcaga cacggttctg    1500
atcctgcgtt gctgtggctg tggctgtggt gtaggccagc agcaaacagc tctgattaga    1560
cccctagcct ggaaacctcc atatgccaca ggtgcagccc taaaaagaca aaaaagaga    1620 aaagacaaaa aaaaaaaaa aaaaaaaaa aaaaaaaaa aaaaaaaaa gaaccccag     1680 aggtatttat ttgttttttgc ctttttttcac tgactgttct ttgtttgttt gtttgagact    1740
gatctagaag actagagatt acaagaaata tggatttggc tcactctaag aaactgcttt    1800
cattccaagg tttgggtcta tccaaaagtg aatagaatc atatgaatac tagtttatga    1860
gtatttagtg agaggaattt caagctcaaa taatgattca gcaagattaa attaaggagg    1920
gaattttcct tgtggctgag tgggttaagg acccaatgtt gtctctgtga ggatgtaggt    1980
tccatcctgg gctttgctca ttaggttaag gatctggcat tgctgcagct cagacccagt    2040
gctgccctgg ttgtggctta ggccaaagct gcagctccaa ttcaatctct ggcctgggaa    2100
cctccatgtg ctacaaggtg cggccttaaa aggaaaaaaa aaaattaaa tcaaggactc    2160 aagagtcttt cattatttgt gttgtggaag ctatatttgt tttaaagtct tagttgtgtt    2220
tagaaagcaa gatgttcttc aactcaaatt tgggagggaa cttgtttcat acatttttaa    2280
tggataagtg gcaaaatttt catgctgagg tgatctatag tgttgtaatg cagaatatag    2340
tcagatcttg aacattttag gaagttggtg agggccaatt gtgtatctgt gccatgctga    2400
taagaatgtc aagggatcac aagaattcgt gttatttgac agcagtcatc tttaaaaggc    2460
atttgagaaa gtccaatttc aaatgcattt ccttctctta aaagataaat tgaagaaaat    2520
aagtctttat ttcccaagta aattgaattg cctctcagtc tgttaaaaga aagaaggaaa    2580
atattggaat catattctcc ctcaccgaaa tgctatttt cagcccacag gaaacccagg    2640
ctggttggag gggacattcc ctgctctggt cgtgttgaag tacaacatgg agacacgtgg    2700
ggcaccgtct gtgattctga cttctctctg gaggcggcca gcgtgctgtg cagggaacta    2760
cagtgcggca cagtgtggtt tccctcctgg ggggagctca cttttggagaa ggaagtggac    2820 agatctgggc tgaagaattc cagtgtgagg ggcacgagtc ccacctttca ctctgcccag    2880
tagcaccccg ccctgacggg acatgtagcc acagcaggga cgtcggcgta gtctgctcaa    2940
gtgagaccca gggaatgtgt tcactttgtt cccatgccat gaagagggta gggttaggta    3000
gtcacagaca tctttttaaa gccctgtctc cttccaggat acacacaaat ccgcttggtg    3060
aatggcaaga ccccatgtga aggaagagtg gagctcaaca ttcttgggtc ctgggggtcc    3120
ctctgcaact ctcactggga catggaagat gcccatgttt tatgccagca gcttaaatgt    3180
ggagttgccc tttctatccc gggaggagca ccttttggga aaggaagtga gcaggtctgg    3240
aggcacatgt ttcactgcac tgggactgag aagcacatgg gagattgttc cgtcactgct    3300
ctgggcgcat cactctgttc ttcagggcaa gtggcctctg taatctgctc aggtaagaga    3360
ataagggcag ccagtgatga gccactcatg acggtgcctt aagagtgggt gtacctagga    3420
gttcccattg tggctcagtg gtaacaaact cgactggtat ccatgagggt atgggtttga    3480
tccctggcct tgctcaatgg gttaaggatc cagcattgct gtgagctgtg gtataggttg    3540
cagactctgc tcaggtccca tgttgctgtg attgtggtgt aggctgactg ctgcagcttc    3600
aatttgaccc ctagcccggg aatttccata ggccacacgt gcagcactaa ggaaggaaaa    3660
```

```
aaagaaaaaa aaaaaaaaag agtgggtgtg cctatagtga agaacagatg taaaagggaa      3720
gtgaaaggga ttcccccatt ctgagggatt gtgagaagtg tgccagaata ttaacttcat      3780
ttgacttgtt acagggaaag taaacttgac tttcacggac ctcctagtta cctggtgctt      3840
actatatgtc ttctcagagt acctgattca ttcccagcct ggttgaccca tcccctatc      3900 tctatggcta tgtttatcca gagcacatct atctaacact ccagctgatc ttcctgacac      3960
agctgtggca accctggatc ctttaaccaa ctgtgccagg ctggagatca aacctaagcc      4020
tctgcagcaa cccaagctgc tgcagtcaga ttttttaaccc cctgtgccac tgtgggtatc      4080
tccgatattt tgtatcttct gtgactgagt ggtttgctgt ttgcagggaa ccagagtcag      4140
acactatccc cgtgcaattc atcatcctcg acccatcaa gctctattat ttcagaagaa      4200
aatggtgttg cctgcatagg tgagaatcag tgaccaacct atgaaaatga tctcaatcct      4260
ctgaaatgca ttttattcat gttttatttc ctctttgcag ggagtggtca acttcgcctg      4320
gtcgatggag gtggtcgttg tgctgggaga gtagaggtct atcatgaggg ctcctggggc      4380
accatctgtg atgacagctg ggacctgaat gatgcccatg tggtgtgcaa acagctgagc      4440
tgtggatggg ccattaatgc cactggttct gctcattttg gggaaggaac agggcccatt      4500
tggctggatg agataaactg taatggaaaa gaatctcata tttggcaatg ccactcacat      4560 ggttggggc ggcacaattg caggcataag gaggatgcag gagtcatctg ctcgg           4615

<210> SEQ ID NO 104
<211> LENGTH: 4866
<212> TYPE: DNA
<213> ORGANISM: Sus scrofa

<400> SEQUENCE: 104
tatagatgac aaggctttgt gtctgatagg ggccagcgaa ctcagtaaag agggaagatg        60
agaaagataa tggcaagaat ttatccctga agtgtagttt tgacaaacca gtcacaaaga       120
ggtctaagaa atttttggtca caagttgtt ttgaatccca ggcattttat ttgcaatgat       180
tgcatatgtt ctggaaagga catctgaacc taagaaatag ttcatttgca ttgtgttata       240
ttttactaag gtctgagaaa taatcttgag atgagaatga actctacttc ttcagagtct       300
ggaaggaata aattatgaaa atgtattaat gcttctttaa accatattgt atatttatct       360
attactaaac aaaaagaagt agctctattt atttatttat ttatttattt atttatgtct       420
tttgtctctt tagggccaca cctgtggcat atggaggttc ccaggctaga ggtccaattg       480
gagatgtagc agccagccta tgccagagcc accgcaacac gggatctgag ccacgtctgt       540
gacttacacc acagctcaca gcaacgcctg atcctcaacc cactgagcga ggccagggat       600
cgaacccatg tcctcatgga tgctagttgg gttcgttaac tgctgagcca tgatgggaac       660
tccaaattaa ttatttctta tatttgttct tcatatattc atttctatag aaagaaataa       720
atacagattc agtaatgat ggcaggtaaa agcttaactt attaatcaaa ggagttaatc       780
caggcacaaa aattcaattc atggctctct gttaaaattt aggtataggt ttagcaggaa       840
gaaaaggtta gtagatgcag actattacat ttagaatgga tggacaatga agtcctacta       900
tacagcacag ggaactatat ccaatctctt gggatagaat atgatggaag acaaaatcag       960
aacaagagag tatatatata tgtgtgtgtg tgtgtgtgtg tgtgtgtgtg tgtgtgtgtg      1020
tgtgtgactg ggtcaccctg cggcacagca gaaattggca gaacattgta aatcaactat      1080
actttaatag gaaaaatact tttaagggct aaatttccaa tattctaacc atgtacacag      1140
```

```
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaagaagat atttatagaa gggacttgtt    1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccag    1680 aggtatttat ttgttttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaattaaa tcaaggactc    2160 aagagtcttt cattatttgt gttgtggaag ctatatttgt tttaaagtct tagttgtgtt   2220
tagaaagcaa gatgttcttc aactcaaatt tgggagggaa cttgtttcat acattttaa    2280 tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt ccttttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt cccttctca cttttcactc tctggcttac     2940
tcctatcatg aaggaaaata ttggaatcat attctccctc accgaaatgc tattttcag    3000 cccacaggaa acccaggctg gttctgtggt ttccctcctg gggggagctc actttggaga   3060
aggaagtgga cagatctggg ctgaagaatt ccagtgtgag gggcacgagt cccacctttc   3120
actctgccca gtagcacccc gccctgacgg gacatgtagc cacagcaggg acgtcggcgt   3180
agtctgctca agtgagaccc agggaatgtg ttcactttgt tcccatgcca tgaagagggt   3240
agggttaggg agtcacagac atcttttaa agccctgtct ccttccagga tacacacaaa    3300
tccgcttggt gaatggcaag accccatgtg aaggaagagt ggagctcaac attcttgggt   3360
cctgggggtc cctctgcaac tctcactggg acatggaaga tgcccatgtt ttatgccagc   3420
agcttaaatg tggagttgcc cttttctatcc cggaggagc accttttggg aaaggaagtg    3480
agcaggtctg gaggcacatg tttcactgca ctgggactga gaagcacatg ggagattgtt   3540
```

| | |
|---|---|
| ccgtcactgc tctgggcgca tcactctgtt cttcagggca agtggcctct gtaatctgct | 3600 |
| caggtaagag aataagggca gccagtgatg agccactcat gacggtgcct aagagtgggg | 3660 |
| tgtacctagg agttcccatt gtggctcagt ggtaacaaac tcgactggta tccatgaggg | 3720 |
| tatgggtttg atccctggcc ttgctcaatg ggttaaggat ccagcattgc tgtgagctgt | 3780 |
| ggtataggtt gcagactctg ctcaggtccc atgttgctgt gattgtggtg taggctgact | 3840 |
| gctgcagctt caatttgacc cctagcccgg gaatttccat aggccacacg tgcagcacta | 3900 |
| aggaaggaaa aaagaaaaa aaaaaaaaaa gagtgggtgt gcctatagtg aagaacagat | 3960 |
| gtaaaaggga agtgaaaggg attcccccat tctgagggat tgtgagaagt gtgccagaat | 4020 |
| attaacttca tttgacttgt tacagggaaa gtaaacttga ctttcacgga cctcctagtt | 4080 |
| acctggtgct tactatatgt cttctcagag tacctgattc attcccagcc tggttgaccc | 4140 |
| atcccctat ctctatggct atgtttatcc agagcacatc tatctaacac tccagctgat | 4200 |
| cttcctgaca cagctgtggc aaccctggat cctttaacca actgtgccag gctggagatc | 4260 |
| aaacctaagc ctctgcagca acccaagctg ctgcagtcag attttaacc ccctgtgcca | 4320 |
| ctgtgggtat ctccgatatt ttgtatcttc tgtgactgag tggtttgctg tttgcaggga | 4380 |
| accagagtca gacactatcc ccgtgcaatt catcatcctc ggacccatca agctctatta | 4440 |
| tttcagaaga aaatggtgtt gcctgcatag gtgagaatca gtgaccaacc tatgaaaatg | 4500 |
| atctcaatcc tctgaaatgc attttattca tgttttattt cctctttgca gggagtggtc | 4560 |
| aacttcgcct ggtcgatgga ggtggtcgtt gtgctgggag agtagaggtc tatcatgagg | 4620 |
| gctcctgggg caccatctgt gatgacagct gggacctgaa tgatgcccat gtggtgtgca | 4680 |
| aacagctgag ctgtgatgg gccattaatg ccactggttc tgctcatttt ggggaaggaa | 4740 |
| cagggcccat ttggctggat gagataaact gtaatggaaa agaatctcat atttggcaat | 4800 |
| gccactcaca tggttggggg cggcacaatt gcaggcataa ggaggatgca ggagtcatct | 4860 |
| gctcgg | 4866 |

<210> SEQ ID NO 105
<211> LENGTH: 4867
<212> TYPE: DNA
<213> ORGANISM: Sus scrofa

<400> SEQUENCE: 105

| | |
|---|---|
| tatagatgac aaggctttgt gtctgatagg ggccagcgaa ctcagtaaag agggaagatg | 60 |
| agaaagataa tggcaagaat ttatccctga agtgtagttt tgacaaacca gtcacaaaga | 120 |
| ggtctaagaa attttggtca caaagttgtt ttgaatccca ggcattttat ttgcaatgat | 180 |
| tgcatatgtt ctgaaagga catctgaacc taagaaatag ttcatttgca ttgtgttata | 240 |
| ttttactaag gtctgagaaa taatcttgag atgagaatga actctacttc ttcagagtct | 300 |
| ggaaggaata aattatgaaa atgtattaat gcttctttaa accatattgt atatttatct | 360 |
| attactaaac aaaagaagt agctctattt atttatttat ttatttattt atttatgtct | 420 |
| tttgtctctt tagggccaca cctgtggcat atggaggttc ccaggctaga ggtccaattg | 480 |
| gagatgtagc agccagccta tgccagagcc accgcaacac gggatctgag ccacgtctgt | 540 |
| gacttacacc acagctcaca gcaacgcctg atcctcaacc cactgagcga ggccagggat | 600 |
| cgaacccatg tcctcatgga tgctagttgg gttcgttaac tgctgagcca tgatgggaac | 660 |
| tccaaattaa ttatttctta tatttgttct tcatatattc atttctatag aaagaaataa | 720 |

```
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag gaactatat ccaatctctt gggatagaat atgatggaag acaaaatcag     960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaagaagat atttatagaa gggacttgtt    1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacgttctg    1500 atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccag    1680 aggtatttat ttgttttgc cttttttcac tgactgttct ttgtttgttt gtttgagact    1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttctttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tattttcag    3000 cccacaggaa acccaggctg gttactgtgg tttccctcct ggggggagct cacttggag    3060 aaggaagtgg acagatctgg gctgaagaat tccagtgtga ggggcacgag tcccaccttt   3120
```

```
cactctgccc agtagcaccc cgccctgacg ggacatgtag ccacagcagg gacgtcggcg      3180
tagtctgctc aagtgagacc cagggaatgt gttcactttg ttcccatgcc atgaagaggg      3240
tagggttagg tagtcacaga catctttta aagccctgtc tccttccagg atacacacaa       3300
atccgcttgg tgaatggcaa gaccccatgt gaaggaagag tggagctcaa cattcttggg      3360
tcctgggggt ccctctgcaa ctctcactgg gacatggaag atgcccatgt tttatgccag      3420
cagcttaaat gtggagttgc cctttctatc ccgggaggag caccttttgg gaaaggaagt      3480
gagcaggtct ggaggcacat gtttcactgc actgggactg agaagcacat gggagattgt      3540
tccgtcactg ctctgggcgc atcactctgt tcttcagggc aagtggcctc tgtaatctgc      3600
tcaggtaaga gaataagggc agccagtgat gagccactca tgacggtgcc ttaagagtgg      3660
gtgtacctag gagttcccat tgtggctcag tggtaacaaa ctcgactggt atccatgagg      3720
gtatgggttt gatccctggc cttgctcaat gggttaagga tccagcattg ctgtgagctg      3780
tggtataggt tgcagactct gctcaggtcc catgttgctg tgattgtggt gtaggctgac      3840
tgctgcagct tcaatttgac ccctagcccg ggaatttcca taggccacac gtgcagcact      3900
aaggaaggaa aaaagaaaa aaaaaaaaa agagtgggtg tgcctatagt gaagaacaga        3960
tgtaaagggg aagtgaaagg gattccccca ttctgaggga ttgtgagaag tgtgccagaa      4020
tattaacttc atttgacttg ttacagggaa agtaaacttg actttcacgg acctcctagt      4080
tacctggtgc ttactatatg tcttctcaga gtacctgatt cattcccagc ctggttgacc      4140 catccccta tctctatggc tatgtttatc cagagcacat ctatctaaca ctccagctga      4200
tcttcctgac acagctgtgg caaccctgga tcctttaacc aactgtgcca ggctggagat      4260
caaacctaag cctctgcagc aacccaagct gctgcagtca gattttaac cccctgtgcc       4320 actgtgggta tctccgatat tttgtatctt ctgtgactga gtggtttgct gtttgcaggg      4380
aaccagagtc agacactatc cccgtgcaat tcatcatcct cggacccatc aagctctatt      4440
atttcagaag aaaatggtgt tgcctgcata ggtgagaatc agtgaccaac ctatgaaaat      4500
gatctcaatc ctctgaaatg cattttattc atgttttatt tcctctttgc agggagtggt      4560
caacttcgcc tggtcgatgg aggtggtcgt tgtgctggga gagtagaggt ctatcatgag      4620
ggctcctggg gcaccatctg tgatgacagc tgggacctga atgatgccca tgtggtgtgc      4680
aaacagctga gctgtggatg ggccattaat gccactggtt ctgctcattt tggggaagga      4740
acagggccca tttggctgga tgagataaac tgtaatggaa aagaatctca tatttggcaa      4800
tgccactcac atggttgggg gcggcacaat tgcaggcata aggaggatgc aggagtcatc      4860
tgctcgg                                                              4867
```

<210> SEQ ID NO 106
<211> LENGTH: 4991
<212> TYPE: DNA
<213> ORGANISM: Sus scrofa
<400> SEQUENCE: 106

```
tatagatgac aaggctttgt gtctgatagg ggccagcgaa ctcagtaaag agggaagatg        60
agaaagataa tggcaagaat ttatccctga agtgtagttt tgacaaacca gtcacaaaga       120
ggtctaagaa attttggtca caaagttgtt ttgaatccca ggcatttat ttgcaatgat        180 tgcatatgtt ctggaaagga catctgaacc taagaaatag ttcatttgca ttgtgttata      240
ttttactaag gtctgagaaa taatcttgag atgagaatga actctacttc ttcagagtct      300
```

```
ggaaggaata aattatgaaa atgtattaat gcttctttaa accatattgt atatttatct    360
attactaaac aaaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
tccaaattaa ttatttctta tatttgttct tcatatattc atttctatag aaagaaataa    720
atacagattc agttaatgat ggcaggtaaa agcttaactt attaatcaaa ggagttaatc    780
caggcacaaa aattcaattc atggctctct gttaaaattt aggtataggt ttagcaggaa    840
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta aatcaactat   1080
actttaatag gaaaaatact tttaaggggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca aatattttag gataaaggaa aaagaagat atttatgaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaagaga   1620
aaagacaaaa aaaaaaaaaa aaaaaaaaa aaaaaaaaa aaaaaaaaa gaaccccccag   1680
aggtatttat ttgttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaaattaaa tcaaggactc   2160
aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
```

-continued

```
gctaaaaagt agagagaatg gatgcatatt atctgtggtc tccaatgtga tgaatgaagt    2760
aggcaaatac tcaaaggaaa gagaaagcat gctccaagaa ttatgggttc agaaggcaa    2820 agtcccagaa ttgtctccag ggaaggacag ggaggtctag aatcggctaa gcccactgta    2880
ggcagaaaaa ccaagaggca tgaatggctt ccctttctca cttttcactc tctggcttac    2940
tcctatcatg aaggaaaata ttggaatcat attctccctc accgaaatgc tattttcag    3000 cccacaggaa acccaggctg ttggagggg acattccctg ctctggtcgt gttgaagtac     3060
aacatggaga cacgtgggc accgtctgtg attctgactt ctctctggag gcggccagcg     3120
tgctgtgcag ggaactacag tgcggcaact gtggtttccc tcctgggggg agctcacttt    3180
ggagaaggaa gtggacagat ctgggctgaa gaattccagt gtgagggca cgagtcccac     3240 cttcactct gcccagtagc accccgcct gacgggacat gtagccacag cagggacgtc       3300
ggcgtagtct gctcaagtga gacccaggga atgtgttcac tttgttccca tgccatgaag    3360
agggtagggt taggtagtca cagacatctt tttaaagccc tgtctccttc caggatacac     3420
acaaatccgc ttggtgaatg caagacccc atgtgaagga agagtggagc tcaacattct      3480
tgggtcctgg gggtccctct gcaactctca ctgggacatg aagatgccc atgttttatg      3540 ccagcagctt aaatgtggag ttgccctttc tatcccggga ggagcacctt tgggaaagg      3600 aagtgagcag gtctggaggc acatgtttca ctgcactggg actgagaagc acatgggaga    3660
ttgttccgtc actgctctgg gcgcatcact ctgttcttca gggcaagtgg cctctgtaat    3720
ctgctcaggt aagagaataa gggcagccag tgatgagcca ctcatgacgg tgccttaaga    3780
gtgggtgtac ctaggagttc ccattgtggc tcagtggtaa caaactcgac tggtatccat    3840
gagggtatgg gtttgatccc tggccttgct caatgggtta aggatccagc attgctgtga    3900
gctgtggtat aggttgcaga ctctgctcag gtcccatgtt gctgtgattg tggtgtaggc    3960
tgactgctgc agcttcaatt tgaccccag cccgggaatt ccataggcc acacgtgcag        4020 cactaaggaa ggaaaaaag aaaaaaaaaa aaaagagtg ggtgtgccta tagtgaagaa       4080
cagatgtaaa agggaagtga aagggattcc cccattctga gggattgtga gaagtgtgcc    4140
agaatattaa cttcatttga cttgttacag ggaaagtaaa cttgactttc acggacctcc    4200
tagttacctg gtgcttacta tatgtcttct cagagtacct gattcattcc cagcctggtt    4260
gacccatccc cctatctcta tggctatgtt tatccagagc acatctatct aacactccag    4320
ctgatcttcc tgacacagct gtggcaaccc tggatccttt aaccaactgt gccaggctgg    4380
agatcaaacc taagcctctg cagcaaccca agctgctgca gtcagatttt taaccccctg    4440
tgccactgtg ggtatctccg atattttgta tcttctgtga ctgagtggtt tgctgtttgc    4500
agggaaccag agtcagacac tatccccgtg caattcatca tcctcggacc catcaagctc    4560
tattatttca gaagaaaatg gtgttgcctg cataggtgag aatcagtgac caacctatga    4620
aaatgatctc aatcctctga aatgcatttt attcatgttt tatttcctct ttgcaggag    4680 tggtcaactt cgcctggtcg atggaggtgg tcgttgtgct gggagagtag aggtctatca    4740
tgagggctcc tggggcacca tctgtgatga cagctgggac ctgaatgatg cccatgtggt    4800
gtgcaaacag ctgagctgtg gatgggccat taatgccact ggttctgctc attttgggga    4860
aggaacaggg cccatttggc tggatgagat aaactgtaat ggaaaagaat ctcatatttg    4920
gcaatgccac tcacatggtt gggggcggca caattgcagg cataaggagg atgcaggagt    4980
catctgctcg g                                                          4991
```

<210> SEQ ID NO 107
<211> LENGTH: 4860
<212> TYPE: DNA
<213> ORGANISM: Sus scrofa

<400> SEQUENCE: 107

| | | | | | |
|---|---|---|---|---|---|
| tatagatgac | aaggctttgt | gtctgatagg | ggccagcgaa | ctcagtaaag | agggaagatg | 60 |
| agaaagataa | tggcaagaat | ttatccctga | agtgtagttt | tgacaaacca | gtcacaaaga | 120 |
| ggtctaagaa | attttggtca | caaagttgtt | ttgaatccca | ggcattttat | ttgcaatgat | 180 |
| tgcatatgtt | ctggaaagga | catctgaacc | taagaaatag | ttcatttgca | ttgtgttata | 240 |
| ttttactaag | gtctgagaaa | taatcttgag | atgagaatga | actctacttc | ttcagagtct | 300 |
| ggaaggaata | aattatgaaa | atgtattaat | gcttctttaa | accatattgt | atatttatct | 360 |
| attactaaac | aaaagaagt | agctctattt | atttatttat | ttatttattt | atttatgtct | 420 |
| tttgtctctt | tagggccaca | cctgtggcat | atggaggttc | ccaggctaga | ggtccaattg | 480 |
| gagatgtagc | agccagccta | tgccagagcc | accgcaacac | gggatctgag | ccacgtctgt | 540 |
| gacttacacc | acagctcaca | gcaacgcctg | atcctcaacc | cactgagcga | ggccagggat | 600 |
| cgaacccatg | tcctcatgga | tgctagttgg | gttcgttaac | tgctgagcca | tgatgggaac | 660 |
| tccaaattaa | ttatttctta | tatttgttct | tcatatattc | atttctatag | aaagaaataa | 720 |
| atacagattc | agttaatgat | ggcaggtaaa | agcttaactt | attaatcaaa | ggagttaatc | 780 |
| caggcacaaa | aattcaattc | atggctctct | gttaaaattt | aggtataggt | ttagcaggaa | 840 |
| gaaaaggtta | gtagatgcag | actattacat | ttagaatgga | tggacaatga | agtcctacta | 900 |
| tacagcacag | ggaactatat | ccaatctctt | gggatagaat | atgatggaag | acaaaatcag | 960 |
| aacaagagag | tatatatata | tgtgtgtgtg | tgtgtgtgtg | tgtgtgtgtg | tgtgtgtgtg | 1020 |
| tgtgtgactg | ggtcaccctg | cggcacagca | gaaattggca | gaacattgta | aatcaactat | 1080 |
| actttaatag | gaaaaatact | tttaagggct | aaatttccaa | tattctaacc | atgtacacag | 1140 |
| agtaaatgtc | ataaggatgc | cagtctgtgt | agagattgat | gtgttactag | cagattcatg | 1200 |
| aaataaaggc | tgaggatgta | gtccccaagt | cacttctgag | tggaagaatt | tctcctttgt | 1260 |
| cctggactca | aatattttag | gataaaggaa | aaagaagat | atttatagaa | gggacttgtt | 1320 |
| ttcaagtact | tgacaaaatt | tcaccattaa | agagaaattt | gtgggagttc | ccatcgtggc | 1380 |
| tcagtggaaa | caaatccaac | taggaaccat | gaggttgtgg | gtttgatccc | tggcctcact | 1440 |
| cagtgggtta | aggatccggt | gttgccgtga | gctgtggtgt | aggttgcaga | cacggttctg | 1500 |
| atcctgcgtt | gctgtggctg | tggctgtggt | gtaggccagc | agcaaacagc | tctgattaga | 1560 |
| ccoctagcct | ggaaacctcc | atatgccaca | ggtgcagccc | taaaaagaca | aaaaagaga | 1620 |
| aaagacaaaa | aaaaaaaaaa | aaaaaaaaa | aaaaaaaaaa | aaaaaaaaaa | gaacccccag | 1680 |
| aggtatttat | ttgttttttgc | ctttttttcac | tgactgttct | ttgtttgttt | gtttgagact | 1740 |
| gatctagaag | actagagatt | acaagaaata | tggatttggc | tcactctaag | aaactgcttt | 1800 |
| cattccaagg | tttgggtcta | tccaaaagtg | gaatagaatc | atatgaatac | tagtttatga | 1860 |
| gtatttagtg | agaggaattt | caagctcaaa | taatgattca | gcaagattaa | attaaggagg | 1920 |
| gaattttcct | tgtggctgag | tgggttaagg | acccaatgtt | gtctctgtga | ggatgtaggt | 1980 |
| tccatcctgg | gctttgctca | ttaggttaag | gatctggcat | tgctgcagct | cagacccagt | 2040 |
| gctgccctgg | ttgtggctta | ggccaaagct | gcagctccaa | ttcaatctct | ggcctgggaa | 2100 |
| cctccatgtg | ctacaaggtg | cggccttaaa | aggaaaaaaa | aaaattaaa | tcaaggactc | 2160 |

```
aagagtctttt cattatttgt gttgtggaag ctatatttgt tttaaagtct tagttgtgtt    2220
tagaaagcaa gatgttcttc aactcaaatt tgggagggaa cttgtttcat acatttttaa    2280
tggataagtg gcaaaatttt catgctgagg tgatctatag tgttgtaatg cagaatatag    2340
tcagatcttg aacattttag gaagttggtg agggccaatt gtgtatctgt gccatgctga    2400
taagaatgtc aagggatcac aagaattcgt gttatttgac agcagtcatc tttaaaaggc    2460
atttgagaaa gtccaatttc aaatgcattt cctttcttta aaagataaat tgaagaaaat    2520
aagtctttat ttcccaagta aattgaattg cctctcagtc tgttaaaaga aactcttacc    2580
ttgatgattg cgctcttaac ctggcaaaga ttgtctttaa atctgagct ccatgtcttc    2640 tgctttattt ctggtgtgcc tttgactcca gattacagta aatggaggac tgagtatagg    2700
gctaaaaagt agagagaatg gatgcatatt atctgtggtc tccaatgtga tgaatgaagt    2760
aggcaaatac tcaaaggaaa gagaaagcat gctccaagaa ttatgggttc agaaggcaa    2820 agtcccagaa ttgtctccag ggaaggacag ggaggtctag aatcggctaa gcccactgta    2880
ggcagaaaaa ccaagaggca tgaatggctt ccctttctca cttttcactc tctggcttac    2940
tcctatcatg aaggaaaata ttggaatcat attctccctc accgaaatgc tattttcag    3000 cccacaggaa acccaggctg gttggagggt cctgggggga gctcactttg gagaaggaag    3060
tggacagatc tgggctgaag aattccagtg tgagggcac gagtcccacc tttcactctg    3120
cccagtagca ccccgccctg acgggacatg tagccacagc agggacgtcg gcgtagtctg    3180
ctcaagtgag acccagggaa tgtgttcact ttgttcccat gccatgaaga gggtagggtt    3240
aggtagtcac agacatcttt ttaaagccct gtctccttcc aggatacaca caaatccgct    3300
tggtgaatgg caagacccca tgtgaaggaa gagtggagct caacattctt gggtcctggg    3360
ggtccctctg caactctcac tgggacatgg aagatgccca tgttttatgc cagcagctta    3420
aatgtggagt tgccctttct atcccgggag gagcaccttt tgggaaagga agtgagcagg    3480
tctggaggca catgtttcac tgcactggga ctgagaagca catgggagat tgttccgtca    3540
ctgctctggg cgcatcactc tgttcttcag ggcaagtggc ctctgtaatc tgctcaggta    3600
agagaataag ggcagccagt gatgagccac tcatgacggt gccttaagag tgggtgtacc    3660
taggagttcc cattgtggct cagtggtaac aaactcgact ggtatccatg agggtatggg    3720
tttgatccct ggccttgctc aatgggttaa ggatccagca ttgctgtgag ctgtggtata    3780
ggttgcagac tctgctcagg tcccatgttg ctgtgattgt ggtgtaggct gactgctgca    3840
gcttcaattt gaccctagc ccgggaattt ccataggcca cacgtgcagc actaaggaag    3900 gaaaaaaga aaaaaaaaa aaaagagtgg gtgtgcctat agtgaagaac agatgtaaaa    3960
gggaagtgaa agggattccc ccattctgag ggattgtgag aagtgtgcca gaatattaac    4020
ttcatttgac ttgttacagg gaaagtaaac ttgactttca cggacctcct agttacctgg    4080
tgcttactat atgtcttctc agagtacctg attcattccc agcctggttg acccatcccc    4140
ctatctctat ggctatgttt atccagagca catctatcta acactccagc tgatcttcct    4200
gacacagctg tggcaaccct ggatccttta accaactgtg ccaggctgga gatcaaacct    4260
aagcctctgc agcaacccaa gctgctgcag tcagattttt aaccccctgt gccactgtgg    4320
gtatctccga tattttgtat cttctgtgac tgagtggttt gctgtttgca gggaaccaga    4380
gtcagacact atccccgtgc aattcatcat cctcggaccc atcaagctct attatttcag    4440
aagaaaatgg tgttgcctgc ataggtgaga atcagtgacc aacctatgaa aatgatctca    4500
```

| | |
|---|---|
| atcctctgaa atgcattta ttcatgtttt atttcctctt tgcagggagt ggtcaacttc | 4560 |
| gcctggtcga tggaggtggt cgttgtgctg ggagagtaga ggtctatcat gagggctcct | 4620 |
| ggggcaccat ctgtgatgac agctgggacc tgaatgatgc ccatgtggtg tgcaaacagc | 4680 |
| tgagctgtgg atgggccatt aatgccactg gttctgctca ttttggggaa ggaacagggc | 4740 |
| ccatttggct ggatgagata aactgtaatg gaaaagaatc tcatatttgg caatgccact | 4800 |
| cacatggttg ggggcggcac aattgcaggc ataaggagga tgcaggagtc atctgctcgg | 4860 |

<210> SEQ ID NO 108
<211> LENGTH: 4858
<212> TYPE: DNA
<213> ORGANISM: Sus scrofa

<400> SEQUENCE: 108

| | |
|---|---|
| tatagatgac aaggctttgt gtctgatagg ggccagcgaa ctcagtaaag agggaagatg | 60 |
| agaaagataa tggcaagaat ttatccctga agtgtagttt tgacaaacca gtcacaaaga | 120 |
| ggtctaagaa attttggtca caagttgtt ttgaatccca ggcattttat ttgcaatgat | 180 |
| tgcatatgtt ctggaaagga catctgaacc taagaaatag ttcatttgca ttgtgttata | 240 |
| ttttactaag gtctgagaaa taatcttgag atgaagatga actctacttc ttcagagtct | 300 |
| ggaaggaata aattatgaaa atgtattaat gcttctttaa accatattgt atatttatct | 360 |
| attactaaac aaaaagaagt agctctattt atttatttat ttatttattt atttatgtct | 420 |
| tttgtctctt tagggccaca cctgtggcat atggaggttc ccaggctaga ggtccaattg | 480 |
| gagatgtagc agccagccta tgccagagcc accgcaacac gggatctgag ccacgtctgt | 540 |
| gacttacacc acagctcaca gcaacgcctg atcctcaacc cactgagcga ggccagggat | 600 |
| cgaacccatg tcctcatgga tgctagttgg gttcgttaac tgctgagcca tgatgggaac | 660 |
| tccaaattaa ttatttctta tatttgttct tcatatattc atttctatag aaagaaataa | 720 |
| atacagattc agtaatgat ggcaggtaaa agcttaactt attaatcaaa ggagttaatc | 780 |
| caggcacaaa aattcaattc atggctctct gttaaaattt aggtataggt ttagcaggaa | 840 |
| gaaaaggtta gtagatgcag actattacat ttagaatgga tggacaatga agtcctacta | 900 |
| tacagcacag ggaactatat ccaatctctt gggatagaat atgatggaag acaaaatcag | 960 |
| aacaagagag tatatatata tgtgtgtgtg tgtgtgtgtg tgtgtgtgtg tgtgtgtgtg | 1020 |
| tgtgtgactg ggtcacccctg cggcacagca gaaattggca gaacattgta aatcaactat | 1080 |
| actttaatag gaaaaatact tttaagggct aaatttccaa tattctaacc atgtacacag | 1140 |
| agtaaatgtc ataaggatgc cagtctgtgt agagattgat gtgttactag cagattcatg | 1200 |
| aaataaaggc tgaggatgta gtccccaagt cacttctgag tggaagaatt tctcctttgt | 1260 |
| cctggactca aatattttag gataaaggaa aaagaagat atttatagaa gggacttgtt | 1320 |
| ttcaagtact tgacaaaatt tcaccattaa agagaaattt gtgggagttc ccatcgtggc | 1380 |
| tcagtggaaa caaatccaac taggaaccat gaggttgtgg gtttgatccc tggcctcact | 1440 |
| cagtgggtta aggatccggt gttgccgtga gctgtggtgt aggttgcaga cacggttctg | 1500 |
| atcctgcgtt gctgtggctg tggctgtggt gtaggccagc agcaaacagc tctgattaga | 1560 |
| cccctagcct ggaaacctcc atatgccaca ggtgcagccc taaaaagaca aaaaagaga | 1620 |
| aaagacaaaa aaaaaaaaaa aaaaaaaaaa aaaaaaaaaa aaaaaaaaaa gaaccccccag | 1680 |
| aggtattat ttgttttgc ctttttttcac tgactgttct ttgtttgttt gtttgagact | 1740 |
| gatctagaag actagagatt acaagaaata tggatttggc tcactctaag aaactgcttt | 1800 |

```
cattccaagg tttgggtcta tccaaaagtg aatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaattaaa tcaaggactc    2160 aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt tgtatctgt gccatgctga    2400 taagaatgtc aagggatcac aagaattcgt gttatttgac agcagtcatc tttaaaaggc   2460
atttgagaaa gtccaatttc aaatgcattt cctttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tattttcag    3000 cccacaggaa acccaggctg gttggagggc tgggggagc tcactttgga gaaggaagtg     3060
gacagatctg ggctgaagaa ttccagtgtg aggggcacga gtcccacctt tcactctgcc   3120
cagtagcacc ccgccctgac gggacatgta gccacagcag ggacgtcggc gtagtctgct   3180
caagtgagac ccagggaatg tgttcactt gttcccatgc catgaagagg gtagggttag    3240
gtagtcacag acatcttttt aaagccctgt ctccttccag gatacacaca aatccgcttg   3300
gtgaatggca agaccccatg tgaaggaaga gtggagctca acattcttgg gtcctggggg   3360
tccctctgca actctcactg ggacatgaa gatgcccatg ttttatgcca gcagcttaaa    3420
tgtggagttg ccctttctat cccgggagga gcaccttttg ggaaaggaag tgagcaggtc   3480
tggaggcaca tgtttcactg cactgggact gagaagcaca tggagattg ttccgtcact    3540 gctctgggcg catcactctg ttcttcaggg caagtggcct ctgtaatctg ctcaggtaag   3600
agaataaggg cagccagtga tgagccactc atgacggtgc cttaagagtg ggtgtaccta   3660
ggagttccca ttgtggctca gtggtaacaa actcgactgg tatccatgag ggtatgggtt   3720
tgatccctgg ccttgctcaa tgggttaagg atccagcatt gctgtgagct gtggtatagg   3780
ttgcagactc tgctcaggtc ccatgttgct gtgattgtgg tgtaggctga ctgctgcagc   3840
ttcaatttga cccctagccc gggaattcc ataggccaca cgtgcagcac taaggaagga    3900 aaaaagaaa aaaaaaaaa aagagtgggt gtgcctatag tgaagaacag atgtaaaagg     3960
gaagtgaaag ggattccccc attctgaggg attgtgagaa gtgtgccaga atattaactt   4020
catttgactt gttacaggga aagtaaactt gactttcacg gacctcctag ttacctggtg   4080
cttactatat gtcttctcag agtacctgat tcattcccag cctggttgac ccatcccct    4140
```

| | |
|---|---|
| atctctatgg ctatgtttat ccagagcaca tctatctaac actccagctg atcttcctga | 4200 |
| cacagctgtg caaccctgg atcctttaac caactgtgcc aggctggaga tcaaacctaa | 4260 |
| gcctctgcag caacccaagc tgctgcagtc agattttaa ccccctgtgc cactgtgggt | 4320 |
| atctccgata ttttgtatct tctgtgactg agtggtttgc tgtttgcagg gaaccagagt | 4380 |
| cagacactat ccccgtgcaa ttcatcatcc tcggacccat caagctctat tatttcagaa | 4440 |
| gaaaatggtg ttgcctgcat aggtgagaat cagtgaccaa cctatgaaaa tgatctcaat | 4500 |
| cctctgaaat gcattttatt catgtttat ttcctctttg cagggagtgg tcaacttcgc | 4560 |
| ctggtcgatg gaggtggtcg ttgtgctggg agagtagagg tctatcatga gggctcctgg | 4620 |
| ggcaccatct gtgatgacag ctgggacctg aatgatgccc atgtggtgtg caaacagctg | 4680 |
| agctgtggat gggccattaa tgccactggt tctgctcatt ttggggaagg aacagggccc | 4740 |
| atttggctgg atgagataaa ctgtaatgga aagaatctc atatttggca atgccactca | 4800 |
| catggttggg ggcggcacaa ttgcaggcat aaggaggatg caggagtcat ctgctcgg | 4858 |

<210> SEQ ID NO 109
<211> LENGTH: 3523
<212> TYPE: DNA
<213> ORGANISM: Sus scrofa

<400> SEQUENCE: 109

| | |
|---|---|
| tatagatgac aaggctttgt gtctgatagg ggccagcgaa ctcagtaaag agggaagatg | 60 |
| agaaagataa tggcaagaat ttatccctga agtgtagttt tgacaaacca gtcacaaaga | 120 |
| ggtctaagaa atttttggtca caaagttgtt ttgaatccca ggcattttat ttgcaatgat | 180 |
| tgcatatgtt ctggaaagga catctgaacc taagaaatag ttcatttgca ttgtgtttata | 240 |
| ttttactaag gtctgagaaa taatcttgag atgagaatga actctacttc ttcagagtct | 300 |
| ggaaggaata aattatgaaa atgtattaat gcttctttaa accatattgt atatttatct | 360 |
| attactaaac aaaagaagt agctctattt attatttat ttatttattt atttatgtct | 420 |
| tttgtctctt tagggccaca cctgtggcat atggaggttc ccaggctaga ggtccaattg | 480 |
| gagatgtagc agccagccta tgccagagcc accgcaacac gggatctgag ccacgtctgt | 540 |
| gacttacacc acagctcaca gcaacgcctg atcctcaacc cactgagcga ggccagggat | 600 |
| cgaacccatg tcctcatgga tgctagttgg gttcgttaac tgctgagcca tgatgggaac | 660 |
| tccaaattaa ttatttctta tatttgttct tcatatattc atttctatag aaagaaataa | 720 |
| atacagattc agttaatgat ggcaggtaaa agcttaactt attaatcaaa ggagttaatc | 780 |
| caggcacaaa aattcaattc atggctctct gttaaaattt aggtataggt ttagcaggaa | 840 |
| gaaaaggtta gtagatgcag actattacat ttagaatgga tggacaatga agtcctacta | 900 |
| tacagcacag ggaactatat ccaatctctt gggatagaat atgatggaag acaaaatcag | 960 |
| aacaagagag tatatatata tgtgtgtgtg tgtgtgtgtg tgtgtgtgtg tgtgtgtgtg | 1020 |
| tgtgtgactg ggtcaccctg cggcacagca gaaattggca gaacattgta aatcaactat | 1080 |
| actttaatag gaaaaatact tttaagggct aaatttccaa tattctaacc atgtacacag | 1140 |
| agtaaatgtc ataaggatgc cagtctgtgt agagattgat gtgttactag cagattcatg | 1200 |
| aaataaaggc tgaggatgta gtccccaagt cacttctgag tggaagaatt tctcctttgt | 1260 |
| cctggactca aatattttag gataaaggaa aaagaagat atttatgaaa gggacttgtt | 1320 |
| ttcaagtact tgacaaaatt tcaccattaa agagaaattt gtgggagttc ccatcgtggc | 1380 |
| tcagtggaaa caaatccaac taggaaccat gaggttgtgg gtttgatccc tggcctcact | 1440 |

```
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaaagaga   1620
aaagacaaaa aaaaaaaaaa aaaaaaaaaa aaaaaaaaaa aaaaaaaaaa gaaccccag    1680
aggtatttat ttgttttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaattaaa tcaaggactc    2160
aagagtcttt cattatttgt gttgtggaag ctatatttgt tttaaagtct tagttgtgtt   2220
tagaaagcaa gatgttcttc aactcaaatt tgggagggaa cttgtttcat acattttttaa  2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gagctgtggt ataggttgca gactctgctc   2460
aggtcccatg ttgctgtgat tgtggtgtag gctgactgct gcagcttcaa tttgaccccct  2520
agcccgggaa tttccatagg ccacacgtgc agcactaagg aaggaaaaaa agaaaaaaaa   2580
aaaaaaagag tgggtgtgcc tatagtgaag aacagatgta aagggaagt gaagggatt     2640
ccccattct gagggattgt gagaagtgtg ccagaatatt aacttcattt gacttgttac    2700
agggaaagta aacttgactt tcacggacct cctagttacc tggtgcttac tatatgtctt   2760
ctcagagtac ctgattcatt cccagcctgg ttgacccatc cccctatctc tatggctatg   2820
tttatccaga gcacatctat ctaacactcc agctgatctt cctgacacag ctgtggcaac   2880
cctggatcct ttaaccaact gtgccaggct ggagatcaaa cctaagcctc tgcagcaacc   2940
caagctgctg cagtcagatt tttaaccccc tgtgccactg tgggtatctc cgatattttg   3000
tatcttctgt gactgagtgg tttgctgttt gcagggaacc agagtcagac actatccccg   3060
tgcaattcat catcctcgga cccatcaagc tctattattt cagaagaaaa tggtgttgcc   3120
tgcataggtg agaatcagtg accaacctat gaaaatgatc tcaatcctct gaaatgcatt   3180
ttattcatgt tttatttcct ctttgcaggg agtggtcaac ttcgcctggt cgatggaggt   3240
ggtcgttgtg ctgggagagt agaggtctat catgagggct cctggggcac catctgtgat   3300
gacagctggg acctgaatga tgcccatgtg gtgtgcaaac agctgagctg tggatgggcc   3360
attaatgcca ctggttctgc tcattttggg aaggaacag ggcccatttg gctggatgag    3420
ataaactgta atgaaaaga atctcatatt tggcaatgcc actcacatgg ttgggggcgg    3480
cacaattgca ggcataagga ggatgcagga gtcatctgct cgg                     3523
```

<210> SEQ ID NO 110
<211> LENGTH: 3603
<212> TYPE: DNA
<213> ORGANISM: Sus scrofa

<400> SEQUENCE: 110

```
tatagatgac aaggctttgt gtctgatagg ggccagcgaa ctcagtaaag agggaagatg      60
agaaagataa tggcaagaat ttatccctga agtgtagttt tgacaaacca gtcacaaaga     120
ggtctaagaa attttggtca caaagttgtt ttgaatccca ggcattttat ttgcaatgat     180
tgcatatgtt ctggaaagga catctgaacc taagaaatag ttcatttgca ttgtgttata     240
ttttactaag gtctgagaaa taatcttgag atgagaatga actctacttc ttcagagtct     300
ggaaggaata aattatgaaa atgtattaat gcttctttaa accatattgt atatttatct     360
attactaaac aaaaagaagt agctctattt atttatttat ttatttattt atttatgtct     420
tttgtctctt tagggccaca cctgtggcat atggaggttc ccaggctaga ggtccaattg     480
gagatgttgt ggagaattcc acaagaattc gtgttatttg acagcagtca tctttaaaag     540
gcatttgaga aagtccaatt tcaaatgcat ttcctttctt taaaagataa attgaagaaa     600
ataagtcttt atttcccaag taaattgaat tgcctctcag tctgttaaaa gaaactctta     660
tatagatgac aaggctttgt gtctgatagg ggccagcgaa ctcagtaaag agggaagatg     720
agaaagataa tggcaagaat ttatccctga agtgtagttt tgacaaacca gtcacaaaga     780
ggtctaagaa attttggtca caaagttgtt ttgaatccca ggcattttat ttgcaatgat     840
tgcatatgtt ctggaaagga catctgaacc taagaaatag ttcatttgca ttgtgttata     900
ttttactaag gtctgagaaa taatcttgag atgagaatga actctacttc ttcagagtct     960
ggaaggaata aattatgaaa atgtattaat gcttctttaa accatattgt atatttatct    1020
attactaaac aaaaagaagt agctctattt atttatttat ttatttattt atttatgtct    1080
tttgtctctt tagggccaca cctgtggcat atggaggttc ccaggctaga ggtccaattg    1140
gagatgttgt ggagaattcc acaagaattc gtgttatttg acagcagtca tctttaaaag    1200
gcatttgaga aagtccaatt tcaaatgcat ttcctttctt taaaagataa attgaagaaa    1260
ataagtcttt atttcccaag taaattgaat tgcctctcag tctgttaaaa gaaactctta    1320
ccttgatgat tgcgctctta acctggcaaa gattgtcttt aaaatctgag ctccatgtct    1380
tctgctttat ttctggtgtg cctttgactc cagattacag taaatggagg actgagtata    1440
gggctaaaaa gtagagagaa tggatgcata ttatctgtgg tctccaatgt gatgaatgaa    1500
gtaggcaaat actcaaagga aagagaaagc atgctccaag aattatgggt tccagaaggc    1560
aaagtcccag aattgtctcc agggaaggac agggaggtct agaatcggct aagcccactg    1620
taggcagaaa aaccaagagg catgaatggc ttcccttcct cacttttcac tctctggctt    1680
actcctatca tgaaggaaaa tattggaatc atattctccc tcaccgaaat gctattttc    1740
agcccacagg aaacccaggc tggttggagg ggacattccc tgctctcact ttggagaagg    1800
aagtggacag atctgggctg aagaattcca gtgtgagggg cacgagtccc acctttcact    1860
ctgcccagta gcacccgcc ctgacgggac atgtagccac agcagggacg tcggcgtagt     1920
ctgctcaagt gagacccagg gaatgtgttc actttgttcc catgccatga agagggtagg    1980
gttaggtagt cacagacatc tttttaaagc cctgtctcct tccaggatac acacaaatcc    2040
gcttggtgaa tggcaagacc ccatgtgaag gaagagtgga gctcaacatt cttgggtcct    2100
gggggtccct ctgcaactct cactgggaca tggaagatgc ccatgtttta tgccagcagc    2160
ttaaatgtgg agttgccctt tctatcccgg gaggagcacc ttttgggaaa ggaagtgagc    2220
aggtctggag gcacatgttt cactgcactg ggactgagaa gcacatggga gattgttccg    2280
tcactgctct gggcgcatca ctctgttctt cagggcaagt ggcctctgta atctgctcag    2340
gtaagagaat aagggcagcc agtgatgagc cactcatgac ggtgccttaa gagtgggtgt    2400
```

```
acctaggagt tcccattgtg gctcagtggt aacaaactcg actggtatcc atgagggtat    2460
gggtttgatc cctggccttg ctcaatgggt taaggatcca gcattgctgt gagctgtggt    2520
ataggttgca gactctgctc aggtcccatg ttgctgtgat tgtggtgtag gctgactgct    2580
gcagcttcaa tttgacccct agcccgggaa tttccatagg ccacacgtgc agcactaagg    2640
aaggaaaaaa agaaaaaaaa aaaaaagag tgggtgtgcc tatagtgaag aacagatgta    2700
aaagggaagt gaaagggatt cccccattct gagggattgt gagaagtgtg ccagaatatt    2760
aacttcattt gacttgttac agggaaagta aacttgactt tcacggacct cctagttacc    2820
tggtgcttac tatatgtctt ctcagagtac ctgattcatt cccagcctgg ttgacccatc    2880
cccctatctc tatggctatg tttatccaga gcacatctat ctaacactcc agctgatctt    2940
cctgacacag ctgtggcaac cctggatcct ttaaccaact gtgccaggct ggagatcaaa    3000
cctaagcctc tgcagcaacc caagctgctg cagtcagatt tttaaccccc tgtgccactg    3060
tgggtatctc cgatattttg tatcttctgt gactgagtgg tttgctgttt gcagggaacc    3120
agagtcagac actatccccg tgcaattcat catcctcgga cccatcaagc tctattattt    3180
cagaagaaaa tggtgttgcc tgcataggtg agaatcagtg accaacctat gaaaatgatc    3240
tcaatcctct gaaatgcatt ttattcatgt tttatttcct ctttgcaggg agtggtcaac    3300
ttcgcctggt cgatggaggt ggtcgttgtg ctgggagagt agaggtctat catgagggct    3360
cctggggcac catctgtgat gacagctggg acctgaatga tgcccatgtg gtgtgcaaac    3420
agctgagctg tggatgggcc attaatgcca ctggttctgc tcattttggg gaaggaacag    3480
ggcccatttg gctggatgag ataaactgta atggaaaaga atctcatatt tggcaatgcc    3540
actcacatgg ttgggggcgg cacaattgca ggcataagga ggatgcagga gtcatctgct    3600
cgg                                                                 3603

<210> SEQ ID NO 111
<211> LENGTH: 4962
<212> TYPE: DNA
<213> ORGANISM: Sus scrofa

<400> SEQUENCE: 111
tatagatgac aaggctttgt gtctgatagg ggccagcgaa ctcagtaaag agggaagatg      60
agaaagataa tggcaagaat ttatccctga agtgtagttt tgacaaacca gtcacaaaga     120
ggtctaagaa attttggtca caagttgtt ttgaatccca ggcatttat ttgcaatgat       180 tgcatatgtt ctgaaaagga catctgaacc taagaaatag ttcatttgca ttgtgttata     240
ttttactaag gtctgagaaa taatcttgag atgagaatga actctacttc ttcagagtct     300
ggaaggaata aattatgaaa atgtattaat gcttctttaa accatattgt atatttatct     360
attactaaac aaaagaagt agctctattt atttatttat ttatttattt atttatgtct      420
tttgtctctt tagggccaca cctgtggcat atggaggttc ccaggctaga ggtccaattg     480
gagatgtagc agccagccta tgccagagcc accgcaacac gggatctgag ccacgtctgt     540
gacttacacc acagctcaca gcaacgcctg atcctcaacc cactgagcga ggccagggat     600
cgaacccatg tcctcatgga tgctagtgg gttcgttaac tgctgagcca tgatgggaac     660
tccaaattaa ttattcctta tatttgttct tcatatattc atttctatag aaagaaataa     720
atacagattc agttaatgat ggcaggtaaa agcttaactt attaatcaaa ggagttaatc     780
caggcacaaa aattcaattc atggctctct gttaaaattt aggtataggt ttagcaggaa     840
```

```
gaaaaggtta gtagatgcag actattacat ttagaatgga tggacaatga agtcctacta    900
tacagcacag ggaactatat ccaatctctt gggatagaat atgatggaag acaaaatcag    960
aacaagagag tatatatata tgtgtgtgtg tgtgtgtgtg tgtgtgtgtg tgtgtgtgtg   1020
tgtgtgactg ggtcaccctg cggcacagca gaaattggca gaacattgta atcaactat   1080 actttaatag gaaaaatact tttaagggct aaatttccaa tattctaacc atgtacacag   1140
agtaaatgtc ataaggatgc cagtctgtgt agagattgat gtgttactag cagattcatg   1200
aaataaaggc tgaggatgta gtccccaagt cacttctgag tggaagaatt tctcctttgt   1260
cctggactca atattttag gataaaggaa aaagaagat atttatagaa gggacttgtt   1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaagaga   1620 aaagacaaaa aaaaaaaaa aaaaaaaaaa aaaaaaaaa aaaaaaaaaa gaacccccag   1680
aggtatttat ttgtttttgc cttttttcac tgactgttct ttgtttgttt gtttgagact   1740
gatctagaag actagagatt acaagaaata tggatttggc tcactctaag aaactgcttt   1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaattaaa tcaaggactc   2160 aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttctttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc cagaaggcaa   2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tatttttcag   3000
cccacaggaa acccaggctg gttggagggg acattccctg ctctggtcgt gttgaagtac   3060
aacatggaga cacgtggggc accgtctgtg attctgactt ctctctggag gcggccagcg   3120
tgctgtgcag ggaactacag tgcgtcactt tggagaagga agtggacaga tctgggctga   3180
agaattccag tgtgaggggc acgagtccca cctttcactc tgcccagtag caccccgccc   3240
```

| | | | | |
|---|---|---|---|---|
| tgacgggaca | tgtagccaca | gcagggacgt | cggcgtagtc | tgctcaagtg | agacccaggg | 3300 |
| aatgtgttca | cttttgttccc | atgccatgaa | gagggtaggg | ttaggtagtc | acagacatct | 3360 |
| ttttaaagcc | ctgtctcctt | ccaggataca | cacaaatccg | cttggtgaat | ggcaagaccc | 3420 |
| catgtgaagg | aagagtggag | ctcaacattc | ttgggtcctg | ggggtccctc | tgcaactctc | 3480 |
| actgggacat | ggaagatgcc | catgttttat | gccagcagct | taaatgtgga | gttgcccttt | 3540 |
| ctatcccggg | aggagcacct | tttgggaaag | gaagtgagca | ggtctggagg | cacatgtttc | 3600 |
| actgcactgg | gactgagaag | cacatgggag | attgttccgt | cactgctctg | ggcgcatcac | 3660 |
| tctgttcttc | agggcaagtg | gcctctgtaa | tctgctcagg | taagagaata | agggcagcca | 3720 |
| gtgatgagcc | actcatgacg | gtgccttaag | agtgggtgta | cctaggagtt | cccattgtgg | 3780 |
| ctcagtggta | acaaactcga | ctggtatcca | tgagggtatg | ggtttgatcc | ctggccttgc | 3840 |
| tcaatgggtt | aaggatccag | cattgctgtg | agctgtggta | taggttgcag | actctgctca | 3900 |
| ggtcccatgt | tgctgtgatt | gtggtgtagg | ctgactgctg | cagcttcaat | ttgacccta | 3960 |
| gcccgggaat | tccataggc | cacacgtgca | gcactaagga | aggaaaaaaa | gaaaaaaaa | 4020 |
| aaaaaagagt | gggtgtgcct | atagtgaaga | acagatgtaa | aagggaagtg | aaagggattc | 4080 |
| ccccattctg | agggattgtg | agaagtgtgc | cagaatatta | acttcatttg | acttgttaca | 4140 |
| gggaaagtaa | acttgacttt | cacggacctc | ctagttacct | ggtgcttact | atatgtcttc | 4200 |
| tcagagtacc | tgattcattc | ccagcctggt | tgacccatcc | ccctatctct | atggctatgt | 4260 |
| ttatccagag | cacatctatc | taacactcca | gctgatcttc | ctgacacagc | tgtggcaacc | 4320 |
| ctggatcctt | taaccaactg | tgccaggctg | gagatcaaac | ctaagcctct | gcagcaaccc | 4380 |
| aagctgctgc | agtcagattt | ttaaccccct | gtgccactgt | gggtatctcc | gatattttgt | 4440 |
| atcttctgtg | actgagtggt | ttgctgtttg | cagggaacca | gagtcagaca | ctatccccgt | 4500 |
| gcaattcatc | atcctcggac | ccatcaagct | ctattatttc | agaagaaaat | ggtgttgcct | 4560 |
| gcataggtga | gaatcagtga | ccaacctatg | aaaatgatct | caatcctctg | aaatgcattt | 4620 |
| tattcatgtt | ttatttcctc | tttgcaggga | gtggtcaact | tcgcctggtc | gatggaggtg | 4680 |
| gtcgttgtgc | tgggagagta | gaggtctatc | atgagggctc | ctggggcacc | atctgtgatg | 4740 |
| acagctggga | cctgaatgat | gcccatgtgg | tgtgcaaaca | gctgagctgt | ggatgggcca | 4800 |
| ttaatgccac | tggttctgct | cattttgggg | aaggaacagg | gcccatttgg | ctggatgaga | 4860 |
| taaactgtaa | tggaaaagaa | tctcatattt | ggcaatgcca | ctcacatggt | tgggggcggc | 4920 |
| acaattgcag | gcataaggag | gatgcaggag | tcatctgctc | gg | | 4962 |

<210> SEQ ID NO 112
<211> LENGTH: 3603
<212> TYPE: DNA
<213> ORGANISM: Sus scrofa

<400> SEQUENCE: 112

| | | | | |
|---|---|---|---|---|
| tatagatgac | aaggctttgt | gtctgatagg | ggccagcgaa | ctcagtaaag | agggaagatg | 60 |
| agaaagataa | tggcaagaat | ttatccctga | agtgtagttt | tgacaaacca | gtcacaaaga | 120 |
| ggtctaagaa | attttggtca | caaagttgtt | ttgaatccca | ggcattttat | ttgcaatgat | 180 |
| tgcatatgtt | ctggaaagga | catctgaacc | taagaaatag | ttcatttgca | ttgtgttata | 240 |
| ttttactaag | gtctgagaaa | taatcttgag | atgagaatga | actctacttc | ttcagagtct | 300 |
| ggaaggaata | aattatgaaa | atgtattaat | gcttctttaa | accatattgt | atatttatct | 360 |

| | |
|---|---|
| attactaaac aaaaagaagt agctctattt atttatttat ttatttattt atttatgtct | 420 |
| tttgtctctt tagggccaca cctgtggcat atggaggttc ccaggctaga ggtccaattg | 480 |
| gagatgtagc agccagccta tgccagagcc accgcaacac gggatctgag ccacgtctgt | 540 |
| gacttacacc acagctcaca gcaacgcctg atcctcaacc cactgagcga ggccagggat | 600 |
| cgaacccatg tcctcatgga tgctagttgg gttcgttaac tgctgagcca tgatgggaac | 660 |
| tccaaattaa ttatttctta tatttgttct tcatatattc atttctatag aaagaaataa | 720 |
| atacagattc agttaatgat ggcaggtaaa agcttaactt attaatcaaa ggagttaatc | 780 |
| caggcacaaa aattcaattc atggctctct gttaaaattt aggtataggt ttagcaggaa | 840 |
| gaaaaggtta gtagatgcag actattacat ttagaatgga tggacaatga agtcctacta | 900 |
| tacagcacag ggaactatat ccaatctctt gggatagaat atgatggaag acaaaatcag | 960 |
| aacaagagag tatatatata tgtgtgtgtg tgtgtgtgtg tgtgtgtgtg tgtgtgtgtg | 1020 |
| tgtgtgactg ggtcaccctg cggcacagca gaaattggca gaacattgta aatcaactat | 1080 |
| actttaatag gaaaaatact tttaagggct aaatttccaa tattctaacc atgtacacag | 1140 |
| agtaaatgtc ataaggatgc agtctgtgt agagattgat gtgttactag cagattcatg | 1200 |
| aaataaaggc tgaggatgta gtccccaagt cacttctgag tggaagaatt tctcctttgt | 1260 |
| cctggactca aatattttag gataaaggaa aaagaagat atttatagaa gggacttgtt | 1320 |
| ttcaagtact tgacaaaatt tcaccattaa agagaaattt gtgggagttc ccatcgtggc | 1380 |
| tcagtggaaa caaatccaac taggaaccat gaggttgtgg gtttgatccc tggcctcact | 1440 |
| cagtgggtta aggatccggt gttgccgtga gctgtggtgt aggttgcaga cacggttctg | 1500 |
| atcctgcgtt gctgtggctg tggctgtggt gtaggccagc agcaaacagc tctgattaga | 1560 |
| cccctagcct ggaaacctcc atatgccaca ggtgcagccc taaaaagaca aaaaagaga | 1620 |
| aaagacaaaa aaaaaaaaa aaaaaaaaa aaaaaaaaa gaaccccag | 1680 |
| aggtatttat ttgttttttgc cttttttcac tgactgttct ttgtttgttt gtttgagact | 1740 |
| gatctagaag actagagatt acaagaaata tggatttggc tcactctaag aaactgcttt | 1800 |
| cattccaagg tttgggtcta tccaaaagtg gaatagaatc atatgaatac tagtttatga | 1860 |
| gtatttagtg agaggaattt caagctcaaa taatgattca gcaagattaa attaaggagg | 1920 |
| gaattttcct tgtggctgag tgggttaagg acccaatgtt gtctctgtga ggatgtaggt | 1980 |
| tccatcctgg gctttgctca ttaggttaag gatctggcat tgctgcagct cagacccagt | 2040 |
| gctgccctgg ttgtggctta ggccaaagct gcagctccaa ttcaatctct ggcctgggaa | 2100 |
| cctccatgtg ctacaaggtg cggccttaaa aggaaaaaaa aaaattaaa tcaaggactc | 2160 |
| aagagtcttt cattatttgt gttgtggaag ctatatttgt tttaaagtct tagttgtgtt | 2220 |
| tagaaagcaa gatgttcttc aactcaaatt tgggagggaa cttgtttcat acatttttaa | 2280 |
| tggataagtg gcaaaatttt catgctgagg tgatctatag tgttgtaatg cagaatatag | 2340 |
| tcagatcttg aacattttag gaagttggtg agggccaatt gtgtatctgt gccatgctga | 2400 |
| taagaatgtc aagggatcac aagaattcgt gttatttgac agcagtcatc tttaaaaggc | 2460 |
| atttgagaaa gtccaatttc aaatgcattt cctttcttta aagataaat tgaagaaaat | 2520 |
| aagtctttat ttcccaagta aattgaattg cctctcagtc tgttaaaaga aactcttacc | 2580 |
| ttgatgattg cgctcttaac ctggcaaaga ttgtctttaa aatctgagct ccatgtcttc | 2640 |
| tgctttattt ctggtgtgcc tttgactcca gattacagta aatggaggac tgagtatagg | 2700 |
| gctaaaaagt agagagaatg gatgcatatt atctgtggtc tccaatgtga tgaatgaagt | 2760 |

```
aggcaaatac tcaaaggaaa gagaaagcat gctccaagaa ttatgggttc cagaaggcaa    2820
agtcccagaa ttgtctccag ggaaggacag ggaggtctag aatcggctaa gcccactgta    2880
ggcagaaaaa ccaagaggca tgaatggctt ccctttctca cttttcactc tctggcttac    2940
tcctatcatg aaggaaaata ttggaatcat attctccctc accgaaatgc tatttttcag    3000
cccacaggaa acccaggctg gttggagggg acattccctg ctctggtcgt gttgaagtac    3060
aacatggaga cacgtggggc accgtctgtg attctgactt ctctctggag gcggccagcg    3120
tgctgtgcag ggaactacag tgcgattcat catcctcgga cccatcaagc tctattattt    3180
cagaagaaaa tggtgttgcc tgcataggtg agaatcagtg accaacctat gaaaatgatc    3240
tcaatcctct gaaatgcatt ttattcatgt tttatttcct ctttgcaggg agtggtcaac    3300
ttcgcctggt cgatggaggt ggtcgttgtg ctgggagagt agaggtctat catgagggct    3360
cctggggcac catctgtgat gacagctggg acctgaatga tgcccatgtg gtgtgcaaac    3420
agctgagctg tggatgggcc attaatgcca ctggttctgc tcattttggg gaaggaacag    3480
ggcccatttg gctggatgag ataaactgta atggaaaaga atctcatatt tggcaatgcc    3540
actcacatgg ttgggggcgg cacaattgca ggcataagga ggatgcagga gtcatctgct    3600
cgg                                                                 3603

<210> SEQ ID NO 113
<211> LENGTH: 3619
<212> TYPE: DNA
<213> ORGANISM: Sus scrofa

<400> SEQUENCE: 113
tatagatgac aaggctttgt gtctgatagg ggccagcgaa ctcagtaaag agggaagatg      60
agaaagataa tggcaagaat ttatccctga agtgtagttt tgacaaacca gtcacaaaga     120
ggtctaagaa attttggtca caaagttgtt tgaatcccca ggcatttat ttgcaatgat      180 tgcatatgtt ctggaaagga catctgaacc taagaaatag ttcatttgca ttgtgttata     240
ttttactaag gtctgagaaa taatcttgag atgagaatga actctacttc ttcagagtct     300
ggaaggaata aattatgaaa atgtattaat gcttctttaa accatattgt atatttatct     360
attactaaac aaaagaagt agctctattt atttatttat ttatttattt atttatgtct      420
tttgtctctt tagggccaca cctgtggcat atggaggttc ccaggctaga ggtccaattg     480
gagatgtagc agccagccta tgccagagcc accgcaacac gggatctgag ccacgtctgt     540
gacttacacc acagctcaca gcaacgcctg atcctcaacc cactgagcga ggccagggat     600
cgaacccatg tcctcatgga tgctagttgg gttcgttaac tgctgagcca tgatgggaac     660
tccaaattaa ttatttctta tatttgttct tcatatattc atttctatag aaagaaataa     720
atacagattc agttaatgat ggcaggtaaa agcttaactt attaatcaaa ggagttaatc     780
caggcacaaa aattcaattc atggctctct gttaaaattt aggtataggt ttagcaggaa     840
gaaaaggtta gtagatgcag actattacat ttagaatgga tggacaatga agtcctacta     900
tacagcacag ggaactatat ccaatctctt gggatagaat atgatggaag acaaaatcag     960
aacaagagag tatatatata tgtgtgtgtg tgtgtgtgtg tgtgtgtgtg tgtgtgtgtg    1020
tgtgtgactg ggtcaccctg cggcacagca gaaattggca gaacattgta aatcaactat    1080
actttaatag gaaaaatact tttaagggct aaatttccaa tattctaacc atgtacacag    1140
agtaaatgtc ataaggatgc cagtctgtgt agagattgat gtgttactag cagattcatg    1200
```

```
aaataaaggc tgaggatgta gtccccaagt cacttctgag tggaagaatt tctcctttgt   1260
cctggactca atattttag gataaaggaa aaagaagat atttatagaa gggacttgtt    1320
ttcaagtact tgacaaaatt tcaccattaa agagaaattt gtgggagttc ccatcgtggc   1380
tcagtggaaa caaatccaac taggaaccat gaggttgtgg gtttgatccc tggcctcact   1440
cagtgggtta aggatccggt gttgccgtga gctgtggtgt aggttgcaga cacggttctg   1500
atcctgcgtt gctgtggctg tggctgtggt gtaggccagc agcaaacagc tctgattaga   1560
cccctagcct ggaaacctcc atatgccaca ggtgcagccc taaaaagaca aaaaagaga    1620 aaagacaaaa aaaaaaaaaa aaaaaaaaa aaaaaaaaa aaaaaaaaa gaaccccag     1680 aggtatttat ttgttttttgc cttttttcac tgactgttct ttgtttgttt gtttgagact   1740
gatctagaag actagagatt acaagaaata tggatttggc tcactctaag aaactgcttt    1800
cattccaagg tttgggtcta tccaaaagtg gaatagaatc atatgaatac tagtttatga   1860
gtatttagtg agaggaattt caagctcaaa taatgattca gcaagattaa attaaggagg   1920
gaattttcct tgtggctgag tgggttaagg acccaatgtt gtctctgtga ggatgtaggt   1980
tccatcctgg gctttgctca ttaggttaag gatctggcat tgctgcagct cagacccagt   2040
gctgccctgg ttgtggctta ggccaaagct gcagctccaa ttcaatctct ggcctgggaa   2100
cctccatgtg ctacaaggtg cggccttaaa aggaaaaaaa aaaattaaa tcaaggactc    2160 aagagtcttt cattatttgt gttgtggaag ctatatttgt tttaaagtct tagttgtgtt   2220
tagaaagcaa gatgttcttc aactcaaatt tgggagggaa cttgtttcat acatttttaa   2280
tggataagtg gcaaaatttt catgctgagg tgatctatag tgttgtaatg cagaatatag   2340
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt cctttctttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctcttaa aatctgagct ccatgtcttc   2640
tgctttattt ctggtgtgcc tttgactcca gattacagta aatggaggac tgagtatagg   2700 gctaaaagt agagagaatg gatgcatatt atctgtggtc tccaatgtga tgaatgaagt    2760
aggcaaatac tcaaggaaa gagaaagcat gctccaagaa ttatgggttc cagaaggcaa    2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tattttttcag  3000 cccacaggaa acccaggctg gttggagggg acattccctg ctctggtcgt gttgaagtac   3060
aacatggaga cacgtgggc accgtctgtg attctgactt ctctctggag gcagccagcg   3120
tgctttgcag ggaaccagag tcagacacta tccccgtgca attcatcatc ctcggaccca   3180
tcaagctcta ttatttcaga agaaaatggt gttgcctgca taggtgagaa tcagtgacca   3240
acctatgaaa atgatctcaa tcctctgaaa tgcattttat tcatgttttta tttcctctttt   3300 gcagggagtg tcaacttcg cctggtcgat ggaggtggtc gttgtgctgg gagagtagag   3360
gtctatcatg agggctcctg gggcaccatc tgtgatgaca gctgggacct gaatgatgcc   3420
catgtggtgt gcaaacagct gagctgtgga tgggccatta atgccactgg ttctgctcat   3480
tttggggaag gaacagggcc catttggctg gatgagataa actgtaatgg aaagaatct    3540 catatttggc aatgccactc acatggttgg gggcggcaca attgcaggca taaggaggat   3600
```
gcaggagtca tctgctcgg                                                  3619

<210> SEQ ID NO 114
<211> LENGTH: 3270
<212> TYPE: DNA
<213> ORGANISM: Sus scrofa

<400> SEQUENCE: 114

| | | | | | |
|---|---|---|---|---|---|
| tatagatgac | aaggctttgt | gtctgatagg | ggccagcgaa | ctcagtaaag | agggaagatg | 60 |
| agaaagataa | tggcaagaat | ttatccctga | agtgtagttt | tgacaaacca | gtcacaaaga | 120 |
| ggtctaagaa | attttggtca | caaagttgtt | ttgaatccca | ggcattttat | ttgcaatgat | 180 |
| tgcatatgtt | ctggaaagga | catctgaacc | taagaaatag | ttcatttgca | ttgtgttata | 240 |
| ttttactaag | gtctgagaaa | taatcttgag | atgagaatga | actctacttc | ttcagagtct | 300 |
| ggaaggaata | aattatgaaa | atgtattaat | gcttctttaa | accatattgt | atatttatct | 360 |
| attactaaac | aaaagaagt | agctctattt | atttatttat | ttatttattt | atttatgtct | 420 |
| tttgtctctt | tagggccaca | cctgtggcat | atggaggttc | ccaggctaga | ggtccaattg | 480 |
| gagatgtagc | agccagccta | tgccagagcc | accgcaacac | gggatctgag | ccacgtctgt | 540 |
| gacttacacc | acagctcaca | gcaacgcctg | atcctcaacc | cactgagcga | ggccagggat | 600 |
| cgaacccatg | tcctcatgga | tgctagttgg | gttcgttaac | tgctgagcca | tgatgggaac | 660 |
| tccaaattaa | ttatttctta | tatttgttct | tcatatattc | atttctatag | aaagaaataa | 720 |
| atacagattc | agtaatgat | ggcaggtaaa | agcttaactt | attaatcaaa | ggagttaatc | 780 |
| caggcacaaa | aattcaattc | atggctctct | gttaaaattt | aggtataggt | ttagcaggaa | 840 |
| gaaaaggtta | gtagatgcag | actattacat | ttagaatgga | tggacaatga | agtcctacta | 900 |
| tacagcacag | ggaactatat | ccaatctctt | gggatagaat | atgatggaag | acaaaatcag | 960 |
| aacaagagag | tatatatata | tgtgtgtgtg | tgtgtgtgtg | tgtgtgtgtg | tgtgtgtgtg | 1020 |
| tgtgtgactg | ggtcaccctg | cggcacagca | gaaattggca | gaacattgta | aatcaactat | 1080 |
| actttaatag | gaaaaatact | tttaagggct | aaatttccaa | tattctaacc | atgtacacag | 1140 |
| agtaaatgtc | ataaggatgc | cagtctgtgt | agagattgat | gtgttactag | cagattcatg | 1200 |
| aaataaaggc | tgaggatgta | gtccccaagt | cacttctgag | tggaagaatt | tctcctttgt | 1260 |
| cctggactca | aatattttag | gataaaggaa | aaagaagat | atttatagaa | gggacttgtt | 1320 |
| ttcaagtact | tgacaaaatt | tcaccattaa | agagaaattt | gtgggagttc | ccatcgtggc | 1380 |
| tcagtggaaa | caaatccaac | taggaaccat | gaggttgtgg | gtttgatccc | tggcctcact | 1440 |
| cagtgggtta | aggatccggt | gttgccgtga | gctgtggtgt | aggttgcaga | cacggttctg | 1500 |
| atcctgcgtt | gctgtggctg | tggctgtggt | gtaggccagc | agcaaacagc | tctgattaga | 1560 |
| cccctagcct | ggaaacctcc | atatgccaca | ggtgcagccc | taaaaagaca | aaaaaagaga | 1620 |
| aaagacaaaa | aaaaaaaaaa | aaaaaaaaaa | aaaaaaaaaa | aaaaaaaaaa | gaaccccag | 1680 |
| aggtatttat | ttgtttttgc | cttttttcac | tgactgttct | ttgtttgttt | gtttgagact | 1740 |
| gatctagaag | actagagatt | acaagaaata | tggatttggc | tcactctaag | aaactgcttt | 1800 |
| cattccaagg | tttgggtcta | tccaaaagtg | gaatagaatc | atatgaatac | tagttttatga | 1860 |
| gtatttagtg | agaggaattt | caagctcaaa | taatgattca | gcaagattaa | attaaggagg | 1920 |
| gaattttcct | tgtggctgag | tgggttaagg | acccaatgtt | gtctctgtga | ggatgtaggt | 1980 |
| tccatcctgg | gctttgctca | ttaggttaag | gatctggcat | tgctgcagct | cagacccagt | 2040 |

```
gctgccctgg ttgtggctta ggccaaagct gcagctccaa ttcaatctct ggcctgggaa    2100
cctccatgtg ctacaaggtg cggccttaaa aggaaaaaaa aaaaattaaa tcaaggactc    2160
aagagtcttt cattatttgt gttgtggaag ctatatttgt tttaaagtct tagttgtgtt    2220
tagaaagcaa gatgttcttc aactcaaatt tgggagggaa cttgtttcat acatttttaa    2280
tggataagtg gcaaaatttt catgctgagg tgatctatag tgttgtaatg cagaatatag    2340
tcagatcttg aacattttag gaagttggtg agggccaatt gtgtatctgt gccatgctga    2400
taagaatgtc aagggatcac aagaattcgt gttatttgac ttgttacagg gaaagtaaac    2460
ttgactttca cggacctcct agttacctgg tgcttactat atgtcttctc agagtacctg    2520
attcattccc agcctggttg acccatcccc ctatctctat ggctatgttt atccagagca    2580
catctatcta acactccagc tgatcttcct gacacagctg tggcaaccct ggatccttta    2640
accaactgtg ccaggctgga gatcaaacct aagcctctgc agcaacccaa gctgctgcag    2700
tcagattttt aacccctgt gccactgtgg gtatctccga tattttgtat cttctgtgac    2760
tgagtggttt gctgtttgca gggaaccaga gtcagacact atccccgtgc aattcatcat    2820
cctcggaccc atcaagctct attatttcag aagaaaatgg tgttgcctgc ataggtgaga    2880
atcagtgacc aacctatgaa aatgatctca atcctctgaa atgcatttta ttcatgtttt    2940
atttcctctt tgcagggagt ggtcaacttc gcctggtcga tggaggtggt cgttgtgctg    3000
ggagagtaga ggtctatcat gagggctcct ggggcaccat ctgtgatgac agctgggacc    3060
tgaatgatgc ccatgtggtg tgcaaacagc tgagctgtgg atgggccatt aatgccactg    3120
gttctgctca ttttggggaa ggaacagggc ccatttggct ggatgagata aactgtaatg    3180
gaaaagaatc tcatatttgg caatgccact cacatggttg ggggcggcac aattgcaggc    3240
ataaggagga tgcaggagtc atctgctcgg                                      3270
```

<210> SEQ ID NO 115
<211> LENGTH: 7
<212> TYPE: DNA
<213> ORGANISM: Sus scrofa

<400> SEQUENCE: 115 tactact                                                                7

<210> SEQ ID NO 116
<211> LENGTH: 12
<212> TYPE: DNA
<213> ORGANISM: Sus scrofa

<400> SEQUENCE: 116
tgtggagaat tc                                                         12

<210> SEQ ID NO 117
<211> LENGTH: 11
<212> TYPE: DNA
<213> ORGANISM: Sus scrofa

<400> SEQUENCE: 117
agccagcgtg c                                                          11

<210> SEQ ID NO 118
<211> LENGTH: 8532
<212> TYPE: DNA
<213> ORGANISM: Sus scrofa

<400> SEQUENCE: 118

-continued

```
tatagatgac aaggctttgt gtctgatagg ggccagcgaa ctcagtaaag agggaagatg    60
agaaagataa tggcaagaat ttatccctga agtgtagttt tgacaaacca gtcacaaaga   120
ggtctaagaa attttggtca caaagttgtt ttgaatccca ggcattttat ttgcaatgat   180
tgcatatgtt ctggaaagga catctgaacc taagaaatag ttcatttgca ttgtgttata   240
ttttactaag gtctgagaaa taatcttgag atgagaatga actctacttc ttcagagtct   300
ggaaggaata aattatgaaa atgtattaat gcttctttaa accatattgt atatttatct   360
attactaaac aaaaagaagt agctctattt atttatttat ttatttattt atttatgtct   420
tttgtctctt tagggccaca cctgtggcat atggaggttc ccaggctaga ggtccaattg   480
gagatgtagc agccagccta tgccagagcc accgcaacac gggatctgag ccacgtctgt   540
gacttacacc acagctcaca gcaacgcctg atcctcaacc cactgagcga ggccagggat   600
cgaacccatg tcctcatgga tgctagttgg gttcgttaac tgctgagcca tgatgggaac   660
tccaaattaa ttatttctta tatttgttct tcatatattc atttctatag aaagaaataa   720
atacagattc agttaatgat ggcaggtaaa agcttaactt attaatcaaa ggagttaatc   780
caggcacaaa aattcaattc atggctctct gttaaaattt aggtataggt ttagcaggaa   840
gaaaaggtta gtagatgcag actattacat ttagaatgga tggacaatga agtcctacta   900
tacagcacag gaactatat ccaatctctt gggatagaat atgatggaag acaaaatcag   960
aacaagagag tatatatata tgtgtgtgtg tgtgtgtgtg tgtgtgtgtg tgtgtgtgtg  1020
tgtgtgactg ggtcaccctg cggcacagca gaaattggca gaacattgta aatcaactat  1080
actttaatag gaaaaatact tttaagggct aaatttccaa tattctaacc atgtacacag  1140
agtaaatgtc ataaggatgc cagtctgtgt agagattgat gtgttactag cagattcatg  1200
aaataaaggc tgaggatgta gtccccaagt cacttctgag tggaagaatt tctcctttgt  1260
cctggactca atatttag gataaaggaa aaagaagat atttatagaa gggacttgtt  1320
ttcaagtact tgacaaaatt tcaccattaa agagaaattt gtgggagttc ccatcgtggc  1380
tcagtggaaa caaatccaac taggaaccat gaggttgtgg gtttgatccc tggcctcact  1440
cagtgggtta aggatccggt gttgccgtga gctgtggtgt aggttgcaga cacggttctg  1500
atcctgcgtt gctgtggctg tggctgtggt gtaggccagc agcaaacagc tctgattaga  1560 ccccctagcct ggaaacctcc atatgccaca ggtgcagccc taaaaagaca aaaaagaga  1620 aaagacaaaa aaaaaaaaaa aaaaaaaaaa aaaaaaaaa aaaaaaaaa gaaccccag  1680 aggtatttat ttgttttttgc cttttttcac tgactgttct ttgtttgttt gtttgagact  1740
gatctagaag actagagatt acaagaaata tggatttggc tcactctaag aaactgcttt  1800
cattccaagg tttgggtcta tccaaaagtg gaatagaatc atatgaatac tagtttatga  1860
gtatttagtg agaggaattt caagctcaaa taatgattca gcaagattaa attaaggagg  1920
gaattttcct tgtggctgag tgggttaagg acccaatgtt gtctctgtga ggatgtaggt  1980
tccatcctgg gctttgctca ttaggttaag gatctggcat tgctgcagct cagacccagt  2040
gctgccctgg ttgtggctta ggccaaagct gcagctccaa ttcaatctct ggcctgggaa  2100
cctccatgtg ctacaaggtg cggccttaaa aggaaaaaaa aaaattaaa tcaaggactc  2160 aagagtcttt cattatttgt gttgtggaag ctatatttgt tttaaagtct tagttgtgtt  2220
tagaaagcaa gatgttcttc aactcaaatt tgggagggaa cttgtttcat acatttttaa  2280
tggataagtg gcaaaatttt catgctgagg tgatctatag tgttgtaatg cagaatatag  2340
```

```
tcagatcttg aacattttag gaagttggtg agggccaatt gtgtatctgt gccatgctga   2400
taagaatgtc aagggatcac aagaattcgt gttatttgac agcagtcatc tttaaaaggc   2460
atttgagaaa gtccaatttc aaatgcattt ccttttcttta aaagataaat tgaagaaaat   2520
aagtctttat ttcccaagta aattgaattg cctctcagtc tgttaaaaga aactcttacc   2580
ttgatgattg cgctcttaac ctggcaaaga ttgtctttaa aatctgagct ccatgtcttc   2640
tgctttattt ctggtgtgcc tttgactcca gattacagta aatggaggac tgagtatagg   2700
gctaaaaagt agagagaatg gatgcatatt atctgtggtc tccaatgtga tgaatgaagt   2760
aggcaaatac tcaaaggaaa gagaaagcat gctccaagaa ttatgggttc agaaggcaa    2820
agtcccagaa ttgtctccag ggaaggacag ggaggtctag aatcggctaa gcccactgta   2880
ggcagaaaaa ccaagaggca tgaatggctt ccctttctca cttttcactc tctggcttac   2940
tcctatcatg aaggaaaata ttggaatcat attctccctc accgaaatgc tattttttcag 3000
cccacaggaa acccaggctg ttggagctg acatgccctg ctctggtcgt gttgaagtaa    3060
aacatgcaga cacgtggggc tccgtctgtg attctgactt ctctctgcat gcggccaacg   3120
tgctgtgcag ggaactaaat tgcggcgatg cgatttccct ctcggtggga gatcactttg   3180
gaaaaggaaa tggactgacc tgggctgaaa aattccagtg tgaggggagc gagacccacc   3240
ttgcactctg cccaatagta caacaccctg aagacacatg tatccacagc agggaagtcg   3300
gcgtagtctg ctcaagtaag agtttactga aaataacact cttaaaatct tgttatgttt   3360
ttattcataa tgtgaatgag tagtagtgga aaataactac cagtttccta agcttataac   3420
ttcgtatagc atacattata cgaagttata agcctgcagg aattctaccg ggtaggggag   3480
gcgcttttcc caaggcagtc tggagcatgc gctttagcag ccccgctggg cacttggcgc   3540
tacacaagtg gcctctggcc tcgcacacat tccacatcca ccgtaggcg ccaaccggct    3600
ccgttctttg gtggccccctt cgcgccacct tctactcctc ccctagtcag gaagttcccc   3660
cccgccccgc agctcgcgtc gtgcaggacg tgacaaatgg aagtagcacg tctcactagt   3720
ctcgtgcaga tggacagcac cgctgagcaa tggaagcggg taggcctttg gggcagcggc   3780
caatagcagc tttgctcctt cgcttttctgg gctcagaggc tgggaagggg tgggtccggg   3840
ggcgggctca ggggcgggct caggggcggg gcgggcgccc gaaggtcctc cggaggcccg   3900
gcattctgca cgcttcaaaa gcgcacgtct gccgcgctgt tctcctcttc ctcatctccg   3960
ggcctttcga cctgcagcca ccatggccat gattgaacag gatggcctgc atgcaggttc   4020
tccagctgcc tgggtggaga gactgtttgg ctatgactgg gcacagcaga ccattggttg   4080
ctctgatgca gcagtgttca gactgtcagc ccagggcagg ccagtcctgt ttgtgaagac   4140
agacctcagt ggggctctca atgagctgca ggatgaggct gccagactct cctggctggc   4200
aacaactggg gtcccctgtg cagctgtcct ggatgtggtc acagaagctg aagggactg    4260
gctcctgctg ggtgaggtgc ctgggcagga cctcctgtcc tctcacctgg ctccagctga   4320
gaaagtgtca atcatggctg atgccatgag aagactccac accctggacc cagccacctg   4380
ccccttttgac caccaggcca agcacaggat tgagagggcc agaaccagga tggaggctgg   4440
cctggtggac caggatgacc tggatgaaga acaccagggc ctggcccctg ctgaactgtt   4500
tgccaggctc aaggcatcca tgccagatgg tgaggacctg gtggtgactc atgggggatgc  4560
ctgcctgccc aacatcatgg tggaaaatgg aaggttctct ggcttcattg actgtggcag   4620
gctgggagtg gctgacaggt accaggacat tgccctggca accagggaca ttgcagaaga   4680
gctgggggga gaatgggcag acaggttcct ggtgctctat ggcattgcag cccctgactc   4740
```

```
ccagagaatt gccttctaca gactgctgga tgagttcttc taaatcgatt ataatcagcc    4800
ataccacatt tgtagaggtt ttacttgctt taaaaaacct cccacacctc ccctgaacc    4860 tgaaacataa aatgaatgca atgttgttgt taaacttgtt tattgcagct tataatggtt    4920
acaaataaag caatagcatc acaaatttca caaataaagc attttttca ctgcattcta    4980 gttgtggttt gtccaaactc atcaatgtgg aaaataacta ccagtttcct aagcttataa    5040
cttcgtatag catacattat acgaagttat aagctagaca aaagtatctt accccaatgg    5100
tagccctgta cccaataaaa gtaggtgttc agtttcatat cctatgaaat accctcttga    5160
tacttttact ttgcatgagg atttagaaga aaaagttttt actataatcc ttaacttagg    5220
aaattctttt gaattggaaa tgaaacacaa attgcttttc attgatatgc catatgatta    5280
tatgaataaa acatgaaatc ttcatattgg attctagtat atacccaagt aaatattttt    5340
tccctagaag agtgccaagt gtgttaaaac cttttggttt aataaagcag aaaaaaataa    5400
actctaaaaa tcataattaa aaatgaaatg cttttattta tagcaattaa ctacaacatg    5460
tttagactta catactatta aatataatat atttaagatc ccctcatgat aaatatgttc    5520
attattttgt aggctgttga tgcactaata tgtatgtaga ttactttgtg aattgcccctt   5580 aataaaattt aaaactttag gctagtaaac ctgtaacact caacttagtt ctgaactatc    5640
tcactattct tttgcaagaa tttacttagg taatgccaac taatttattc caaggccaaa    5700
aagatgacaa tgtcttatat attataaaaa ctaataaaaa ccattttaaa acctagtata    5760
aatttaaagg tacttgctct tctggttcat ctcttctttt gtttacttct gctttcaaaa    5820 acttattat tgtgaccata ttctttactt ccatttattg ttataattta taagatacta     5880
tacttgcaag caataaatgt tatcttttta gcttttaaat ggtctcattt gaaaagaata    5940
tataattagt aagtcatagc tactttaaat aaaaacttat tctttaagag attaaacact    6000
tctccaagtg atctgttttt ctttaattaa aacgttatta actcccaaaa tgatgttatt    6060
gtttttttat aatcttaaat accaataatt accaggtcta ttttgatttt gatacaggat    6120
aaaaactact attaattact taagaatgtg ttctttttta tatgtaccat tttcatgatc    6180
aaagttggtg atatgactga ggttttgatt attattaaac agatagttaa tatgatatat    6240 tcctcattt tccaaatgaa aggaaaaatg tcttatatgg aggaaaagat tggggcaggg    6300
ggattagtaa attattactt aaatatctga ataggaggat ttttcaatga aaggataaag    6360
gaagaatgat tgtatcatct gaatctttcc ctcccttttcc tggagtttgt cctttcaacc    6420
cagtatacct accactccct tcatcaccta ctttcccatt acagtcccta tgtgttgggt    6480
ggtaactatt ttgttttggt gttaatatcc aagtttccct taataacacc tagtgaatgg    6540
aggaaggatg agcatacta cccatcagac atatttagcc accatattta atcaacaagc     6600
atgaagaaag gaagctagcc tctccccttc ctttcctcct gcctctctct ctcttctctg    6660
tcctcgctcc ctttcttccc atcaatattt tcagagcacc tcttatgcgc caggcattgg    6720
gatactcaaa ctggaggaaa caagaaaaaa aaaaaaaaaa ggcgaagacc tcagggaaat    6780
ttatattgct gctatatttt tttgagccta gtgtaaatta aaattcctta atgctgtgcc    6840
ttttaaaaac acaaataagc aaaatagttt atttcttcaa cagttaaatc cttagggtag    6900
gaaagtgatt caggatctat tgctactatt aactcttctt tcattttcac acaggataca    6960
cacaaatccg cttggtgaat ggcaagaccc catgtgaagg aagagtggag ctcaacattc    7020
ttgggtcctg ggggtccctc tgcaactctc actgggacat ggaagatgcc catgttttat    7080
```

```
gccagcagct taaatgtgga gttgcccttt ctatcccggg aggagcacct tttgggaaag    7140
gaagtgagca ggtctggagg cacatgtttc actgcactgg gactgagaag cacatgggag    7200
attgttccgt cactgctctg ggcgcatcac tctgttcttc agggcaagtg gcctctgtaa    7260
tctgctcagg taagagaata agggcagcca gtgatgagcc actcatgacg gtgccttaag    7320
agtgggtgta cctaggagtt cccattgtgg ctcagtggta acaaactcga ctggtatcca    7380
tgagggtatg ggtttgatcc ctggccttgc tcaatgggtt aaggatccag cattgctgtg    7440
agctgtggta taggttgcag actctgctca ggtcccatgt tgctgtgatt gtggtgtagg    7500
ctgactgctg cagcttcaat ttgacccta gcccgggaat ttccataggc cacacgtgca    7560
gcactaagga aggaaaaaaa gaaaaaaaaa aaaaagagt gggtgtgcct atagtgaaga    7620
acagatgtaa aagggaagtg aaagggattc ccccattctg agggattgtg agaagtgtgc    7680
cagaatatta acttcatttg acttgttaca gggaaagtaa acttgacttt cacggacctc    7740
ctagttacct ggtgcttact atatgtcttc tcagagtacc tgattcattc ccagcctggt    7800
tgacccatcc ccctatctct atggctatgt ttatccagag cacatctatc taacactcca    7860
gctgatcttc ctgacacagc tgtggcaacc ctggatcctt taaccaactg tgccaggctg    7920
gagatcaaac ctaagcctct gcagcaaccc aagctgctgc agtcagattt ttaaccccct    7980
gtgccactgt gggtatctcc gatattttgt atcttctgtg actgagtggt ttgctgtttg    8040
cagggaacca gagtcagaca ctatcccgt gcaattcatc atcctcggac ccatcaagct    8100
ctattatttc agaagaaaat ggtgttgcct gcataggtga gaatcagtga ccaacctatg    8160
aaaatgatct caatcctctg aaatgcattt tattcatgtt ttatttcctc tttgcaggga    8220
gtggtcaact tcgcctggtc gatggaggtg gtcgttgtgc tgggagagta gaggtctatc    8280
atgagggctc ctggggcacc atctgtgatg acagctggga cctgaatgat gcccatgtgg    8340
tgtgcaaaca gctgagctgt ggatgggcca ttaatgccac tggttctgct cattttgggg    8400
aaggaacagg gcccatttgg ctggatgaga taaactgtaa tggaaaagaa tctcatattt    8460
ggcaatgcca ctcacatggt tggggcggc acaattgcag gcataaggag gatgcaggag    8520
tcatctgctc gg                                                        8532
```

<210> SEQ ID NO 119
<211> LENGTH: 4538
<212> TYPE: DNA
<213> ORGANISM: Sus scrofa

<400> SEQUENCE: 119

```
tatagatgac aaggctttgt gtctgatagg ggccagcgaa ctcagtaaag agggaagatg     60
agaaagataa tggcaagaat ttatccctga agtgtagttt tgacaaacca gtcacaaaga    120
ggtctaagaa attttggtca caaagttgtt ttgaatccca ggcatttat ttgcaatgat    180
tgcatatgtt ctggaaagga catctgaacc taagaaatag ttcatttgca ttgtgttata    240
ttttactaag gtctgagaaa taatcttgag atgagaatga actctacttc ttcagagtct    300
ggaaggaata aattatgaaa atgtattaat gcttctttaa accatattgt atatttatct    360
attactaaac aaaagaagt agctctattt atttatttat ttatttattt atttatgtct    420
tttgtctctt tagggccaca cctgtggcat atggaggttc ccaggctaga ggtccaattg    480
gagatgtagc agccagccta tgccagagcc accgcaacac gggatctgag ccacgtctgt    540
gacttacacc acagctcaca gcaacgcctg atcctcaacc cactgagcga ggccagggat    600
cgaacccatg tcctcatgga tgctagttgg gttcgttaac tgctgagcca tgatgggaac    660
```

```
tccaaattaa ttatttctta tatttgttct tcatatattc atttctatag aaagaaataa      720
atacagattc agttaatgat ggcaggtaaa agcttaactt attaatcaaa ggagttaatc      780
caggcacaaa aattcaattc atggctctct gttaaaattt aggtataggt ttagcaggaa      840
gaaaaggtta gtagatgcag actattacat ttagaatgga tggacaatga agtcctacta      900
tacagcacag ggaactatat ccaatctctt gggatagaat atgatggaag acaaaatcag      960
aacaagagag tatatatata tgtgtgtgtg tgtgtgtgtg tgtgtgtgtg tgtgtgtgtg     1020
tgtgtgactg ggtcaccctg cggcacagca gaaattggca gaacattgta aatcaactat     1080
actttaatag gaaaaatact tttaagggct aaatttccaa tattctaacc atgtacacag     1140
agtaaatgtc ataaggatgc cagtctgtgt agagattgat gtgttactag cagattcatg     1200
aaataaaggc tgaggatgta gtccccaagt cacttctgag tggaagaatt tctcctttgt     1260
cctggactca aatattttag gataaaggaa aaagaagat atttatagaa gggacttgtt      1320
ttcaagtact tgacaaaatt tcaccattaa agagaaattt gtgggagttc ccatcgtggc     1380
tcagtggaaa caaatccaac taggaaccat gaggttgtgg gtttgatccc tggcctcact     1440
cagtgggtta aggatccggt gttgccgtga gctgtggtgt aggttgcaga cacggttctg     1500
atcctgcgtt gctgtggctg tggctgtggt gtaggccagc agcaaacagc tctgattaga     1560
cccctagcct ggaaacctcc atatgccaca ggtgcagccc taaaaagaca aaaaagaga      1620 aaagacaaaa aaaaaaaaa aaaaaaaaa aaaaaaaaa aaaaaaaaa gaaccccag          1680 aggtatttat ttgttttgc cttttttcac tgactgttct ttgtttgttt gtttgagact      1740
gatctagaag actagagatt acaagaaata tggatttggc tcactctaag aaactgcttt     1800
cattccaagg tttgggtcta tccaaaagtg gaatagaatc atatgaatac tagtttatga     1860
gtatttagtg agaggaattt caagctcaaa taatgattca gcaagattaa attaaggagg     1920
gaattttcct tgtggctgag tgggttaagg acccaatgtt gtctctgtga ggatgtaggt     1980
tccatcctgg gctttgctca ttaggttaag gatctggcat tgctgcagct cagacccagt     2040
gctgccctgg ttgtggctta ggccaaagct gcagctccaa ttcaatctct ggcctgggaa     2100
cctccatgtg ctacaaggtg cggccttaaa aggaaaaaaa aaaattaaa tcaaggactc      2160 aagagtcttt cattatttgt gttgtggaag ctatatttgt tttaaagtct tagttgtgtt     2220
tagaaagcaa gatgttcttc aactcaaatt tgggaggaa cttgtttcat acatttttaa      2280
tggataagtg gcaaaatttt catgctgagg tgatctatag tgttgtaatg cagaatatag     2340
tcagatcttg aacattttag gaagttggtg agggccaatt gtgtatctgt gccatgctga     2400
taagaatgtc aagggatcac aagaattcgt gttatttgac agcagtcatc tttaaaaggc     2460
atttgagaaa gtccaatttc aaatgcattt cctttcttta aaagataaat tgaagaaaat     2520
aagtctttat ttcccaagta aattgaattg cctctcagtc tgttaaaaga aactcttacc     2580
ttgatgattg cgctcttaac ctggcaaaga ttgtctttaa aatctgagct ccatgtcttc     2640
tgctttattt ctggtgtgcc tttgactcca gattacagta aatggaggac tgagtatagg     2700
gctaaaaagt agagagaatg gatgcatatt atctgtggtc tccaatgtga tgaatgaagt     2760
aggcaaatac tcaaaggaaa gagaaagcat gctccaagaa ttatgggttc cagaaggcaa     2820
agtcccagaa ttgtctccag ggaaggacag ggaggtctag aatcggctaa gcccactgta     2880
ggcagaaaaa ccaagaggca tgaatggctt ccctttctca cttttcactc tctggcttac     2940
tcctatcatg aaggaaaata ttggaatcat attctccctc accgaaatgc tatttttcag     3000
```

```
cccacaggaa acccagctca acattcttgg gtcctggggg tccctctgca actctcactg    3060
ggacatggaa gatgcccatg ttttatgcca gcagcttaaa tgtggagttg ccctttctat    3120
cccgggagga gcacctttg ggaaaggaag tgagcaggtc tggaggcaca tgtttcactg     3180
cactgggact gagaagcaca tgggagattg ttccgtcact gctctgggcg catcactctg    3240
ttcttcaggg caagtggcct ctgtaatctg ctcaggtaag agaataaggg cagccagtga    3300
tgagccactc atgacggtgc cttaagagtg ggtgtaccta ggagttccca ttgtggctca    3360
gtggtaacaa actcgactgg tatccatgag ggtatgggtt tgatccctgg ccttgctcaa    3420
tgggttaagg atccagcatt gctgtgagct gtggtatagg ttgcagactc tgctcaggtc    3480
ccatgttgct gtgattgtgg tgtaggctga ctgctgcagc ttcaatttga ccctagccc     3540
gggaatttcc ataggccaca cgtgcagcac taaggaagga aaaaagaaa aaaaaaaa      3600
aagagtgggt gtgcctatag tgaagaacag atgtaaaagg gaagtgaaag ggattccccc    3660
attctgaggg attgtgagaa gtgtgccaga atattaactt catttgactt gttacaggga    3720
aagtaaactt gactttcacg gacctcctag ttacctggtg cttactatat gtcttctcag    3780
agtacctgat tcattcccag cctggttgac ccatcccct atctctatgg ctatgtttat     3840
ccagagcaca tctatctaac actccagctg atcttcctga cacagctgtg gcaaccctgg    3900
atcctttaac caactgtgcc aggctggaga tcaaacctaa gcctctgcag caacccaagc    3960
tgctgcagtc agatttttaa ccccctgtgc cactgtgggt atctccgata ttttgtatct    4020
tctgtgactg agtggtttgc tgtttgcagg gaaccagagt cagacactat ccccgtgcaa    4080
ttcatcatcc tcggacccat caagctctat tatttcagaa gaaaatggtg ttgcctgcat    4140
aggtgagaat cagtgaccaa cctatgaaaa tgatctcaat cctctgaaat gcattttatt    4200
catgttttat ttcctctttg cagggagtgg tcaacttcgc ctggtcgatg gaggtggtcg    4260
ttgtgctggg agagtagagg tctatcatga gggctcctgg ggcaccatct gtgatgacag    4320
ctgggacctg aatgatgccc atgtggtgtg caaacagctg agctgtggat gggccattaa    4380
tgccactggt tctgctcatt tggggaagg aacagggccc atttggctgg atgagataaa     4440
ctgtaatgga aaagaatctc atatttggca atgccactca catggttggg ggcggcacaa    4500
ttgcaggcat aaggaggatg caggagtcat ctgctcgg                           4538
```

<210> SEQ ID NO 120
<211> LENGTH: 101
<212> TYPE: PRT
<213> ORGANISM: Sus scrofa

<400> SEQUENCE: 120

```
Pro Arg Leu Val Gly Gly Asp Ile Pro Cys Ser Gly Arg Val Glu Val
1               5                   10                  15

Gln His Gly Asp Thr Trp Gly Thr Val Cys Asp Ser Asp Phe Ser Leu
            20                  25                  30

Glu Ala Ala Ser Val Leu Cys Arg Glu Leu Gln Cys Gly Thr Val Val
        35                  40                  45

Ser Leu Leu Gly Gly Ala His Phe Gly Glu Gly Ser Gly Gln Ile Trp
    50                  55                  60

Ala Glu Glu Phe Gln Cys Glu Gly His Glu His Leu Ser Leu Cys
65                  70                  75                  80

Pro Val Ala Pro Arg Pro Asp Gly Thr Cys Ser His Ser Arg Asp Val
                85                  90                  95

Gly Val Val Cys Ser
            100
```

-continued

```
<210> SEQ ID NO 121
<211> LENGTH: 100
<212> TYPE: PRT
<213> ORGANISM: Homo sapiens

<400> SEQUENCE: 121

Leu Arg Leu Val Asp Gly Asp Ser Arg Cys Ala Gly Arg Val Glu Ile
1               5                   10                  15

Tyr His Asp Gly Phe Trp Gly Thr Ile Cys Asp Asp Gly Trp Asp Leu
            20                  25                  30

Ser Asp Ala His Val Val Cys Gln Lys Leu Gly Cys Gly Val Ala Phe
        35                  40                  45

Asn Ala Thr Val Ser Ala His Phe Gly Glu Gly Ser Gly Pro Ile Trp
    50                  55                  60

Leu Asp Leu Asn Cys Thr Gly Met Glu Ser His Leu Trp Gln Cys
65                  70                  75                  80

Pro Ser Arg Gly Trp Gly Gln His Asp Cys Arg His Lys Glu Asp Ala
                85                  90                  95

Gly Val Ile Cys
            100
```